(12) United States Patent
Ballard et al.

(10) Patent No.: US 9,708,259 B2
(45) Date of Patent: Jul. 18, 2017

(54) INDOL AND INDAZOL DERIVATIVES

(71) Applicant: Hoffmann-La Roche Inc., Little Falls, NJ (US)

(72) Inventors: Theresa M. Ballard, Lutter (FR); Katrin Groebke Zbinden, Liestal (CH); Emmanuel Pinard, Linsdorf (FR); Thomas Ryckmans, Rosenau (FR); Herve Schaffhauser, Habsheim (FR); Jean-Baptiste Blanc, Sierentz (FR)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/082,754

(22) Filed: Mar. 28, 2016

(65) Prior Publication Data

US 2016/0207885 A1    Jul. 21, 2016

Related U.S. Application Data

(63) Continuation of application No. PCT/EP2014/070092, filed on Sep. 22, 2014.

(30) Foreign Application Priority Data

Sep. 27, 2013   (EP) .................................... 13186458

(51) Int. Cl.
| | | |
|---|---|---|
| *C07D 209/42* | (2006.01) |
| *C07D 409/12* | (2006.01) |
| *C07D 401/06* | (2006.01) |
| *C07D 405/10* | (2006.01) |
| *C07D 493/08* | (2006.01) |
| *C07D 401/14* | (2006.01) |
| *C07D 405/14* | (2006.01) |
| *C07D 417/14* | (2006.01) |
| *C07D 413/14* | (2006.01) |
| *C07D 405/12* | (2006.01) |
| *C07D 471/04* | (2006.01) |
| *C07D 403/10* | (2006.01) |

(52) U.S. Cl.
CPC ......... *C07D 209/42* (2013.01); *C07D 401/06* (2013.01); *C07D 401/14* (2013.01); *C07D 403/10* (2013.01); *C07D 405/10* (2013.01); *C07D 405/12* (2013.01); *C07D 405/14* (2013.01); *C07D 409/12* (2013.01); *C07D 413/14* (2013.01); *C07D 417/14* (2013.01); *C07D 471/04* (2013.01); *C07D 493/08* (2013.01)

(58) Field of Classification Search
None
See application file for complete search history.

(56) References Cited

U.S. PATENT DOCUMENTS

2015/0126487 A1    5/2015   Sakamoto et al.

FOREIGN PATENT DOCUMENTS

| JP | 2013-514358 A | 4/2013 | |
|---|---|---|---|
| WO | 2011/084368 A1 | 7/2011 | |
| WO | WO 2013/106795 A1 * | 7/2013 | ........... A61K 31/415 |
| WO | 2013/129622 A1 | 9/2013 | |

OTHER PUBLICATIONS

ISR for PCT/EP 2014/070092, mailed Nov. 27, 2014.
Written Opinion for PCT/EP 2014/070092, mailed Aug. 26, 2015.

* cited by examiner

*Primary Examiner* — Brian J Davis
(74) *Attorney, Agent, or Firm* — Genentech, Inc.; Mark D. Kafka

(57) ABSTRACT

The present invention relates to compounds of formula I or pharmaceutically acceptable addition salts, racemic mixtures or the corresponding enantiomers and optical isomers thereof. The compounds may be used for the treatment or prophylaxis of Alzheimer's disease, cognitive impairment, schizophrenia, pain and sleep disorder.

13 Claims, No Drawings

INDOL AND INDAZOL DERIVATIVES

CROSS REFERENCE TO RELATED APPLICATIONS

This application is a continuation of International Application No. PCT/EP2014/070092 having an International Filing Date of 22 Sep. 2014, the entire contents of which are incorporated herein by reference, and which claims the benefit of priority under 35 U.S.C. §119 to EP 13186458.9 filed 27 Sep. 2013.

The present invention relates to compounds of formula wherein
A is

R is lower alkyl, $-(CH_2)_z-C_{3-7}$-cycloalkyl or $-(CH_2)_z-C_{4-6}$-heterocycloalkyl, which are optionally substituted by one to three hydroxy, lower alkyl, lower alkoxy or halogen, or is (endo)-7-oxabicyclo[2.2.1]heptan-2-yl;
X is CH or N;
$Y^1$ is $CR^3$ or N;
$Y^2$ is $CR^4$; or
or $Y^1$ and $Y^2$ may form together with the carbon atoms to which they are attach $Y^3$ is N;
$Y^4$ is N;
$Y^5$ is $NR^7$;
$R^1$ is hydrogen or halogen;
$R^2$ is hydrogen, halogen, cycloalkyl, lower alkyl or lower alkoxy;
$R^3$ is hydrogen, halogen, CN, $-C(O)NH_2$, $-C(O)NHCH_3$ or $-C(O)N(CH_3)_2$;
$R^4$ is hydrogen, a 5 or 6 membered heteroaryl or heterocyclyl group, selected from the group consisting of or is phenyl, $-C(O)NH_2$, $-CH_2C(O)NH_2$, $-C(O)NHCH_3$, $-C(O)NH$-cycloalkyl, $-C(O)N(CH_3)_2$, $-NHC(O)O$-lower alkyl, CN, lower alkoxy, lower alkoxy substituted by halogen, halogen or $S(O)_2CH_3$;
$R^5$ is phenyl;
$R^6$ is phenyl or thiazol-2-yl;
$R^7$ is pyridin-2-yl or pyrimidin-4-yl;

p is 0 or 1;
m is 1, 2 or 3;
z is 0 or 1;
or to a pharmaceutically acceptable acid addition salt, to a racemic mixture or to its corresponding enantiomer and/or optical isomers thereof.

WO 2013/106795 describes a very broad scope of partially similar compounds for treating neurological and psychiatric disorders associated with muscarinic acetylcholine receptor dysfunction. The activity ($EC_{50}$, in nM) is very low between 2400 and >10000, and therefore these compounds are not suitable for the development of corresponding drugs.

The compounds of the present invention are muscarinic M1 receptor positive allosteric modulators (PAM) and hence are useful in the treatment of diseases, mediated by the muscarinic M1 receptor, such as Alzheimer's disease, cognitive impairment, schizophrenia, pain or sleep disorders. Acetylcholine (ACh) is a neurotransmitter which activates both nicotinic (ligand-gated ion channel) and muscarinic (metabotropic) receptors in the CNS and in the periphery.

The muscarinic receptors (mAChRs) are members of the class A G-protein-coupled receptors. To date, five distinct subtypes of mAChRs (M1-M5) have been cloned and sequenced. The muscarinic M1 receptors are predominantly distributed in the brain, with the highest expression in the cortex, thalamus, striatum and hippocampus. In clinical studies, Xanomeline, a M1/M4-preferring agonist, demonstrated robust efficacy on positive, negative and cognitive symptoms in schizophrenic patients and improved cognitive scores and reduced psychotic-like behaviors in patients with Alzheimer's disease (AD). The M1 receptor has been implicated in memory and learning processes, regulation of dopamine and NMDA receptor activity and has thus been proposed as a potential target for the treatment of AD and schizophrenia.

AD is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length by processing of the beta-amyloid precursor protein (APP) by the beta-amyloid protein cleaving enzyme. The processing leads to accumulation of Abeta in the brain.

M1 receptors are abundantly expressed postsynaptically in cortex, hippocampus and striatum which are important brain regions involved for cognition. Based on the cholinergic hypothesis i.e. degeneration of presynaptic cholinergic nerve terminals in hippocampus and cortical regions, M1 activation should rescue the cognitive deficits which occur in AD, thus providing symptomatic treatment of this neurodegenerative disorder. Postmortem studies in AD cortical tissues have shown that M1 receptor expression are not reduced, thus providing evidence for target availability in a critical brain region. Moreover, preclinical studies have shown that M1 activation has potential as a disease-modifying therapy for AD by shifting the APP processing towards the non-amyloidogenic α-secretase pathway and by decreasing tau hyperphosphorylation. Therefore, M1 PAMs provide an approach to target both symptomatic and disease-modifying treatment of AD.

Schizophrenia is a severe, disabling, lifelong disorder that affects 1% of the population and is characterized by positive symptoms (such as hallucinations, delusions and paranoia), negative symptoms (such as social withdrawal and apathy) and cognitive impairment (for example, deficits in working memory, executive function and attention). Schizophrenia is a neurodevelopmental disorder with genetic risk factors and neuropathological changes. Aberrant activity occurs within the prefrontal hippocampal thalamic network in brains of schizophrenia patients. Positive symptoms of schizophrenia are suggested to be caused by dopaminergic system dysfunction, particularly increased dopamine activity within subcortical brain regions such as the striatum. Negative symptoms are thought to occur due to impaired signaling within the neurocircuitry of the ventral tegmental area and ventral striatum. Decreased NMDA receptor function in pyramidal neurons coupled with sub-optimal dopamine release in critical regions such as dorsolateral prefrontal cortex may account for some of the cognitive deficits.

M1 receptors are located in regions which are affected in schizophrenia, such as the hippocampus, cortex and striatum, in particular in the medium spiny neurons. Several reports have shown a reduction in muscarinic receptors in the prefrontal cortex and hippocampus, regions where M1 is densely expressed, in a subset of schizophrenic patients. Furthermore, preclinical studies have shown that M1 knock-out mice have enhanced amphetamine-induced activity and increased striatal dopamine levels. Electrophysiology studies have revealed that activation of M1 receptors potentiates NMDA mediated hippocampal activity, modulates activity of medium spiny neurons and increases activity of medial prefrontal cortex neurons. Overall, activation of M1 receptors should modulate dysfunctional dopaminergic and glutamatergic signaling within the underlying neurocircuitry resulting in improvements in the symptoms of schizophrenia.

The clinical effects of Xanomeline and other muscarinic M1 agonist agents were however always associated with adverse effects attributed to their insufficient M1 muscarinic receptor subtype selectivity. The typical observed side effects, including sweating, salivation, gastrointestinal distress and bradycardia have been attributed to the non-specific activation of peripheral M2 and M3 mAChRs. Despite a tremendous effort from a number of companies, the search for highly M1 selective agonists has failed because of the high degree of conservation between muscarinic receptor subtypes at their orthosteric acetylcholine ligand binding sites.

To circumvent the selectivity and safety issues associated with targeting the highly conserved orthosteric ACh site, an alternative approach consists of developing M1 PAMs that act at the less highly conserved allosteric binding sites.

Recently, Merck and Vanderbilt University reported M1 PAMs from different chemical classes exhibiting, as rationalized, a good level of M1 subtype selectivity. Importantly, similar to the preclinical profile of Xanomeline and other unselective M1 agonists, these M1 allosteric agents demonstrated pro-cognitive effects (in scopolamine-induced memory deficit in mice, scopolamine impaired non-human primates and in transgenic AD mice). PQCA and ML169 have been shown to promote non-amyloidogenic APP processing. Electrophysiology studies have shown that M1 PAMs potentiate carbachol-induced activity in the medial prefrontal cortex and medium spiny neurons. Moreover, unlike unselective agonists, M1 PAMs do not appear to produce side effects such as salivation at therapeutic effective doses. Additionally, they are expected to be devoid of liabilities such as receptor desensitization/internalization following chronic dosing previously reported for orthosteric receptor agonists. In summary, the PAM approach, by activating in a truly selective manner M1 receptors, is a highly promising novel strategy to deliver both efficacious and safe therapeutic agents for the treatment of schizophrenia (positive, negative and cognitive symptoms) as well as AD (symptomatic and disease modifying).

Thus, the compounds of the invention, which are muscarinic M1 receptor positive allosteric modulators, are believed to be useful in the treatment of Alzheimer's disease and other diseases mediated by the muscarinic M1 receptor, without side effects.

Therefore, the object of the present invention was to identify compounds that are muscarinic M1 receptor positive allosteric modulators. It has been found that the compounds of formula I are active in this area and they may therefore be used for the treatment of Alzheimer's disease, cognitive impairment, schizophrenia, pain or sleep disorders The present invention relates to compounds of formula I and to their pharmaceutically acceptable salts, to these compounds as pharmaceutically active substances, to the processes for their production, as well as to the use in the treatment or prevention of disorders, relating to muscarinic M1 receptor positive allosteric modulators, and to pharmaceutical compositions containing the compounds of formula I.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, isopropyl, n-butyl, i-butyl, 2-butyl, t-butyl and the like.

As used therein, the term "$C_{3-7}$-cycloalkyl" denotes a saturated carbon ring, containing from 3 to 7 carbon ring atoms, for example cyclopropyl, cyclobutyl, cyclopentyl, cyclohexyl or cycloheptyl.

The term "alkoxy" denotes a group —O—R' wherein R' is lower alkyl as defined above.

The term "halogen" denotes chlorine, bromine, fluorine or iodine.

The term "lower alkoxy substituted by halogen" denotes an alkyl group as defined above, wherein at least one hydrogen atoms is replaced by halogen, for example $OCF_3$, $OCH_2F$, $OCH_2CF_3$, $OCH_2CH_2CF_3$, $OCH_2CF_2CF_3$ and the like.

The term "$C_{4-6}$-heterocycloalkyl" denotes a non-aromatic heterocyclic ring with 4 to 6 ring atoms, containing at least one O atom, for example tetrahydropyran-4-yl, tetrahydrothiopyran, thiane 1,1-dioxide, tetrahydropyran-3-yl, oxolan-3-yl, oxetan-3-yl, oxetan-2-yl or tetrahydrofuran-2-yl.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like One embodiment of the present invention are compounds of formula I, wherein R is —$(CH_2)_z$—$C_{4-6}$-cycloalkyl, which is optionally substituted by one to three hydroxy, lower alkyl, lower alkoxy or halogen or 8endo)-7-oxabicyclo[2.2.1]heptan-2-yl; and p is 0 or 1, and the other substituents are as described above, for example the following compounds:

4-fluoro-1-(2-fluoro-4-(1-methyl-1H-pyrazol-4-yl)benzyl)-N-((1S,2S)-2-hydroxycyclohexyl)-1H-indole-3-carboxamide 4-fluoro-1-(2-fluoro-4-(1-methyl-1H-pyrazol-4-yl)benzyl)-N-((1R,2R)-2-hydroxycyclohexyl)-1H-indole-3-carboxamide 4-fluoro-1-(2-fluoro-4-(1-methyl-1H-pyrazol-4-yl)benzyl)-N-((1S,2S)-2-hydroxycyclohexyl)-1H-indazole-3-carboxamide 4-fluoro-1-(2-fluoro-4-(1-methyl-1H-pyrazol-4-yl)benzyl)-N-((1R,2R)-2-hydroxycyclohexyl)-1H-indazole-3-carboxamide N-(3,3-difluorocyclobutyl)-4-fluoro-1-(4-(1-methyl-1H-pyrazol-4-yl)benzyl)-1H-indole-3-carboxamide N-cyclobutyl-4-fluoro-1-(4-(1-methyl-1H-pyrazol-4-yl)benzyl)-1H-indole-3-carboxamide 4-fluoro-1-(2-fluoro-4-(1-methyl-1H-pyrazol-4-yl)benzyl)-N-((1S,2S)-2-hydroxycyclopentyl)-1H-indole-3-carboxamide 4-fluoro-1-(2-fluoro-4-(1-methyl-1H-pyrazol-4-yl)benzyl)-N-((1SR,2SR)-2-hydroxy-2-methylcyclohexyl)-1H-indole-3-carboxamide N-cyclohexyl-4-fluoro-1-(2-fluoro-4-(1-methyl-1H-pyrazol-4-yl)benzyl)-1H-indole-3-carboxamide 4-fluoro-1-(2-fluoro-4-(1-methyl-1H-pyrazol-4-yl)benzyl)-N-((1SR,2RS)-2-hydroxy-2-methylcyclohexyl)-1H-indole-3-carboxamide 4-fluoro-1-(2-fluoro-4-(1-methyl-1H-pyrazol-4-yl)benzyl)-N-((1S,2R)-2-hydroxycyclopentyl)-1H-indole-3-carboxamide N-(2,2-difluorocyclohexyl)-4-fluoro-1-(2-fluoro-4-(1-methyl-1H-pyrazol-4-yl)benzyl)-1H-indole-3-carboxamide 4,5,6,7-tetrafluoro-1-(2-fluoro-4-(1-methyl-1H-pyrazol-4-yl)benzyl)-N-((1S,2S)-2-hydroxycyclohexyl)-1H-indole-3-carboxamide 4,5,6,7-tetrafluoro-N-((1S,2S)-2-hydroxycyclohexyl)-1-((6-(1-methyl-1H-pyrazol-4-yl)pyridin-3-yl)methyl)-1H-indole-3-carboxamide 4-fluoro-1-(2-fluoro-4-methoxybenzyl)-N-((1S,2S)-2-hydroxycyclohexyl)-1H-indole-3-carboxamide 1-(4-(difluoromethoxy)benzyl)-4-fluoro-N-((1S,2S)-2-hydroxycyclohexyl)-1H-indole-3-carboxamide 4-fluoro-N-((1S,2S)-2-hydroxycyclohexyl)-1-((6-(1-methyl-1H-pyrazol-4-yl)pyridin-3-yl)methyl)-1H-indole-3-carboxamide 4-fluoro-N-((1S,2S)-2-hydroxycyclohexyl)-1-(4-methoxybenzyl)-1H-indole-3-carboxamide 1-(4-cyanobenzyl)-4-fluoro-N-((1S,2S)-2-hydroxycyclohexyl)-1H-indole-3-carboxamide 4-fluoro-1-(3-fluoro-4-methoxybenzyl)-N-((1S,2S)-2-hydroxycyclohexyl)-1H-indole-3-carboxamide 4-fluoro-N-((1S,2S)-2-hydroxycyclohexyl)-1-(4-(trifluoromethoxy)benzyl)-1H-indole-3-carboxamide 4-fluoro-N-((1S,2S)-2-hydroxycyclohexyl)-1-(3-(1-methyl-1H-pyrazol-4-yl)benzyl)-1H-indole-3-carboxamide 4-fluoro-N-((1S,2S)-2-hydroxycyclohexyl)-1-(4-(4-methyl-1H-imidazol-1-yl)benzyl)-1H-indole-3-carboxamide 4-fluoro-N-((1S,2S)-2-hydroxycyclohexyl)-1-((1-methyl-1H-indazol-5-yl)methyl)-1H-indole-3-carboxamide 1-(4-chlorobenzyl)-4-fluoro-N-((1S,2S)-2-hydroxycyclohexyl)-1H-indole-3-carboxamide 1-(3-chlorobenzyl)-4-fluoro-N-((1S,2S)-2-hydroxycyclohexyl)-1H-indole-3-carboxamide 1-(3-cyanobenzyl)-4-fluoro-N-((1S,2S)-2-hydroxycyclohexyl)-1H-indole-3-carboxamide
1-(3,4-difluorobenzyl)-4-fluoro-N-((1S,2S)-2-hydroxycyclohexyl)-1H-indole-3-carboxamide
4-fluoro-1-(4-fluorobenzyl)-N-((1S,2S)-2-hydroxycyclohexyl)-1H-indole-3-carboxamide
1-(3,5-difluorobenzyl)-4-fluoro-N-((1S,2S)-2-hydroxycyclohexyl)-1H-indole-3-carboxamide
4-fluoro-N-((1S,2S)-2-hydroxycyclohexyl)-1-(4-(1-methyl-1H-pyrazol-4-yl)benzyl)-1H-indole-3-carboxamide
4-fluoro-1-(2-fluoro-4-(1-methyl-1H-pyrazol-4-yl)benzyl)-N-((1S,2S)-2-hydroxycyclohexyl)-7-methyl-1H-indole-3-carboxamide
4-fluoro-N-((1S,2S)-2-hydroxycyclohexyl)-7-methyl-1-(4-(1-methyl-1H-pyrazol-4-yl)benzyl)-1H-indole-3-carboxamide
1-benzyl-4-fluoro-N-((1S,2S)-2-hydroxycyclohexyl)-1H-indole-3-carboxamide
4-fluoro-N-((1S,2S)-2-hydroxycyclohexyl)-1-(4-(3-methyl-1H-pyrazol-1-yl)benzyl)-1H-indole-3-carboxamide
4,5,6,7-tetrafluoro-N-((1S,2S)-2-hydroxycyclohexyl)-1-(4-(1-methyl-1H-pyrazol-4-yl)benzyl)-1H-indole-3-carboxamide
4-fluoro-N-((1S,2S)-2-hydroxycyclohexyl)-1-((1-methyl-1H-benzo[d]imidazol-5-yl)methyl)-1H-indole-3-carboxamide
4,5-difluoro-N-((1S,2S)-2-hydroxycyclohexyl)-1-(4-(1-methyl-1H-pyrazol-4-yl)benzyl)-1H-indole-3-carboxamide
4,5-difluoro-N-((1S,2S)-2-hydroxycyclohexyl)-1-((6-(1-methyl-1H-pyrazol-4-yl)pyridin-3-yl)methyl)-1H-indole-3-carboxamide
4-fluoro-N-((1S,2S)-2-hydroxycyclohexyl)-1-(4-(methylcarbamoyl)benzyl)-1H-indole-3-carboxamide
4,5-difluoro-N-((1S,2S)-2-hydroxycyclohexyl)-1-(4-(4-methyl-1H-imidazol-1-yl)benzyl)-1H-indole-3-carboxamide
4,5-difluoro-N-((1S,2S)-2-hydroxycyclohexyl)-1-(4-(3-methyl-1H-pyrazol-1-yl)benzyl)-1H-indole-3-carboxamide
4,7-difluoro-1-(2-fluoro-4-(1-methyl-1H-pyrazol-4-yl)benzyl)-N-((1S,2S)-2-hydroxycyclohexyl)-1H-indazole-3-carboxamide
4,7-difluoro-N-((1S,2S)-2-hydroxycyclohexyl)-1-((6-(1-methyl-1H-pyrazol-4-yl)pyridin-3-yl)methyl)-1H-indazole-3-carboxamide
4-fluoro-N-((1S,2S)-2-hydroxycyclohexyl)-1-(4-(methylcarbamoyl)benzyl)-1H-indole-3-carboxamide
1-(4-carbamoylbenzyl)-4-fluoro-N-((1S,2S)-2-hydroxycyclohexyl)-1H-indole-3-carboxamide
1-(4-(2-amino-2-oxoethyl)benzyl)-4-fluoro-N-((1S,2S)-2-hydroxycyclohexyl)-1H-indole-3-carboxamide
1-(3-carbamoylbenzyl)-4-fluoro-N-((1S,2S)-2-hydroxycyclohexyl)-1H-indole-3-carboxamide
4-fluoro-N-((1S,2S)-2-hydroxycyclohexyl)-1-(4-(methylsulfonyl)benzyl)-1H-indole-3-carboxamide
ethyl 4-((4-fluoro-3-((1S,2S)-2-hydroxycyclohexylcarbamoyl)-1H-indol-1-yl)methyl)phenylcarbamate
4-fluoro-1-(2-fluoro-4-(methylcarbamoyl)benzyl)-N-((1S,2S)-2-hydroxycyclohexyl)-1H-indole-3-carboxamide
4-fluoro-N-((1S,2S)-2-hydroxycyclohexyl)-1-((6-(methylcarbamoyl)pyridin-3-yl)methyl)-1H-indole-3-carboxamide
4-fluoro-1-(3-fluoro-4-(methylcarbamoyl)benzyl)-N-((1S,2S)-2-hydroxycyclohexyl)-1H-indole-3-carboxamide
4-fluoro-N-((1S,2S)-2-hydroxycyclohexyl)-1-(3-(methylcarbamoyl)benzyl)-1H-indole-3-carboxamide
1-(3-(dimethylcarbamoyl)benzyl)-4-fluoro-N-((1S,2S)-2-hydroxycyclohexyl)-1H-indole-3-carboxamide
2-(4-fluoro-1-(2-fluoro-4-(1-methyl-1H-pyrazol-4-yl)benzyl)-1H-indol-3-yl)-N-((1S,2S)-2-hydroxycyclohexyl)acetamide
4-fluoro-1-(2-fluoro-4-(1-methyl-1H-pyrazol-4-yl)benzyl)-N-((1-hydroxycyclopropyl)methyl)-1H-indole-3-carboxamide
4-((4-fluoro-3-(2-((1S,2S)-2-hydroxycyclohexylamino)-2-oxoethyl)-1H-indol-1-yl)methyl)-N-methylbenzamide
N-((1R,2S)-3,3-difluoro-2-hydroxycyclohexyl)-4-fluoro-1-(4-(1-methyl-1H-pyrazol-4-yl)benzyl)-1H-indole-3-carboxamide
N-((1S,2R)-3,3-difluoro-2-hydroxycyclohexyl)-4-fluoro-1-(4-(1-methyl-1H-pyrazol-4-yl)benzyl)-1H-indole-3-carboxamide
N-((1R,2S)-3,3-difluoro-2-hydroxycyclohexyl)-4-fluoro-1-(2-fluoro-4-(1-methyl-1H-pyrazol-4-yl)benzyl)-1H-indole-3-carboxamide
N-((1S,2R)-3,3-difluoro-2-hydroxycyclohexyl)-4-fluoro-1-(2-fluoro-4-(1-methyl-1H-pyrazol-4-yl)benzyl)-1H-indole-3-carboxamide
7-cyclopropyl-4-fluoro-N-((1S,2S)-2-hydroxycyclohexyl)-1-(4-(1-methyl-1H-pyrazol-4-yl)benzyl)-1H-indole-3-carboxamide
N-cyclopropyl-4-fluoro-1-[[4-(methylcarbamoyl)phenyl]methyl]indole-3-carboxamide
N-cyclobutyl-4-fluoro-1-[[4-(methylcarbamoyl)phenyl]methyl]indole-3-carboxamide
N-cyclopentyl-4-fluoro-1-[[4-(methylcarbamoyl)phenyl]methyl]indole-3-carboxamide
N-cyclohexyl-4-fluoro-1-[[4-(methylcarbamoyl)phenyl]methyl]indole-3-carboxamide
N-cyclohexyl-4-fluoro-1-[[4-(methylcarbamoyl)phenyl]methyl]indole-3-carboxamide
N-(cyclopropylmethyl)-4-fluoro-1-[[4-(methylcarbamoyl)phenyl]methyl]indole-3-carboxamide
N-(4,4-difluorocyclohexyl)-4-fluoro-1-[[4-(methylcarbamoyl)phenyl]methyl]indole-3-carboxamide
N-(3,3-difluorocyclohexyl)-4-fluoro-1-[[4-(methylcarbamoyl)phenyl]methyl]indole-3-carboxamide
N-(3,3-difluorocyclohexyl)-4-fluoro-[[4-(methylcarbamoyl)phenyl]methyl]indole-3-carboxamide
4-fluoro-N-(2-fluorocyclohexyl)-1-[[4-(methylcarbamoyl)phenyl]methyl]indole-3-carboxamide
4-fluoro-1-(3-fluoro-4-(methylcarbamoyl)benzyl)-N-(2-fluorocyclohexyl)-1H-indole-3-carboxamide
4-fluoro-1-(3-fluoro-4-(methylcarbamoyl)benzyl)-N-(2-fluorocyclohexyl)-1H-indole-3-carboxamide
4-fluoro-N-((1S,2S)-2-hydroxycyclohexyl)-1-((6-phenylpyridin-3-yl)methyl)-1H-indole-3-carboxamide
4-fluoro-N-((1S,2S)-2-hydroxycyclohexyl)-1-(4-(pyrimidin-2-yl)benzyl)-1H-indole-3-carboxamide
4-fluoro-N-((1S,2S)-2-hydroxycyclohexyl)-1-(4-(oxazol-5-yl)benzyl)-1H-indole-3-carboxamide
4-fluoro-N-((1S,2S)-2-hydroxycyclohexyl)-1-(4-(isoxazol-5-yl)benzyl)-1H-indole-3-carboxamide
4-fluoro-N-((1S,2S)-2-hydroxycyclohexyl)-1-((2-phenylpyrimidin-5-yl)methyl)-1H-indole-3-carboxamide
4-fluoro-N-((1S,2S)-2-hydroxycyclohexyl)-1-((5-phenylpyridin-2-yl)methyl)-1H-indole-3-carboxamideyl)benzyl)-1H-indole-3-carboxamide
4-fluoro-N-((1S,2S)-2-hydroxycyclohexyl)-1-((5-(thiazol-2-yl)pyridin-2-yl)methyl)-1H-indole-3-carboxamide
1-((6-(1H-imidazol-1-yl)pyridin-3-yl)methyl)-4-fluoro-N-((1S,2S)-2-hydroxycyclohexyl)-1H-indole-3-carboxamide 4-fluoro-N-((1S,2S)-2-hydroxycyclohexyl)-1-((1-(pyrimidin-4-yl)piperidin-4-yl)methyl)-1H-indole-3-carboxamide
4-fluoro-N-((1S,2S)-2-hydroxycyclohexyl)-1-(imidazo[1,2-a]pyridin-7-ylmethyl)-1H-indole-3-carboxamide
4-fluoro-N-((1S,2S)-2-hydroxycyclohexyl)-1-(imidazo[1,2-a]pyridin-6-ylmethyl)-1H-indole-3-carboxamide
1-(4-(cyclopropylcarbamoyl)benzyl)-4-fluoro-N-((1S,2S)-2-hydroxycyclohexyl)-1H-indole-3-carboxamide
4-fluoro-N-((1S,2S)-2-hydroxycyclohexyl)-7-methoxy-1-(4-(1-methyl-1H-pyrazol-4-yl)benzyl)-1H-indole-3-carboxamide
4-fluoro-1-(2-fluoro-4-(1-methyl-1H-pyrazol-4-yl)benzyl)-N-((1S,2S)-2-hydroxycyclohexyl)-7-methoxy-1H-indole-3-carboxamide
1-(4-(1H-Pyrazol-5-yl)benzyl)-4-fluoro-N-((1S,2S)-2-hydroxycyclohexyl)-1H-indole-3-carboxamide
1-(4-(1H-1,2,4-triazol-3-yl)benzyl)-4-fluoro-N-((1S,2S)-2-hydroxycyclohexyl)-1H-indole-3-carboxamide
4-Fluoro-N-((1S,2S)-2-hydroxycyclohexyl)-1-(4-(pyrimidin-5-yl)benzyl)-1H-indole-3-carboxamide
4-Fluoro-N-((1S,2S)-2-hydroxycyclohexyl)-1-(4-(pyridin-3-yl)benzyl)-1H-indole-3-carboxamide
4-Fluoro-N-((1S,2S)-2-hydroxycyclohexyl)-1-((1-(pyridin-2-yl)piperidin-4-yl)methyl)-1H-indole-3-carboxamide
4-fluoro-N-((1S,2S)-2-hydroxycyclohexyl)-1-(4-(pyrrolidin-1-yl)benzyl)-1H-indole-3-carboxamide
4-fluoro-N-((1S,2S)-2-hydroxycyclohexyl)-1-((6-(pyrrolidin-1-yl)pyridin-3-yl)methyl)-1H-indole-3-carboxamide or
N-(2,2-difluorocyclohexyl)-4-fluoro-1-(3-fluoro-4-(methylcarbamoyl)benzyl)-1H-indole-3-carboxamide.

One further embodiment of the present invention are compounds of formula I, wherein R is —$(CH_2)_z$—$C_{4-6}$-heterocycloalkyl, which are optionally substituted by one to three hydroxy, lower alkyl, lower alkoxy or halogen or (endo)-7-oxabicyclo[2.2.1]heptan-2-yl; p is 0 or 1; and the other substituents are as described above, for example the following compounds:

4-fluoro-1-(2-fluoro-4-(1-methyl-1H-pyrazol-4-yl)benzyl)-N-((3RS,4RS)-3-hydroxytetrahydro-2H-pyran-4-yl)-1H-indole-3-carboxamide
4-fluoro-1-(2-fluoro-4-(1-methyl-1H-pyrazol-4-yl)benzyl)-N-((3RS,4SR)-3-hydroxytetrahydro-2H-pyran-4-yl)-1H-indazole-3-carboxamide
4-fluoro-N-[(3S,4R)-4-methoxyoxolan-3-yl]-1-[[4-(1-methylpyrazol-4-yl)phenyl]methyl]indole 3-carboxamide
(R)-4-fluoro-1-(4-(1-methyl-1H-pyrazol-4-yl)benzyl)-N-((tetrahydrofuran-2-yl)methyl)-1H-indole-3-carboxamide
4-fluoro-1-(4-(1-methyl-1H-pyrazol-4-yl)benzyl)-N-(tetrahydro-2H-pyran-3-yl)-1H-indole-3-carboxamide
4-fluoro-1-(4-(1-methyl-1H-pyrazol-4-yl)benzyl)-N-(oxetan-3-ylmethyl)-1H-indole-3-carboxamide
4-fluoro-1-(4-(1-methyl-1H-pyrazol-4-yl)benzyl)-N-(oxetan-2-ylmethyl)-1H-indole-3-carboxamide
1-(4-carbamoylbenzyl)-4-fluoro-N-((3RS,4SR)-3-hydroxytetrahydro-2H-pyran-4-yl)-1H-indole 3-carboxamide
1-(4-cyanobenzyl)-4-fluoro-N-((3RS,4SR)-3-hydroxytetrahydro-2H-pyran-4-yl)-1H-indole-3-carboxamide
4-fluoro-1-(2-fluoro-4-(1-methyl-1H-pyrazol-4-yl)benzyl)-N-(tetrahydro-2H-pyran-3-yl)-1H indole-3-carboxamide
4-fluoro-1-(2-fluoro-4-(1-methyl-1H-pyrazol-4-yl)benzyl)-N-((3S,4 S)-4-hydroxytetrahydro-2H pyran-3-yl)-1H-indole-3-carboxamide
4-fluoro-1-(2-fluoro-4-(1-methyl-1H-pyrazol-4-yl)benzyl)-N-(tetrahydro-2H-pyran-4-yl)-1H indole-3-carboxamide
4-fluoro-7-methyl-1-(4-(1-methyl-1H-pyrazol-4-yl)benzyl)-N-(tetrahydro-2H-pyran-3-yl)-1H indole-3-carboxamide
4-fluoro-7-methyl-1-(4-(1-methyl-1H-pyrazol-4-yl)benzyl)-N-(tetrahydro-2H-pyran-4-yl)-1H indole-3-carboxamide
4-fluoro-N-((3R,4S) or (3S,4R)-3-hydroxytetrahydro-2H-pyran-4-yl)-1-(4-(4-methyl-1H imidazol-1-yl)benzyl)-1H-indole-3-carboxamide
4-fluoro-N-((3R,4S) or (3S,4R)-3-hydroxytetrahydro-2H-pyran-4-yl)-1-((1-methyl-1H-indazol 5-yl)methyl)-1H-indole-3-carboxamide
1-(4-cyanobenzyl)-4-fluoro-N-((3R,4S) or (3S,4R)-3-hydroxytetrahydro-2H-pyran-4-yl)-1H indole-3-carboxamide
4-fluoro-N-((3R,4S) or (3S,4R)-3-hydroxytetrahydro-2H-pyran-4-yl)-1-(4-(1-methyl-1H pyrazol-4-yl)benzyl)-1H-indole-3-carboxamide
4,5,6,7-tetrafluoro-N-((3S,4R) or (3R,4S))-3-hydroxytetrahydro-2H-pyran-4-yl)-1-(4-(1-methyl-1H-pyrazol-4-yl)benzyl)-1H-indole-3-carboxamide
4,5,6,7-tetrafluoro-N-((3R,4S) or (3S,4R)-3-hydroxytetrahydro-2H-pyran-4-yl)-1-(4-(1-methyl-1H-pyrazol-4-yl)benzyl)-1H-indole-3-carboxamide
4,5,6,7-tetrafluoro-1-(2-fluoro-4-(1-methyl-1H-pyrazol-4-yl)benzyl)-N-((3R,4S) or (3S,4R))-3-hydroxytetrahydro-2H-pyran-4-yl)-1H-indole-3-carboxamide
4-fluoro-1-(4-(1-methyl-1H-pyrazol-4-yl)benzyl)-N-(tetrahydro-2H-pyran-4-yl)-1H-indole-3-carboxamide
4-fluoro-1-((1-methyl-1H-indazol-5-yl)methyl)-N-(tetrahydro-2H-pyran-4-yl)-1H-indole-3-carboxamide
4-fluoro-1-(4-(4-methyl-1H-imidazol-1-yl)benzyl)-N-(tetrahydro-2H-pyran-4-yl)-1H-indole-3-carboxamide
4-fluoro-1-((6-(1-methyl-1H-pyrazol-4-yl)pyridin-3-yl)methyl)-N-(tetrahydro-2H-pyran-4-yl)-1H-indole-3-carboxamide
4-fluoro-1-(4-(1-methyl-1H-pyrazol-4-yl)benzyl)-N-(tetrahydro-2H-pyran-4-yl)-1H-indazole-3-carboxamide
4-fluoro-1-(2-fluoro-4-(1-methyl-1H-pyrazol-4-yl)benzyl)-N-((3S,4R) or (3R,4S)-3-hydroxytetrahydro-2H-pyran-4-yl)-1H-indole-3-carboxamide
4-fluoro-1-(2-fluoro-4-(1-methyl-1H-pyrazol-4-yl)benzyl)-N-((3R,4S) or (3S,4R)-3-hydroxytetrahydro-2H-pyran-4-yl)-1H-indole-3-carboxamide
4,7-difluoro-1-(2-fluoro-4-(1-methyl-1H-pyrazol-4-yl)benzyl)-N-((3R,4S)-3-hydroxytetrahydro-2H-pyran-4-yl)-1H-indazole-3-carboxamide
4,7-difluoro-N-((3R,4S)-3-hydroxytetrahydro-2H-pyran-4-yl)-1-((6-(1-methyl-1H-pyrazol-4-yl)pyridin-3-yl)methyl)-1H-indazole-3-carboxamide
1-((6-(1H-1,2,4-triazol-1-yl)pyridin-3-yl)methyl)-4-fluoro-N-((3R,4S)-3-hydroxytetrahydro-2H-pyran-4-yl)-1H-indole-3-carboxamide
4-fluoro-N-((3R,4S)-3-hydroxytetrahydro-2H-pyran-4-yl)-1-(4-(thiazol-2-yl)benzyl)-1H-indole-3-carboxamide
4-fluoro-N-((3R,4S)-3-hydroxytetrahydro-2H-pyran-4-yl)-1-(4-(5-methyl-1,2,4-oxadiazol-3-yl)benzyl)-1H-indole-3-carboxamide
4-fluoro-N-((3R,4S)-3-hydroxytetrahydro-2H-pyran-4-yl)-1-(4-(2-oxopyrrolidin-1-yl)benzyl)-1H-indole-3-carboxamide
4-fluoro-1-(2-fluoro-4-(methylcarbamoyl)benzyl)-N-((1S,2S)-2-hydroxycyclohexyl)-1H-indole-3-carboxamide
2-[4-fluoro-1-[[2-fluoro-4-(1-methylpyrazol-4-yl)phenyl]methyl]indol-3-yl]-N-[(3R,4S)-3-hydroxyoxan-4-yl]acetamide
4,7-difluoro-1-((1-methyl-1H-indazol-5-yl)methyl)-N-(tetrahydro-2H-pyran-4-yl)-1H-indole-3-carboxamide 4,7-difluoro-1-(4-(1-methyl-1H-pyrazol-4-yl)benzyl)-N-(tetrahydro-2H-pyran-4-yl)-1H-indole-3-carboxamide 4,7-difluoro-1-(2-fluoro-4-(1-methyl-1H-pyrazol-4-yl)benzyl)-N-(tetrahydro-2H-pyran-4-yl)-1H-indole-3-carboxamide 4-((4-fluoro-3-(2-(((3R,4S)-3-hydroxytetrahydro-2H-pyran-4-ylamino)-2-oxoethyl)-1H-indol-1-yl)methyl)-N-methylbenzamide 7-cyclopropyl-4-fluoro-N-((3R,4S)-3-hydroxytetrahydro-2H-pyran-4-yl)-1-(4-(1-methyl-1H-pyrazol-4-yl)benzyl)-1H-indole-3-carboxamide 7-cyclopropyl-4-fluoro-1-(2-fluoro-4-(1-methyl-1H-pyrazol-4-yl)benzyl)-N-((3R,4S)-3-hydroxytetrahydro-2H-pyran-4-yl)-1H-indole-3-carboxamide 7-ethyl-4-fluoro-1-(4-(1-methyl-1H-pyrazol-4-yl)benzyl)-N-(tetrahydro-2H-pyran-4-yl)-1H-indole-3-carboxamide 7-ethyl-4-fluoro-N-((3R,4S)-3-hydroxytetrahydro-2H-pyran-4-yl)-1-(4-(1-methyl-1H-pyrazol-4-yl)benzyl)-1H-indole-3-carboxamide N-(2,2-dimethyloxan-4-yl)-4-fluoro-[[4-(methylcarbamoyl)phenyl]methyl]indole-3-carboxamide 4-fluoro-1-[[4-(methylcarbamoyl)phenyl]methyl]-N-(oxan-3-yl)indole-3-carboxamide 4-fluoro-1-[[4-(methylcarbamoyl)phenyl]methyl]-N-(4-methyloxan-4-yl)indole-3-carboxamide 4-fluoro-1-[[4-(methylcarbamoyl)phenyl]methyl]-N-(thian-4-yl)indole-3-carboxamide N-(1,1-dioxothian-4-yl)-4-fluoro-1-[[4-(methylcarbamoyl)phenyl]methyl]indole-3-carboxamide 4-fluoro-1-[[4-(methylcarbamoyl)phenyl]methyl]-N-(3-methyloxan-4-yl)indole-3-carboxamide 4-fluoro-1-[[4-(methylcarbamoyl)phenyl]methyl]-N-(2-methyloxan-4-yl)indole-3-carboxamide 7-ethyl-4-fluoro-1-((1-methyl-1H-indazol-5-yl)methyl)-N-(tetrahydro-2H-pyran-4-yl)-1H-indole-3-carboxamide 4-fluoro-1-(4-(methylcarbamoyl)benzyl)-N-(tetrahydro-2H-pyran-4-yl)-1H-indole-3-carboxamide 4-fluoro-1-(2-fluoro-4-(1-methyl-1H-pyrazol-4-yl)benzyl)-7-methyl-N-(tetrahydro-2H-pyran-4-yl)-1H-indole-3-carboxamide 4-fluoro-7-methyl-1-((1-methyl-1H-indazol-5-yl)methyl)-N-(tetrahydro-2H-pyran-4-yl)-1H-indole-3-carboxamide 4-fluoro-N-((3R,4S)-3-hydroxytetrahydro-2H-pyran-4-yl)-1-((1-(pyridin-2-yl)piperidin-4-yl)methyl)-1H-indole-3-carboxamide 4-fluoro-1-((6-(methylcarbamoyl)pyridin-3-yl)methyl)-N-(tetrahydro-2H-pyran-4-yl)-1H-indole-3-carboxamide 4-fluoro-N-((3R,4S)-3-hydroxytetrahydro-2H-pyran-4-yl)-7-methoxy-1-(4-(1-methyl-1H-pyrazol-4-yl)benzyl)-1H-indole-3-carboxamide 4-fluoro-7-methoxy-1-(4-(1-methyl-1H-pyrazol-4-yl)benzyl)-N-(tetrahydro-2H-pyran-4-yl)-1H-indole-3-carboxamide 4-fluoro-1-(2-fluoro-4-(1-methyl-1H-pyrazol-4-yl)benzyl)-7-methoxy-N-(tetrahydro-2H-pyran-4-yl)-1H-indole-3-carboxamide 4-fluoro-1-(2-fluoro-4-(1-methyl-1H-pyrazol-4-yl)benzyl)-N-((3R,4S)-3-hydroxytetrahydro-2H-pyran-4-yl)-7-methoxy-1H-indole-3-carboxamide 4-fluoro-7-methoxy-1-((1-methyl-1H-indazol-5-yl)methyl)-N-(tetrahydro-2H-pyran-4-yl)-1H-indole-3-carboxamide 1-(4-(1H-1,2,4-triazol-3-yl)benzyl)-4-fluoro-N-(tetrahydro-2H-pyran-4-yl)-1H-indole-3-carboxamide 4-Fluoro-1-(3-fluoro-4-(methylcarbamoyl)benzyl)-N-(tetrahydro-2H-pyran-4-yl)-1H-indole-3-carboxamide 4-Fluoro-1-(2-fluoro-4-(methylcarbamoyl)benzyl)-N-(tetrahydro-2H-pyran-4-yl)-1H-indole-3-carboxamide N-(2,2-dimethyltetrahydro-2H-pyran-4-yl)-4-fluoro-1-(3-fluoro-4-(methylcarbamoyl)benzyl)-1H-indole-3-carboxamide 4-fluoro-1-(3-fluoro-4-(methylcarbamoyl)benzyl)-N-(tetrahydro-2H-thiopyran-4-yl)-1H-indole-3-carboxamide or 4-fluoro-1-(3-fluoro-4-(methylcarbamoyl)benzyl)-N-(3-methyltetrahydro-2H-pyran-4-yl)-1H-indole-3-carboxamide.

One embodiment of the invention are compounds of formula I, wherein X is N, for example the following compounds 4-fluoro-1-(2-fluoro-4-(1-methyl-1H-pyrazol-4-yl)benzyl)-N-((1S,2S)-2-hydroxycyclohexyl)1H-indazole-3-carboxamide 4-fluoro-1-(2-fluoro-4-(1-methyl-1H-pyrazol-4-yl)benzyl)-N-((1R,2R)-2-hydroxycyclohexyl)1H-indazole-3-carboxamide 4-fluoro-1-(2-fluoro-4-(1-methyl-1H-pyrazol-4-yl)benzyl)-N-((3RS,4SR)-3-hydroxytetrahydro 2H-pyran-4-yl)-1H-indazole-3-carboxamide 4-fluoro-1-(4-(1-methyl-1H-pyrazol-4-yl)benzyl)-N-(tetrahydro-2H-pyran-4-yl)-1H-indazole-3-carboxamide 4,7-difluoro-1-(2-fluoro-4-(1-methyl-1H-pyrazol-4-yl)benzyl)-N-((1S,2S)-2-hydroxycyclohexyl)-1H-indazole-3-carboxamide 4,7-difluoro-1-(2-fluoro-4-(1-methyl-1H-pyrazol-4-yl)benzyl)-N-((3R,4S)-3-hydroxytetrahydro-2H-pyran-4-yl)-1H-indazole-3-carboxamide 4,7-difluoro-N-((3R,4S)-3-hydroxytetrahydro-2H-pyran-4-yl)-1-((6-(1-methyl-1H-pyrazol-4-yl)pyridin-3-yl)methyl)-1H-indazole-3-carboxamide or 4,7-difluoro-N-((1S,2S)-2-hydroxycyclohexyl)-1-((6-(1-methyl-1H-pyrazol-4-yl)pyridin-3-yl)methyl)-1H-indazole-3-carboxamide.

One embodiment of the invention are compounds of formula I, wherein $Y^1$ is N, for example the following compounds 4,5,6,7-tetrafluoro-N-((1S,2S)-2-hydroxycyclohexyl)-1-((6-(1-methyl-1H-pyrazol-4-yl)pyridine 3-yl)methyl)-1H-indole-3-carboxamide 4, 5-difluoro-N-((1S,2S)-2-hydroxycyclohexyl)-1-((6-(1-methyl-1H-pyrazol-4-yl)pyridine-3-yl)methyl)-1H-indole-3-carboxamide 4-fluoro-1-((6-(1-methyl-1H-pyrazol-4-yl)yridine-3-yl)methyl)-N-(tetrahydro-2H-pyran-4-yl)-1H-indole-3-carboxamide 4,7-difluoro-N-((3R,4S)-3-hydroxytetrahydro-2H-pyran-4-yl)-1-((6-(1-methyl-1H-pyrazol-4-yl)yridine-3-yl)methyl)-1H-indazole-3-carboxamide 4,7-difluoro-N-((1S,2S)-2-hydroxycyclohexyl)-1-((6-(1-methyl-1H-pyrazol-4-yl)yridine-3-yl)methyl)-1H-indazole-3-carboxamide 1-((6-(1H-1,2,4-triazol-1-yl)yridine-3-yl)methyl)-4-fluoro-N-((3R,4S)-3-hydroxytetrahydro-2H-pyran-4-yl)-1H-indole-3-carboxamide 4-fluoro-N-((1S,2S)-2-hydroxycyclohexyl)-1-((6-(methylcarbamoyl)yridine-3-yl)methyl)-1H-indole-3-carboxamide One embodiment of the invention are compounds of formula I, wherein $Y^1$ and $Y^2$ may form together with the carbon atoms to which they are attach

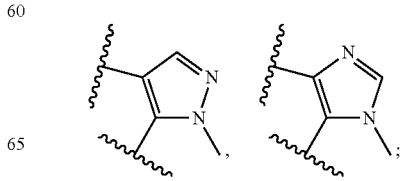

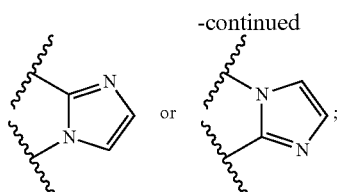

for example the following compounds
4-fluoro-N-((1S,2S)-2-hydroxycyclohexyl)-1-((1-methyl-1H-indazol-5-yl)methyl)-1H-indole-3-carboxamide
4-fluoro-N-((3R,4S) or (3S,4R)-3-hydroxytetrahydro-2H-pyran-4-yl)-1-((1-methyl-1H-indazol-5-yl)methyl)-1H-indole-3-carboxamide
4-fluoro-N-((1S,2S)-2-hydroxycyclohexyl)-1-((1-methyl-1H-benzo[d]yridine-5-yl)methyl)1H-indole-3-carboxamide
4-fluoro-1-((1-methyl-1H-indazol-5-yl)methyl)-N-(tetrahydro-2H-pyran-4-yl)-1H-indole-3-Carboxamide
4,7-difluoro-1-((1-methyl-1H-indazol-5-yl)methyl)-N-(tetrahydro-2H-pyran-4-yl)-1H-indole-3 carboxamide
7-ethyl-4-fluoro-1-((1-methyl-1H-indazol-5-yl)methyl)-N-(tetrahydro-2H-pyran-4-yl)-1H indole-3-carboxamide
4-fluoro-7-methyl-1-((1-methyl-1H-indazol-5-yl)methyl)-N-(tetrahydro-2H-pyran-4-yl)-1H indole-3-carboxamide
4-fluoro-N-((1S,2S)-2-hydroxycyclohexyl)-1-(imidazo[1,2-a]pyridin-7-ylmethyl)-1H-indole-3 carboxamide
4-fluoro-N-((1S,2S)-2-hydroxycyclohexyl)-1-(imidazo[1,2-a]pyridin-6-ylmethyl)-1H-indole-3 Carboxamide
4-fluoro-7-methoxy-1-((1-methyl-1H-indazol-5-yl)methyl)-N-(tetrahydro-2H-pyran-4-yl)-1H indole-3-carboxamide
One embodiment of the invention are compounds of formula I, wherein the five-membered heteroaryl group for $R^4$ is not a pyrazole group, substituted by methyl, for example the following compounds
1-(4-carbamoylbenzyl)-4-fluoro-N-((3RS,4SR)-3-hydroxytetrahydro-2H-pyran-4-yl)-1H-indole-3-carboxamide
1-(4-cyanobenzyl)-4-fluoro-N-((3RS,4SR)-3-hydroxytetrahydro-2H-pyran-4-yl)-1H-indole-3-carboxamide
4-fluoro-1-(2-fluoro-4-methoxybenzyl)-N-((1S,2S)-2-hydroxycyclohexyl)-1H-indole-3-carboxamide
1-(4-(difluoromethoxy)benzyl)-4-fluoro-N-((1S,2S)-2-hydroxycyclohexyl)-1H-indole-3-carboxamide
4-fluoro-N-((1S,2S)-2-hydroxycyclohexyl)-1-(4-methoxybenzyl)-1H-indole-3-carboxamide
1-(4-cyanobenzyl)-4-fluoro-N-((1S,2S)-2-hydroxycyclohexyl)-1H-indole-3-carboxamide
4-fluoro-1-(3-fluoro-4-methoxybenzyl)-N-((1S,2S)-2-hydroxycyclohexyl)-1H-indole-3-carboxamide
4-fluoro-N-((1S,2S)-2-hydroxycyclohexyl)-1-(4-(trifluoromethoxy)benzyl)-1H-indole-3-carboxamide
4-fluoro-N-((1S,2S)-2-hydroxycyclohexyl)-1-(3-(1-methyl-1H-pyrazol-4-yl)benzyl)-1H-indole 3-carboxamide
4-fluoro-N-((1S,2S)-2-hydroxycyclohexyl)-1-(4-(4-methyl-1H-imidazol-1-yl)benzyl)-1H-indole 3-carboxamide
4-fluoro-N-((1S,2S)-2-hydroxycyclohexyl)-1-((1-methyl-1H-indazol-5-yl)methyl)-1H-indole-3-carboxamide
1-(4-chlorobenzyl)-4-fluoro-N-((1S,2S)-2-hydroxycyclohexyl)-1H-indole-3-carboxamide
1-(3-chlorobenzyl)-4-fluoro-N-((1S,2S)-2-hydroxycyclohexyl)-1H-indole-3-carboxamide
1-(3-cyanobenzyl)-4-fluoro-N-((1S,2S)-2-hydroxycyclohexyl)-1H-indole-3-carboxamide
1-(3,4-difluorobenzyl)-4-fluoro-N-((1S,2S)-2-hydroxycyclohexyl)-1H-indole-3-carboxamide
4-fluoro-1-(4-fluorobenzyl)-N-((1S,2S)-2-hydroxycyclohexyl)-1H-indole-3-carboxamide
1-(3,5-difluorobenzyl)-4-fluoro-N-((1S,2S)-2-hydroxycyclohexyl)-1H-indole-3-carboxamide
1-benzyl-4-fluoro-N-((1S,2S)-2-hydroxycyclohexyl)-1H-indole-3-carboxamide
4-fluoro-N-((3R,4S) or (3S,4R)-3-hydroxytetrahydro-2H-pyran-4-yl)-1-(4-(4-methyl-1H-yridine-1-yl)benzyl)-1H-indole-3-carboxamide
4-fluoro-N-((3R,4S) or (3S,4R)-3-hydroxytetrahydro-2H-pyran-4-yl)-1-((1-methyl-1H-indazol-5-yl)methyl)-1H-indole-3-carboxamide
1-(4-cyanobenzyl)-4-fluoro-N-((3R,4S) or (3S,4R)-3-hydroxytetrahydro-2H-pyran-4-yl)-1H-indole-3-carboxamide
4-fluoro-N-((1S,2S)-2-hydroxycyclohexyl)-1-((1-methyl-1H-benzo[d]yridine-5-yl)methyl)-1H-indole-3-carboxamide
4-fluoro-N-((1S,2S)-2-hydroxycyclohexyl)-1-(4-(methylcarbamoyl)benzyl)-1H-indole-3-carboxamide
4,5-difluoro-N-((1S,2S)-2-hydroxycyclohexyl)-1-(4-(4-methyl-1H-imidazol-1-yl)benzyl)-1H-indole-3-carboxamide
4-fluoro-1-((1-methyl-1H-indazol-5-yl)methyl)-N-(tetrahydro-2H-pyran-4-yl)-1H-indole-3-carboxamide
4-fluoro-1-(4-(4-methyl-1H-imidazol-1-yl)benzyl)-N-(tetrahydro-2H-pyran-4-yl)-1H-indole-3-carboxamide
4-fluoro-N-((1S,2S)-2-hydroxycyclohexyl)-1-(4-(methylcarbamoyl)benzyl)-1H-indole-3-carboxamide
1-(4-carbamoylbenzyl)-4-fluoro-N-((1S,2S)-2-hydroxycyclohexyl)-1H-indole-3-carboxamide
1-((6-(1H-1,2,4-triazol-1-yl)yridine-3-yl)methyl)-4-fluoro-N-((3R,4S)-3-hydroxytetrahydro-2H-pyran-4-yl)-1H-indole-3-carboxamide
1-(4-(2-amino-2-oxoethyl)benzyl)-4-fluoro-N41S,2S)-2-hydroxycyclohexyl)-1H-indole-3-carboxamide
1-(3-carbamoylbenzyl)-4-fluoro-N-((1S,2S)-2-hydroxycyclohexyl)-1H-indole-3-carboxamide
4-fluoro-N-((1S,2S)-2-hydroxycyclohexyl)-1-(4-(methylsulfonyl)benzyl)-1H-indole-3-carboxamide
4-fluoro-N-((3R,4S)-3-hydroxytetrahydro-2H-pyran-4-yl)-1-(4-(5-methyl-1,2,4-oxadiazol-3-yl)benzyl)-1H-indole-3-carboxamide
4-fluoro-N-((3R,4S)-3-hydroxytetrahydro-2H-pyran-4-yl)-1-(4-(2-oxopyrrolidin-1-yl)benzyl)-1H-indole-3-carboxamide
ethyl 4-((4-fluoro-3-((1S,2S)-2-hydroxycyclohexylcarbamoyl)-1H-indol-1-yl)methyl)phenylcarbamate
4-fluoro-1-(2-fluoro-4-(methylcarbamoyl)benzyl)-N-((1S,2S)-2-hydroxycyclohexyl)-1H-indole-3-carboxamide
4-fluoro-N-((1S,2S)-2-hydroxycyclohexyl)-1-((6-(methylcarbamoyl)yridine-3-yl)methyl)-1H-indole-3-carboxamide
4-fluoro-1-(3-fluoro-4-(methylcarbamoyl)benzyl)-N-((1S,2S)-2-hydroxycyclohexyl)-1H-indole-3-carboxamide
4-fluoro-N-((1S,2S)-2-hydroxycyclohexyl)-1-(3-(methylcarbamoyl)benzyl)-1H-indole-3-carboxamide
1-(3-(dimethylcarbamoyl)benzyl)-4-fluoro-N-((1S,2S)-2-hydroxycyclohexyl)-1H-indole-3-carboxamide
4-fluoro-1-(2-fluoro-4-(methylcarbamoyl)benzyl)-N-((1S,2S)-2-hydroxycyclohexyl)-1H-indole-3-carboxamide
4-fluoro-N-((1S,2S)-2-hydroxycyclohexyl)-1-(4-(oxazol-5-yl)benzyl)-1H-indole-3-carboxamide
4-fluoro-N-((1S,2S)-2-hydroxycyclohexyl)-1-(4-(isoxazol-5-yl)benzyl)-1H-indole-3-carboxamide
1-(4-(1H-Pyrazol-5-yl)benzyl)-4-fluoro-N-((1S,2S)-2-hydroxycyclohexyl)-1H-indole-3-carboxamide 1-(4-(1H-1,2,4-triazol-3-yl)benzyl)-4-fluoro-N-((1S,2S)-2-hydroxycyclohexyl)-1H-indole-3-carboxamide or
1-(4-(1H-1,2,4-triazol-3-yl)benzyl)-4-fluoro-N-(tetrahydro-2H-pyran-4-yl)-1H-indole-3-carboxamide.

One further embodiment of the invention are compounds of formula IA which compounds are

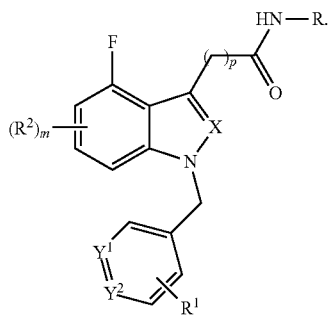

4-fluoro-1-(2-fluoro-4-(1-methyl-1H-pyrazol-4-yl)benzyl)-N-((1S,2S)-2-hydroxycyclohexyl)-1H-indole-3-carboxamide
4-fluoro-1-(2-fluoro-4-(1-methyl-1H-pyrazol-4-yl)benzyl)-N-((1R,2R)-2-hydroxycyclohexyl)-1H-indole-3-carboxamide
4-fluoro-1-(2-fluoro-4-(1-methyl-1H-pyrazol-4-yl)benzyl)-N-((1S,2S)-2-hydroxycyclohexyl)-1H-indazole-3-carboxamide  4-fluoro-1-(2-fluoro-4-(1-methyl-1H-pyrazol-4-yl)benzyl)-N-((1R,2R)-2-hydroxycyclohexyl)-1H-indazole-3-carboxamide
4,6-difluoro-1-(2-fluoro-4-(1-methyl-1H-pyrazol-4-yl)benzyl)-N-((1S,2S)-2-hydroxycyclohexyl)-1H-indole-3-carboxamide
4-fluoro-1-(2-fluoro-4-(1-methyl-1H-pyrazol-4-yl)benzyl)-N-((3RS,4RS)-3-hydroxytetrahydro-2H-pyran-4-yl)-1H-indole-3-carboxamide
4-fluoro-1-(2-fluoro-4-(1-methyl-1H-pyrazol-4-yl)benzyl)-N-((3RS,4SR)-3-hydroxytetrahydro-2H-pyran-4-yl)-1H-indazole-3-carboxamide
4-fluoro-N-[(3S,4R)-4-methoxyoxolan-3-yl]-1-[[4-(1-methylpyrazol-4-yl)phenyl]methyl]indole-3-carboxamide
N-(3,3-difluorocyclobutyl)-4-fluoro-1-(4-(1-methyl-1H-pyrazol-4-yl)benzyl)-1H-indole-3-carboxamide
(R)-4-fluoro-1-(4-(1-methyl-1H-pyrazol-4-yl)benzyl)-N-((tetrahydrofuran-2-yl)methyl)-1H-indole-3-carboxamide
N-cyclobutyl-4-fluoro-1-(4-(1-methyl-1H-pyrazol-4-yl)benzyl)-1H-indole-3-carboxamide
4-fluoro-1-(4-(1-methyl-1H-pyrazol-4-yl)benzyl)-N-(tetrahydro-2H-pyran-3-yl)-1H-indole-3-carboxamide
4-fluoro-1-(4-(1-methyl-1H-pyrazol-4-yl)benzyl)-N-(oxetan-3-ylmethyl)-1H-indole-3-carboxamide
4-fluoro-1-(4-(1-methyl-1H-pyrazol-4-yl)benzyl)-N-(oxetan-2-ylmethyl)-1H-indole-3-carboxamide
1-(4-carbamoylbenzyl)-4-fluoro-N-((3RS,4SR)-3-hydroxytetrahydro-2H-pyran-4-yl)-1H-indole-3-carboxamide
1-(4-cyanobenzyl)-4-fluoro-N-((3RS,4SR)-3-hydroxytetrahydro-2H-pyran-4-yl)-1H-indole-3-carboxamide
4-fluoro-1-(2-fluoro-4-(1-methyl-1H-pyrazol-4-yl)benzyl)-N-((1S,2S)-2-hydroxycyclopentyl)-1H-indole-3-carboxamide
4-fluoro-1-(2-fluoro-4-(1-methyl-1H-pyrazol-4-yl)benzyl)-N-((1SR,2SR)-2-hydroxy-2-methylcyclohexyl)-1H-indole-3-carboxamide
4-fluoro-1-(2-fluoro-4-(1-methyl-1H-pyrazol-4-yl)benzyl)-N-(tetrahydro-2H-pyran-3-yl)-1H-indole-3-carboxamide
N-cyclohexyl-4-fluoro-1-(2-fluoro-4-(1-methyl-1H-pyrazol-4-yl)benzyl)-1H-indole-3-carboxamide
4-fluoro-1-(2-fluoro-4-(1-methyl-1H-pyrazol-4-yl)benzyl)-N-((3S,4S)-4-hydroxytetrahydro-2H-pyran-3-yl)-1H-indole-3-carboxamide
4-fluoro-1-(2-fluoro-4-(1-methyl-1H-pyrazol-4-yl)benzyl)-N-(tetrahydro-2H-pyran-4-yl)-1H-indole-3-carboxamide
4-fluoro-1-(2-fluoro-4-(1-methyl-1H-pyrazol-4-yl)benzyl)-N-((1SR,2RS)-2-hydroxy-2-methylcyclohexyl)-1H-indole-3-carboxamide
4-fluoro-1-(2-fluoro-4-(1-methyl-1H-pyrazol-4-yl)benzyl)-N-((1S,2R)-2-hydroxycyclopentyl)-1H-indole-3-carboxamide
N-(2,2-difluorocyclohexyl)-4-fluoro-1-(2-fluoro-4-(1-methyl-1H-pyrazol-4-yl)benzyl)-1H-indole-3-carboxamide
4,5,6,7-tetrafluoro-1-(2-fluoro-4-(1-methyl-1H-pyrazol-4-yl)benzyl)-N-((1S,2S)-2-hydroxycyclohexyl)-1H-indole-3-carboxamide
4,5,6,7-tetrafluoro-N-((1S,2S)-2-hydroxycyclohexyl)-1-((6-(1-methyl-1H-pyrazol-4-yl)pyridine-3-yl)methyl)-1H-indole-3-carboxamide
4-fluoro-1-(2-fluoro-4-methoxybenzyl)-N-((1S,2S)-2-hydroxycyclohexyl)-1H-indole-3-carboxamide
1-(4-(difluoromethoxy)benzyl)-4-fluoro-N-((1S,2S)-2-hydroxycyclohexyl)-1H-indole-3-carboxamide
4-fluoro-N-((1S,2S)-2-hydroxycyclohexyl)-1-((6-(1-methyl-1H-pyrazol-4-yl)pyridine-3-yl)methyl)-1H-indole-3-carboxamide
4-fluoro-N-((1S,2S)-2-hydroxycyclohexyl)-1-(4-methoxybenzyl)-1H-indole-3-carboxamide
1-(4-cyanobenzyl)-4-fluoro-N-((1S,2S)-2-hydroxycyclohexyl)-1H-indole-3-carboxamide
4-fluoro-1-(3-fluoro-4-methoxybenzyl)-N-((1S,2S)-2-hydroxycyclohexyl)-1H-indole-3-carboxamide
4-fluoro-N-((1S,2S)-2-hydroxycyclohexyl)-1-(4-(trifluoromethoxy)benzyl)-1H-indole-3-carboxamide
4-fluoro-N-((1S,2S)-2-hydroxycyclohexyl)-1-(3-(1-methyl-1H-pyrazol-4-yl)benzyl)-1H-indole-3-carboxamide
4-fluoro-N-((1S,2S)-2-hydroxycyclohexyl)-1-(4-(4-methyl-1H-imidazol-1-yl)benzyl)-1H-indole-3-carboxamide
4-fluoro-N-((1S,2S)-2-hydroxycyclohexyl)-1-((1-methyl-1H-indazol-5-yl)methyl)-1H-indole-3-carboxamide
1-(4-chlorobenzyl)-4-fluoro-N-((1S,2S)-2-hydroxycyclohexyl)-1H-indole-3-carboxamide
1-(3-chlorobenzyl)-4-fluoro-N-((1S,2S)-2-hydroxycyclohexyl)-1H-indole-3-carboxamide
1-(3-cyanobenzyl)-4-fluoro-N-((1S,2S)-2-hydroxycyclohexyl)-1H-indole-3-carboxamide
1-(3,4-difluorobenzyl)-4-fluoro-N-((1S,2S)-2-hydroxycyclohexyl)-1H-indole-3-carboxamide
4-fluoro-1-(4-fluorobenzyl)-N-((1S,2S)-2-hydroxycyclohexyl)-1H-indole-3-carboxamide
1-(3,5-difluorobenzyl)-4-fluoro-N-((1S,2S)-2-hydroxycyclohexyl)-1H-indole-3-carboxamide
4-fluoro-N-((1S,2S)-2-hydroxycyclohexyl)-1-(4-(1-methyl-1H-pyrazol-4-yl)benzyl)-1H-indole-3-carboxamide
4-fluoro-1-(2-fluoro-4-(1-methyl-1H-pyrazol-4-yl)benzyl)-N-((1S,2S)-2-hydroxycyclohexyl)-7-methyl-1H-indole-3-carboxamide
4-fluoro-N-((1S,2S)-2-hydroxycyclohexyl)-7-methyl-1-(4-(1-methyl-1H-pyrazol-4-yl)benzyl)-1H-indole-3-carboxamide
1-benzyl-4-fluoro-N-((1S,2S)-2-hydroxycyclohexyl)-1H-indole-3-carboxamide 4-fluoro-7-methyl-1-(4-(1-methyl-1H-pyrazol-4-yl)benzyl)-N-(tetrahydro-2H-pyran-3-yl)-1H-indole-3-carboxamide
4-fluoro-7-methyl-1-(4-(1-methyl-1H-pyrazol-4-yl)benzyl)-N-(tetrahydro-2H-pyran-4-yl)-1H-indole-3-carboxamide
4-fluoro-N-((1S,2S)-2-hydroxycyclohexyl)-1-(4-(3-methyl-1H-pyrazol-1-yl)benzyl)-1H-indole-3-carboxamide
4-fluoro-N-((3R,4S) or (3S,4R)-3-hydroxytetrahydro-2H-pyran-4-yl)-1-(4-(4-methyl-1H-imidazol-1-yl)benzyl)-1H-indole-3-carboxamide
4-fluoro-N-((3R,4S) or (3S,4R)-3-hydroxytetrahydro-2H-pyran-4-yl)-1-((1-methyl-1H-indazol-5-yl)methyl)-1H-indole-3-carboxamide
4,5,6,7-tetrafluoro-N-((1S,2S)-2-hydroxycyclohexyl)-1-(4-(1-methyl-1H-pyrazol-4-yl)benzyl)-1H-indole-3-carboxamide
1-(4-cyanobenzyl)-4-fluoro-N-((3R,4S) or (3S,4R)-3-hydroxytetrahydro-2H-pyran-4-yl)-1H-indole-3-carboxamide
4-fluoro-N-((3R,4S) or (3S,4R)-3-hydroxytetrahydro-2H-pyran-4-yl)-1-(4-(1-methyl-1H-pyrazol-4-yl)benzyl)-1H-indole-3-carboxamide
4-fluoro-N-((1S,2S)-2-hydroxycyclohexyl)-1-((1-methyl-1H-benzo[d]yridine-5-yl)methyl)-1H-indole-3-carboxamide
4,5-difluoro-N-((1S,2S)-2-hydroxycyclohexyl)-1-(4-(1-methyl-1H-pyrazol-4-yl)benzyl)-1H-indole-3-carboxamide
4,5-difluoro-N-((1S,2S)-2-hydroxycyclohexyl)-1-((6-(1-methyl-1H-pyrazol-4-yl)pyridine-3-yl)methyl)-1H-indole-3-carboxamide
4-fluoro-N-((1S,2S)-2-hydroxycyclohexyl)-1-(4-(methylcarbamoyl)benzyl)-1H-indole-3-carboxamide
4,5-difluoro-N-((1S,2S)-2-hydroxycyclohexyl)-1-(4-(4-methyl-1H-imidazol-1-yl)benzyl)-1H-indole-3-carboxamide
4,5-difluoro-N-((1S,2S)-2-hydroxycyclohexyl)-1-(4-(3-methyl-1H-pyrazol-1-yl)benzyl)-1H-indole-3-carboxamide
4,5,6,7-Tetrafluoro-N-((3S,4R) or (3R,4S))-3-hydroxytetrahydro-2H-pyran-4-yl)-1-(4-(1-methyl-1H-pyrazol-4-yl)benzyl)-1H-indole-3-carboxamide
4,5,6,7-Tetrafluoro-N-((3R,4S) or (3S,4R))-3-hydroxytetrahydro-2H-pyran-4-yl)-1-(4-(1-methyl-1H-pyrazol-4-yl)benzyl)-1H-indole-3-carboxamide
4,5,6,7-Tetrafluoro-1-(2-fluoro-4-(1-methyl-1H-pyrazol-4-yl)benzyl)-N-((3R,4S) or (3S,4R))-3-hydroxytetrahydro-2H-pyran-4-yl)-1H-indole-3-carboxamide
Fluoro-1-(4-(1-methyl-1H-pyrazol-4-yl)benzyl)-N-(tetrahydro-2H-pyran-4-yl)-1H-indole-3-carboxamide
4-fluoro-1-((1-methyl-1H-indazol-5-yl)methyl)-N-(tetrahydro-2H-pyran-4-yl)-1H-indole-3-carboxamide
4-fluoro-1-(4-(4-methyl-1H-imidazol-1-yl)benzyl)-N-(tetrahydro-2H-pyran-4-yl)-1H-indole-3-carboxamide
4-fluoro-1-((6-(1-methyl-1H-pyrazol-4-yl)yridine-3-yl)methyl)-N-(tetrahydro-2H-pyran-4-yl)-1H-indole-3-carboxamide
4-fluoro-1-(4-(1-methyl-1H-pyrazol-4-yl)benzyl)-N-(tetrahydro-2H-pyran-4-yl)-1H-indazole-3-carboxamide
4-fluoro-1-(2-fluoro-4-(1-methyl-1H-pyrazol-4-yl)benzyl)-N-((3S,4R) or (3R,4S)-3-hydroxytetrahydro-2H-pyran-4-yl)-1H-indole-3-carboxamide
4-Fluoro-1-(2-fluoro-4-(1-methyl-1H-pyrazol-4-yl)benzyl)-N-((3R,4S) or (3S,4R)-3-hydroxytetrahydro-2H-pyran-4-yl)-1H-indole-3-carboxamide
4,7-difluoro-1-(2-fluoro-4-(1-methyl-1H-pyrazol-4-yl)benzyl)-N-((1S,2S)-2-hydroxycyclohexyl)-1H-indazole-3-carboxamide
4,7-difluoro-1-(2-fluoro-4-(1-methyl-1H-pyrazol-4-yl)benzyl)-N-((3R,4S)-3-hydroxytetrahydro-2H-pyran-4-yl)-1H-indazole-3-carboxamide
4,7-difluoro-N-((3R,4S)-3-hydroxytetrahydro-2H-pyran-4-yl)-1-((6-(1-methyl-1H-pyrazol-4-yl)yridine-3-yl)methyl)-1H-indazole-3-carboxamide
4,7-difluoro-N-((1S,2S)-2-hydroxycyclohexyl)-1-((6-(1-methyl-1H-pyrazol-4-yl)yridine-3-yl)methyl)-1H-indazole-3-carboxamide
4-fluoro-N-((1S,2S)-2-hydroxycyclohexyl)-1-(4-(methylcarbamoyl)benzyl)-1H-indole-3-carboxamide
1-(4-carbamoylbenzyl)-4-fluoro-N-((1S,2S)-2-hydroxycyclohexyl)-1H-indole-3-carboxamide
1-((6-(1H-1,2,4-triazol-1-yl)yridine-3-yl)methyl)-4-fluoro-N-((3R,4S)-3-hydroxytetrahydro-2H-pyran-4-yl)-1H-indole-3-carboxamide
4-fluoro-N-((3R,4S)-3-hydroxytetrahydro-2H-pyran-4-yl)-1-(4-(thiazol-2-yl)benzyl)-1H-indole-3-carboxamide
1-(4-(2-amino-2-oxoethyl)benzyl)-4-fluoro-N41 S,2S)-2-hydroxycyclohexyl)-1H-indole-3-carboxamide
1-(3-carbamoylbenzyl)-4-fluoro-N-((1S,2S)-2-hydroxycyclohexyl)-1H-indole-3-carboxamide
4-fluoro-N-((1S,2S)-2-hydroxycyclohexyl)-1-(4-(methyl sulfonyl)benzyl)-1H-indole-3-carboxamide
4-fluoro-N-((3R,4S)-3-hydroxytetrahydro-2H-pyran-4-yl)-1-(4-(5-methyl-1,2,4-oxadiazol-3-yl)benzyl)-1H-indole-3-carboxamide
4-fluoro-N-((3R,4S)-3-hydroxytetrahydro-2H-pyran-4-yl)-1-(4-(2-oxopyrrolidin-1-yl)benzyl)-1H-indole-3-carboxamide
ethyl 4-((4-fluoro-3-((1S,2S)-2-hydroxycyclohexyl carbamoyl)-1H-indol-1-yl)methyl)phenylcarbamate
4-fluoro-1-(2-fluoro-4-(methylcarbamoyl)benzyl)-N-((1S,2S)-2-hydroxycyclohexyl)-1H-indole-3-carboxamide
4-fluoro-N-((1S,2S)-2-hydroxycyclohexyl)-1-((6-(methylcarbamoyl)pyridin-3-yl)methyl)-1H-indole-3-carboxamide
4-fluoro-1-(3-fluoro-4-(methylcarbamoyl)benzyl)-N-((1S,2S)-2-hydroxycyclohexyl)-1H-indole-3-carboxamide
4-fluoro-N-((1S,2S)-2-hydroxycyclohexyl)-1-(3-(methylcarbamoyl)benzyl)-1H-indole-3-carboxamide
1-(3-(dimethylcarbamoyl)benzyl)-4-fluoro-N-((1S,2S)-2-hydroxycyclohexyl)-1H-indole-3-carboxamide
4-fluoro-1-(2-fluoro-4-(methylcarbamoyl)benzyl)-N-((1S,2S)-2-hydroxycyclohexyl)-1H-indole-3-carboxamide
2-[4-fluoro-1-[[2-fluoro-4-(1-methylpyrazol-4-yl)phenyl]methyl]indol-3-yl]-N-[(3R,4S)-3-hydroxyoxan-4-yl]acetamide
2-(4-fluoro-1-(2-fluoro-4-(1-methyl-1H-pyrazol-4-yl)benzyl)-1H-indol-3-yl)-N-((1S,2S)-2-hydroxycyclohexyl)acetamide
4,7-difluoro-1-((1-methyl-1H-indazol-5-yl)methyl)-N-(tetrahydro-2H-pyran-4-yl)-1H-indole-3-carboxamide
4,7-difluoro-1-(4-(1-methyl-1H-pyrazol-4-yl)benzyl)-N-(tetrahydro-2H-pyran-4-yl)-1H-indole-3-carboxamide
4,7-difluoro-1-(2-fluoro-4-(1-methyl-1H-pyrazol-4-yl)benzyl)-N-(tetrahydro-2H-pyran-4-yl)-1H-indole-3-carboxamide
4,7-difluoro-1-(2-fluoro-4-(1-methyl-1H-pyrazol-4-yl)benzyl)-N-(tetrahydro-2H-pyran-4-yl)-1H-indole-3-carboxamide
4-((4-fluoro-3-(2-((3R,4S)-3-hydroxytetrahydro-2H-pyran-4-ylamino)-2-oxoethyl)-1H-indol-1-yl)methyl)-N-methylbenzamide
4-((4-fluoro-3-(2-((1S,2S)-2-hydroxycyclohexylamino)-2-oxoethyl)-1H-indol-1-yl)methyl)-N-methylbenzamide N-((1R,2S)-3,3-difluoro-2-hydroxycyclohexyl)-4-fluoro-1-(4-(1-methyl-1H-pyrazol-4-yl)benzyl)-1H-indole-3-carboxamide
N-((1S,2R)-3,3-difluoro-2-hydroxycyclohexyl)-4-fluoro-1-(4-(1-methyl-1H-pyrazol-4-yl)benzyl)-1H-indole-3-carboxamide
N-((1R,2S)-3,3-difluoro-2-hydroxycyclohexyl)-4-fluoro-1-(2-fluoro-4-(1-methyl-1H-pyrazol-4-yl)benzyl)-1H-indole-3-carboxamide
N-((1S,2R)-3,3-difluoro-2-hydroxycyclohexyl)-4-fluoro-1-(2-fluoro-4-(1-methyl-1H-pyrazol-4-yl)benzyl)-1H-indole-3-carboxamide
N-((endo)-7-oxabicyclo[2.2.1]heptan-2-yl)-4-fluoro-1-(2-fluoro-4-(1-methyl-1H-pyrazol-4-yl)benzyl)-1H-indole-3-carboxamide
7-cyclopropyl-4-fluoro-N-((1S,2S)-2-hydroxycyclohexyl)-1-(4-(1-methyl-1H-pyrazol-4-yl)benzyl)-1H-indole-3-carboxamide
7-cyclopropyl-4-fluoro-N-((3R,4S)-3-hydroxytetrahydro-2H-pyran-4-yl)-1-(4-(1-methyl-1H-pyrazol-4-yl)benzyl)-1H-indole-3-carboxamide
7-cyclopropyl-4-fluoro-1-(2-fluoro-4-(1-methyl-1H-pyrazol-4-yl)benzyl)-N-((3R,4S)-3-hydroxytetrahydro-2H-pyran-4-yl)-1H-indole-3-carboxamide
7-ethyl-4-fluoro-1-(4-(1-methyl-1H-pyrazol-4-yl)benzyl)-N-(tetrahydro-2H-pyran-4-yl)-1H-indole-3-carboxamide
7-ethyl-4-fluoro-N-((3R,4S)-3-hydroxytetrahydro-2H-pyran-4-yl)-1-(4-(1-methyl-1H-pyrazol-4-yl)benzyl)-1H-indole-3-carboxamide
4-fluoro-N-methyl-1-[[4-(methylcarbamoyl)phenyl]methyl]indole-3-carboxamide
N-cyclopropyl-4-fluoro-1-[[4-(methylcarbamoyl)phenyl]methyl]indole-3-carboxamide
N-cyclobutyl-4-fluoro-1-[[4-(methylcarbamoyl)phenyl]methyl]indole-3-carboxamide
N-cyclopentyl-4-fluoro-1-[[4-(methylcarbamoyl)phenyl]methyl]indole-3-carboxamide
N-cyclohexyl-4-fluoro-1-[[4-(methylcarbamoyl)phenyl]methyl]indole-3-carboxamide
N-cycloheptyl-4-fluoro-1-[[4-(methylcarbamoyl)phenyl]methyl]indole-3-carboxamide
N-(cyclopropylmethyl)-4-fluoro-1-[[4-(methylcarbamoyl)phenyl]methyl]indole-3-carboxamide
N-(4,4-difluorocyclohexyl)-4-fluoro-1-[[4-(methylcarbamoyl)phenyl]methyl]indole-3-carboxamide
N-(3,3-difluorocyclohexyl)-4-fluoro-1-[[4-(methylcarbamoyl)phenyl]methyl]indole-3-carboxamide
N-(2,2-dimethyloxan-4-yl)-4-fluoro-1-[[4-(methylcarbamoyl)phenyl]methyl]indole-3-carboxamide
N-(2,2-difluorocyclohexyl)-4-fluoro-1-[[4-(methylcarbamoyl)phenyl]methyl]indole-3-carboxamide
4-fluoro-N-(2-fluorocyclohexyl)-1-[[4-(methylcarbamoyl)phenyl]methyl]indole-3-carboxamide
4-fluoro-1-[[4-(methylcarbamoyl)phenyl]methyl]-N-(oxan-3-yl)indole-3-carboxamide
4-fluoro-1-[[4-(methylcarbamoyl)phenyl]methyl]-N-(4-methyloxan-4-yl)indole-3-carboxamide
4-fluoro-1-[[4-(methylcarbamoyl)phenyl]methyl]-N-(thian-4-yl)indole-3-carboxamide
N-(1,1-dioxothian-4-yl)-4-fluoro-1-[[4-(methylcarbamoyl)phenyl]methyl]indole-3-carboxamide
4-fluoro-1-[[4-(methylcarbamoyl)phenyl]methyl]-N-(3-methyloxan-4-yl)indole-3-carboxamide
4-fluoro-1-[[4-(methylcarbamoyl)phenyl]methyl]-N-(2-methyloxan-4-yl)indole-3-carboxamide
7-ethyl-4-fluoro-1-((1-methyl-1H-indazol-5-yl)methyl)-N-(tetrahydro-2H-pyran-4-yl)-1H-indole-3-carboxamide
4-fluoro-1-(3-fluoro-4-(methylcarbamoyl)benzyl)-N-(2-fluorocyclohexyl)-1H-indole-3-carboxamide
N-(3,3-difluorocyclohexyl)-4-fluoro-1-(3-fluoro-4-(methylcarbamoyl)benzyl)-1H-indole-3-carboxamide
4-fluoro-N-((1S,2S)-2-hydroxycyclohexyl)-1-((6-phenylpyridin-3-yl)methyl)-1H-indole-3-carboxamide
4-fluoro-1-(4-(methylcarbamoyl)benzyl)-N-(tetrahydro-2H-pyran-4-yl)-1H-indole-3-carboxamide
4-fluoro-1-(2-fluoro-4-(1-methyl-1H-pyrazol-4-yl)benzyl)-7-methyl-N-(tetrahydro-2H-pyran-4-yl)-1H-indole-3-carboxamide
4-fluoro-7-methyl-1-((1-methyl-1H-indazol-5-yl)methyl)-N-(tetrahydro-2H-pyran-4-yl)-1H-indole-3-carboxamide
4-fluoro-N-((1S,2S)-2-hydroxycyclohexyl)-1-(4-(pyrimidin-2-yl)benzyl)-1H-indole-3-carboxamide
4-fluoro-N-((1S,2S)-2-hydroxycyclohexyl)-1-(4-(oxazol-5-yl)benzyl)-1H-indole-3-carboxamide
4-fluoro-N-((1S,2S)-2-hydroxycyclohexyl)-1-(4-(isoxazol-5-yl)benzyl)-1H-indole-3-carboxamide
1-((6-(1H-imidazol-1-yl)pyridin-3-yl)methyl)-4-fluoro-N-((1S,2S)-2-hydroxycyclohexyl)-1H-indole-3-carboxamide
4-fluoro-N-((1S,2S)-2-hydroxycyclohexyl)-1-(imidazo[1,2-a]pyridin-7-ylmethyl)-1H-indole-3-carboxamide
4-fluoro-N-((1S,2S)-2-hydroxycyclohexyl)-1-(imidazo[1,2-a]pyridin-6-ylmethyl)-1H-indole-3-carboxamide
1-(4-(cyclopropylcarbamoyl)benzyl)-4-fluoro-N-((1S,2S)-2-hydroxycyclohexyl)-1H-indole-3-carboxamide
4-fluoro-1-((6-(methylcarbamoyl)pyridin-3-yl)methyl)-N-(tetrahydro-2H-pyran-4-yl)-1H-indole-3-carboxamide
4-fluoro-N-((1S,2S)-2-hydroxycyclohexyl)-7-methoxy-1-(4-(1-methyl-1H-pyrazol-4-yl)benzyl)-1H-indole-3-carboxamide
4-fluoro-1-(2-fluoro-4-(1-methyl-1H-pyrazol-4-yl)benzyl)-N-((1S,2S)-2-hydroxycyclohexyl)-7-methoxy-1H-indole-3-carboxamide
4-fluoro-N-((3R,4S)-3-hydroxytetrahydro-2H-pyran-4-yl)-7-methoxy-1-(4-(1-methyl-1H-pyrazol-4-yl)benzyl)-1H-indole-3-carboxamide
4-fluoro-7-methoxy-1-(4-(1-methyl-1H-pyrazol-4-yl)benzyl)-N-(tetrahydro-2H-pyran-4-yl)-1H-indole-3-carboxamide
4-fluoro-1-(2-fluoro-4-(1-methyl-1H-pyrazol-4-yl)benzyl)-7-methoxy-N-(tetrahydro-2H-pyran-4-yl)-1H-indole-3-carboxamide
4-fluoro-1-(2-fluoro-4-(1-methyl-1H-pyrazol-4-yl)benzyl)-N-((3R,4S)-3-hydroxytetrahydro-2H-pyran-4-yl)-7-methoxy-1H-indole-3-carboxamide
4-fluoro-7-methoxy-1-((1-methyl-1H-indazol-5-yl)methyl)-N-(tetrahydro-2H-pyran-4-yl)-1H-indole-3-carboxamide
1-(4-(1H-Pyrazol-5-yl)benzyl)-4-fluoro-N4-(1S,2S)-2-hydroxycyclohexyl)-1H-indole-3-carboxamide
1-(4-(1H-1,2,4-triazol-3-yl)benzyl)-4-fluoro-N-((1S,2S)-2-hydroxycyclohexyl)-1H-indole-3-carboxamide
1-(4-(1H-1,2,4-triazol-3-yl)benzyl)-4-fluoro-N-(tetrahydro-2H-pyran-4-yl)-1H-indole-3-carboxamide
4-Fluoro-N-((1S,2S)-2-hydroxycyclohexyl)-1-(4-(pyrimidin-5-yl)benzyl)-1H-indole-3-carboxamide
4-Fluoro-N-((1S,2S)-2-hydroxycyclohexyl)-1-(4-(pyridin-3-yl)benzyl)-1H-indole-3-carboxamide
4-fluoro-N-((1S,2S)-2-hydroxycyclohexyl)-1-(4-(pyrrolidin-1-yl)benzyl)-1H-indole-3-carboxamide
4-fluoro-N-((1S,2S)-2-hydroxycyclohexyl)-1-((6-(pyrrolidin-1-yl)pyridin-3-yl)methyl)-1H-indole-3-carboxamide
4-Fluoro-1-(3-fluoro-4-(methylcarbamoyl)benzyl)-N-(tetrahydro-2H-pyran-4-yl)-1H-indole-3-carboxamide 4-Fluoro-1-(2-fluoro-4-(methylcarbamoyl)benzyl)-N-(tetrahydro-2H-pyran-4-yl)-1H-indole-3-carboxamide N-(2,2-difluorocyclohexyl)-4-fluoro-1-(3-fluoro-4-(methylcarbamoyl)benzyl)-1H-indole-3-carboxamide N-(2,2-dimethyltetrahydro-2H-pyran-4-yl)-4-fluoro-1-(3-fluoro-4-(methylcarbamoyl)benzyl)-1H-indole-3-carboxamide 4-fluoro-1-(3-fluoro-4-(methylcarbamoyl)benzyl)-N-(tetrahydro-2H-thiopyran-4-yl)-1H-indole-3-carboxamide or 4-fluoro-1-(3-fluoro-4-(methylcarbamoyl)benzyl)-N-(3-methyltetrahydro-2H-pyran-4-yl)-1H-indole-3-carboxamide.

One further embodiment of the invention are compounds of formula IB

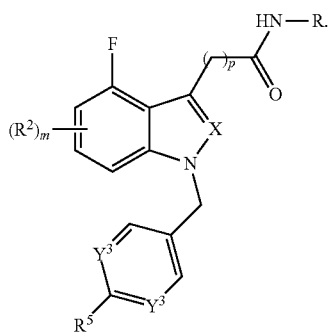

which compound is
4-fluoro-N-((1S,2S)-2-hydroxycyclohexyl)-1-((2-phenylpyrimidin-5-yl)methyl)-1H-indole-3-carboxamide.

One further embodiment of the invention are compounds of formula IC

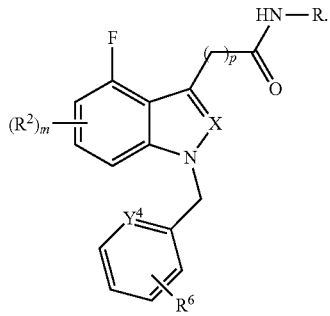

which compounds are
4-fluoro-N-((1S,2S)-2-hydroxycyclohexyl)-1-((2-phenylpyrimidin-5-yl)methyl)-1H-indole-3-carboxamide or 4-fluoro-N-((1S,2S)-2-hydroxycyclohexyl)-1-((5-(thiazol-2-yl)pyridin-2-yl)methyl)-1H-indole-3-carboxamide.

One further embodiment of the invention are compounds of formula ID

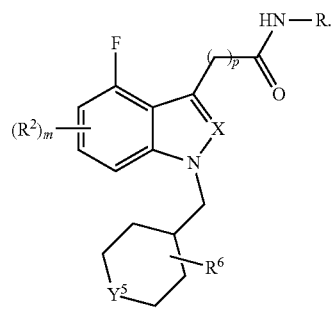

which compounds are
4-fluoro-N-((3R,4S)-3-hydroxytetrahydro-2H-pyran-4-yl)-1-((1-(pyridin-2-yl)piperidin-4-yl)methyl)-1H-indole-3-carboxamide 4-fluoro-N-((1S,2S)-2-hydroxycyclohexyl)-1-((1-(pyrimidin-4-yl)piperidin-4-yl)methyl)-1H-indole-3-carboxamide or 4-Fluoro-N-((1S,2S)-2-hydroxycyclohexyl)-1-((1-(pyridin-2-yl)piperidin-4-yl)methyl)-1H-indole-3-carboxamide.

The present compounds of formula I and their pharmaceutically acceptable salts can be prepared by methods known in the art, for example, by processes described below, which process comprises a) reacting a compound of formula

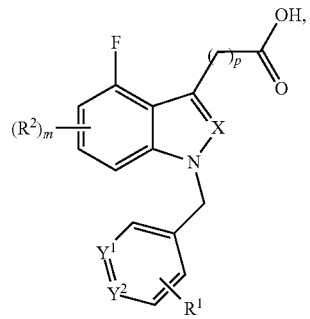

IIA

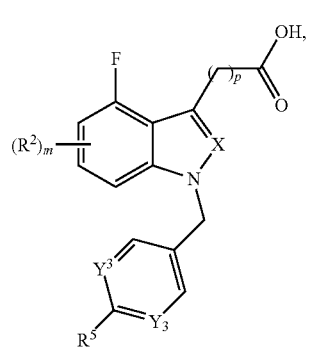

IIB

-continued

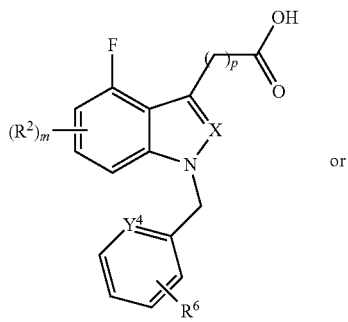
IIC or

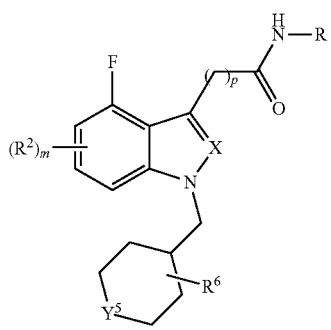
IID with a compound of formula

RNH$_2$ in the presence of an activating agent such as BOP (benzotriazol-1-yloxy)tris(dimethylamino)phosphonium hexafluorophosphate or thionyl chloride to a compound of formula

IA

IB

-continued

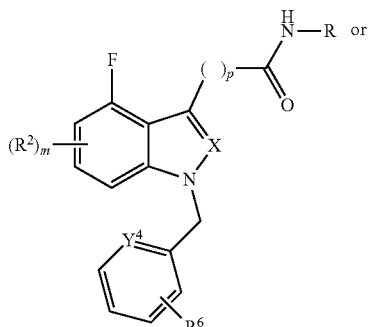
IC

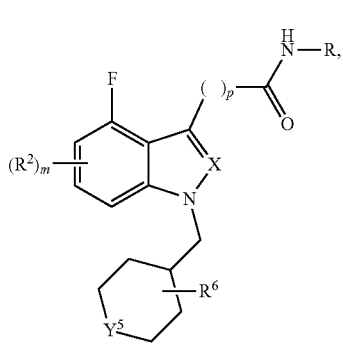
ID wherein the substituents are as defined above, or b) reacting a compound of formula

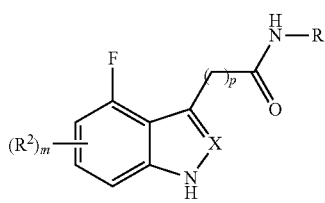
III with a compound of formula

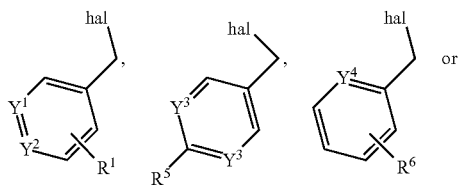

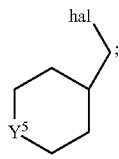

in the presence of base like cesium carbonate or sodium hydride to a compound of formula

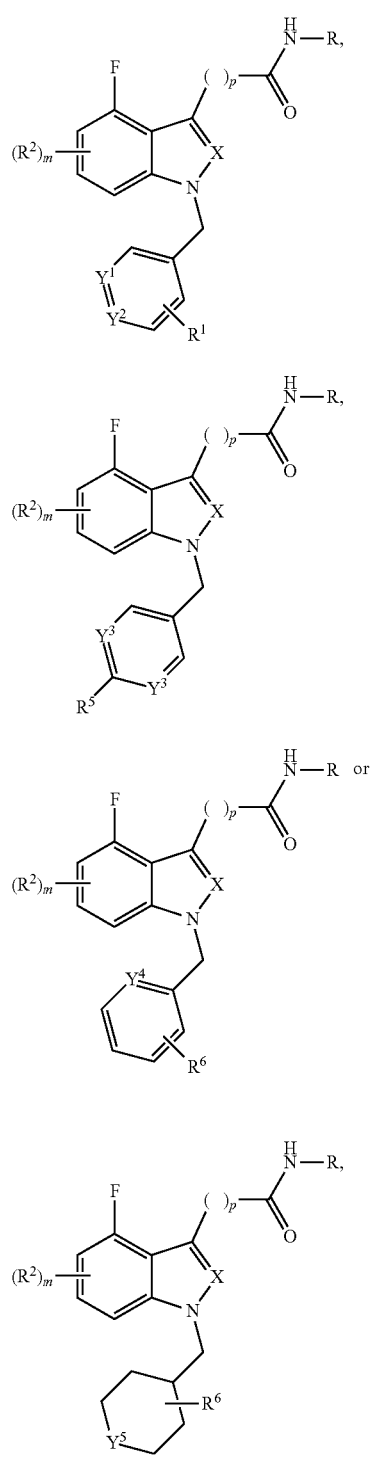

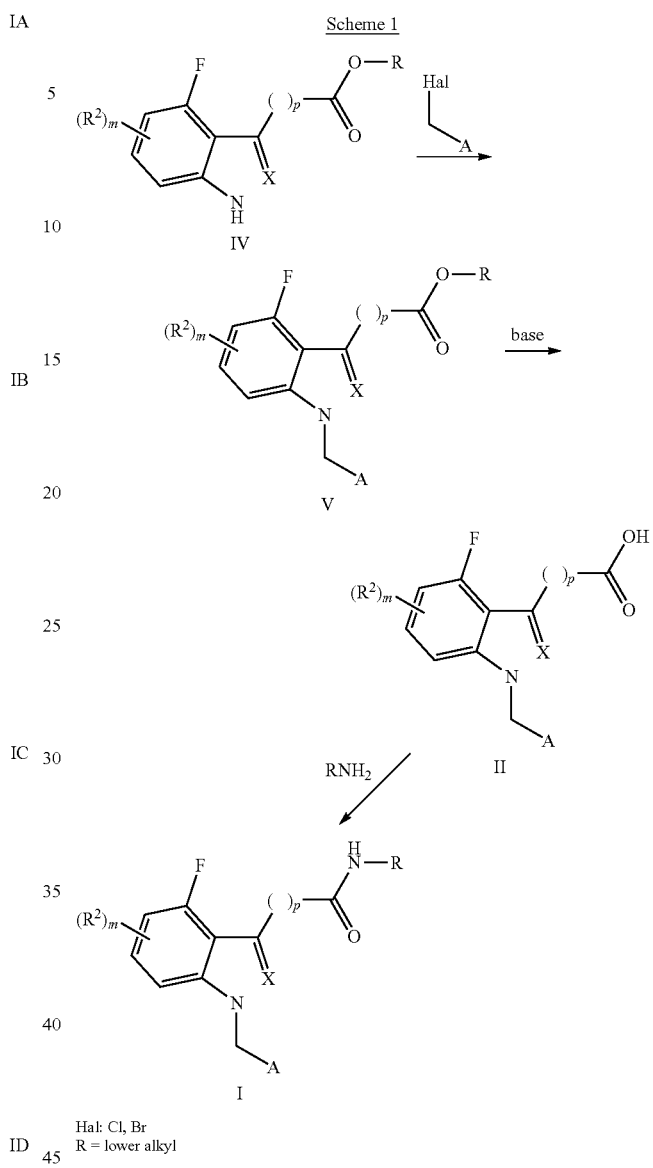

Scheme 1

Hal: Cl, Br
R = lower alkyl

The substituents are as described above.

Compounds of general formula I can be prepared by reacting ester derivatives of formula IV with an alkylating agent in the presence of a base such as sodium hydride to provide V followed by a saponification of V in the presence of a base such as lithium hydroxide and coupling of the resulting acid II with an amine RNH$_2$.

wherein Hal is halogen and the other substituents are as defined above, and, if desired, converting the compounds obtained into pharmaceutically acceptable acid addition salts.

The compounds of formula I may be prepared in accordance with process variant a) or b) and with the following schemes 1-2. The starting material is commercially available or may be prepared in accordance with known methods.

Scheme 2

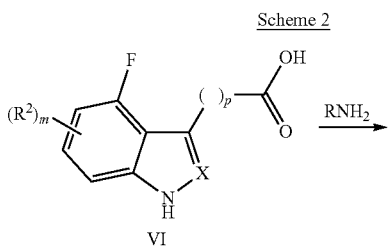

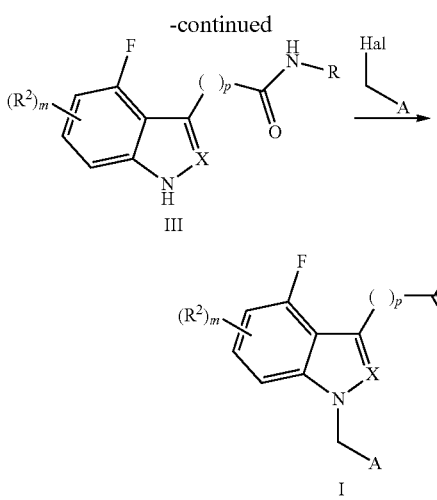

The substituents are as described above.

Compounds of general formula I can be prepared by coupling acid derivatives of formula VI with an amine RNH$_2$ to provide amide III followed by reaction of III with an alkylating agent in the presence of a base such as cesium carbonate or sodium hydride.

All reactions are typically performed in a suitable solvent and under an atmosphere of argon or nitrogen.

Some substituents substituents R$^1$ may be derived from another precursor substituent at the end of the reaction sequence. For instance, a compound of formula I may be synthesized bearing an ester group as R$^1$, which is converted to a carboxamide substituent by standard procedures.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

M1 PAM Assay

The assay is designed to select compounds that possess modulator activity at the acetylcholine muscarinic receptor expressed in CHO cells by measuring the intracellular calcium with a Fluorometric Imaging Plate Reader System (FLIPR, Molecular Devices). The assay study the effect of several concentrations of test compounds on basal or acetylcholine-stimulated Ca$^{2+}$ levels using FLIPR.

CHO human M1 are plated the day before the experiments at 2×10$^5$ cells/ml in PDL BioCoat 96 well black/clear plate (Becton 35 4640). The cells are grown at 37° C. and 5% CO$_2$ in the following medium: F12 Nut Mix (Gibco 21765), 10% FCS heat inactivated (GIBCO 16000-044), 1% Pen Strep (Gibco,15140) and 200 μg/ml Geneticin (Gibco 11811). On the day of the experiment, the medium was removed and replaced by 100 ml of dye loading buffer containing Hanks Balanced Salt solution (HBSS, 14065-049, Gibco) with 20 mM HEPES (Gibco 15630-056), 2 mM Probenicid (Sigma P8761), 2 mM Fluo-4AM ester (Molecular Probes F-14202), 10% Pluronic acid Molecular Probes P-3000) pH=7.4 and incubated at 37° C. After 60 minutes extracellular dye was removed and the cells were washed five times with FLIPR buffer containing HBSS (Gibco 14065-049) with 20 mM HEPES (Gibco, 15630-056), 2 mM Probenicid (Sigma P8761) pre-warmed at 37° C. using and Ebml cell washer leaving 100 ml of FLIPR buffer in each well. The cell plate and the diluted compounds (1% DMSO final concentration) are placed on the platform of the FLIPR and the door closed. A signal test to check background fluorescence and basal fluorescence signal is performed. Laser intensity is adjusted if necessary. Two minutes preincubation with the diluted test compounds is provide to determine any agonist activity on the M1 receptor by comparison to 30 nM Acetylcholine control. In order to determine any modulator activity the diluted compounds were added to cells and after two minutes preincubation, the EC$_{20}$ of acetylcholine is added followed by another two minutes preincubation before the measurement of intracellular Ca$^{2+}$ with a FLIPR (Molecular Devices).

| Table with activity data | |
|---|---|
| Example | hM1 EC$_{50}$/ratM1 EC$_{50}$ |
| 1 | 0.00564/0.06265 |
| 2 | 0.03897/0.20758 |
| 3 | 0.02518/0.09056 |
| 4 | 0.29451/1.29408 |
| 5 | 0.08375/0.23056 |
| 6 | 0.07002/0.14723 |

Table with activity data

| Example | hM1 EC$_{50}$/ratM1 EC$_{50}$ |
|---|---|
| 7 | 0.07002/0.14723 |
| 8 | 0.27812/0.4268 |
| 9 | 0.36503/0.41052 |
| 10 | 0.25567/0.39796 |
| 11 | 0.41296/0.61775 |
| 12 | 0.12931/0.39801 |
| 13 | 0.19182/0.24956 |
| 14 | 0.12088/0.19809 |
| 15 | 0.01243/0.00961 |
| 16 | 0.23702/0.3368 |
| 17 | 0.1004/0.1694 |
| 18 | 0.06116/0.18456 |
| 19 | 0.22859/0.57922 |
| 20 | 0.20379/0.42486 |
| 21 | 0.06054/0.175 |
| 22 | 0.01776/0.06046 |
| 23 | 0.01495/0.02579 |
| 24 | 0.04629/0.08446 |
| 25 | 0.35873/— |
| 26 | 0.08061/0.20053 |
| 27 | 0.05596/0.08072 |
| 28 | 0.27196/— |
| 29 | 0.22564/— |
| 30 | 0.01324/0.01411 |
| 31 | 0.09063/0.16046 |
| 32 | 0.1047/0.22344 |
| 33 | 0.10375/0.22165 |
| 34 | 0.34213/— |
| 35 | 0.22606/— |
| 36 | 0.01546/0.02591 |
| 37 | 0.04381/0.03954 |
| 38 | 0.13074/0.38163 |
| 39 | 0.20524/— |
| 40 | 0.47648/— |
| 41 | 0.21875/0.45572 |
| 42 | 0.11046/0.20003 |
| 43 | 0.48838/0.63158 |
| 44 | 0.006/0.0098 |
| 45 | 0.03613/0.07408 |
| 46 | 0.0103/0.02216 |
| 47 | 0.11766/0.39292 |
| 48 | 0.25074/0.52781 |
| 49 | 0.04448/0.05247 |
| 50 | 0.01831/0.01388 |
| 51 | 0.01228/0.01116 |
| 52 | 0.01786/0.027 |
| 53 | 0.04414/0.04752 |
| 54 | 0.06964/0.1218 |
| 55 | 0.00211/0.00282 |
| 56 | 0.13603/0.28466 |
| 57 | 0.13923/— |
| 58 | 0.17359/10 |
| 59 | 0.00433/0.00435 |
| 60 | 0.10092/0.18255 |
| 61 | 0.34281/0.51525 |
| 62 | 0.43262/0.56325 |
| 63 | 0.01955/0.05425 |
| 64 | 0.0547/0.07993 |
| 65 | 0.03236/0.05995 |
| 66 | 0.21649/0.41204 |
| 67 | 0.08278/0.18328 |
| 68 | 0.26659/0.18163 |
| 69 | 0.34401/— |
| 70 | 0.10203/0.28411 |
| 71 | 0.00592/0.01202 |
| 72 | 0.0428/0.133 |
| 73 | 0.0658/0.0943 |
| 74 | 0.0548/0.0489 |
| 75 | 0.0401/0.046 |
| 76 | 0.00433/0.00435 |
| 77 | 0.00221/0.00247 |
| 78 | 0.522/0.728 |
| 79 | 0.0168/0.0256 |
| 80 | 0.11/0.263 |
| 81 | 0.351/— |
| 82 | 0.435/— |
| 83 | 0.184/0.16 |
| 84 | 0.182/0.169 |
| 85 | 0.0429/— |
| 86 | 0.00691/0.013 |
| 87 | 0.0734/0.12 |
| 88 | 0.0143/0.0158 |
| 89 | 0.319/— |
| 90 | 0.341/— |
| 91 | 0.0249/— |
| 92 | 0.035/0.057 |
| 93 | 0.191/1.881 |
| 94 | 0.066/0.141 |
| 95 | 0.027/0.05 |
| 96 | 0.028/0.073 |
| 97 | 0.465/1.886 |
| 98 | 0.032 0.134 |
| 99 | 0.054/0.195 |
| 100 | 0.004/0.015 |
| 101 | 0.014/0.042 |
| 102 | 0.029/0.088 |
| 103 | 0.007/0.032 |
| 104 | 0.165/0.196 |
| 105 | 0.288/0.627 |
| 106 | 0.189/0.187 |
| 107 | 0.482/0.767 |
| 108 | 0.414/0.952 |
| 109 | 0.061/0.079 |
| 110 | 0.141/0.482 |
| 111 | 0.127/0.408 |
| 112 | 0.072/0.168 |
| 113 | 0.034/0.077 |
| 114 | 0.017/0.015 |
| 115 | 0.05/0.028 |
| 116 | 0.074/0.32 |
| 117 | 0.014/0.029 |
| 118 | 0.009/0.029 |
| 119 | 0.006/0.012 |
| 120 | 0.015/0.032 |
| 121 | 0.006/0.017 |
| 122 | 0.062/0.154 |
| 123 | 0.364/0.68 |
| 124 | 0.011/0.024 |
| 125 | 0.166/0.623 |
| 126 | 0.019/0.051 |
| 127 | 0.019/0.026 |
| 128 | 0.289/1.238 |
| 129 | 0.027/0.066 |
| 130 | 0.034/0.058 |
| 131 | 0.036/0.152 |
| 132 | 0.003/0.022 |
| 133 | 0.048/0.084 |
| 134 | 0.025/0.076 |
| 135 | 0.097/0.384 |
| 136 | 0.134/0.428 |
| 137 | 0.009/0.034 |
| 138 | 0.016/0.038 |
| 139 | 0.423/2.627 |
| 140 | 0.103/0.518 |
| 141 | 0.155/0.453 |
| 142 | 0.075/0.21 |
| 143 | 0.409/1.072 |
| 144 | 0.07/0.172 |
| 145 | 0.017/0.036 |
| 146 | 0.002/0.005 |
| 147 | 0.197/0.323 |
| 148 | 0.084/0.139 |
| 149 | 0.438/0.348 |
| 150 | 0.05/0.034 |
| 151 | 0.194/0.299 |
| 152 | 0.26/0.609 |
| 153 | 0.056/0.056 |
| 154 | 0.272/0.837 |
| 155 | 0.011/0.005 |
| 156 | 0.003/0.01 |

-continued

Table with activity data

| Example | hM1 $EC_{50}$/ratM1 $EC_{50}$ |
|---------|-------------------------------|
| 157 | 0.095/0.117 |
| 158 | 0.023/0.061 |
| 159 | 0.02/0.047 |
| 160 | 0.196/— |
| 161 | 0.121/0.307 |
| 162 | 0.214/0.751 |
| 163 | 0.059/0.082 |
| 164 | 0.048/0.088 |
| 165 | 0.043/— |
| 166 | 0.035/— |
| 167 | 0.047/— |
| 168 | 0.097/— |

The 168 compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelantine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelantine capsules. Suitable carriers for soft gelantine capsules are, for example, vegetable oils, waxes, fats, semi-solid and liquid polyols and the like; depending on the nature of the active substance no carriers are, however, usually required in the case of soft gelantine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula (I) or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Pharmaceutical Compositions Comprising Compounds of the Invention

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXPERIMENTAL PART

Preparation of Intermediates

Example A.1

4-Fluoro-1-(2-fluoro-4-(1-methyl-1H-pyrazol-4-yl)benzyl)-1H-indole-3-carboxylic acid

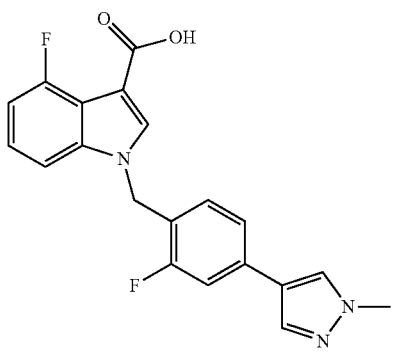 [SMILES: Cn1cc(-c2ccc(Cn3cc(C(=O)O)c4c(F)cccc43)c(F)c2)cn1]

Step 1: Methyl 4-fluoro-1-(2-fluoro-4-(1-methyl-1H-pyrazol-4-yl)benzyl)-1H-indole-3-carboxylate A suspension of methyl 4-fluoro-1H-indole-3-carboxylate (150 mg, 777 µmol) in N,N-dimethylformamide (2 ml) was cooled in ice-bath. Sodium hydride 60% dispersion in oil (37.3 mg, 932 µmol) was added at once. The mixture was stirred at 0° C. for 15 minutes. 4-(4-(chloromethyl)-3-fluorophenyl)-1-methyl-1H-pyrazole (example B.2) (174 mg, 777 µmol) was added at once. The mixture was stirred at 0° C. for 1 hour, quenched with a 20% ammonium chloride solution, diluted with water and extracted with ethyl acetate. The combined extracts were dried over sodium sulfate, filtered and concentrated in vacuo. The crude oil was purified with a flash column chromatography on silica (10 g) eluting with a gradient formed from n-heptane and ethyl acetate (0 to 100%) to provide 208 mg (70%) of the title compound as a light brown solid. MS (m/e): 382.5 (M+H)$^+$.

Step 2: 4-Fluoro-1-(2-fluoro-4-(1-methyl-1H-pyrazol-4-yl)benzyl)-1H-indole-3-carboxylic acid To a solution of methyl 4-fluoro-1-(2-fluoro-4-(1-methyl-1H-pyrazol-4-yl)benzyl)-1H-indole-3-carboxylate (195.9 mg, 514 µmol) in THF (1.6 ml), MeOH (0.8 ml) and water (0.8 ml) was added lithium hydroxide monohydrate (64.7 mg, 1.54 mmol). The mixture was stirred at room temperature for 1 hr, then heated to 50° C. for 5 hrs and finally stirred at room temperature for 2 days. The mixture was diluted with water and the solvent was evaporated in vacuo. The residue was taken up in water and HCl2N was added dropwise to adjust the pH to 2-3. The solid was filtered and dried to provide the title compound (170 mg, 90%) as a white solid. MS (m/e): 366.2 (M−H)$^-$.

Example A.2

4-Fluoro-1-(2-fluoro-4-(1-methyl-1H-pyrazol-4-yl)benzyl)-1H-indazole-3-carboxylic acid

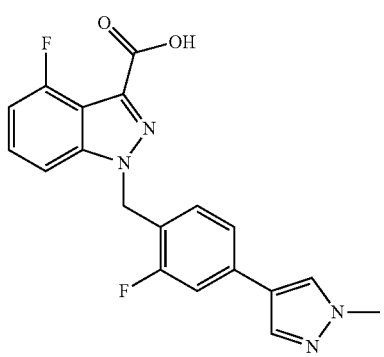 [SMILES: Cn1cc(-c2ccc(Cn3nc(C(=O)O)c4c(F)cccc43)c(F)c2)cn1]

In analogy to the procedures described for the synthesis of example A.1, the title compound was prepared from methyl 4-fluoro-1H-indazole-3-carboxylate (CAS 1427504-03-7) and 4-(4-(chloromethyl)-3-fluorophenyl)-1-methyl-1H-pyrazole (example B.2) White solid. MS (m/e): 369.4 (M+H)$^+$.

Example A.3

4,6-Difluoro-1-(2-fluoro-4-(1-methyl-1H-pyrazol-4-yl)benzyl)-1H-indole-3-carboxylic acid

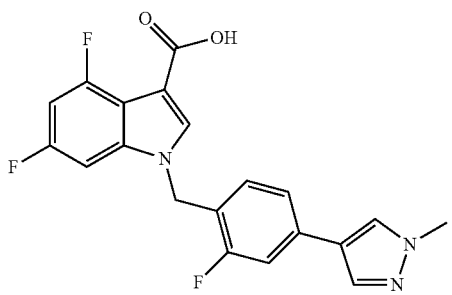 [SMILES: Cn1cc(-c2ccc(Cn3cc(C(=O)O)c4c(F)cc(F)cc43)c(F)c2)cn1]

In analogy to the procedures described for the synthesis of example A.1, the title compound was prepared from ethyl 4,6-difluoro-1H-indole-3-carboxylate and 4-(4-(chloromethyl)-3-fluorophenyl)-1-methyl-1H-pyrazole (example B.2). White solid. MS (m/e): 386.4 (M+H)$^+$.

Example A.4

4,5,6,7-Tetrafluoro-1H-indole-3-carboxylic acid ((1S,2S)-2-hydroxy-cyclohexyl)-amide

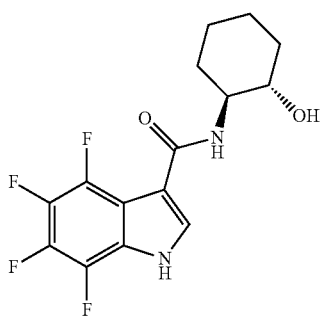 [SMILES: O=C(N[C@H]1CCCC[C@@H]1O)c1c[nH]c2c(F)c(F)c(F)c(F)c12]

In a 10 mL pear-shaped flask, 4,5,6,7-tetrafluoro-1H-indole-3-carboxylic acid (200 mg, 815 μmol), (1S,2S)-(+)-2-aminocyclohexanol hydrochloride (136 mg, 897 μmol) and (1H-benzo[d][1,2,3]triazol-1-yloxy)tris(dimethylamino)phosphonium hexafluorophosphate(V) (469 mg, 1.1 mmol) were combined with $CH_2Cl_2$ (4.9 ml) and triethylamine (330 mg, 452 μl, 3.26 mmol) to give an off-white suspension. The reaction mixture was stirred at r.t. for 2 days. The reaction mixture diluted with $H_2O$ and extracted with $CH_2Cl_2$. The aqueous layer extracted with EtOAc. This organic layer was dried over $MgSO_4$, filtrated and concentrated to give the title compound (390 mg, 70% pure) as an off-white solid. MS (m/e): 331.4 (M+H)⁻.

Example A.5

4-Fluoro-1-(2-fluoro-4-(1-methyl-1H-pyrazol-4-yl)benzyl)-1H-indole-3-carbonyl chloride

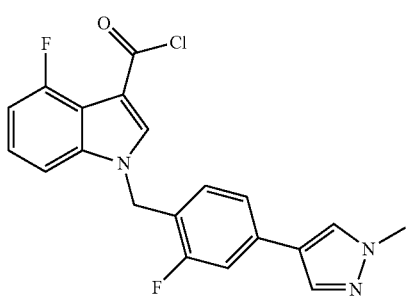 [SMILES: Cn1cc(-c2ccc(Cn3cc(C(=O)Cl)c4c(F)cccc43)c(F)c2)cn1]

To a solution of 4-fluoro-1-(2-fluoro-4-(1-methyl-1H-pyrazol-4-yl)benzyl)-1H-indole-3-carboxylic acid (Example A.1) (200 mg, 544 μmol) in dichloroethane (2 ml) under nitrogen at room temperature, was added 1 drop of N,N-dimethylformamide, followed by oxalyl chloride (212 mg, 143 μl, 1.63 mmol). The reaction mixture was stirred at room temperature for 3.5 hours. The mixture was evaporated to dryness to provide the title compound (222 mg, 106%) as an off-white solid.

Example A.6

4-Fluoro-N-((1S,2S)-2-hydroxycyclohexyl)-1H-indole-3-carboxamide

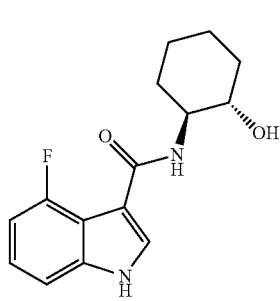 [SMILES: O=C(N[C@H]1CCCC[C@@H]1O)c1c[nH]c2cccc(F)c12]

To a stirred suspension of 4-fluoro-1H-indole-3-carboxylic acid (1 g, 5.58 mmol; CAS 23077-42-1) at r.t. in dichloromethane (60 ml) under an argon atmosphere were added (1S,2S)-2-aminocyclohexanol hydrochloride (931 mg, 6.14 mmol), BOP (2.96 g, 6.7 mmol) and triethylamine (2.26 g, 3.1 ml, 22.3 mmol). The resulting light brown solution was stirred at r.t. for 17 hrs. The mixture was concentrated and the residue was purified by silica gel chromatography (50 g) chromatography using a $CH_2Cl_2$/MeOH 9:1 gradient as eluent. The product-containing fractions were combined and concentrated to leave a viscous oil. It was triturated in $CH_2Cl_2$/n-heptane 3:2 (25 ml). The resulting suspension was stirred at r.t. for 1 hr. The product was collected by filtration, washed with a 1:1 mixture of $CH_2Cl_2$ and n-heptane, and dried to give the title compound (1.2 g, 75%) as an off-white solid. MS (m/e): 275.3 (M–H)⁻

Example A.7

4-Fluoro-7-methyl-1H-indole-3-carboxylic acid ((1S,2S)-2-hydroxy-cyclohexyl)-amide

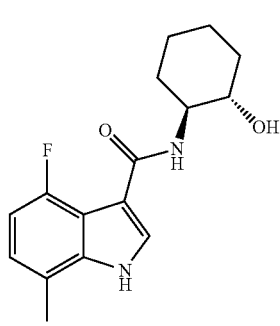 [SMILES: Cc1ccc(F)c2c(C(=O)N[C@H]3CCCC[C@@H]3O)c[nH]c12]

In analogy to the procedure described for the synthesis of example A.6, the title compound was prepared from 4-fluoro-7-methyl-1H-indole-3-carboxylic acid and (1S,2S)-(+)-2-amino-cyclohexanol hydrochloride. White solid.

Example A.8

4-Fluoro-N-(tetrahydro-2H-pyran-4-yl)-1H-indole-3-carboxamide

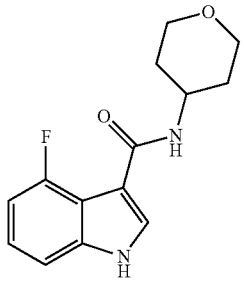 [SMILES: O=C(NC1CCOCC1)c1c[nH]c2cccc(F)c12]

In analogy to the procedure described for the synthesis of example A.6, the title compound was prepared from 4-fluoro-1H-indole-3-carboxylic acid (CAS 23077-42-1) and tetrahydro-2H-pyran-4-amine. White solid. MS (m/e): 263.2 (M+H)$^+$.

Example A.9

4-Fluoro-1-(4-(1-methyl-1H-pyrazol-4-yl)benzyl)-1H-indole-3-carboxylic acid

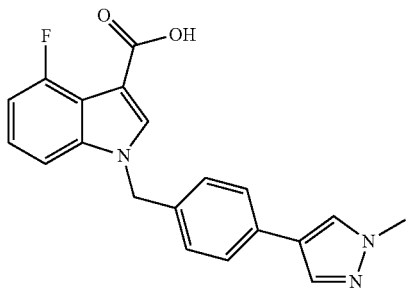 [SMILES: Cn1cc(-c2ccc(Cn3cc(C(=O)O)c4c(F)cccc43)cc2)cn1]

In analogy to the procedures described for the synthesis of example A.1, the title compound was prepared from methyl 4-fluoro-1H-indole-3-carboxylate and 4-(4-(chloromethyl)phenyl)-1-methyl-1H-pyrazole (example B.5). Off-white solid. MS (m/e): 350.6 (M+H)$^+$.

Example A.10

4-Fluoro-7-methyl-1H-indole-3-carboxylic acid (tetrahydro-pyran-3-yl)-amide

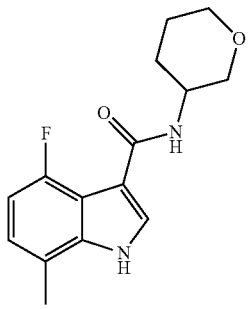 [SMILES: Cc1ccc(F)c2c(C(=O)NC3CCCOC3)c[nH]c12]

In analogy to the procedure described for the synthesis of example A.6, the title compound was prepared from 4-fluoro-7-methyl-1H-indole-3-carboxylic acid and tetrahydro-pyran-3-yl amine. Light yellow solid.

Example A.11

4-Fluoro-7-methyl-1H-indole-3-carboxylic acid (tetrahydro-pyran-4-yl)-amide

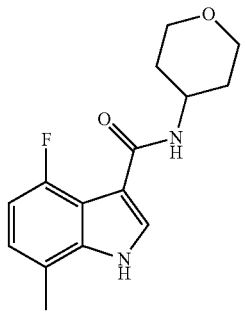 [SMILES: Cc1ccc(F)c2c(C(=O)NC3CCOCC3)c[nH]c12]

In analogy to the procedure described for the synthesis of example A.6, the title compound was prepared from 4-fluoro-7-methyl-1H-indole-3-carboxylic acid and tetrahydro-pyran-4-ylamine. White foam. MS (m/e): 277.2 (M+H)$^+$.

Example A.12

4-fluoro-N-((3R,4S) or (3S,4R)-3-hydroxytetrahydro-2H-pyran-4-yl)-1H-indole-3-carboxamide

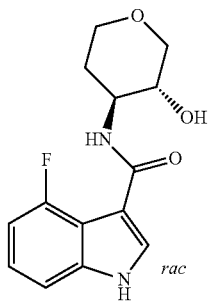 [SMILES: O=C(N[C@H]1CCOC[C@@H]1O)c1c[nH]c2cccc(F)c12]

Step 1: 4-Fluoro-N-((3RS,4SR)-3-hydroxytetrahydro-2H-pyran-4-yl)-1H-indole-3-carboxamide In analogy to the procedure described for the synthesis of example A.6, the title compound was prepared from methyl 4-fluoro-1H-indole-3-carboxylate and (3RS,4SR)-4-aminotetrahydro-2H-pyran-3-ol (CAS 215940-92-4). Light yellow solid. MS (m/e): 279.4 (M+H)$^+$.

Step 2: 4-Fluoro-N-((3R,4S) or (3S,4R)-3-hydroxytetrahydro-2H-pyran-4-yl)-1H-indole-3-carboxamide 4-Fluoro-N-((3RS,4SR)-3-hydroxytetrahydro-2H-pyran-4-yl)-1H-indole-3-carboxamide (310 mg, 1.1 mmol) was separated on a Reprosil Chiral NR column to provide 136 mg (44%) of the title compound as an off-white solid (+ enantiomer). MS (m/e): 279.4 (M+H)$^+$.

Example A.13

4,5,6,7-Tetrafluoro-1H-indole-3-carboxylic acid ((3RS,4SR)-3-hydroxy-tetrahydro-pyran-4-yl)-amide

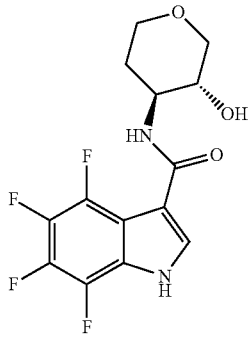 [SMILES: O=C(N[C@H]1CCOC[C@@H]1O)c1c[nH]c2c(F)c(F)c(F)c(F)c12]

In analogy to the procedure described for the synthesis of example A.6, the title compound was prepared from 4,5,6,7-tetrafluoro-1H-indole-3-carboxylic acid and (3RS,4SR)-4-amino-tetrahydro-2H-pyran-3-ol (CAS 215940-92-4). White solid.

Example A.14

4,5-Difluoro-1H-indole-3-carboxylic acid ((1S,2S)-2-hydroxy-cyclohexyl)-amide

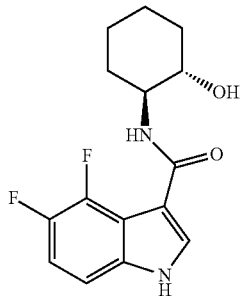 [SMILES: O=C(N[C@H]1CCCC[C@@H]1O)c1c[nH]c2ccc(F)c(F)c12]

In analogy to the procedure described for the synthesis of example A.6, the title compound was prepared from 4,5-difluoro-1H-indole-3-carboxylic acid and (1S,2S)-(+)-2-aminocyclohexanol hydrochloride. Light brown solid.

Example A.15

4,7-Difluoro-1-(2-fluoro-4-(1-methyl-1H-pyrazol-4-yl)benzyl)-1H-indazole-3-carboxylic acid

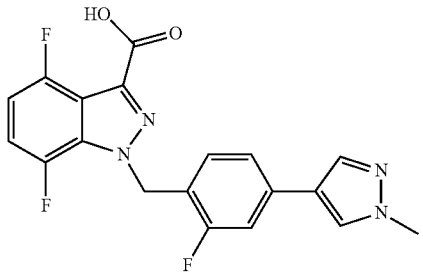 [SMILES: Cn1cc(-c2ccc(Cn3nc(C(=O)O)c4c(F)ccc(F)c43)c(F)c2)cn1]

Step 1: 4,7-Difluoro-1H-indazole-3-carboxylic acid

A solution of 4,7-difluoroindoline-2,3-dione (2.0 g, 10.9 mmol) in 1N NaOH (11.8 ml) was stirred at 50° C. for 30 mins. The solution was allowed to cool to r.t. and maintained for 1 hr. The reaction mixture was cooled to 0° C. and treated with a pre-cooled (0° C.) solution of sodium nitrite (754 mg in 2.8 ml $H_2O$). This solution was added to a stirred solution of $H_2SO_4$ (1.2 ml in 22 ml $H_2O$) at 0° C. and the reaction mixture was maintained at that temperature for 30 min. A cold (0° C.) solution of $SnCl_2$ (5.9 g, 26.2 mmol) in concentrated HCl (4.2 ml) was slowly added to the reaction mixture within 10 min; and the reaction mixture was maintained for 60 min. The reaction mixture was extracted with 15% MeOH/$CH_2Cl_2$. Evaporation of the solvent provided the title compound as a brown sticky solid (600 mg, 55%) which was used in the next step without purification.

Step 2: Methyl 4,7-difluoro-1H-indazole-3-carboxylate

A solution of 4,7-difluoro-1H-indazole-3-carboxylic acid (4.5 g, 22.7 mmol) in MeOH (45 ml) was treated with $H_2SO_4$ (0.41 ml) and stirred at 50° C. over night. After completion of the reaction, the reaction mixture was concentrated. The crude product was purified by silica gel chromatography using 15% EtOAc in hexane as eluent to provide the title compound as an off-white solid (500 mg, 10%).

Step 3: Methyl 4,7-difluoro-1-(2-fluoro-4-(1-methyl-1H-pyrazol-4-yl)benzyl)-1H-indazole-3-carboxylate To a stirred solution of methyl 4,7-difluoro-1H-indazole-3-carboxylate (250 mg, 1.2 mmol) at 0° C. in DMF (3.00 ml) under an argon atmosphere was added sodium hydride 60% dispersion in mineral oil (47.1 mg, 1.2 mmol) in one portion. After stirring for 15 min at 0° C., 4-(4-(chloromethyl)-3-fluorophenyl)-1-methyl-1H-pyrazole (example B.2; 265 mg, 1.2 mmol) was added in one portion. The ice bath was removed, and stirring at r.t. was continued for 17 hrs. The reaction mixture was taken up in $H_2O$ (10 ml) and sat. aq. NaCl (10 ml) and extracted with EtOAc. The aqueous phase was back-extracted with EtOAc (10 ml). The combined organics were washed with water (20 ml) and brine (20 ml), dried over $MgSO_4$, filtered and concentrated. The crude product was purified by silica gel chromatography using a EtOAc/heptane gradient as eluent providing the title compound (251 mg, 53 mg) as yellow solid, along with its regioisomer (103 mg, 22 mg) methyl 4,7-difluoro-2-(2-fluoro-4-(1-methyl-1H-pyrazol-4-yl)benzyl)-2H-indazole-3-carboxylate. MS (m/e): 401.1 $(M+H)^+$.

Step 4: 4,7-Difluoro-1-(2-fluoro-4-(1-methyl-1H-pyrazol-4-yl)benzyl)-1H-indazole-3-carboxylic acid To a stirred solution of methyl 4,7-difluoro-1-(2-fluoro-4-(1-methyl-1H-pyrazol-4-yl)benzyl)-1H-indazole-3-carboxylate (246 mg, 614 μmol) at r.t. in THF (2 ml) and methanol (1 ml) under an argon atmosphere were added water (1.7 ml) and 1 N NaOH (1.23 ml, 1.23 mmol). Stirring at r.t. was continued for 17 hrs. The mixture (clear orange solution) was treated with 1 N HCl (1.2 ml). The light yellow suspension was stirred at r.t. for 1 hr. The solid was collected by filtration, washed with $H_2O$ and dried to provide the title compound (221 mg, 93%) as light yellow solid. MS (m/e): 385.1 $(M-H)^-$.

Example A.16

4,7-Difluoro-1-[[6-(1-methylpyrazol-4-yl)pyridine-3-yl]methyl]indazole-3-carboxylic acid

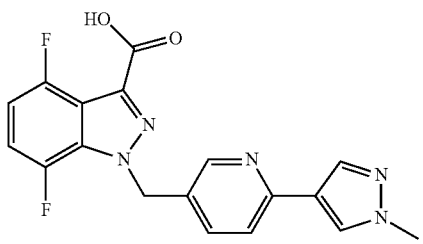 [SMILES: Cn1cc(-c2ccc(Cn3nc(C(=O)O)c4c(F)ccc(F)c43)cn2)cn1]

The title compound was prepared in analogy to the procedures described in example A.15, using 5-(chloromethyl)-2-(1-methyl-1H-pyrazol-4-yl)pyridine (example B.1) as alkylating agent in the 3$^{rd}$ step. Off-white solid. MS (m/e): 368.2

Example A.17

4,7-Difluoro-1-((1-methyl-1H-indazol-5-yl)methyl)-1H-indole-3-carboxylic acid

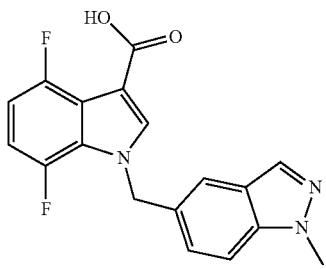 [SMILES: Cn1ncc2cc(Cn3cc(C(=O)O)c4c(F)ccc(F)c43)ccc21]

Step 1: Methyl 4,7-difluoro-1-((1-methyl-1H-indazol-5-yl)methyl)-1H-indole-3-carboxylate The title compound was obtained in analogy to the procedure described in example 26, reacting methyl 4,7-difluoro-1H-indole-3-carboxylate and 5-(bromomethyl)-1-methyl-1H-indazole hydrobromide. White solid. MS (m/e): 356.5 (M+H)$^+$.

Step 2: 4,7-Difluoro-1-((1-methyl-1H-indazol-5-yl)methyl)-1H-indole-3-carboxylic acid The title compound was obtained in analogy to the procedure described in example A.1, step 2. White solid. MS (m/e): 342.5 (M+H)$^+$.

Example A.18

4,7-Difluoro-1-(4-(1-methyl-1H-pyrazol-4-yl)benzyl)-1H-indole-3-carboxylic acid

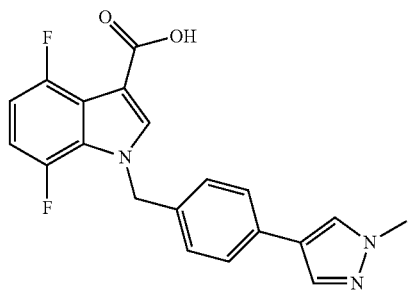 [SMILES: Cn1cc(-c2ccc(Cn3cc(C(=O)O)c4c(F)ccc(F)c43)cc2)cn1]

In analogy to the procedures described for the synthesis of example A.17, the title compound was prepared from methyl 4,7-difluoro-1H-indole-3-carboxylate and 4-(4-(chloromethyl)phenyl)-1-methyl-1H-pyrazole (example B.5). White solid. MS (m/e): 368.5 (M+H)$^+$.

Example A.19

4,7-Difluoro-1-(2-fluoro-4-(1-methyl-1H-pyrazol-4-yl)benzyl)-1H-indole-3-carboxylic acid

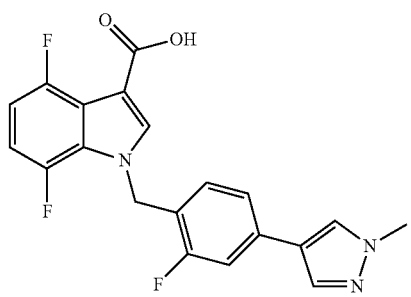 [SMILES: Cn1cc(-c2ccc(Cn3cc(C(=O)O)c4c(F)ccc(F)c43)c(F)c2)cn1]

In analogy to the procedures described for the synthesis of example A.17, the title compound was prepared from methyl 4,7-difluoro-1H-indole-3-carboxylate and 4-(4-(chloromethyl)-3-fluorophenyl)-1-methyl-1H-pyrazole (example B.2). White solid. MS (m/e): 386.5 (M+H)$^+$.

Example A.20

2-(4-Fluoro-1-(4-(methylcarbamoyl)benzyl)-1H-indol-3-yl)acetic acid

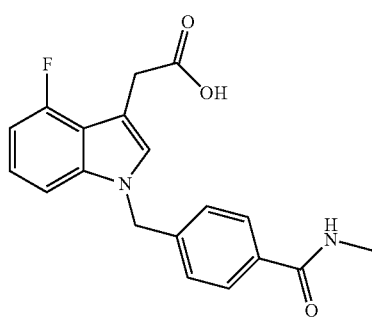 [SMILES: CNC(=O)c1ccc(Cn2cc(CC(=O)O)c3c(F)cccc32)cc1]

In analogy to the procedures described for the synthesis of example A.17, the title compound was prepared from ethyl 2-(4-fluoro-1H-indol-3-yl)acetate (CAS 919295-78-6) and 4-(chloromethyl)-N-methylbenzamide (example B.6). Brown solid. MS (m/e): 341.2 (M+H)⁺.

Example A.21

7-Cyclopropyl-4-fluoro-1-(4-(1-methyl-1H-pyrazol-4-yl)benzyl)-1H-indole-3-carboxylic acid

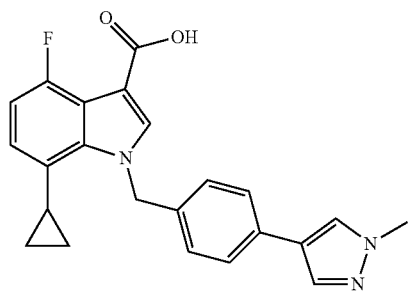 [SMILES: Cn1cc(-c2ccc(Cn3cc(C(=O)O)c4c(F)ccc(C5CC5)c43)cc2)cn1]

Step 1: 1-(7-Bromo-4-fluoro-1H-indol-3-yl)-2,2,2-trifluoro-ethanone

To a solution of 7-bromo-4-fluoro-1H-indole (23 g, 107.4 mmol) in DMF (220 ml) under nitrogen at room temperature was added trifluoro acetic anhydride (29.8 ml, 214.95 mmol). The reaction mixture was stirred at 40° C. for 8 hours, cooled to room temperature, diluted with water (250 ml) and extracted with ethyl acetate (2×500 ml). The combined organic layers were washed with brine (250 ml), aqueous sodium carbonate solution (200 ml) and dried over sodium sulfate, filtered and concentrated. The residue was purified with flash column chromatography on silica eluting with 15% ethyl acetate in hexane to provide 20 g (60%) of the title compound as an off-white solid. LC-MS (ESI): 310 (M).

Step 2: 7-Bromo-4-fluoro-1H-indole-3-carboxylic acid

To a solution of 1-(7-bromo-4-fluoro-1H-indol-3-yl)-2,2,2-trifluoro-ethanone (5 g, 16.12 mmol) in methanol (60 ml) and water (60 ml) under nitrogen at room temperature was added NaOH (9.6 g, 241.93 mmol). The mixture was stirred at 140° C. for 16 hours, cooled to room temperature and concentrated. The residue was diluted with water (150 ml) and washed with ethyl acetate (100 ml). The aqueous layer was treated with 50% aqueous HCl until pH-4 and extracted with ethyl acetate (2×200 ml). The combined organics were washed with brine (100 ml) and aqueous sodium carbonate solution (100 ml), dried over sodium sulfate, filtered and concentrated to provide the title compound as a off white-solid (2.3 g, 55%). LC-MS (ESI): 256 (M–H)⁻.

Step 3: Methyl 7-bromo-4-fluoro-1H-indole-3-carboxylate

HCl gas was bubbled through a solution of 7-bromo-4-fluoro-1H-indole-3-carboxylic acid (11.2 g, 43.4 mmol) in methanol (200 ml) at room temperature for 30 min. The reaction mixture was then stirred at 60° C. for 16 hours and concentrated. The residue was diluted with water (200 ml) and extracted with ethyl acetate (2×500 ml). The combined organics were washed with brine (250 ml) and aqueous sodium carbonate solution (250 ml), dried over sodium sulfate, filtered and concentrated. The residue was purified with flash column chromatography on silica eluting with 20% ethyl acetate in hexane to provide the title compound as a brown solid (7.1 g, 60%). LC-MS (ESI): 271 (M–H)⁻.

Step 4: Methyl 7-cyclopropyl-4-fluoro-1H-indole-3-carboxylate

To a solution of 7-bromo-4-fluoro-1H-indole-3-carboxylic acid methyl ester (4.5 g, 16.5 mmol) in toluene (200 ml) were added cyclopropyl boronic acid (2.8 g, 33.08 mmol), tricyclohexylphosphine (0.232 g, 0.827 mmol), and K₃PO₄ (7.01 g, 33.08 mmol). The reaction mixture was purged with argon for 20 min. Pd(OAc)₂ (0.371 g, 1.65 mmol) was added and the mixture was purged with argon for another 10 min. The reaction mixture was then heated to 100° C. and stirred at this temperature for 16 hours in a sealed tube. The mixture was cooled to room temperature and filtered through a celite pad which was washed with EtOAc (100 ml). Water (200 ml) was added to the filtrate. The aqueous layer was extracted with EtOAc (3×200 ml). The combined organics were washed with water (100 ml) and brine (100 ml), dried over Na₂SO₄ and concentrated. The residue was purified with flash column chromatography on silica eluting with 20% ethyl acetate in hexane to provide the title compound as a grey solid (2.3 g, 60%) %). LC-MS (ESI): 234 (M+H)⁺.

Step 5: 7-Cyclopropyl-4-fluoro-1-(4-(1-methyl-1H-pyrazol-4-yl)benzyl)-1H-indole-3-carboxylic acid In analogy to the procedures described for the synthesis of example A.17, the title compound was prepared from methyl 7-cyclopropyl-4-fluoro-1H-indole-3-carboxylate and 4-(4-(chloromethyl)phenyl)-1-methyl-1H-pyrazole (example B.5). Off-white solid. MS (m/e): 388.3 (M–H)⁻.

Example A.22

7-Cyclopropyl-4-fluoro-1-(2-fluoro-4-(1-methyl-1H-pyrazol-4-yl)benzyl)-1H-indole-3-carboxylic acid

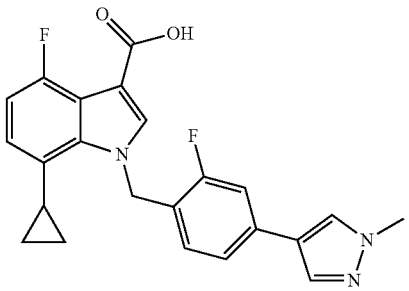 [SMILES: Cn1cc(-c2ccc(Cn3cc(C(=O)O)c4c(F)ccc(C5CC5)c43)c(F)c2)cn1]

In analogy to the procedures described for the synthesis of example A.21, the title compound was prepared from methyl 7-cyclopropyl-4-fluoro-1H-indole-3-carboxylate and 4-(4-(chloromethyl)-3-fluorophenyl)-1-methyl-1H-pyrazole (example B.2). Off-white solid. MS (m/e): 406.2 (M–H)⁻.

Example A.23

7-Ethyl-4-fluoro-1-(4-(1-methyl-1H-pyrazol-4-yl)benzyl)-1H-indole-3-carboxylic acid

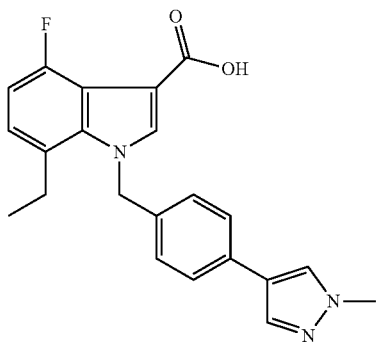 [SMILES: CCc1ccc(F)c2c(C(=O)O)cn(Cc3ccc(-c4cnn(C)c4)cc3)c12]

Step 1: Methyl 4-fluoro-7-vinyl-1H-indole-3-carboxylate

To a solution of methyl 7-bromo-4-fluoro-1H-indole-3-carboxylate (example A.21, step 3) (1.0 g, 3.68 mmol) and 4,4,5,5-tetramethyl-2-vinyl-[1,3,2]dioxaborolane (1.13 g, 7.35 mmol) at room temperature in 1,4-dioxane (30 ml) and water (3 ml) was added $Cs_2CO_3$ (2.39 g, 7.35 mmol) and the mixture was purged with argon for 10 min. [1,1'-bis(diphenylphosphino)ferrocene]dichloropalladium(II) dichloromethane adduct (0.08 g, 0.37 mmol) was added and the reaction mixture was purged with argon for another 10 min. The reaction mixture was then heated to 80° C. and stirred at this temperature for 16 hours under argon. The reaction mixture was cooled to room temperature, filtered through a celite pad which was washed with EtOAc (50 ml). The filtrate was diluted with water (100 ml) and extracted with EtOAc (2×100 ml). The combined organics were washed with water (50 ml) and brine (50 ml), dried over $Na_2SO_4$ and concentrated. The residue was purified with flash column chromatography on silica eluting with 20% ethyl acetate in hexane to provide the title compound as a white solid (500 mg, 62%). LC-MS (ESI): 220 (M+H)$^+$.

Step 2: Methyl 7-ethyl-4-fluoro-1H-indole-3-carboxylate

A mixture of methyl 4-fluoro-7-vinyl-1H-indole-3-carboxylate (500 mg, 2.28 mmol) and 10% palladium on activated charcoal (4 mg, 0.039 mmol) in methanol (10 ml) was stirred for 4 hours at room temperature under hydrogen atmosphere (balloon pressure). The palladium catalyst was filtered off and the filtrate was concentrated. The residue was purified with flash column chromatography on silica eluting with 20% ethyl acetate in hexane to provide the title compound as an off-white solid (450 mg, 89%). LC-MS (ESI): 220 (M–H)$^-$.

Step 3: 7-Ethyl-4-fluoro-1-(4-(1-methyl-1H-pyrazol-4-yl)benzyl)-1H-indole-3-carboxylic acid In analogy to the procedures described for the synthesis of example A.17, the title compound was prepared from methyl 7-ethyl-4-fluoro-1H-indole-3-carboxylate and 4-(4-(chloromethyl)phenyl)-1-methyl-1H-pyrazole (example B.5). White solid. MS (m/e): 378.2 (M+H)$^+$.

Example A.24

4-Fluoro-1-{[4-(methylcarbamoyl)phenyl]methyl}-1H-indole-3-carboxylic acid

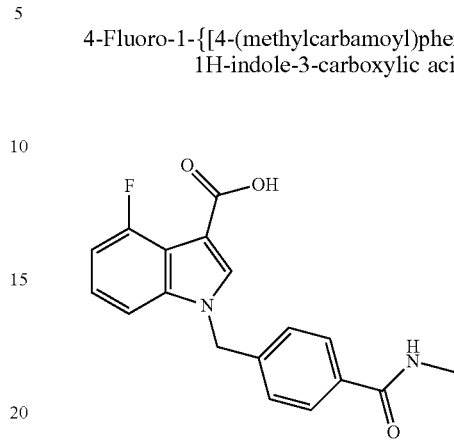

In analogy to the procedures described for the synthesis of example A.17, the title compound was prepared from methyl 4-fluoro-1H-indole-3-carboxylate and 4-(chloromethyl)-N-methylbenzamide (example B.6). Off-white solid. LC-MS (ESI): 327.0 (M+H)$^+$.

Example A.25

7-Ethyl-4-fluoro-1-((1-methyl-1H-indazol-5-yl)methyl)-1H-indole-3-carboxylic acid

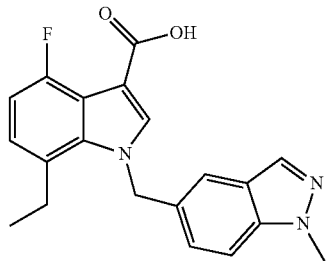 [SMILES: CCc1ccc(F)c2c(C(=O)O)cn(Cc3ccc4c(cnn4C)c3)c12]

In analogy to the procedures described for the synthesis of example A.17, the title compound was prepared from methyl 7-ethyl-4-fluoro-1H-indole-3-carboxylate and 5-(bromomethyl)-1-methyl-1H-indazole hydrobromide. White solid. MS (m/e): 355.2 (M+H)$^+$.

Example A.26

4-Fluoro-1-(3-fluoro-4-(methylcarbamoyl)benzyl)-1H-indole-3-carboxylic acid

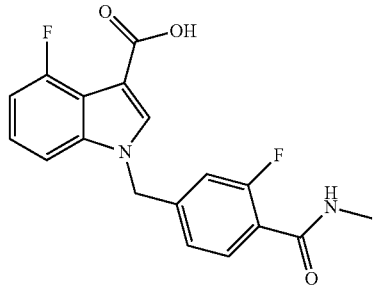 [SMILES: CNC(=O)c1ccc(Cn2cc(C(=O)O)c3c(F)cccc32)cc1F]

In analogy to the procedures described for the synthesis of example A.17, the title compound was prepared from methyl 4-fluoro-1H-indole-3-carboxylate and 4-(chloromethyl)-2-fluoro-N-methylbenzamide (example B.7). Off-white solid. MS (m/e): 345.1 (M+H)+.

Example A.27

4-Fluoro-N-((1S,2S)-2-hydroxycyclohexyl)-7-methoxy-1H-indole-3-carboxamide

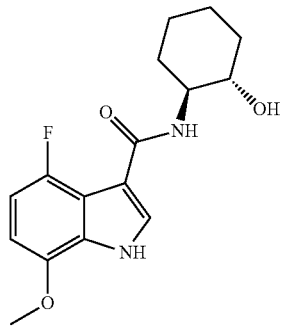 [SMILES: COc1ccc(F)c2c(C(=O)N[C@H]3CCCC[C@@H]3O)c[nH]c12]

To a stirred solution of (1S,2S)-2-aminocyclohexanol hydrochloride (CAS 13374-30-6) (111 mg, 734 µmol) at room temperature in dichloromethane (5 ml) under an argon atmosphere were added 4-fluoro-7-methoxy-1H-indole-3-carboxylic acid (150 mg, 667 µmol), (benzotriazol-1-yloxy)tris(dimethylamino)phosphonium hexafluorophosphate (BOP) (354 mg, 800 µmol) and triethylamine (270 mg, 370 µl, 2.67 mmol). Stirring at r.t. was continued for 17 hours. The reaction mixture was concentrated and the residue was purified with flash column chromatography on silica eluting with a gradient formed from dichloromethane and methanol (0 to 10%) to provide the title compound as an off-white solid (162 mg, 79%). MS (m/e): 305.2 (M−H)−.

Example A.28

4-Fluoro-N-((3R,4S)-3-hydroxytetrahydro-2H-pyran-4-yl)-7-methoxy-1H-indole-3-carboxamide

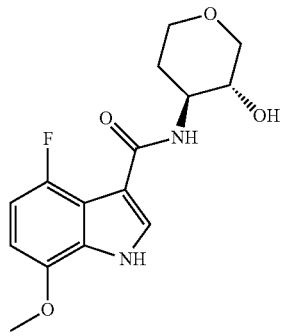 [SMILES: COc1ccc(F)c2c(C(=O)N[C@H]3CCOC[C@@H]3O)c[nH]c12]

In analogy to the procedure described for the synthesis of example A.27, the title compound was prepared from 4-fluoro-7-methoxy-1H-indole-3-carboxylic acid and (3R,4S)-4-aminotetrahydropyran-3-ol hydrochloride (example C.1). Off-white solid. MS (m/e): 307.1 (M−H)−.

Example A.29

4-Fluoro-7-methoxy-N-(tetrahydro-2H-pyran-4-yl)-1H-indole-3-carboxamide

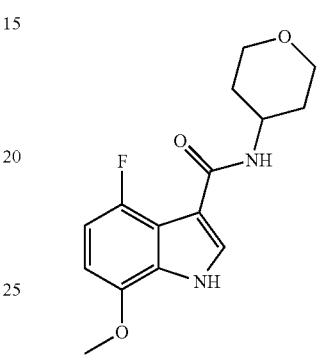

In analogy to the procedure described for the synthesis of example A.27, the title compound was prepared from 4-fluoro-7-methoxy-1H-indole-3-carboxylic acid and 4-aminotetrahydropyran. Off-white solid. MS (m/e): 291.2 (M−H)−.

Example A.30

1-(4-Bromobenzyl)-4-fluoro-N-((1S,2S)-2-hydroxycyclohexyl)-1H-indole-3-carboxamide

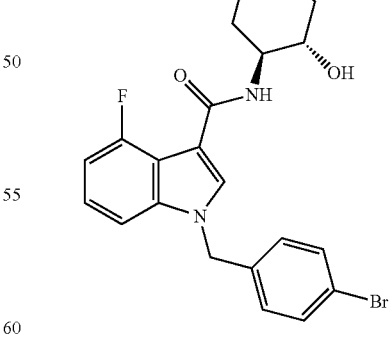

In analogy to the procedure described for the synthesis of example A.17, step 1, the title compound was prepared from 4-fluoro-N-((1S,2S)-2-hydroxycyclohexyl)-1H-indole-3-carboxamide (example A.6) and 1-bromo-4-(bromomethyl)benzene. White solid. MS (m/e): 445.3 (M+H)+.

Example A.31

4-Fluoro-N-((1S,2S)-2-hydroxycyclohexyl)-1-(piperidin-4-ylmethyl)-1H-indole-3-carboxamide

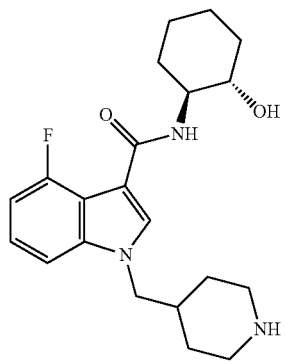 [SMILES: O=C(N[C@H]1CCCC[C@@H]1O)c1cn(CC2CCNCC2)c2cccc(F)c12]

Step 1: tert-Butyl 4-((4-fluoro-3-((1S,2S)-2-hydroxycyclohexylcarbamoyl)-1H-indol-1-yl)methyl)piperidine-1-carboxylate In analogy to the procedure described for the synthesis of example A.17, step 1, the title compound was prepared from 4-fluoro-N-((1S,2S)-2-hydroxycyclohexyl)-1H-indole-3-carboxamide (example A.6) and 4-methanesulfonyloxymethylpiperidine-1-carboxylic acid tert-butyl ester (CAS 161975-39-9). White solid. MS (m/e): 474.4 (M+H)⁻.

Step 2: 4-Fluoro-N-((1S,2S)-2-hydroxycyclohexyl)-1-(piperidin-4-ylmethyl)-1H-indole-3-carboxamide To a solution of tert-butyl 4-((4-fluoro-3-((1S,2S)-2-hydroxycyclohexylcarbamoyl)-1H-indol-1-yl)methyl)piperidine-1-carboxylate (200 mg, 422 µmol) at 0° C. in dioxane (5 ml) under an argon atmosphere was added HCl 4M solution in dioxane (528 µl, 2.11 mmol). The mixture was stirred at room temperature for 5 hours. The reaction mixture was cooled again to 0° C. and HCl 4M solution in dioxane (528 µl, 2.11 mmol) was added and the mixture was stirred at room temperature for another 17 hours. The mixture was concentrated. The residue was dissolved in CH$_2$Cl$_2$/MeOH (95:5) and washed with aqueous saturated Na$_2$CO$_3$ solution. The organic layer was dried over MgSO$_4$, filtered and concentrated to provide the title compound as a light yellow solid (149 mg, 89%). MS (m/e): 374.3 (M+H)⁺.

Example A.32

1-((6-Bromopyridin-3-yl)methyl)-4-fluoro-N-((1S,2S)-2-hydroxycyclohexyl)-1H-indole-3-carboxamide

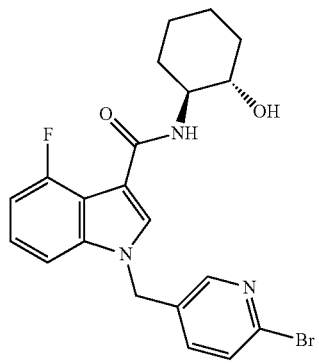 [SMILES: O=C(N[C@H]1CCCC[C@@H]1O)c1cn(Cc2ccc(Br)nc2)c2cccc(F)c12]

In analogy to the procedure described for the synthesis of example A.17, step 1, the title compound was prepared from 4-fluoro-N-((1S,2S)-2-hydroxycyclohexyl)-1H-indole-3-carboxamide (example A.6) and 2-bromo-5-pyridylmethyl chloride. White solid. MS(m/e): 448.2 (M+H)⁺.

Example A.33

Methyl 2-fluoro-4-((4-fluoro-3-(tetrahydro-2H-pyran-4-ylcarbamoyl)-1H-indol-1-yl)methyl)benzoate

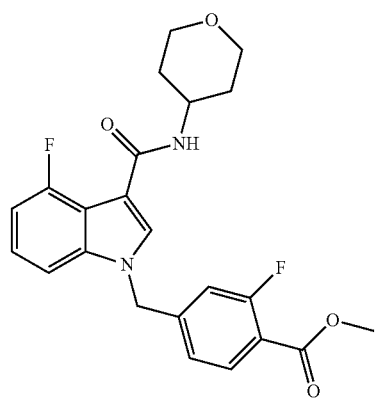 [SMILES: COC(=O)c1ccc(Cn2cc(C(=O)NC3CCOCC3)c3c(F)cccc32)cc1F]

In analogy to the procedure described for the synthesis of example A.17, step 1, the title compound was prepared from 4-fluoro-N-(tetrahydro-2H-pyran-4-yl)-1H-indole-3-carboxamide (example A.8) and methyl 4-(bromomethyl)-2-fluorobenzoate. White solid. MS (m/e): 429.3 (M+H)⁺.

Example A.34

4-Fluoro-N-((3R,4S)-3-hydroxytetrahydro-2H-pyran-4-yl)-1H-indole-3-carboxamide

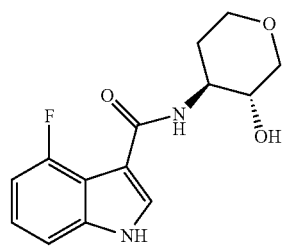 [SMILES: O=C(N[C@H]1CCOC[C@@H]1O)c1c[nH]c2cccc(F)c12]

In analogy to the procedure described for the synthesis of example A.27, the title compound was prepared from 4-fluoro-indole-3-carboxylic acid (CAS 23077-42-1) and (3R,4S)-4-aminotetrahydropyran-3-ol hydrochloride (example C.1). Light-yellow solid. MS (m/e): 279.1 (M+H)⁺.

Example A.35

1-(4-Carbamoyl-benzyl)-4-fluoro-1H-indole-3-carboxylic acid

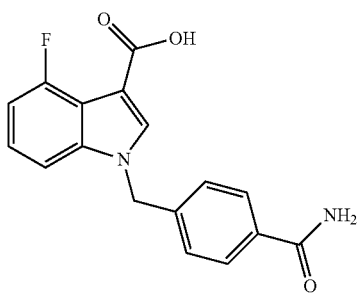 [SMILES: NC(=O)c1ccc(Cn2cc(C(=O)O)c3c(F)cccc32)cc1]

In analogy to the procedure described for the synthesis of example A.1 (step: 1 and 2), the title compound was prepared from methyl 4-fluoro-1H-indole-3-carboxylate and 4-chloromethyl-benzonitrile. MS (m/e): 313.4 (M+H)⁻.

Example A.36

1-(4-Cyanobenzyl)-4-fluoro-1H-indole-3-carboxylic acid

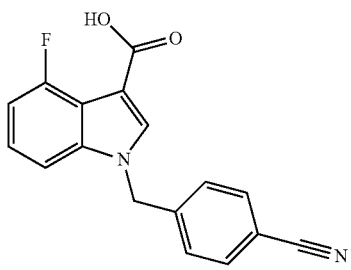 [SMILES: N#Cc1ccc(Cn2cc(C(=O)O)c3c(F)cccc32)cc1]

Step 1: Methyl 1-(4-cyanobenzyl)-4-fluoro-1H-indole-3-carboxylate

In analogy to the procedure described for the synthesis of example A.1 (step 1), the title compound was prepared from methyl 4-fluoro-1H-indole-3-carboxylate and 4-chloromethyl-benzonitrile.

Step 2: 1-(4-Cyanobenzyl)-4-fluoro-1H-indole-3-carboxylic acid

In a sealed tube, methyl 1-(4-cyanobenzyl)-4-fluoro-1H-indole-3-carboxylate (187 mg, 607 μmol) and lithium iodide (812 mg, 6.1 mmol) were combined with pyridine (8.7 ml). The reaction mixture was stirred at 135° C. for 19 hrs, then treated with water and HCl 2N. The precipitate was filtered, washed with water and dried to provide 85 mg (48%) of the title compound as an off white solid. MS (m/e): 295.4 (M+H)⁺.

Example A.37

4-Fluoro-N-tetrahydropyran-4-yl-1H-indazole-3-carboxamide

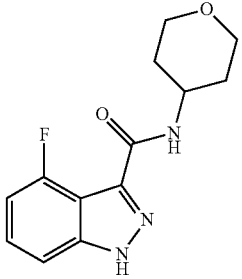 [SMILES: O=C(NC1CCOCC1)c1n[nH]c2cccc(F)c12]

In analogy to the procedure described for the synthesis of example A.6, the title compound was prepared from 4-fluoro-1H-indazole-3-carboxylic acid and tetrahydropyran-4-yl amine. MS (m/e): 264.4 (M+H)⁺.

Example B.1

5-(Chloromethyl)-2-(1-methyl-1H-pyrazol-4-yl)pyridine

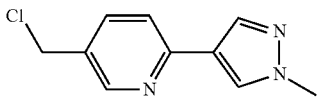

Step 1: (6-(1-Methyl-1H-pyrazol-4-yl)pyridine-3-yl)methanol

To a solution of (6-chloropyridin-3-yl)methanol (1 g, 6.8 mmol) in dioxane (20 ml) under nitrogen at room temperature was added 1-methyl-4-(4,4,5,5-tetramethyl-1,3,2-dioxaborolan-2-yl)-1H-pyrazole (2.16 g, 10.2 mmol) followed by [1,1'-bis(diphenylphosphino)ferrocene]dichloropalladium(II) dichloromethane adduct (276 mg, 341 μmol). A solution of sodium carbonate (2.17 g, 20.5 mmol) in water (16 ml) was added to the mixture. The reaction mixture was stirred at 80° C. for 1 hour and cooled to room temperature. Ethyl acetate (20 ml) and water (10 ml) were added. The aqueous layer was extracted with ethyl acetate. The combined organic layers were dried over sodium sulfate and concentrated. The crude brown solid was purified with flash column chromatography on silica eluting with a gradient formed from n-heptane and ethyl acetate (0 to 100%) to provide 1 g (77%) of the title compound as a grey solid. MS (m/e): 190.2 (M+H)⁺.

Step 2: 5-(Chloromethyl)-2-(1-methyl-1H-pyrazol-4-yl)pyridine

To a 0° C. solution of (6-(1-methyl-1H-pyrazol-4-yl)pyridine-3-yl)methanol (1 g, 5.3 mmol) in dichloromethane (30 ml) was added a solution of thionyl chloride (1.27 g, 775 μl, 10.6 mmol) in dichloromethane (5 ml). The reaction mixture was stirred at room temperature for 3 hours and quenched with a saturated solution of sodium hydrogen carbonate (30 ml). The aqueous layer was extracted with dichloromethane. The combined organic layers were dried over sodium sulfate and evaporated. The crude material was purified with flash column chromatography on silica eluting with a gradient formed from n-heptane and ethyl acetate (0 to 20%) to provide 930 mg (85%) of the title compound as a light grey solid. MS (m/e): 208.2 (M+H)$^+$.

Example B.2

4-(4-(Chloromethyl)-3-fluorophenyl)-1-methyl-1H-pyrazole

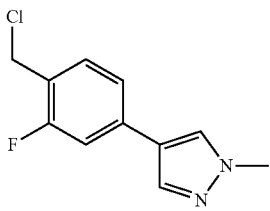

In analogy to the procedures described for the synthesis of example B.1, the title compound was prepared from 4-bromo-2-fluorophenyl)-methanol. MS (m/e): 225.4 (M+H)$^+$.

Example B.3

4-(3-(Chloromethyl)phenyl)-1-methyl-1H-pyrazole

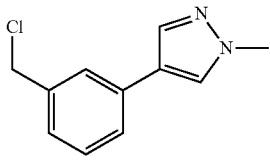

In analogy to the procedure described for the synthesis of example B.1, the title compound was prepared from 3-bromophenyl-methanol. MS (m/e): 207.4 (M+H)$^+$.

Example B.4

1-(4-Chloromethyl-phenyl)-4-methyl-1H-imidazole

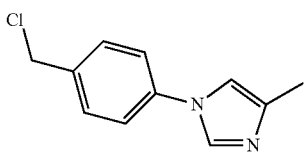

In analogy to the procedure described for the synthesis of example B.1 (step 2), the title compound was prepared from (4-(4-methyl-1H-imidazol-1-yl)phenyl)methanol. MS (m/e): 207.3 (M+H)$^+$.

Example B.5

4-(4-(Chloromethyl)phenyl)-1-methyl-1H-pyrazole

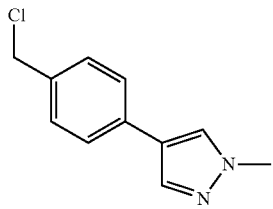

In analogy to the procedure described for the synthesis of example B.1, the title compound was prepared from 4-bromophenyl-methanol. MS (m/e): 207.4 (M+H)$^+$.

Example B.6

4-(Chloromethyl)-N-methylbenzamide

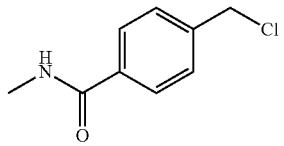

To a stirred, cooled solution of 4-(chloromethyl)benzoyl chloride (1.6 g, 8.49 mmol) at 0° C. in dichloromethane (15 ml) under an argon atmosphere were added methylamine hydrochloride (521 mg, 7.72 mmol). A solution of triethylamine (3.12 g, 4.28 ml, 30.9 mmol) in dichloromethane (15 ml) was added dropwise. Stirring at 0° C. was continued for 44 hrs. The mixture was concentrated and the residue was purified with flash column chromatography on silica eluting with a gradient formed from dichloromethane and methanol (0 to 10%) to provide 10 mg (y: 0.6%) of the title compound as a white solid. MS (m/e): 184.2 (M+H)$^+$.

Example B.7

4-(Chloromethyl)-2-fluoro-N-methylbenzamide

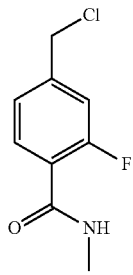

Step 1: 2-Fluoro-4-formyl-N-methylbenzamide

To a stirred suspension of 2-fluoro-4-formylbenzoic acid (1 g, 5.95 mmol) at r.t. in dichloromethane (3 ml) under an argon atmosphere was added dropwise thionyl chloride (849 mg, 521 μl, 7.14 mmol). DMF (0.25 ml) was then added dropwise. The mixture was then refluxed for 2 hours. The mixture was cooled to room temperature and it was added dropwise to stirred, cooled (0° C.) methylamine 40% solution in water (1.66 g, 1.85 ml, 21.4 mmol) for 15 min. When the addition was complete, stirring at 0° C. was continued for 1 hour. The mixture was concentrated and the residue was purified with flash column chromatography on silica eluting with a gradient formed from dichloromethane and methanol (0 to 10%) to provide the title compound as an off-white solid (330 mg, 36%). MS (m/e): 182.1 (M+H)$^+$.

Step 2:
2-Fluoro-4-(hydroxymethyl)-N-methylbenzamide

To a stirred, cooled (0° C.) solution of 2-fluoro-4-formyl-N-methylbenzamide (320 mg, 1.77 mmol) in dichloromethane (8 ml) and methanol (2 ml) under an argon atmosphere was added portionwise sodium borohydride (134 mg, 3.53 mmol). The cooling bath was removed and stirring at room temperature was continued for 6 hours. The mixture was concentrated and the residue was purified with flash column chromatography on silica eluting with a gradient formed from dichloromethane and methanol (0 to 10%) to provide the title compound as an off-white solid (288 mg, 89%). MS (m/e): 184.1 (M+H)$^+$.

Step 3:
4-(Chloromethyl)-2-fluoro-N-methylbenzamide

To a stirred, cooled (0° C.) suspension of 2-fluoro-4-(hydroxymethyl)-N-methylbenzamide (275 mg, 1.5 mmol) in dichloromethane (10 ml) under an argon atmosphere was added dropwise a solution of thionyl chloride (357 mg, 219 µl, 3.00 mmol) in dichloromethane (2 ml). The cooling bath was removed and stirring at room temperature was continued for 6 hours.

The mixture was concentrated and the residue was purified with flash column chromatography on silica eluting with a gradient formed from dichloromethane and methanol (0 to 10%) to provide the title compound as a white solid (255 mg, 84%). MS (m/e): (M+H)$^+$.

Example B.8

5-(4-Bromomethyl-phenyl)-oxazole

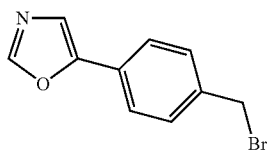 [SMILES: BrCc1ccc(-c2cnco2)cc1]

To a stirred solution of 5-(4-methylphenyl)-1,3-oxazole (2 g) at room temperature in tetrachloromethane (60 ml) were added NBS (2.9 g) and dibenzoylperoxide (150 mg). The mixture was stirred at 77° C. under a 150 watt lamp for 6 hours and then cooled to room temperature. The insoluble material was filtered off. The filtrate was washed with water and aqueous NaHCO$_3$ solution, dried (MgSO$_4$), filtered and concentrated. The residue was purified with flash column chromatography on silica eluting with 50% heptane in diisopropylether to provide the title compound (1.35 g, 45%). MS (m/e): 237 (M).

Example B.9

2-(4-(Chloromethyl)phenyl)thiazole

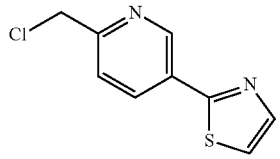 [SMILES: ClCc1ccc(-c2nccs2)cn1]

To a solution at 0° of (5-(thiazol-2-yl)pyridin-2-yl)methanol (65 mg, 338 µmol) in dichloromethane (5 ml) was added under an argon atmosphere sulfurous dichloride (80.5 mg, 49.1 µl, 676 µmol). The mixture was stirred at r.t for 3 h. The solvent was evaporated. The residue was purified with flash column chromatography on silica eluting with a gradient formed from dichloromethane and methanol (0 to 5%) to provide the title compound (40 mg, 56%) as light yellow solid. MS (m/e): 211.1 (M+H)$^+$.

Example B.10

(1-(Pyrimidin-4-yl)piperidin-4-yl)methyl methanesulfonate

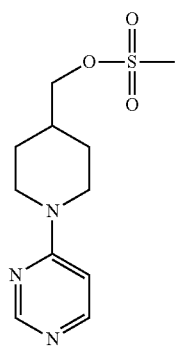 [SMILES: CS(=O)(=O)OCC1CCN(c2ccncn2)CC1]

Step 1: Ethyl 1-(pyrimidin-4-yl)piperidine-4-carboxylate

A mixture of 4-bromopyrimidine hydrochloride (200 mg, 1.02 mmol), cesium carbonate (333 mg, 1.02 mmol) and ethyl piperidine-4-carboxylate (161 mg, 158 µl, 1.02 mmol) in 1,4-dioxane (5 ml) under an argon atmosphere was stirred at 100° for 17 hours. The reaction mixture was cooled to room temperature and concentrated. The residue was purified with flash column chromatography on silica eluting with a gradient formed from dichloromethane and methanol (0 to 5%) to provide the title compound as a light yellow viscous oil (153 mg, 63%). MS (m/e): 236.3 (M+H)$^+$.

Step 2: (1-(Pyrimidin-4-yl)piperidin-4-yl)methanol

To a solution of ethyl 1-(pyrimidin-4-yl)piperidine-4-carboxylate (150 mg, 638 µmol) in methanol (5 ml) and dichloromethane (5 ml) at 0° C. under argon was added sodium borohydride (145 mg, 3.83 mmol) in one portion. The cooling bath was removed and the mixture was stirred at room temperature for 4 hours. The mixture was cooled again to 0° C. and sodium borohydride (145 mg, 3.83 mmol) was added in one portion. The mixture was stirred at room temperature for 17 hr and concentrated. The residue was purified with flash column chromatography on silica eluting with a gradient formed from dichloromethane and methanol (0 to 5%) to provide the title compound as a white solid (80 mg, 65%). MS (m/e): 194.2 (M+H)⁻.

Step 3: (1-(Pyrimidin-4-yl)piperidin-4-yl)methyl methanesulfonate

To a stirred solution of (1-(pyrimidin-4-yl)piperidin-4-yl) methanol (80 mg, 414 μmol) and triethylamine (83.8 mg, 115 μl, 828 μmol) in dichloromethane (2 ml) at 0° C. under argon was added dropwise a solution of methanesulfonyl chloride (94.8 mg, 64.3 μl, 828 μmol) in dichloromethane (2 ml). The reaction mixture was stirred at room temperature for 3 hours. Sodium bicarbonate (34.8 mg, 414 μmol) was added and the mixture was stirred for 5 min and filtered. The filtrate was concentrated and the residue was purified with flash column chromatography on silica eluting with a gradient formed from dichloromethane and methanol (0 to 5%) to provide the title compound as a yellow viscous oil (34.5 mg, 31%). MS (m/e): 272.2 (M+H)⁺.

Example B.11

5-(Chloromethyl)-N-methylpicolinamide

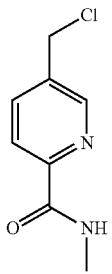

In analogy to the procedures described for the synthesis of example B.10, step 2 and example B.9, the title compound was prepared from methyl 6-(methylcarbamoyl)nicotinate (CAS 173371-36-3). Off-white solid. MS (m/e): 185.1 (M+H)⁺.

Example B.12

5-(4-(Chloromethyl)phenyl)-1-(4-methoxybenzyl)-1H-pyrazole

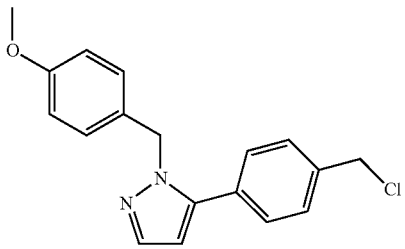 [SMILES: COc1ccc(Cn2nccc2-c2ccc(CCl)cc2)cc1]

Step 1: 5-Iodo-1-(4-methoxybenzyl)-1H-pyrazole

To a solution of 5-iodo-1H-pyrazole (0.2 g, 1.03 mmol) in dimethyl acetamide (3 ml) at 0° C. under argon was added sodium hydride 60% dispersion in mineral oil (41.2 mg, 1.03 mmol) in one portion. After stirring at 0° C. for 15 min, 1-(bromomethyl)-4-methoxybenzene (207 mg, 1.03 mmol) was added in one portion. The cooling bath was removed and the mixture was stirred at room temperature for 17 hours. The mixture was diluted with ethyl acetate, and washed with water. The aqueous phase was back extracted with ethyl acetate. The combined organics were washed with water, dried over MgSO₄, filtered and evaporated. The residue was purified with flash column chromatography on silica eluting with a gradient formed from heptane and ethyl acetate (0 to 50%) to provide the title compound as a colorless viscous oil (270 mg, 83%). MS (m/e): 315.1 (M+H)⁺.

Step 2: (4-(1-(4-Methoxybenzyl)-1H-pyrazol-5-yl) phenyl)methanol

A mixture of 5-iodo-1-(4-methoxybenzyl)-1H-pyrazole (0.27 g, 860 μmol) and 4-(hydroxymethyl)phenylboronic acid (170 mg, 1.12 mmol) at room temperature in 1,2-dimethoxyethane (6 ml) and 2M aqueous Na₂CO₃ solution (1.43 ml, 2.86 mmol) was purged with argon in an ultrasonic bath for 5 min. Then triphenylphosphine (45.1 mg, 172 μmol) and palladium(II) acetate (19.3 mg, 86.0 μmol) were added and the mixture was stirred at 85° C. under argon for 17 hr. The mixture was cooled to room temperature, poured onto water and extracted with ethyl acetate. The organic layer was washed with water, dried with MgSO₄, filtered and evaporated. The residue was purified with flash column chromatography on silica eluting with a gradient formed from heptane and ethyl acetate (0 to 50%) to provide the title compound as a colorless viscous oil (160 mg, 63%). MS (m/e): 295.2 (M+H)⁺.

Step 3: 5-(4-(Chloromethyl)phenyl)-1-(4-methoxybenzyl)-1H-pyrazole

In analogy to the procedures described for the synthesis of example B.9, the title compound was prepared from (4-(1-(4-methoxybenzyl)-1H-pyrazol-5-yl)phenyl)methanol. Off-white solid. MS (m/e): 313.2 (M+H)⁺.

Example B.13

3-(4-(Chloromethyl)phenyl)-1-(4-methoxybenzyl)-1H-1,2,4-triazole

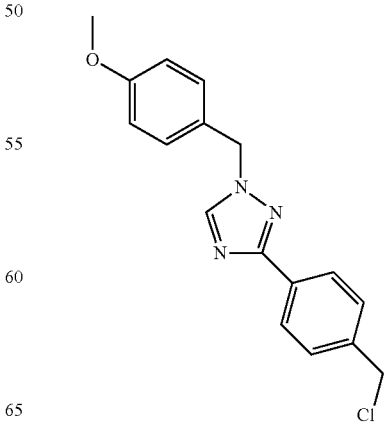

In analogy to the procedures described for the synthesis of example B.13, the title compound was prepared from 5-bromo-1H-1,2,4-triazole. White solid. MS (m/e): 314.2 (M+H)+.

Example C.1

(3R,4S)-4-Aminotetrahydropyran-3-ol hydrochloride

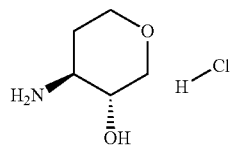

Step 1: Methanesulfonic acid tetrahydro-pyran-4-yl ester

To a solution of tetrahydro-2H-pyran-4-ol (25 g, 245 mmol) and triethyl amine (40.1 ml, 294 mmol) in CH$_2$Cl$_2$ (500 ml) at 0° C. was added dropwise methanesulfonylchloride (20.7 ml, 269 mmol) over a period of 40 min, keeping the temperature between 0°-4° C. The reaction mixture was then allowed to stir at 0° C. for 1 hr. The cooling bath was removed and the mixture was stirred for another 90 mins at 25° C. The mixture was washed with water (2×125 ml), dried over anhydrous Na$_2$SO$_4$, filtered and concentrated under vacuum to get methanesulfonic acid tetrahydro-pyran-4-yl ester (38 g, 86%; crude) as a liquid that was used in the next step without any further purification.

Step 2: 3, 6-Dihydro-2H-pyran

A mixture of tetrahydro-2H-pyran-4-yl methanesulfonate (20 g, 111 mmol) and DBU (18.8 ml, 125.6 mmol) was distilled under normal atmospheric pressure. The fraction at 90°-96° C. was 6-dihydro-2H-pyran (6 g, 64%) as a colourless liquid.

Step 3: (1SR, 6RS)-3,7-Dioxa-bicyclo[4.1.0]heptane

To a solution of 3,6-dihydro-2H-pyran (6 g, 71.4 mmol) in CH$_2$Cl$_2$ (300 ml) was added 3-chloroperbenzoic acid (25 g, 107.1 mmol) portionwise at 25° C., and stirred at that temperature for 21 hrs. The resultant white suspension was diluted with water (250 ml) and then with aqueous solution of Na$_2$SO$_3$. The mixture was stirred at 25° C. for 10 min, then basified by addition of saturated aqueous solution of NaHCO$_3$. The organic layer was separated, and the aqueous layer was re-extracted with CH$_2$Cl$_2$. The combined organic layers were washed with saturated aqueous solution of NaHCO$_3$ (100 ml), and brine (80 ml), dried over anhydrous Na$_2$SO$_4$, filtered and concentrated in vacuo to afford the title compound (5 g, 70%; crude) as a yellow liquid.

Step 4: (3SR,4RS)-4-Azidotetrahydropyran-3-ol

To a solution of (1SR,6RS)-3,7-dioxabicyclo[4.1.0]heptane (5 g, 49.9 mmol) in MeOH (50 ml) were added sodium azide (24.3 g, 374.6 mmol), ammonium chloride (20 g, 374.6 mmol) and water (5 ml), and the resultant mixture was stirred at 25° C. for 19 hrs, and then at 70° C. for 2 hrs. The mixture was cooled 0° C., and the precipitated solid was filtered and washed with methanol. The filtrate was concentrated in vacuo. Resultant residue was taken in ethyl acetate, and filtered. Removal of the filtrate in vacuo yielded the title compound (5 g, 70%; crude) as a yellow liquid.

Step 5: (3SR,4RS)-4-Aminotetrahydropyran-3-ol

To a solution of (3SR,4RS)-4-azidotetrahydropyran-3-ol (5 g, 35 mmol) in ethyl acetate (50 ml), was added Pd(OH)$_2$ on charcoal (1.25 g, 1.4 mmol). The mixture was purged with argon, and then allowed to stir under a balloon pressure of hydrogen for 21 hrs at 25° C. Removal of the catalyst by filtration followed by evaporation of the filtrate in vacuo afforded the title compound (4 g, crude).

Step 6: (3S,4R)-3-Hydroxy-tetrahydro-pyran-4-yl)-carbamic acid benzyl ester and ((3R,4S)-3-hydroxy-tetrahydro-pyran-4-yl)-carbamic acid benzyl ester To a solution of (3SR,4RS)-4-aminotetrahydropyran-3-ol (10 g, 85.4 mmol) and Et$_3$N (23.6 ml, 170.9 mmol) in CH$_2$Cl$_2$ (100 ml) was added benzyl chloroformate (9.8 ml, 59.9 mmol) dropwise at 0° C. After completion of addition, the mixture was stirred at 25° C. for 2 hrs. The mixture was washed with water (60 ml). The aqueous layer was re-extracted with CH$_2$Cl$_2$. The combined organic layers were dried over anhydrous Na$_2$SO$_4$, filtered and concentrated in vacuo to get the mixture the two regioisomeric pairs of enantiomers (16 g). This crude product was purified by silica gel chromatography using 45% EtOAc in hexane as eluent to get the pair of enantiomers with the desired regioisomery as white solid (4.5 g, 21%). This enantiomeric mixture was subject to chiral separation by SFC to afford (3S,4R)-3-hydroxy-tetrahydro-pyran-4-yl)-carbamic acid benzyl ester (1.7 g, 8%) and ((3R,4S)-3-hydroxy-tetrahydro-pyran-4-yl)-carbamic acid benzyl ester (1.7 g, 8%) both as a white solid.

Step 7: (3R,4S)-4-Amino-tetrahydro-pyran-3-ol hydrochloride

To a solution of ((3R,4S)-3-hydroxy-tetrahydro-pyran-4-yl)-carbamic acid benzyl ester (1.1 g, 4.4 mmol) in MeOH (50 ml) was added 10% palladium on charcoal (140 mg, 0.13 mmol), and stirred the reaction mixture under hydrogen atmosphere for 1 hr. The catalyst was filtered off. The filtrate was acidified with 1.25 M HCl in MeOH and concentrated in vacuo to get (3R,4S)-4-amino-tetrahydro-pyran-3-ol hydrochloride as an off white solid (500 mg, 97%).

DESCRIPTION OF EXAMPLES

Example 1

4-Fluoro-1-(2-fluoro-4-(1-methyl-1H-pyrazol-4-yl)benzyl)-N-((1S,2S)-2-hydroxycyclohexyl)-1H-indole-3-carboxamide

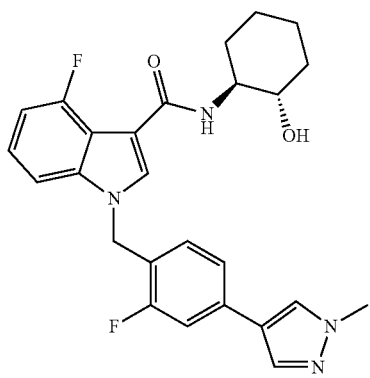 [SMILES: Cn1cc(-c2ccc(Cn3cc(C(=O)N[C@H]4CCCC[C@@H]4O)c4c(F)cccc43)c(F)c2)cn1]

To a suspension of 4-fluoro-1-(2-fluoro-4-(1-m ethyl-1H-pyrazol-4-yl)benzyl)-1H-indole-3-carboxylic acid (example A.1) (30 mg, 81.7 μmol) in N,N-dimethylformamide (1 ml) was added triethylamine (41.3 mg, 56.8 μl, 408 μmol). The mixture was stirred at room temperature for 15 minutes. (Benzotriazol-1-yloxy)tris(dimethylamino)phosphonium hexafluorophosphate (BOP) (47.0 mg, 106 μmol) was added. The suspension was stirred at room temperature for 1 hour. (1S,2S)-2-Aminocyclohexanol hydrochloride (12.4 mg, 81.7 μmol) was added. The mixture was stirred at room temperature for 16 hours. The solvent was removed in vacuo. The residue was taken in water. The aqueous layer was extracted with ethyl acetate. The combined extracts were dried over sodium sulfate, filtered and concentrated in vacuo. The crude oil was purified with flash column chromatography on silica eluting with a gradient formed from heptane and ethyl acetate (0 to 100%) to provide 10 mg (25%) of the title compound as a light yellow solid. MS (m/e): 465.5 (M+H)$^+$.

In analogy to example 1, examples 2 to 16 of the following table were prepared by coupling an acid derivative with an amine.

| Example No. | Structure | Systematic Name | Starting materials | MW found (MH$^+$) |
|---|---|---|---|---|
| 2 | 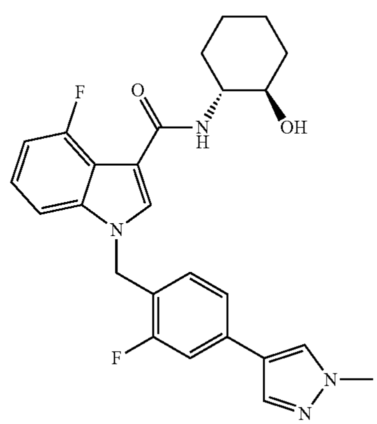 [SMILES: Cn1cc(-c2ccc(Cn3cc(C(=O)N[C@@H]4CCCC[C@H]4O)c4c(F)cccc43)c(F)c2)cn1] | 4-fluoro-1-(2-fluoro-4-(1-methyl-1H-pyrazol-4-yl)benzyl)-N-((1R,2R)-2-hydroxycyclohexyl)-1H-indazole-3-carboxamide | 4-fluoro-1-(2-fluoro-4-(1-methyl-1H-pyrazol-4-yl)benzyl)-1H-indole-3-carboxylic acid (example A.1) and aminocyclohexanol hydrochloride | 465.5 |
| 3 | 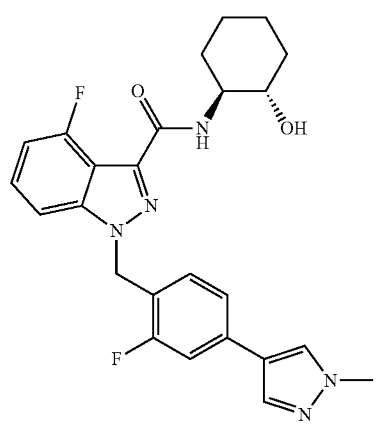 [SMILES: Cn1cc(-c2ccc(Cn3nc(C(=O)N[C@H]4CCCC[C@@H]4O)c4c(F)cccc43)c(F)c2)cn1] | 4-fluoro-1-(2-fluoro-4-(1-methyl-1H-pyrazol-4-yl)benzyl)-N-((1S,2S)-2-hydroxycyclohexyl)-1H-indazole-3-carboxamide | 4-fluoro-1-(2-fluoro-4-(1-methyl-1H-pyrazol-4-yl)benzyl)-1H-indazole-3-carboxylic acid (example A.2) and (1S,2S)-2-aminocyclohexanol hydrochloride | 466.5 |

| Example No. | Structure | Systematic Name | Starting materials | MW found (MH+) |
|---|---|---|---|---|
| 4 | 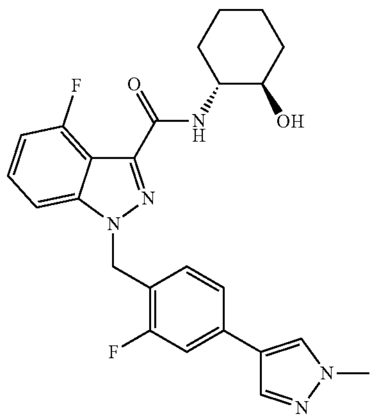 [SMILES: Cn1cc(-c2ccc(Cn3nc(C(=O)N[C@@H]4CCCC[C@H]4O)c4c(F)cccc43)c(F)c2)cn1] | 4-fluoro-1-(2-fluoro-4-(1-methyl-1H-pyrazol-4-yl)benzyl)-N-((1R,2R)-2-hydroxycyclohexyl)-1H-indazole-3-carboxamide | 4-fluoro-1-(2-fluoro-4-(1-methyl-1H-pyrazol-4-yl)benzyl)-1H-indazole-3-carboxylic acid (example A.2) and (1R,2R)-2-aminocyclohexanol hydrochloride | 466.5 |
| 5 | 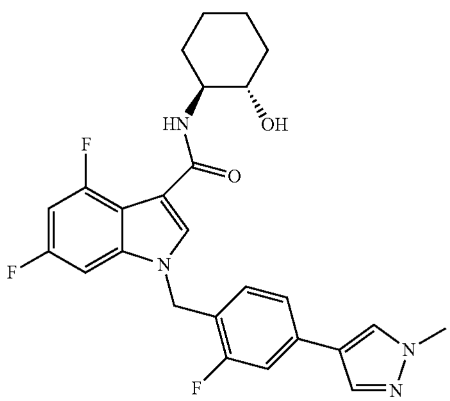 [SMILES: Cn1cc(-c2ccc(Cn3cc(C(=O)N[C@H]4CCCC[C@@H]4O)c4c(F)cc(F)cc43)c(F)c2)cn1] | 4,6-difluoro-1-(2-fluoro-4-(1-methyl-1H-pyrazol-4-yl)benzyl)-N-((1S,2S)-2-hydroxycyclohexyl)-1H-indole-3-carboxamide | 4,6-difluoro-1-(2-fluoro-4-(1-methyl-1H-pyrazol-4-yl)benzyl)-1H-indole-3-carboxylic acid (example A.3) and (1S,2S)-2-aminocyclohexanol hydrochloride | 483.6 |
| 6 | 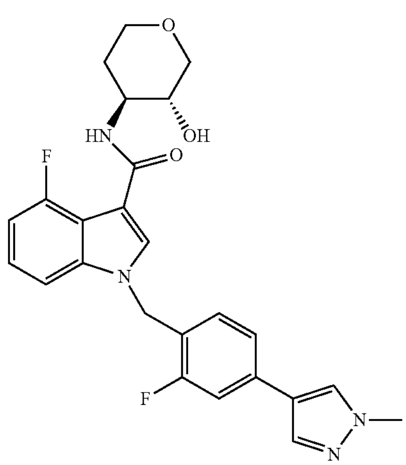 [SMILES: Cn1cc(-c2ccc(Cn3cc(C(=O)N[C@H]4CCOC[C@@H]4O)c4c(F)cccc43)c(F)c2)cn1] | 4-fluoro-1-(2-fluoro-4-(1-methyl-1H-pyrazol-4-yl)benzyl)-N-((3R,4RS)-3-hydroxytetrahydro-2H-pyran-4-yl)-1H-indole-3-carboxamide | 4-fluoro-1-(2-fluoro-4-(1-methyl-1H-pyrazol-4-yl)benzyl)-1H-indole-3-carboxylic acid (example A.1) and (3RS,4SR)-4-aminotetrahydro-2H-pyan-3-ol (CAS: 215940-92-4) | 467.5 |

| Example No. | Structure | Systematic Name | Starting materials | MW found (MH⁺) |
|---|---|---|---|---|
| 7 | 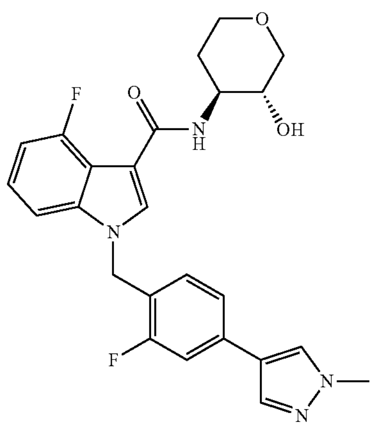 [SMILES: Cn1cc(-c2ccc(Cn3cc(C(=O)N[C@H]4CCOC[C@@H]4O)c4c(F)cccc43)c(F)c2)cn1] | 4-fluoro-1-(2-fluoro-4-(1-methyl-1H-pyrazol-4-yl)benzyl)-N-((3RS,4SR)-3-hydroxytetrahydro-2H-pyran-4-yl)-1H-indazole-3-carboxamide | 4-fluoro-1-(2-fluoro-4-(1-methyl-1H-pyrazol-4-yl)benzyl)-1H-indazole-3-carboxylic acid (example A.2) and (3RS,4SR)-4-aminotetrahydro-2H-pyran-3-ol (CAS: 215940-92-4) | 468.5 |
| 8 | 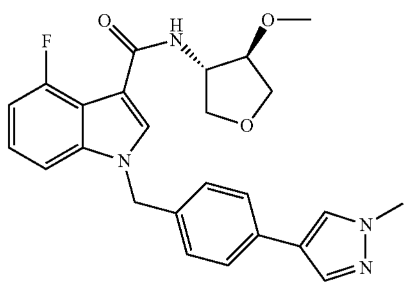 [SMILES: CO[C@H]1COC[C@@H]1NC(=O)c1cn(Cc2ccc(-c3cnn(C)c3)cc2)c2cccc(F)c12] | 4-fluoro-N-[(3S,4R)-4-methoxyoxolan-3-yl]-1-[[4-(1-methylpyrazol-4-yl)phenyl]methyl]indole-3-carboxamide | 4-fluoro-1-(4-(1-methyl-1H-pyrazol-4-yl)benzyl)-1H-indole-3-carboxylic acid (example A.9) and (3S,4R)-4-methoxy-tetrahydro-furan-3-ylamine | 419.5 |
| 9 | 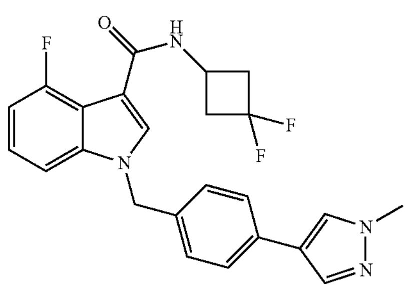 [SMILES: Cn1cc(-c2ccc(Cn3cc(C(=O)NC4CC(F)(F)C4)c4c(F)cccc43)cc2)cn1] | N-(3,3-difluorocyclobutyl)-4-fluoro-1-(4-(1-methyl-1H-pyrazol-4-yl)benzyl)-1H-indole-3-carboxamide | 4-fluoro-1-(4-(1-methyl-1H-pyrazol-4-yl)benzyl)-1H-indole-3-carboxylic acid (example A.9) and 3,3-difluoro-cyclobutylamine | 439.6 |
| 10 | 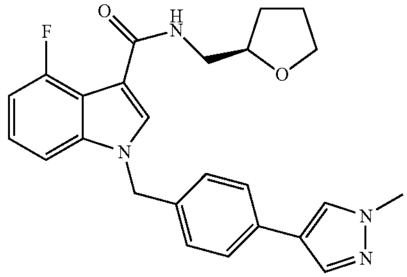 [SMILES: Cn1cc(-c2ccc(Cn3cc(C(=O)NC[C@H]4CCCO4)c4c(F)cccc43)cc2)cn1] | (R)-4-fluoro-1-(4-(1-methyl-1H-pyrazol-4-yl)benzyl)-N-((tetrahydrofuran-2-yl)methyl)-1H-indole-3-carboxamide | (R) 4-fluoro-1-(4-(1-methyl-1H-pyrazol-4-yl)benzyl)-1H-indole-3-carboxylic acid (example A.9) and [1-(tetrahydrofuran-2-yl)]-methylamine | 433.7 |

-continued

| Example No. | Structure | Systematic Name | Starting materials | MW found (MH+) |
|---|---|---|---|---|
| 11 | 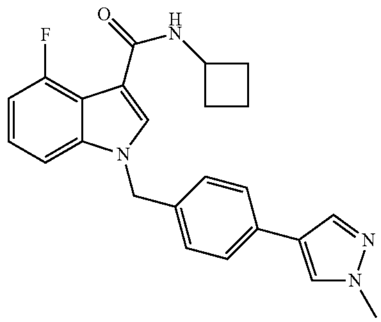 [SMILES: Cn1cc(-c2ccc(Cn3cc(C(=O)NC4CCC4)c4c(F)cccc43)cc2)cn1] | N-cyclobutyl-4-fluoro-1-(4-(1-methyl-1H-pyrazol-4-yl)benzyl)-1H-indole-3-carboxamide | 4-fluoro-1-(4-(1-methyl-1H-pyrazol-4-yl)benzyl)-1H-indole-3-carboxamide acid (example A.9) and cyclobutylamine | 403.6 |
| 12 | 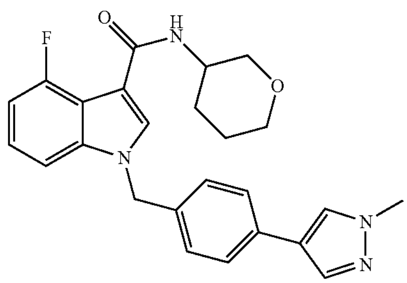 [SMILES: Cn1cc(-c2ccc(Cn3cc(C(=O)NC4CCCOC4)c4c(F)cccc43)cc2)cn1] | 4-fluoro-1-(4-(1-methyl-1H-pyrazol-4-yl)benzyl)-N-(tetrahydro-2H-pyran-3-yl)-1H-indole-3-carboxamide | 4-fluoro-1-(4-(1-methyl-1H-pyrazol-4-yl)benzyl)-1H-indole-3-carboxamide acid (example A.9) and tetrahydro-pyran-3-ylamine | 433.7 |
| 13 | 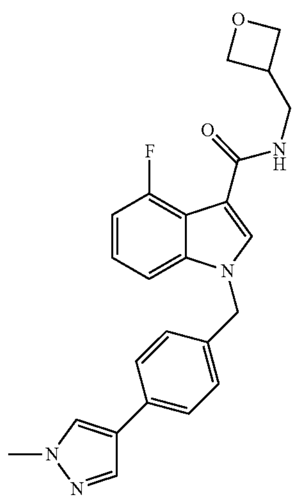 [SMILES: Cn1cc(-c2ccc(Cn3cc(C(=O)NCC4COC4)c4c(F)cccc43)cc2)cn1] | 4-fluoro-1-(4-(1-methyl-1H-pyrazol-4-yl)benzyl)-N-(oxetan-3-ylmethyl)-1H-indole-3-carboxamide | 4-fluoro-1-(4-(1-methyl-1H-pyrazol-4-yl)benzyl)-1H-indole-3-carboxylic acid (example A.9) and oxetan-3-yl-methylamine | 419.6 |
| 14 | 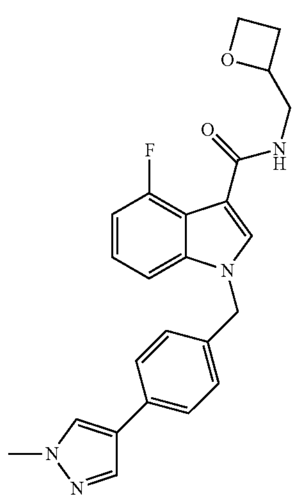 [SMILES: Cn1cc(-c2ccc(Cn3cc(C(=O)NCC4CCO4)c4c(F)cccc43)cc2)cn1] | 4-fluoro-1-(4-(1-methyl-1H-pyrazol-4-yl)benzyl)-N-(oxetan-2-ylmethyl)-1H-indole-3-carboxamide | 4-fluoro-1-(4-(1-methyl-1H-pyrazol-4-yl)benzyl)-1H-indole-3-carboxylic acid (example A.9) and oxetan-2-yl-methyalmine | 419.6 |

| Example No. | Structure | Systematic Name | Starting materials | MW found (MH+) |
|---|---|---|---|---|
| 15 | rac | 1-(4-carbamoylbenzyl)-4-fluoro-N-((3RS,4SR)-3-hydroxytetrahydro-2H-pyran-4-yl)-1H-indole-3-carboxamide | 1-(4-carbamoyl-benzyl)-4-fluoro-1H-indole-3-carboxylic acid (example A.35) and (3RS,4SR)-4-aminotetrahydro-2H-pyran-3-ol (CAS: 215940-92-4) | 412.5 |
| 16 | rac | 1-(4-cyanobenzyl)-4-fluoro-N-((3RS,4SR)-3-hydroxytetrahydro-2H-pyran-4-yl)-1H-indole-3-carboxamide | 1-(4-cyanobenzyl)-4-fluoro-1H-indole-3-carboxylic acid (example A.36) and (3RS,4SR)-4-aminotetrahydro-2H-pyran-3-ol (CAS: 215940-92-4) | 394.6 |

Example 17

4-Fluoro-1-(2-fluoro-4-(1-methyl-1H-pyrazol-4-yl)benzyl)-N-((1S,2S)-2-hydroxycyclopentyl)-1H-indole-3-carboxamide

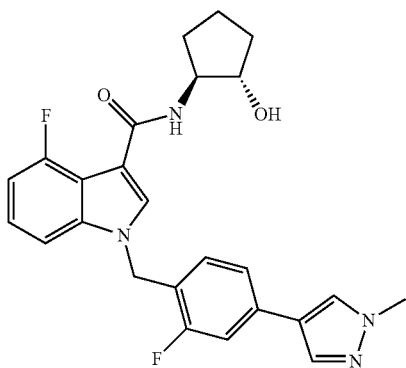 [SMILES: Cn1cc(-c2ccc(Cn3cc(C(=O)N[C@H]4CCC[C@@H]4O)c4c(F)cccc43)c(F)c2)cn1]

To a solution of 4-fluoro-1-(2-fluoro-4-(1-methyl-1H-pyrazol-4-yl)benzyl)-1H-indole-3-carbonyl chloride (example A.5) (30 mg, 77.8 μmol) and triethylamine (31.5 mg, 43.3 μl, 311 μmol) in dichloromethane (1.2 ml) was added (1S,2S)-2-aminocyclopentanol hydrochloride (12.3 mg, 85.5 μmol). The mixture was stirred at room temperature overnight. The solvent was removed in vacuo. Water was added. The resulting precipitate was filtrated, washed with diethyl ether and dried to provide 26 mg (74%) of the title compound as an off-white solid. MS (m/e): 451.4 (M+H)+.

In analogy to Example 17, compounds 18 to 25 of the following table were prepared from 4-fluoro-1-(2-fluoro-4-(1-methyl-1H-pyrazol-4-yl)benzyl)-1H-indole-3-carbonyl-chloride (example A.5) and an amine derivative:

| Expl. No. | Structure | Systematic Name | Starting materials | MW found (MH+) |
|---|---|---|---|---|
| 18 | rac | 4-fluoro-1-(2-fluoro-4-(1-methyl-1H-pyrazol-4-yl)benzyl)-N-((1SR,2SR)-2-hydroxy-2-methylcyclohexyl)-1H-indole-3-carboxamide | 4-fluoro-1-(2-fluoro-4-(1-methyl-1H-pyrazol-4-yl)benzyl)-1H-indole-3-carbonyl chloride (example A.5) and (1SR,2SR)-2-amino-1-methylcyclohexanol hydrochloride | 479.5 |
| 19 | 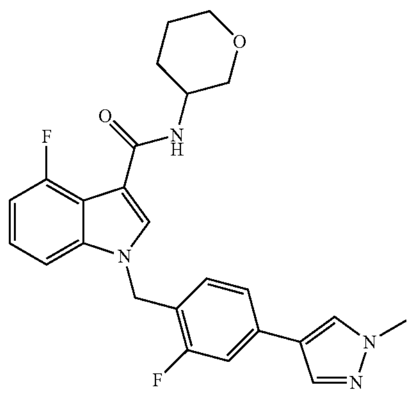 [SMILES: Cn1cc(-c2ccc(Cn3cc(C(=O)NC4CCCOC4)c4c(F)cccc43)c(F)c2)cn1] | 4-fluoro-1-(2-fluoro-4-(1-methyl-1H-pyrazol-4-yl)benzyl)-N-(tetrahydro-2H-pyran-3-yl)-1H-indole-3-carboxamide | 4-fluoro-1-(2-fluoro-4-(1-methyl-1H-pyrazol-4-yl)benzyl)-1H-indole-3-carbonyl chloride (example A.5) and tetrahydro-2H-pyran-3-amine hydrochloride | 451.4 |
| 20 | 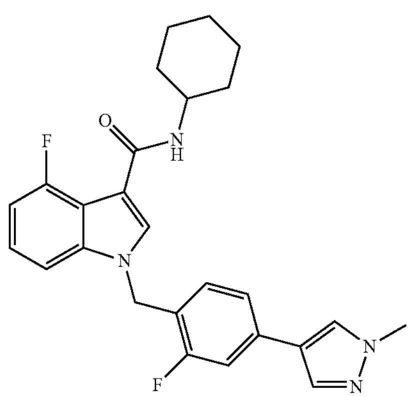 [SMILES: Cn1cc(-c2ccc(Cn3cc(C(=O)NC4CCCCC4)c4c(F)cccc43)c(F)c2)cn1] | N-cyclohexyl-4-fluoro-1-(2-fluoro-4-(1-methyl-1H-pyrazol-4-yl)benzyl)-1H-indole-3-carboxamide | 4-fluoro-1-(2-fluoro-4-(1-methyl-1H-pyrazol-4-yl)benzyl)-1H-indole-3-carbonyl chloride (example A.5) and cyclohexanamine | 449.5 |
| 21 | 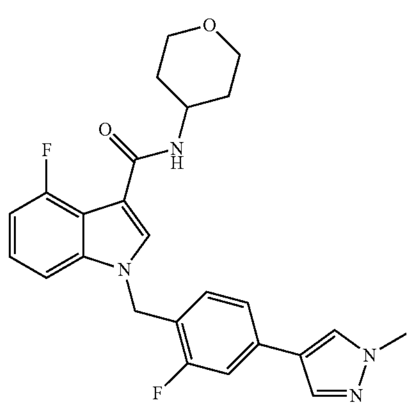 [SMILES: Cn1cc(-c2ccc(Cn3cc(C(=O)NC4CCOCC4)c4c(F)cccc43)c(F)c2)cn1] | 4-fluoro-1-(2-fluoro-4-(1-methyl-1H-pyrazol-4-yl)benzyl)-N-(tetrahydro-2H-pyran-4-yl)-1H-indole-3-carboxamide | 4-fluoro-1-(2-fluoro-4-(1-methyl-1H-pyrazol-4-yl)benzyl)-1H-indole-3-carbonyl chloride (example A.5) and tetrahydro-2H-pyran-4-amine | 451.4 |

-continued

| Expl. No. | Structure | Systematic Name | Starting materials | MW found (MH+) |
|---|---|---|---|---|
| 22 | 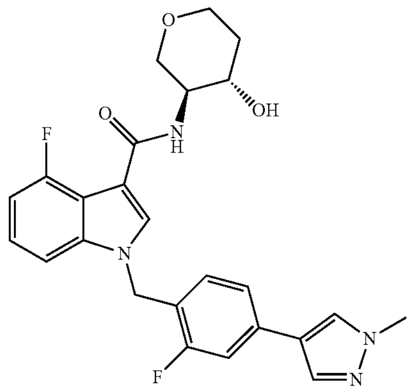 [SMILES: Cn1cc(-c2ccc(Cn3cc(C(=O)N[C@H]4COCC[C@@H]4O)c4c(F)cccc43)c(F)c2)cn1] | 4-fluoro-1-(2-fluoro-4-(1-methyl-1H-pyrazol-4-yl)benzyl)-N-((3S,4S)-4-hydroxytetrahydro-2H-pyran-3-yl)-1H-indole-3-carboxamide | 4-fluoro-1-(2-fluoro-4-(1-methyl-1H-pyrazol-4-yl)benzyl)-1H-indole-3-carbonyl chloride (example A.5) and (3S,4S)-3-aminotetrahydro-2H-pyran-4-ol | 467.5 |
| 23 | 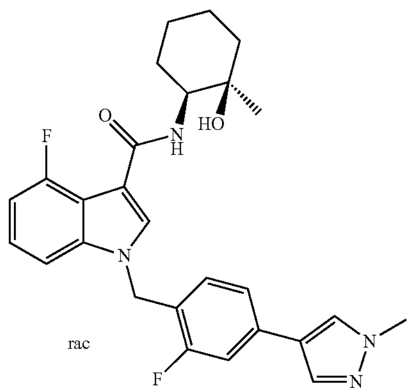 [SMILES: Cn1cc(-c2ccc(Cn3cc(C(=O)N[C@H]4CCCC[C@@]4(C)O)c4c(F)cccc43)c(F)c2)cn1] | 4-fluoro-1-(2-fluoro-4-(1-methyl-1H-pyrazol-4-yl)benzyl)-N-((1SR,2RS)-2-hydroxy-2-methylcyclohexyl)-1H-indole-3-carboxamide | 4-fluoro-1-(2-fluoro-4-(1-methyl-1H-pyrazol-4-yl)benzyl)-1H-indole-3-carbonyl chloride (example A.5) and (1RS,2SR)-2-amino-1-methylcyclohexanol hydrochloride | 479.4 |
| 24 | 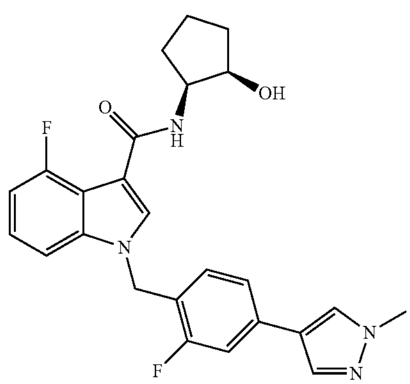 [SMILES: Cn1cc(-c2ccc(Cn3cc(C(=O)N[C@H]4CCC[C@H]4O)c4c(F)cccc43)c(F)c2)cn1] | 4-fluoro-1-(2-fluoro-4-(1-methyl-1H-pyrazol-4-yl)benzyl)-N-((1S,2R)-2-hydroxycyclopentyl)-1H-indole-3-carboxamide | 4-fluoro-1-(2-fluoro-4-(1-methyl-1H-pyrazol-4-yl)benzyl)-1H-indole-3-carbonyl chloride (example A.5) and (1S,2R)-2-aminocyclopentanol hydrochloride | 451.4 |
| 25 | 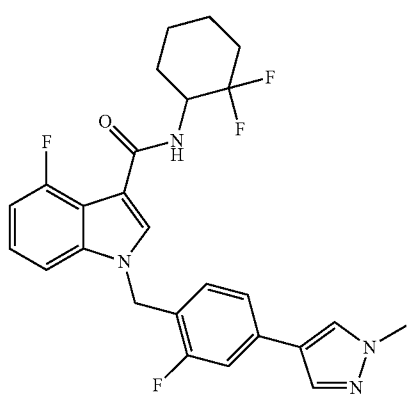 [SMILES: Cn1cc(-c2ccc(Cn3cc(C(=O)NC4CCCCC4(F)F)c4c(F)cccc43)c(F)c2)cn1] | N-(2,2-difluorocyclohexyl)-4-fluoro-1-(2-fluoro-4-(1-methyl-1H-pyrazol-4-yl)benzyl)-1H-indole-3-carboxamide | 4-fluoro-1-(2-fluoro-4-(1-methyl-1H-pyrazol-4-yl)benzyl)-1H-indole-3-carbonyl chloride (example A.5) and 2,2-difluorocyclohexanamine hydrochloride | 485.4 |

Example 26

4,5,6,7-Tetrafluoro-1-(2-fluoro-4-(1-methyl-1H-pyrazol-4-yl)benzyl)-N-((1S,2S)-2-hydroxycyclohexyl)-1H-indole-3-carboxamide Chiral

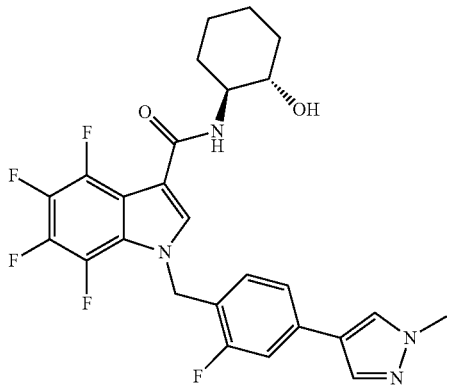

In a microwave tube, 4,5,6,7-tetrafluoro-N-((1S,2S)-2-hydroxycyclohexyl)-1H-indole-3-carboxamide (50 mg, 104 µmol; example A.4), 4-(4-(chloromethyl)-3-fluorophenyl)-1-methyl-1H-pyrazole (34 mg, 151 µmol; example B.2) and cesium carbonate (98.7 mg, 303 µmol) were combined with N,N-dimethylaceamide (633 µl) to give a colorless suspension. The reaction mixture was stirred at r.t. for 2 days, then was taken up in $H_2O$ and extracted with EtOAc. The organic layers were washed $H_2O$ and then with saturated NaCl solution, dried over MgSO4 and concentrated in vacuo. The crude material was purified by silica gel chromatography using a $CH_2Cl_2$/MeOH gradient as eluent to provide the title compound (39 mg, 72%) as colorless solid. MS (m/e): 519.4 $(M+H)^+$ In analogy to Example 26, compounds 27 to 61 of the following table were prepared by reaction of the indicated amides with an alkylating agent.

| Expl. No. | Structure | Systematic Name | Starting materials | MW found (MH+) |
|---|---|---|---|---|
| 27 | 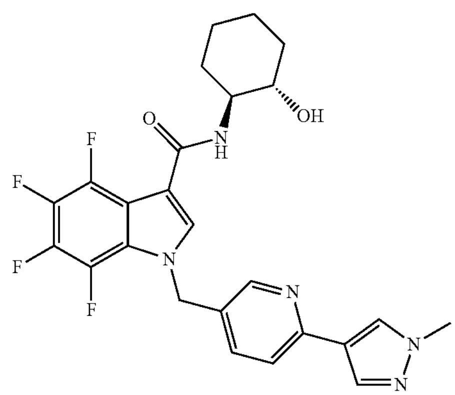 [SMILES: Cn1cc(-c2ccc(Cn3cc(C(=O)N[C@H]4CCCC[C@@H]4O)c4c(F)c(F)c(F)c(F)c43)cn2)cn1] | 4,5,6,7-tetrafluoro-N-((1S,2S)-2-hydroxycyclohexyl)-1-((6-(1-methyl-1H-pyrazol-4-yl)pyridine-3-yl)methyl)-1H-indole-3-carboxamide | 4,5,6,7-tetrafluoro-1H-indole-3-carboxylic acid ((1S,2S)-2-hydroxy-cyclohexyl)-amide (example A.4) and 5-(chloromethyl)-2-(1-methyl-1H-pyrazol-4-yl)pyridine (example B.1) | 502.4 |
| 28 | 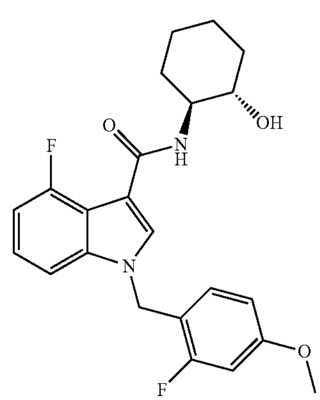 [SMILES: COc1ccc(Cn2cc(C(=O)N[C@H]3CCCC[C@@H]3O)c3c(F)cccc32)c(F)c1] | 4-fluoro-1-(2-fluoro-4-methoxybenzyl)-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 1-(chloromethyl)-2-fluoro-4-methoxybenzene | 415.5 |

-continued

| Expl. No. | Structure | Systematic Name | Starting materials | MW found (MH+) |
|---|---|---|---|---|
| 29 | 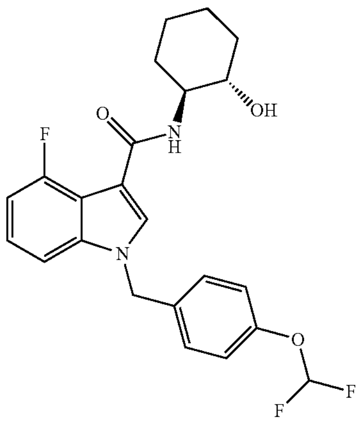 [SMILES: O=C(N[C@H]1CCCC[C@@H]1O)c1cn(Cc2ccc(OC(F)F)cc2)c2cccc(F)c12] | 1-(4-(difluoromethoxy)benzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 1-(bromomethyl)-4-(difluoromethoxy)benzene | 433.4 |
| 30 | 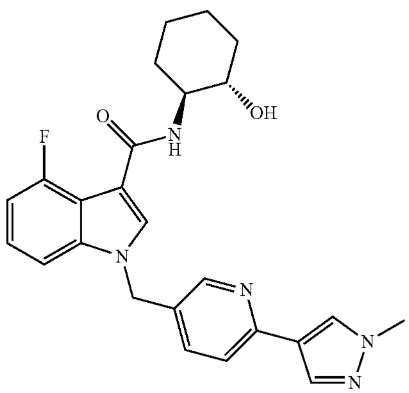 [SMILES: Cn1cc(-c2ccc(Cn3cc(C(=O)N[C@H]4CCCC[C@@H]4O)c4c(F)cccc43)cn2)cn1] | 4-fluoro-N-((1S,2S)-2-hydroxycyclohexyl)-1-((6-(1-methyl-1H-pyrazol-4-yl)pyridine-3-yl)methyl)-1H-indole-3-carboxamide | 4-fluoro-N-((1S,2S)-2-hydroxycyclohexyl)-1H-indole-3-carboxamide (example A.6) and 5-(chloromethyl)-2-(1-methyl-1H-pyrazol-4-yl)pyridine (example B.1) | 448.5 |
| 31 | 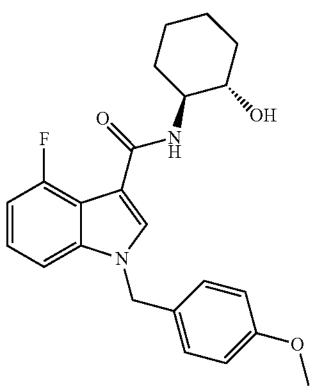 [SMILES: COc1ccc(Cn2cc(C(=O)N[C@H]3CCCC[C@@H]3O)c3c(F)cccc32)cc1] | 4-fluoro-N-((1S,2S)-2-hydroxycyclohexyl)-1-(4-methoxybenzyl)-1H-indole-3-carboxamide | 4-fluoro-N-((1S,2S)-2-hydroxycyclohexyl)-1H-indole-3-carboxamide (example A.6) and 1-(bromomethyl)-4-methoxybenzene | 397.5 |
| 32 | 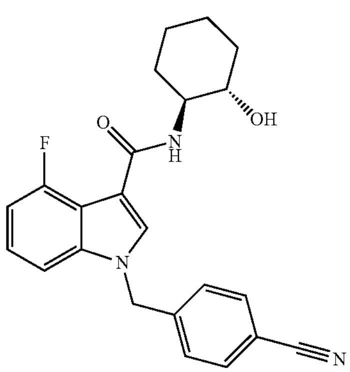 [SMILES: N#Cc1ccc(Cn2cc(C(=O)N[C@H]3CCCC[C@@H]3O)c3c(F)cccc32)cc1] | 1-(4-cyanobenzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 4-(chloromethyl)benzonitrile | 392.5 |

-continued

| Expl. No. | Structure | Systematic Name | Starting materials | MW found (MH+) |
|---|---|---|---|---|
| 33 | 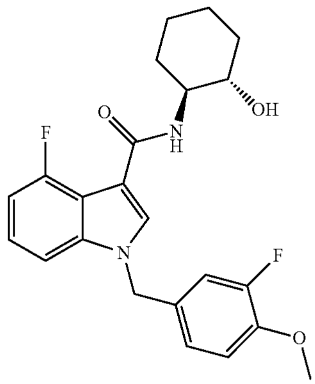 [SMILES: COc1ccc(Cn2cc(C(=O)N[C@H]3CCCC[C@@H]3O)c3c(F)cccc32)cc1F] | 4-fluoro-1-(3-fluoro-4-methoxybenzyl)-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 4-(bromomethyl)-2-fluoro-1-methoxybenzene | 415.5 |
| 43 | 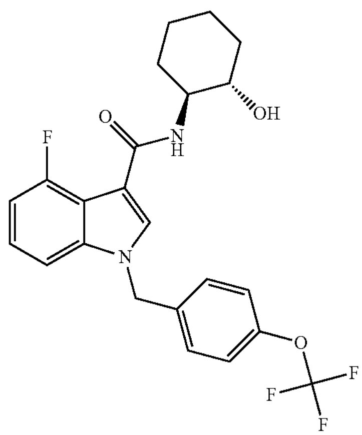 [SMILES: O=C(N[C@H]1CCCC[C@@H]1O)c1cn(Cc2ccc(OC(F)(F)F)cc2)c2cccc(F)c12] | 4-fluoro-N-((1S,2S)-2-hydroxycyclohexyl)-1-(4-(trifluoromethoxy)benzyl)-1H-indole-3-carboxamide | 4-fluoro-N-((1S,2S)-2-hydroxycyclohexyl)-1H-indole-3-carboxamide (example A.6) and 1-(bromomethyl)-4-(trifluoromethoxy)benzene | 451.4 |
| 35 | 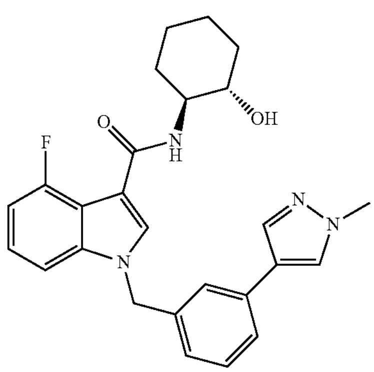 [SMILES: Cn1cc(-c2cccc(Cn3cc(C(=O)N[C@H]4CCCC[C@@H]4O)c4c(F)cccc43)c2)cn1] | 4-fluoro-N-((1S,2S)-2-hydroxycyclohexyl)-1-(3-(1-methyl-1H-pyrazol-4-yl)benzyl)-1H-indole-3-carboxamide | 4-fluoro-N-((1S,2S)-2-hydroxycyclohexyl)-1H-indole-3-carboxamide (example A.6) and 4-(3-(chloromethyl)phenyl)-1-methyl-1H-pyrazole (example B.3) | 447.5 |
| 36 | 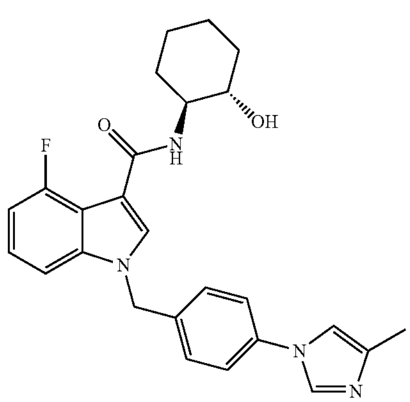 [SMILES: Cc1cn(-c2ccc(Cn3cc(C(=O)N[C@H]4CCCC[C@@H]4O)c4c(F)cccc43)cc2)cn1] | 4-fluoro-N-((1S,2S)-2-hydroxycyclohexyl)-1-(4-(4-methyl-1H-imidazol-1-yl)benzyl)-1H-indole-3-carboxamide | 4-fluoro-N-((1S,2S)-2-hydroxycyclohexyl)-1H-indole-3-carboxamide (example A.6) and 1-(4-chloromethyl-phenyl)-4-methyl-1H-imidazole (example B.4) | 447.5 |

| Expl. No. | Structure | Systematic Name | Starting materials | MW found (MH+) |
|---|---|---|---|---|
| 37 | 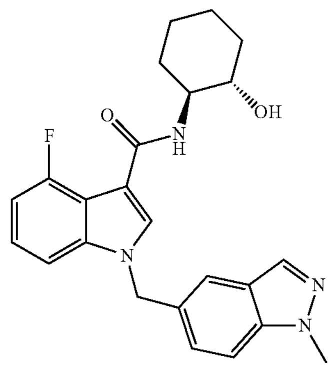 [SMILES: Cn1ncc2cc(Cn3cc(C(=O)N[C@H]4CCCC[C@@H]4O)c4c(F)cccc43)ccc21] | 4-fluoro-N-((1S,2S)-2-hydroxycyclohexyl)-1-((1-methyl-1H-indazol-5-yl)methyl)-1H-indole-3-carboxamide | 4-fluoro-N-((1S,2S)-2-hydroxycyclohexyl)-1H-indole-3-carboxamide (example A.6) and 5-(bromomethyl)-1-methyl-1H-indazole hydrobromide | 421.5 |
| 38 | 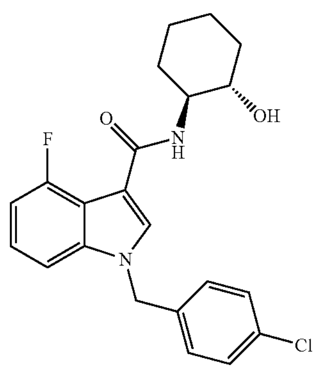 [SMILES: O=C(N[C@H]1CCCC[C@@H]1O)c1cn(Cc2ccc(Cl)cc2)c2cccc(F)c12] | 1-(4-chlorobenzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 1-chloro-4-(chloromethyl)benzene | 401.4 |
| 39 | 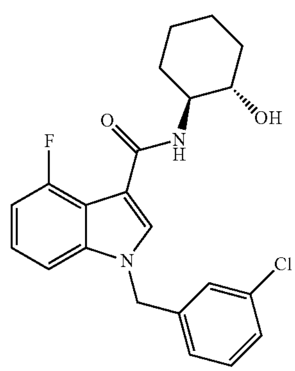 [SMILES: O=C(N[C@H]1CCCC[C@@H]1O)c1cn(Cc2cccc(Cl)c2)c2cccc(F)c12] | 1-(3-chlorobenzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 1-chloro-3-(chloromethyl)benzene | 401.4 |
| 40 | 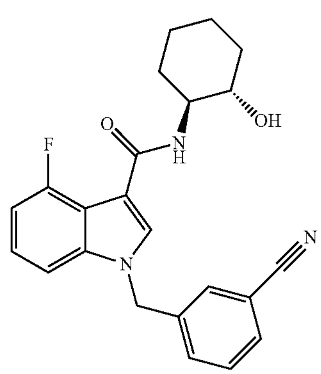 [SMILES: N#Cc1cccc(Cn2cc(C(=O)N[C@H]3CCCC[C@@H]3O)c3c(F)cccc32)c1] | 1-(3-cyanobenzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 3-(bromomethyl)benzonitrile | 392.5 |

-continued

| Expl. No. | Structure | Systematic Name | Starting materials | MW found (MH+) |
|---|---|---|---|---|
| 41 | 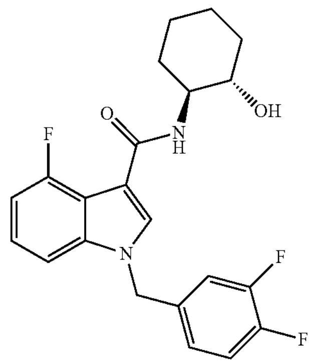 [SMILES: O=C(N[C@H]1CCCC[C@@H]1O)c1cn(Cc2ccc(F)c(F)c2)c2cccc(F)c12] | 1-(3,4-difluorobenzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 4-(chloromethyl)-1,2-difluorobenzene | 403.4 |
| 42 | 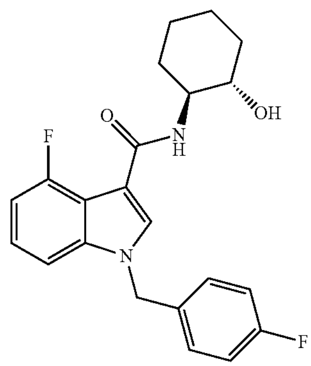 [SMILES: O=C(N[C@H]1CCCC[C@@H]1O)c1cn(Cc2ccc(F)cc2)c2cccc(F)c12] | 4-fluoro-1-(4-fluorobenzyl)-N-((1S,2S)-2-hydroxycyclohexyl)-1H-indole-3-carboxamide | 4-fluoro-4-((1S,2S)-2-hydroxycyclohexyl)-1H-indole-3-carboxamide (example A.6) and 1-(chloromethyl)-4-fluorobenzene | 385.5 |
| 43 | 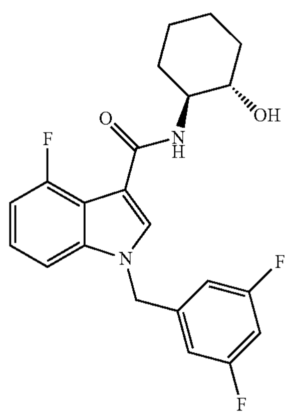 [SMILES: O=C(N[C@H]1CCCC[C@@H]1O)c1cn(Cc2cc(F)cc(F)c2)c2cccc(F)c12] | 1-(3,5-difluorobenzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 1-(chloromethyl)-3,5-difluorobenzene | 403.5 |
| 44 | 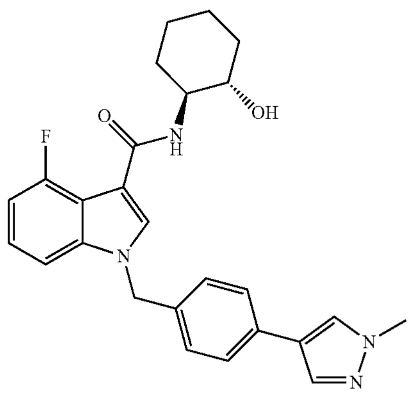 [SMILES: Cn1cc(-c2ccc(Cn3cc(C(=O)N[C@H]4CCCC[C@@H]4O)c4c(F)cccc43)cc2)cn1] | 4-fluoro-N-((1S,2S)-2-hydroxycyclohexyl)-1-(4-(1-methyl-1H-pyrazol-4-yl)benzyl)-1H-indole-3-carboxamide | 4-fluoro-N-((1S,2S)-2-hydroxycyclohexyl)-1H-indole-3-carboxamide (example A.6) and 4-(4-(chloromethyl)phenyl)-1-methyl-1H-pyrazole (example B.5) | 447.5 |

| Expl. No. | Structure | Systematic Name | Starting materials | MW found (MH+) |
|---|---|---|---|---|
| 45 | 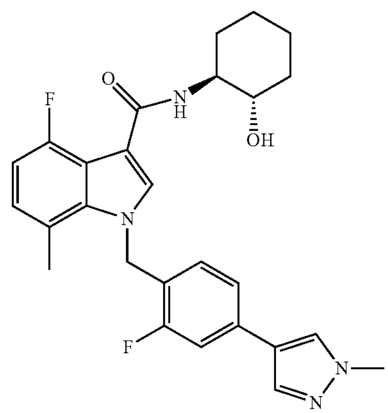 [SMILES: Cc1ccc(F)c2c(C(=O)N[C@H]3CCCC[C@@H]3O)cn(Cc3ccc(-c4cnn(C)c4)cc3F)c12] | 4-fluoro-1-(2-fluoro-4-(1-methyl-1H-pyrazol-4-yl)benzyl)-N-((1S,2S)-2-hydroxycyclohexyl)-7-methyl-1H-indole-3-carboxamide | 4-fluoro-7-methyl-1H-indole-3-carboxylic acid ((1S,2S)-2-hydroxy-cyclohexyl)-amide (example A.7) and 4-(4-(chloromethyl)-3-fluorophenyl)-1-methyl-1H-pyrazole (example B.2) | 479.6 |
| 46 | 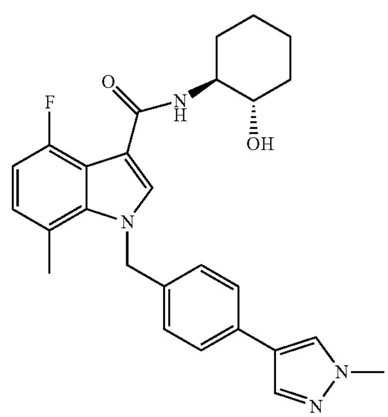 [SMILES: Cc1ccc(F)c2c(C(=O)N[C@H]3CCCC[C@@H]3O)cn(Cc3ccc(-c4cnn(C)c4)cc3)c12] | 4-fluoro-N-((1S,2S)-2-hydroxycyclohexyl)-7-methyl-1-(4-(1-methyl-1H-pyrazol-4-yl)benzyl)-1H-indole-3-carboxamide | 4-fluoro-7-methyl-1H-indole-3-carboxylic acid ((1S,2S)-2-hydroxy-cyclohexyl)-amide (example A.7) and 4-(4-(chloromethyl)phenyl)-1-methyl-1H-pyrazole (example B.5) | 461.7 |
| 47 | 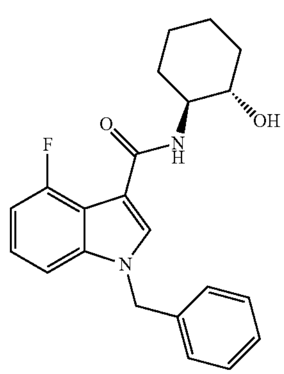 [SMILES: O=C(N[C@H]1CCCC[C@@H]1O)c1cn(Cc2ccccc2)c2cccc(F)c12] | 1-benzyl-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and (bromomethyl)benzene | 367.5 |
| 48 | 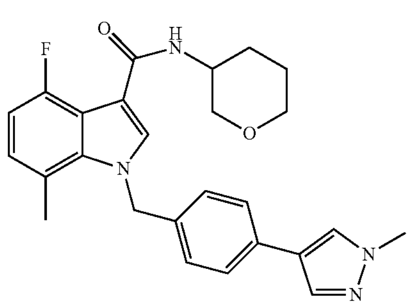 [SMILES: Cc1ccc(F)c2c(C(=O)NC3CCCOC3)cn(Cc3ccc(-c4cnn(C)c4)cc3)c12] | 4-fluoro-7-methyl-1-(4-(1-methyl-1H-pyrazol-4-yl)benzyl)-N-(tetrahydro-2H-pyran-3-yl)-1H-indole-3-carboxamide | 4-fluoro-7-methyl-1H-indole-3-carboxylic acid (tetrahydro-pyran-3-yl)-amide (example A.10) and 4-(4-(chloromethyl)phenyl)-1-methyl-1H-pyrazole (example B.5) | 447.5 |

-continued

| Expl. No. | Structure | Systematic Name | Starting materials | MW found (MH+) |
|---|---|---|---|---|
| 49 | 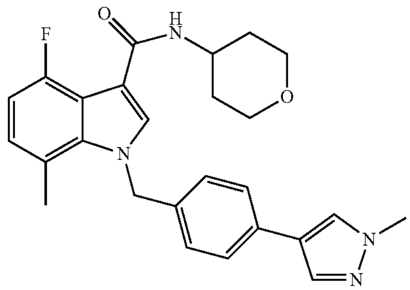 [SMILES: Cc1ccc(F)c2c(C(=O)NC3CCOCC3)cn(Cc3ccc(-c4cnn(C)c4)cc3)c12] | 4-fluoro-7-methyl-1-(4-(1-methyl-1H-pyrazol-4-yl)benzyl)-N-(tetrahydro-2H-pyran-4-yl)-1H-indole-3-carboxamide | 4-fluoro-7-methyl-1H-indole-3-carboxylic acid (tetrahydro-pyran-4-yl)-amide (example A.11) and 4-(4-(chloromethyl)phenyl)-1-methyl-1H-pyrazole (example B.5) | 447.7 |
| 50 | 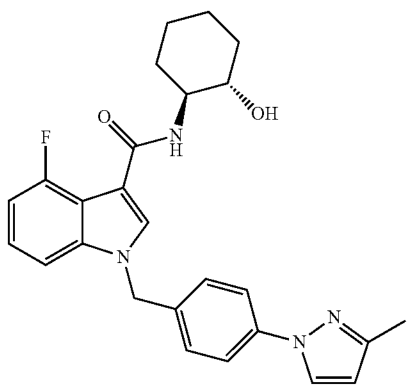 [SMILES: Cc1ccn(-c2ccc(Cn3cc(C(=O)N[C@H]4CCCC[C@@H]4O)c4c(F)cccc43)cc2)n1] | 4-fluoro-N-((1S,2S)-2-hydroxycyclohexyl)-1-(4-(3-methyl-1H-pyrazol-1-yl)benzyl)-1H-indole-3-carboxamide | 4-fluoro-N-((1S,2S)-2-hydroxycyclohexyl)-1H-indole-3-carboxamide (example A.6) and 1-(4-chloromethyl-phenyl)-3-methyl-1H-pyrazole | 447.4 |
| 51 | 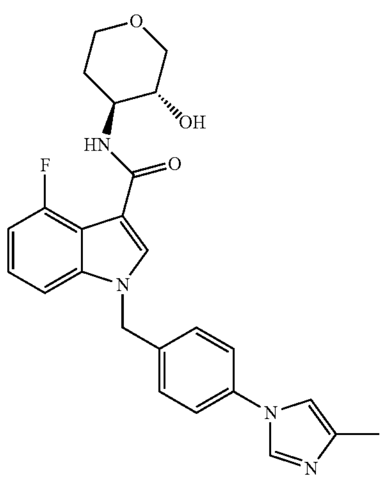 [SMILES: Cc1cn(-c2ccc(Cn3cc(C(=O)N[C@H]4CCOC[C@@H]4O)c4c(F)cccc43)cc2)cn1] | 4-fluoro-N-((3R,4S) or (3S,4R)-3-hydroxytetrahydro-2H-pyran-4-yl)-1-(4-(4-methyl-1H-imidazol-1-yl)benzyl)-1H-indole-3-carboxamide | 4-fluoro-N-((3R,4S) or (3S,4R)-3-hydroxytetrahydro-2H-pyran-4-yl)-1H-indole-3-carboxamide (example A.12) and 1-(4-chloromethyl-phenyl)-4-methyl-1H-imidazole (example B.4) | 449.4 |
| 52 | 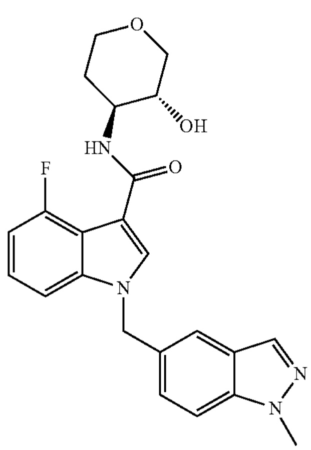 [SMILES: Cn1ncc2cc(Cn3cc(C(=O)N[C@H]4CCOC[C@@H]4O)c4c(F)cccc43)ccc21] | 4-fluoro-N-((3R,4S) or (3S,4R)-3-hydroxytetrahydro-2H-pyran-4-yl)-1-((1-methyl-1H-indazol-5-yl)methyl)-1H-indole-3-carboxamide | 4-fluoro-N-((3R,4S) or (3S,4R)-3-hydroxytetrahydro-2H-pyran-4-yl)-1H-indole-3-carboxamide (example A.12) and 5-(bromomethyl)-1-methyl-1H-indazole hydrobromide | 441.2 |

| Expl. No. | Structure | Systematic Name | Starting materials | MW found (MH+) |
|---|---|---|---|---|
| 53 | 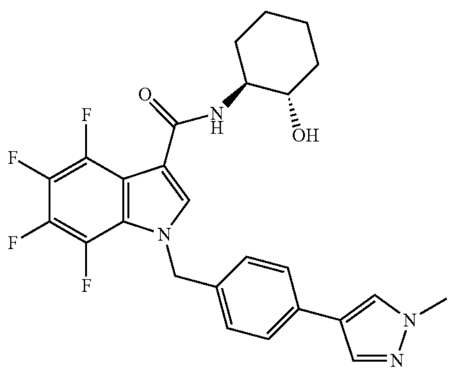 [SMILES: Cn1cc(-c2ccc(Cn3cc(C(=O)N[C@H]4CCCC[C@@H]4O)c4c(F)c(F)c(F)c(F)c43)cc2)cn1] | 4,5,6,7-tetrafluoro-N-((1S,2S)-2-hydroxycyclohexyl)-1-(4-(1-methyl-1H-pyrazol-4-yl)benzyl)-1H-indole-3-carboxamide | 4,5,6,7-tetrafluoro-1H-indole-3-carboxylic acid ((1S,2S)-2-hydroxy-cyclohexyl)-amide (example A.4) and 4-(4-(chloromethyl)phenyl)-1-methyl-1H-pyrazole (example B.5) | 501.6 |
| 54 | 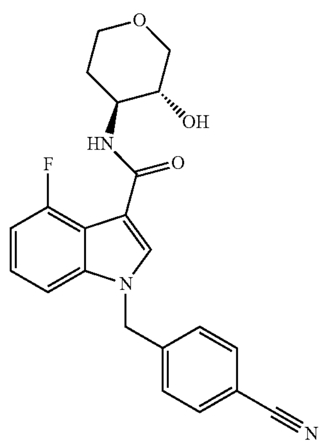 [SMILES: N#Cc1ccc(Cn2cc(C(=O)N[C@H]3CCOC[C@@H]3O)c3c(F)cccc32)cc1] | 1-(4-cyanobenzyl)-4-fluoro-N-((3R,4S) or (3S,4R)-3-hydroxytetrahydro-2H-pyran-4-yl)-1H-indole-3-carboxamide | 4-fluoro-N-((3R,4S) or (3S,4R)-3-hydroxytetrahydro-2H-pyran-4-yl)-1H-indole-3-carboxamide (example A.12) and 4-(chloromethyl)benzonitrile | 394.5 |
| 55 | 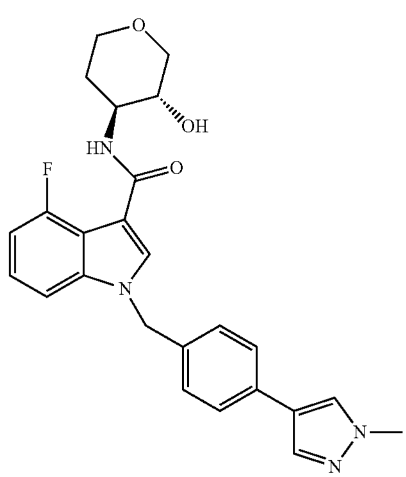 [SMILES: Cn1cc(-c2ccc(Cn3cc(C(=O)N[C@H]4CCOC[C@@H]4O)c4c(F)cccc43)cc2)cn1] | 4-fluoro-N-((3R,4S) or (3S,4R)-3-hydroxytetrahydro-2H-pyran-4-yl)-1-(4-(1-methyl-1H-pyrazol-4-yl)benzyl)-1H-indole-3-carboxamide | 4-fluoro-N-((3R,4S) or (3S,4R)-3-hydroxytetrahydro-2H-pyran-4-yl)-1H-indole-3-carboxamide (example A.12) and 4-(4-(chloromethyl)phenyl)-1-methyl-1H-pyrazole (example B.5) | 449.4 |

-continued

| Expl. No. | Structure | Systematic Name | Starting materials | MW found (MH+) |
|---|---|---|---|---|
| 56 | 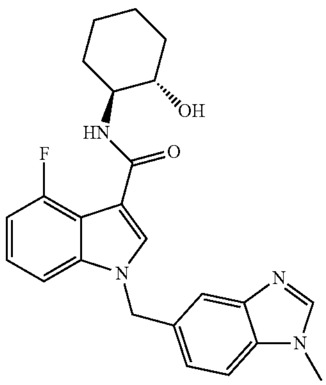 [SMILES: Cn1cnc2cc(Cn3cc(C(=O)N[C@H]4CCCC[C@@H]4O)c4c(F)cccc43)ccc21] | 4-fluoro-N-((1S,2S)-2-hydroxycyclohexyl)-1-((1-methyl-1H-benzo[d]yridine-5-yl)methyl)-1H-indole-3-carboxamide | 4-fluoro-N-((1S,2S)-2-hydroxycyclohexyl)-1H-indole-3-carboxamide (example A.6) and 5-(chloromethyl)-1-methyl-1H-benzo[d]imidazole | 421.5 |
| 57 | 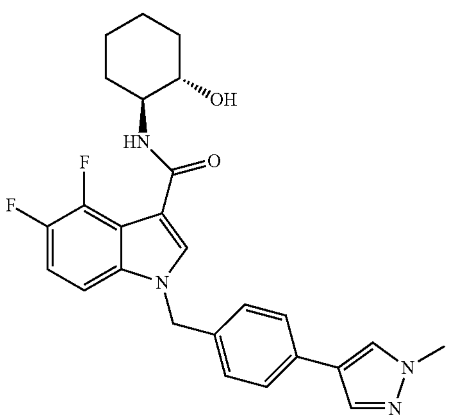 [SMILES: Cn1cc(-c2ccc(Cn3cc(C(=O)N[C@H]4CCCC[C@@H]4O)c4c(F)c(F)ccc43)cc2)cn1] | 4,5-difluoro-N-((1S,2S)-2-hydroxycyclohexyl)-1-(4-(1-methyl-1H-pyrazol-4-yl)benzyl)-1H-indole-3-carboxamide | 4,5-difluoro-1H-indole-3-carboxylic acid ((1S,2S)-2-hydroxy-cyclohexyl)-amide (example A.14) and 4-(4-(chloromethyl)phenyl)-1-methyl-1H-pyrazole (example B.5) | 465.5 |
| 58 | 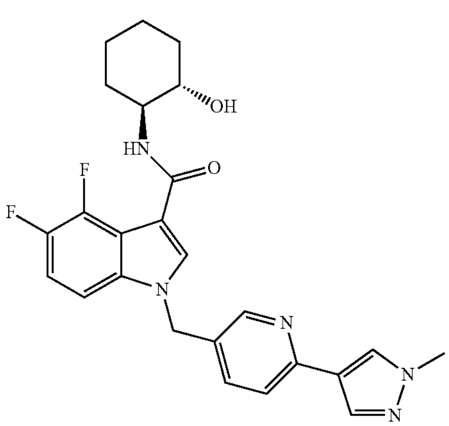 [SMILES: Cn1cc(-c2ccc(Cn3cc(C(=O)N[C@H]4CCCC[C@@H]4O)c4c(F)c(F)ccc43)cn2)cn1] | 4,5-difluoro-N-((1S,2S)-2-hydroxycyclohexyl)-1-((6-(1-methyl-1H-pyrazol-4-yl)pyridine-3-yl)methyl)-1H-indole-3-carboxamide | 4,5-difluoro-1H-indole-3-carboxylic acid ((1S,2S)-2-hydroxy-cyclohexyl)-amide (example A.14) and 5-(chloromethyl)-2-(1-methyl-1H-pyrazol-4-yl)pyridine (example B.1) | 466.7 |

-continued

| Expl. No. | Structure | Systematic Name | Starting materials | MW found (MH+) |
|---|---|---|---|---|
| 59 | 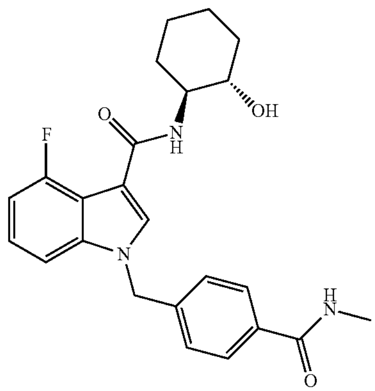 [SMILES: CNC(=O)c1ccc(Cn2cc(C(=O)N[C@H]3CCCC[C@@H]3O)c3c(F)cccc32)cc1] | 4-fluoro-N-((1S,2S)-2-hydroxycyclohexyl)-1-(4-(methylcarbamoyl)benzyl)-1H-indole-3-carboxamide | 4-fluoro-N-((1S,2S)-2-hydroxycyclohexyl)-1H-indole-3-carboxamide (example A.6) and 4-(chloromethyl)-N-methylbenzamide (example B.6) | 424.7 |
| 60 | 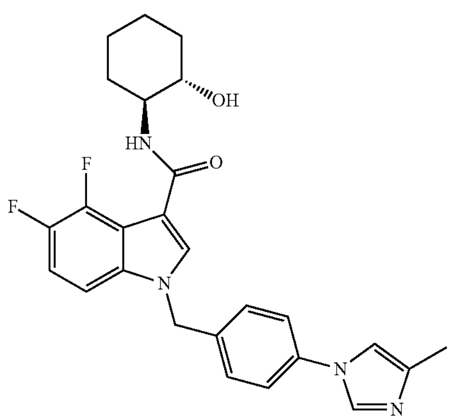 [SMILES: Cc1cn(-c2ccc(Cn3cc(C(=O)N[C@H]4CCCC[C@@H]4O)c4c(F)c(F)ccc43)cc2)cn1] | 4,5-difluoro-N-((1S,2S)-2-hydroxycyclohexyl)-1-(4-(4-methyl-1H-imidazol-1-yl)benzyl)-1H-indole-3-carboxamide | 4,5-difluoro-1H-indole-3-carboxylic acid ((1S,2S)-2-hydroxy-cyclohexyl)-amide (example A.14) and 1-(4-chloromethyl-phenyl)-4-methyl-1H-imidazole (example B.4) | 465.5 |
| 61 | 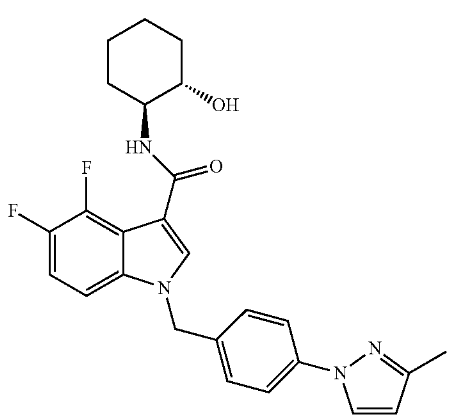 [SMILES: Cc1ccn(-c2ccc(Cn3cc(C(=O)N[C@H]4CCCC[C@@H]4O)c4c(F)c(F)ccc43)cc2)n1] | 4,5-difluoro-N-((1S,2S)-2-hydroxycyclohexyl)-1-(4-(3-methyl-1H-pyrazol-1-yl)benzyl)-1H-indole-3-carboxamide | 4,5-Difluoro-1H-indole-3-carboxylic acid ((1S,2S)-2-hydroxy-cyclohexyl)-amide (example A.14) and 1-(4-chloromethyl-phenyl)-4-methyl-1H-imidazole (example B.4) and 1-(4-(chloromethyl)phenyl)-3-methyl-1H-pyrazole | 465.5 |

Example 62

4,5,6,7-Tetrafluoro-N-((3S,4R) or (3R,4S))-3-hydroxytetrahydro-2H-pyran-4-yl)-1-(4-(1-methyl-1H-pyrazol-4-yl)benzyl)-1H-indole-3-carboxamide and

Example 63

4,5,6,7-Tetrafluoro-N-((3R,4S) or (3S,4R)-3-hydroxytetrahydro-2H-pyran-4-yl)-1-(4-(1-methyl-1H-pyrazol-4-yl)benzyl)-1H-indole-3-carboxamide

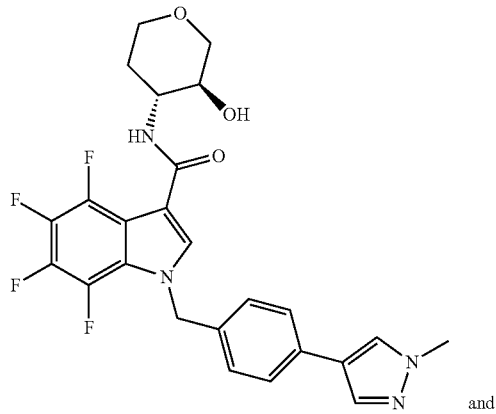

and

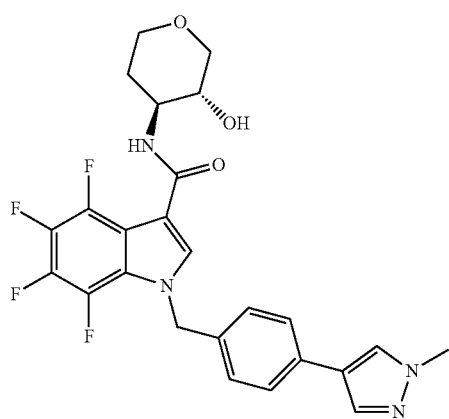 [SMILES: Cn1cc(-c2ccc(Cn3cc(C(=O)N[C@H]4CCOC[C@@H]4O)c4c(F)c(F)c(F)c(F)c43)c(F)c2)cn1]

In analogy to the procedure described for the synthesis of example 26, the title compounds were prepared from 4,5,6,7-tetrafluoro-1H-indole-3-carboxylic acid ((3RS,4SR)-3-hydroxy-tetrahydro-pyran-4-yl)-amide (example A.13) and 4-(4-(chloromethyl)phenyl)-1-methyl-1H-pyrazole (example B.5) followed by chiral separation on a Reprosil chiral NR column. Example 62: (−) enantiomer, MS (m/e): 503.4 (M+H)⁻ and example 63: (+) enantiomer, MS (m/e): 503.4 (M+H)⁺.

Example 64

4,5,6,7-Tetrafluoro-1-(2-fluoro-4-(1-methyl-1H-pyrazol-4-yl)benzyl)-N-((3R,4S) or (3S,4R))-3-hydroxytetrahydro-2H-pyran-4-yl)-1H-indole-3-carboxamide

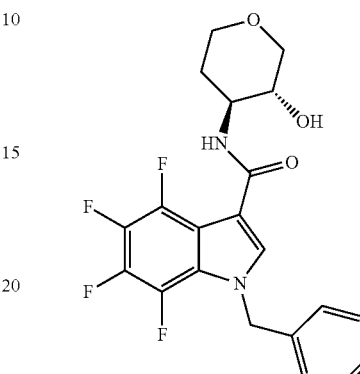

In analogy to the procedure described for the synthesis of example 26, the title compound was prepared from the chiral version of 4,5,6,7-tetrafluoro-1H-indole-3-carboxylic acid ((3RS,4SR)-3-hydroxy-tetrahydro-pyran-4-yl)-amide (example A.13) and 4-(4-(chloromethyl)-3-fluorophenyl)-1-methyl-1H-pyrazole (example B.2) followed by purification with separation chromatography with a gradient formed from methylene chloride and methanol (0-5%) to provide 53 mg (44%) of the title compound as a white solid. MS (m/e): 519.5 (M+H)⁺.

Example 65

Fluoro-1-(4-(1-methyl-1H-pyrazol-4-yl)benzyl)-N-(tetrahydro-2H-pyran-4-yl)-1H-indole-3-carboxamide

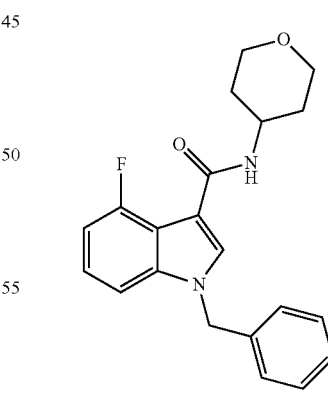

To a suspension of 4-fluoro-N-(tetrahydro-2H-pyran-4-yl)-1H-indole-3-carboxamide (example A.8) (50 mg, 191 μmol) in N,N-dimethylformamide (500 μl) under nitrogen at 0° C. was added sodium hydride 60% dispersion in oil (9.15 mg, 229 μmol). The mixture was stirred at 0° C. for 15 minutes. After this time, 4-(4-(chloromethyl)phenyl)-1- methyl-1H-pyrazole (example B.5) (39.4 mg, 191 μmol) was added at once. The mixture was stirred under ice-bath cooling for 5 hours, quenched with a 20% ammonium chloride solution and diluted with water. The crude material was purified with flash column chromatography on amine eluting with a gradient formed from n-heptane and ethyl acetate (0 to 80%) to provide 60 mg (73%) of the title compound as a white solid. MS (m/e): 433.5 (M+H)$^+$.

In analogy to Example 65, compounds 66 to 69 of the following table were prepared by reaction of the indicated amides with an alkylating agent.

| Expl. No. | Structure | Systematic Name | Starting materials | MW found (MH$^+$) |
|---|---|---|---|---|
| 66 | 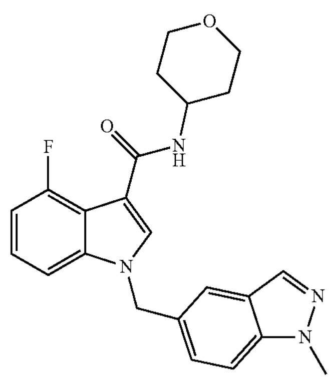 [SMILES: Cn1ncc2cc(Cn3cc(C(=O)NC4CCOCC4)c4c(F)cccc43)ccc21] | 4-fluoro-1-((1-methyl-1H-indazol-5-yl)methyl)-N-(tetrahydro-2H-pyran-4-yl)-1H-indole-3-carboxamide | 4-fluoro-N-(tetrahydro-2H-pyran-4-yl)-1H-indole-3-carboxamide (example A.8) and 5-(bromomethyl)-1-methyl-1H-indazole hydrobromide | 407.5 |
| 67 | 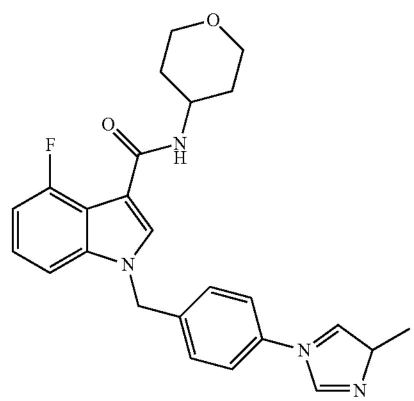 | 4-fluoro-1-(4-(4-methyl-1H-imidazol-1-yl)benzyl)-N-(tetrahydro-2H-pyran-4-yl)-1H-indole-3-carboxamide | 4-fluoro-N-(tetrahydro-2H-pyran-4-yl)-1H-indole-3-carboxamide (example A.8) and 1-(4-chloromethyl-phenyl)-4-methyl-1H-imidazole (example B.4) | 433.5 |
| 68 | 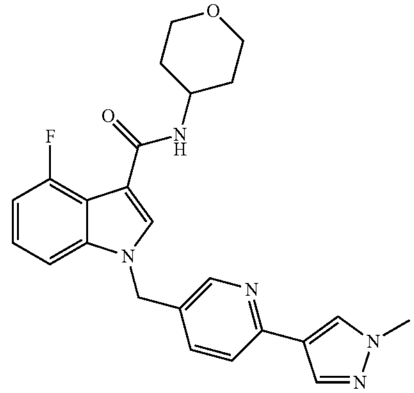 [SMILES: Cn1cc(-c2ccc(Cn3cc(C(=O)NC4CCOCC4)c4c(F)cccc43)cn2)cn1] | 4-fluoro-1-((6-(1-methyl-1H-pyrazol-4-yl)yridine-3-yl)methyl)-N-(tetrahydro-2H-pyran-4-yl)-1H-indole-3-carboxamide | 4-fluoro-N-(tetrahydro-2H-pyran-4-yl)-1H-indole-3-carboxamide (example A.8) and 5-(chloromethyl)-2-(1-methyl-1H-pyrazol-4-yl)pyridine (example B.1) | 434.4 |

| Expl. No. | Structure | Systematic Name | Starting materials | MW found (MH+) |
|---|---|---|---|---|
| 69 | 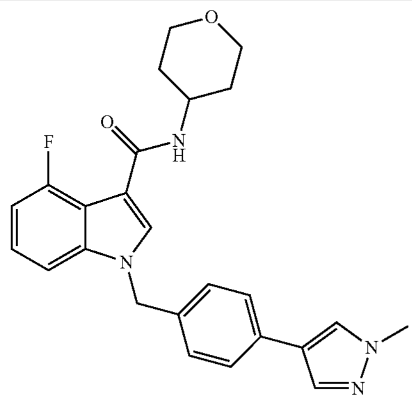 [SMILES: Cn1cc(-c2ccc(Cn3cc(C(=O)NC4CCOCC4)c4c(F)cccc43)cc2)cn1] | 4-fluoro-1-(4-(1-methyl-1H-pyrazol-4-yl)benzyl)-N-(tetrahydro-2H-pyran-4-yl)-1H-indole-3-carboxamide | 4-fluoro-N-(tetrahydro-2H-pyran-4-yl)-1H-indazole-3-carboxamide (example A.37) and 4-(4-(chloromethyl)phenyl)-1-methyl-1H-pyrazole (example B.5) | 434.5 |

Example 70

4-Fluoro-1-(2-fluoro-4-(1-methyl-1H-pyrazol-4-yl)benzyl)-N-((3S,4R) or (3R,4S)-3-hydroxytetrahydro-2H-pyran-4-yl)-1H-indole-3-carboxamide and

Example 71

4-Fluoro-1-(2-fluoro-4-(1-methyl-1H-pyrazol-4-yl)benzyl)-N-((3R,4S) or (3S,4R)-3-hydroxytetrahydro-2H-pyran-4-yl)-1H-indole-3-carboxamide

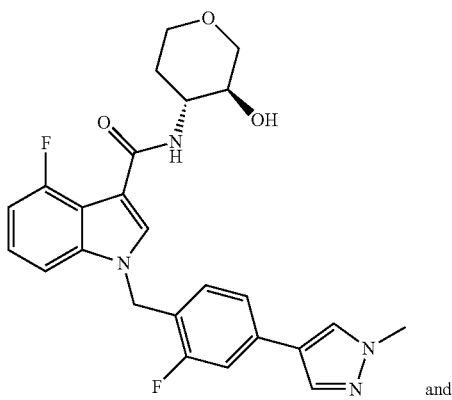

and

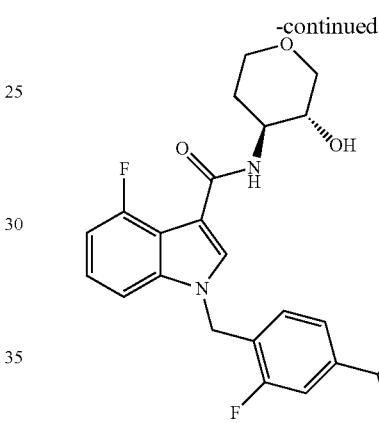

4-Fluoro-1-(2-fluoro-4-(1-methyl-1H-pyrazol-4-yl)benzyl)-N-((3RS,4SR)-3-hydroxytetrahydro-2H-pyran-4-yl)-1H-indole-3-carboxamide (example 6) (220 mg) was separated on a Reprosil Chiral NR column to provide 94 mg (43%) of the title compound (example 81, (−) enantiomer) as an off-white solid, MS (m/e): 467.3 (M+H)+ and 91 mg (41%) of the compound (example 82, (+) enantiomer) as an off-white solid. MS (m/e): 467.4 (M+H)+.

In analogy to example 1, examples 72 to 75 of the following table were prepared by coupling an acid derivative with an amine.

| Example No. | Structure | Systematic Name | Starting materials | MW found (MH+) |
|---|---|---|---|---|
| 72 | 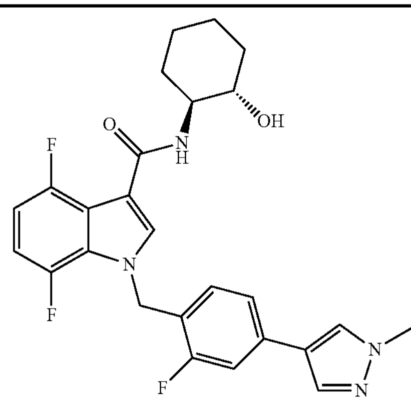 | 4,7-difluoro-1-(2-fluoro-4-(1-methyl-1H-pyrazol-4-yl)benzyl)-N-((1S,2S)-2-hydroxycyclohexyl)-1H-indazole-3-carboxamide | 4,7-difluoro-1-(2-fluoro-4-(1-methyl-1H-pyrazol-4-yl)benzyl)-1H-indazole-3-carboxylic acid (example A.15) and (1S,2S)-2-aminocyclohexanol hydrochloride | 484.2 |

-continued

| Example No. | Structure | Systematic Name | Starting materials | MW found (MH+) |
|---|---|---|---|---|
| 73 | 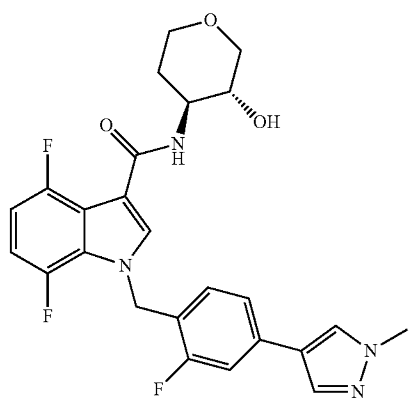 [SMILES: Cn1cc(-c2ccc(Cn3cc(C(=O)N[C@H]4CCOC[C@@H]4O)c4c(F)ccc(F)c43)c(F)c2)cn1] | 4,7-difluoro-1-(2-fluoro-4-(1-methyl-1H-pyrazol-4-yl)benzyl)-N-((3R,4S)-3-hydroxytetrahydro-2H-pyran-4-yl)-1H-indazole-3-carboxamide | 4,7-difluoro-1-(2-fluoro-4-(1-methyl-1H-pyrazol-4-yl)benzyl)-1H-indazole-3-carboxylic acid (example A.15) and (3R,4S)-4-aminotetrahydropyran-3-ol hydrochloride (example C.1) | 486.1 |
| 74 | 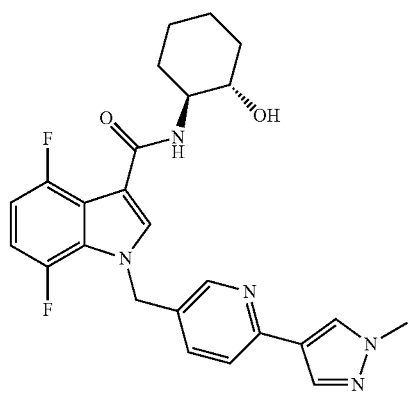 [SMILES: Cn1cc(-c2ccc(Cn3cc(C(=O)N[C@H]4CCCC[C@@H]4O)c4c(F)ccc(F)c43)cn2)cn1] | 4,7-difluoro-N-((3R,4S)-3-hydroxytetrahydro-2H-pyran-4-yl)-1-((6-(1-methyl-1H-pyrazol-4-yl)yridine-3-yl)methyl)-1H-indazole-3-carboxamide | 4,7-difluoro-1-[[6-(1-methylpyrazol-4-yl)yridine-3-yl]methyl]indazole-3-carboxylic acid (A.16) and (1S,2S)-2-aminocyclohexanol hydrochloride | 469.3 |
| 75 | 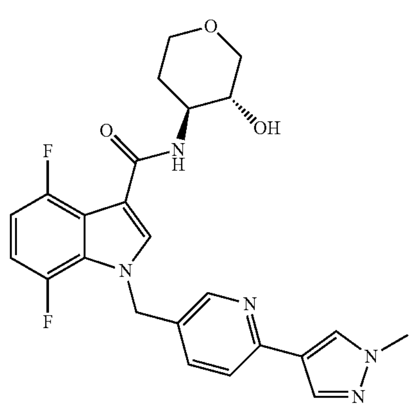 [SMILES: Cn1cc(-c2ccc(Cn3cc(C(=O)N[C@H]4CCOC[C@@H]4O)c4c(F)ccc(F)c43)cn2)cn1] | 4,7-difluoro-N-((1S,2S)-2-hydroxycyclohexanol)-1-((6-(1-methyl-1H-pyrazol-4-yl)yridine-3-yl)methyl)-1H-indazole-3-carboxamide | 4,7-difluoro-1-[[6-(1-methylpyrazol-4-yl)yridine-3-yl]methyl]indazole-3-carboxylic acid (A.16) and (3R,4S)-4-aminotetrahydropyran-3-ol hydrochloride (example C.1) | 467.3 |

In analogy to Example 26, compounds 76 to 85 following table were prepared by reaction of the indicated amides with an alkylating agent.

| Expl. No. | Structure | Systematic Name | Starting materials | MW found (MH+) |
|---|---|---|---|---|
| 76 | 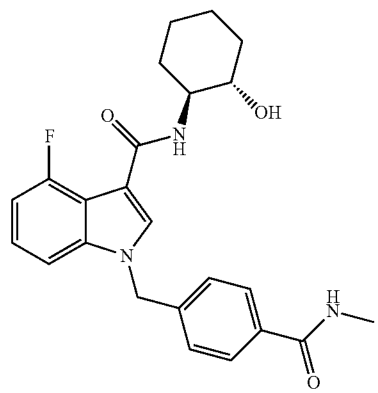 [SMILES: CNC(=O)c1ccc(Cn2cc(C(=O)N[C@H]3CCCC[C@@H]3O)c3c(F)cccc32)cc1] | 4-fluoro-N-((1S,2S)-2-hydroxycyclohexyl)-1-(4-(methylcarbamoyl)benzyl)-1H-indole-3-carboxamide | 4-fluoro-N-((1S,2S)-2-hydroxycyclohexyl)-1H-indole-3-carboxamide (example A.6) and 4-(chloromethyl)-N-methylbenzamide (CAS 220875-88-7) | 424.7 |
| 77 | 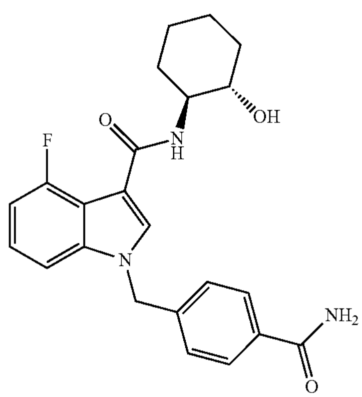 [SMILES: NC(=O)c1ccc(Cn2cc(C(=O)N[C@H]3CCCC[C@@H]3O)c3c(F)cccc32)cc1] | 1-(4-carbamoylbenzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 4-(chloromethyl)benzamide (CAS 84545-14-2) | 410.3 |
| 78 | 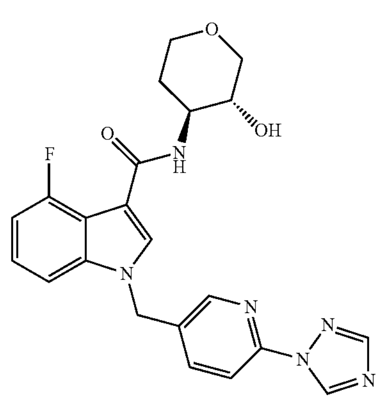 [SMILES: O=C(N[C@H]1CCOC[C@@H]1O)c1cn(Cc2ccc(-n3cncn3)nc2)c2cccc(F)c12] | 1-((6-(1H-1,2,4-triazol-1-yl)yridine-3-yl)methyl)-4-fluoro-N-((3R,4S)-3-hydroxytetrahydro-2H-pyran-4-yl)-1H-indole-3-carboxamide | 4-fluoro-N-((3R,4S) or (3S,4R)-3-hydroxytetrahydro-2H-pyran-4-yl)-1H-indole-3-carboxamide (A.12) and 5-(chloromethyl)-2-(1H-1,2,4-triazol-1-yl)pyridine (CAS 1250524-50-5) | 437.3 |

| Expl. No. | Structure | Systematic Name | Starting materials | MW found (MH+) |
|---|---|---|---|---|
| 79 | 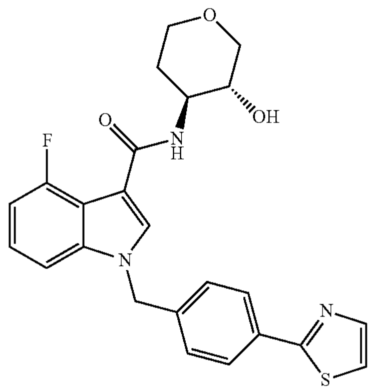 [SMILES: O=C(N[C@H]1CCOC[C@@H]1O)c1cn(Cc2ccc(-c3nccs3)cc2)c2cccc(F)c12] | 4-fluoro-N-((3R,4S)-3-hydroxytetrahydro-2H-pyran-4-yl)-1-(4-(thiazol-2-yl)benzyl)-1H-indole-3-carboxamide | 4-fluoro-N-((3R,4S) or (3S,4R)-3-hydroxytetrahydro-2H-pyran-4-yl)-1H-indole-3-carboxamide (A.12) and 2-(4-(chloromethyl)phenyl)thiazole (CAS 906352-61-2) | 452.3 |
| 80 | 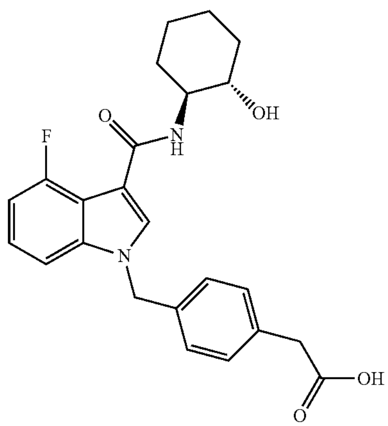 [SMILES: O=C(O)Cc1ccc(Cn2cc(C(=O)N[C@H]3CCCC[C@@H]3O)c3c(F)cccc32)cc1] | 1-(4-(2-amino-2-oxoethyl)benzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 2-(4-(bromomethyl)phenyl)acetamide (CAS 847486-99-1) | 424.3 |
| 81 | 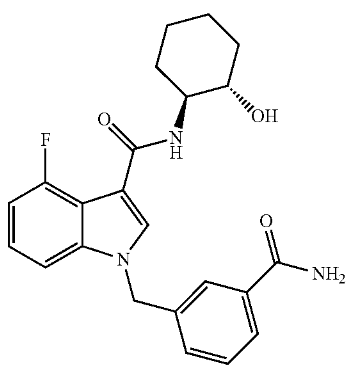 [SMILES: NC(=O)c1cccc(Cn2cc(C(=O)N[C@H]3CCCC[C@@H]3O)c3c(F)cccc32)c1] | 1-(3-carbamoylbenzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 3-(chloromethyl)benzamide (CAS 135654-16-9) | 410.3 |
| 82 | 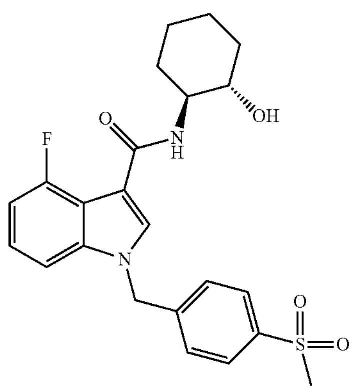 [SMILES: CS(=O)(=O)c1ccc(Cn2cc(C(=O)N[C@H]3CCCC[C@@H]3O)c3c(F)cccc32)cc1] | 4-fluoro-N-((1S,2S)-2-hydroxycyclohexyl)-1-(4-(methylsulfonyl)benzyl)-1H-indole-3-carboxamide | 4-fluoro-N-((1S,2S)-2-hydroxycyclohexyl)-1H-indole-3-carboxamide (example A.6) and 1-(bromomethyl)-4-(methylsulfonyl)benzene (CAS 53606-06-7 | 445.2 |

-continued

| Expl. No. | Structure | Systematic Name | Starting materials | MW found (MH+) |
|---|---|---|---|---|
| 83 | 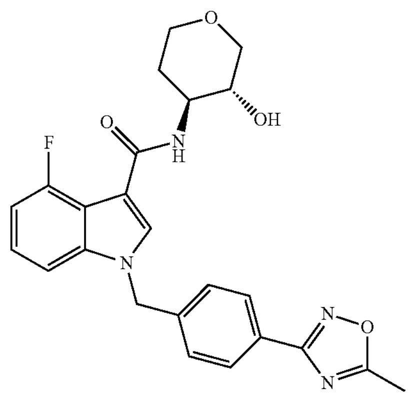 [SMILES: Cc1nc(-c2ccc(Cn3cc(C(=O)N[C@H]4CCOC[C@@H]4O)c4c(F)cccc43)cc2)no1] | 4-fluoro-N-((3R,4S)-3-hydroxytetrahydro-2H-pyran-4-yl)-1-(4-(5-methyl-1,2,4-oxadiazol-3-yl)benzyl)-1H-indole-3-carboxamide | 4-fluoro-N-((3R,4S) or (3S,4R)-3-hydroxytetrahydro-2H-pyran-4-yl)-1H-indole-3-carboxamide (A.12) and 3-(4-(chloromethyl)phenyl)-5-methyl-1,2,4-oxadiazole (CAS 449209-35-2) | 451.3 |
| 84 | 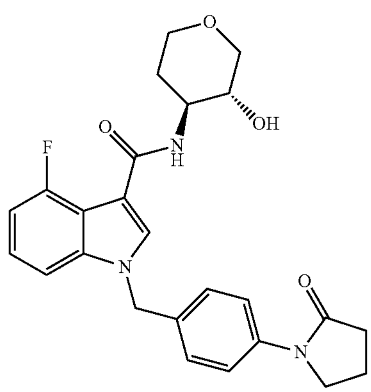 [SMILES: O=C(N[C@H]1CCOC[C@@H]1O)c1cn(Cc2ccc(N3CCCC3=O)cc2)c2cccc(F)c12] | 4-fluoro-N-((3R,4S)-3-hydroxytetrahydro-2H-pyran-4-yl)-1-(4-(2-oxopyrrolidin-1-yl)benzyl)-1H-indole-3-carboxamide | 4-fluoro-N-((3R,4S) or (3S,4RF)-3-hydroxytetrahydro-2H-pyran-4-yl)-1H-indole-3-carboxamide (A.12) and 1-(4-(chloromethyl)phenyl)pyrrolidin-2-one (CAS 36152-29-1) | 452.3 |
| 85 | 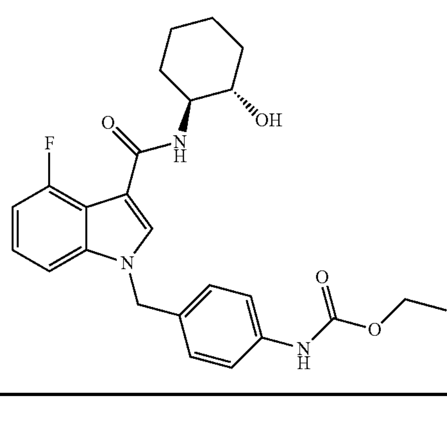 | ethyl 4-((4-fluoro-3-((1S,2S)-2-hydroxycyclohexylcarbamoyl)-1H-indol-1-yl)methyl)phenylcarbamate | 4-fluoro-N-((1S,2S)-2-hydroxycyclohexyl)-1H-indole-3-carboxamide (example A.6) and (4-chloromethyl-phenyl)-carbamic acid ethyl ester (CAS 873372-18-0) | 452.4 |

Example 86

Preparation of 4-fluoro-1-(2-fluoro-4-(methylcarbamoyl)benzyl)-N-((1S,2S)-2-hydroxycyclohexyl)-1H-indole-3-carboxamide

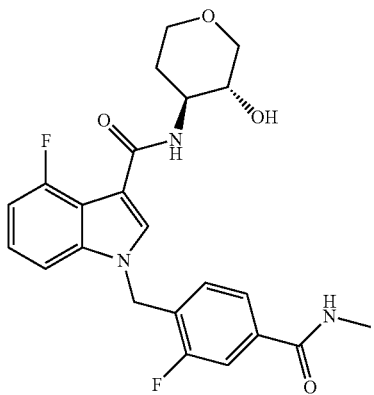 [SMILES: CNC(=O)c1ccc(Cn2cc(C(=O)N[C@H]3CCOC[C@@H]3O)c3c(F)cccc32)c(F)c1]

Step 1: Methyl 3-fluoro-4-((4-fluoro-3-((1S,2S)-2-hydroxycyclohexylcarbamoyl)-1H-indol-1-yl)methyl)benzoate The title compound was obtained in analogy to the procedure described in example 26, reacting 4-fluoro-N-((1S,2S)-2-hydroxycyclohexyl)-1H-indole-3-carboxamide (example A.6) and 4-bromomethyl-3-fluoro-benzoic acid methyl ester (CAS 128577-47-9). Off-white solid. MS (m/e): 443.5 (M+H)$^+$.

Step 2: 4-Fluoro-1-(2-fluoro-4-(methylcarbamoyl)benzyl)-N-((1S,2S)-2-hydroxycyclohexyl)-1H-indole-3-carboxamide To a stirred suspension of methylamine hydrochloride (22.9 mg, 339 μmol) at r.t. in dioxane (3 ml) under an argon atmosphere was added trimethylaluminum 2M solution in toluene (170 μl, 339 μmol) in one portion. After stirring for 2 hrs at r.t., methyl 3-fluoro-4-((4-fluoro-3-((1S,2S)-2-hydroxycyclohexylcarbamoyl)-1H-indol-1-yl)methyl)benzoate (50 mg, 113 μmol) was added in one portion. The reaction mixture was heated to 100° C. and stirring at that temperature was continued overnight. The orange slurry was cooled to r.t. and treated with 0.5 ml of water. Then, MgSO$_4$ was added. After stirring for 15 min at r.t., the mixture was filtered and the cake was washed with methanol. The filtrate was concentrated. The crude product was purified by silica gel chromatography using a CH$_2$Cl$_2$/MeOH gradient as eluent to provide the title compound (18 mg, 36%) as white solid. MS (m/e): 442.2 (M+H)$^+$.

In analogy to Example 86, compounds 87 to 90 of the following table were prepared by reaction of the indicated amides with an alkylating agent, followed by conversion of the ester with methyl- or dimethylamine hydrochloride in the presence of trimethylaluminium.

| Expl. No. | Structure | Systematic Name | Starting materials | MW found (MH$^+$) |
|---|---|---|---|---|
| 87 | 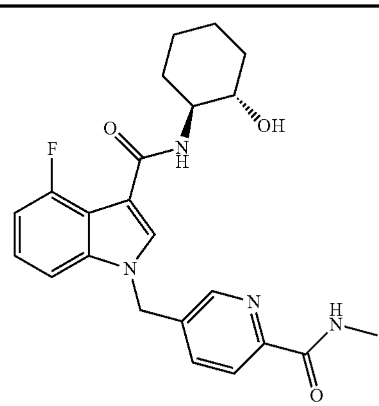 | 4-fluoro-N-((1S,2S)-2-hydroxycyclohexyl)-1-((6-(methylcarbamoyl)pyridin-3-yl)methyl)-1H-indole-3-carboxamide | 4-fluoro-N-((1S,2S)-2-hydroxycyclohexyl)-1H-indole-3-carboxamide (example A.6) and 5-chloromethyl-pyridine-2-carboxylic acid ethyl ester (CAS 39977-48-5), then methylamine hydrochloride | 425.3 |
| 88 | 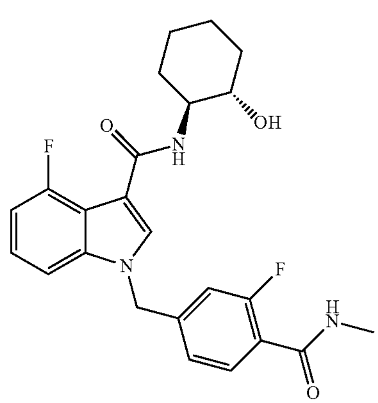 [SMILES: CNC(=O)c1ccc(Cn2cc(C(=O)N[C@H]3CCCC[C@@H]3O)c3c(F)cccc32)cc1F] | 4-fluoro-1-(3-fluoro-4-(methylcarbamoyl)benzyl)-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and methyl 4-(bromomethyl)-2-fluorobenzoate (CAS 85070-57-1), then methylamine hydrochloride | 442.3 |

| Expl. No. | Structure | Systematic Name | Starting materials | MW found (MH+) |
|---|---|---|---|---|
| 89 | 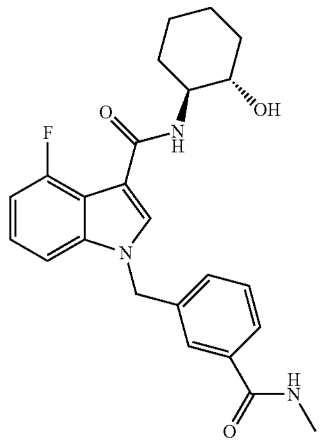 [SMILES: CNC(=O)c1cccc(Cn2cc(C(=O)N[C@H]3CCCC[C@@H]3O)c3c(F)cccc32)c1] | 4-fluoro-N-((1S,2S)-2-hydroxycyclohexyl)-1-(3-(methylcarbamoyl)benzyl)-1H-indole-3-carboxamide | 4-fluoro-N-((1S,2S)-2-hydroycyclohexyl)-1H-indole-3-carboxamide (example A.6) and methyl 3-(bromomethyl)benzoate (CAS 1129-28-8), then methylamine hydrochloride | 424.3 |
| 90 | 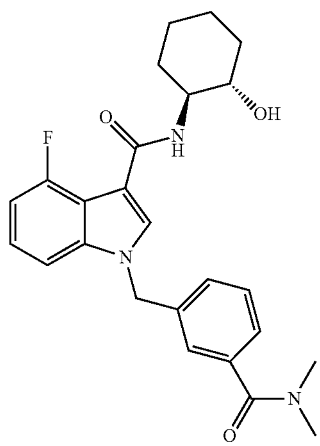 [SMILES: CN(C)C(=O)c1cccc(Cn2cc(C(=O)N[C@H]3CCCC[C@@H]3O)c3c(F)cccc32)c1] | 1-(3-(dimethylcarbamoyl)benzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and methyl 3-(bromomethyl)benzoate (CAS 1129-28-8), then dimethylamine hydrochloride | 438.3 |

Example 91

Preparation of 4-fluoro-1-(2-fluoro-4-(methylcarbamoyl)benzyl)-N-((1S,2S)-2-hydroxycyclohexyl)-1H-indole-3-carboxamide

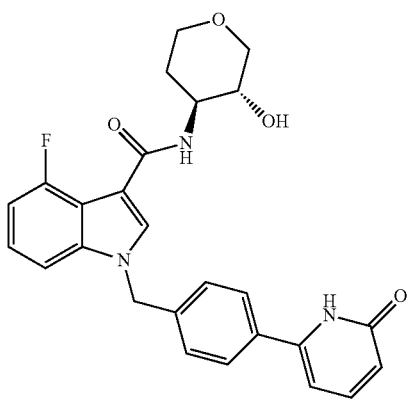 [SMILES: O=C(N[C@H]1CCOC[C@@H]1O)c1cn(Cc2ccc(-c3cccc(=O)[nH]3)cc2)c2cccc(F)c12]

Step 1: 1-(4-Bromobenzyl)-4-fluoro-N-((3R,4S)-3-hydroxytetrahydro-2H-pyran-4-yl)-1H-indole-3-carboxamide The title compound was obtained in analogy to the procedures described in example 26, reacting 4-fluoro-N-((1S,2S)-2-hydroxycyclohexyl)-1H-indole-3-carboxamide (example A.12) and 1-bromo-4-(chloromethyl)benzene. White solid. MS (m/e): 447.1 (M+H)+.

Step 2: 4-fluoro-N-((3R,4S)-3-hydroxytetrahydro-2H-pyran-4-yl)-1-(4-(6-methoxypyridin-2-yl)benzyl)-1H-indole-3-carboxamide To a solution of 1-(4-bromobenzyl)-4-fluoro-N-((3R,4S)-3-hydroxytetrahydro-2H-pyran-4-yl)-1H-indole-3-carboxamide (128 mg, 286 μmol) and 6-methoxypyridin-2-ylboronic acid (65.7 mg, 429 μmol) in 1,2-dimethoxyethane (2 ml) under an argon atmosphere was added cesium carbonate (186 mg, 572 μmol), water (0.2 ml) and tetrakis(triphenylphosphine)palladium(0) (9.9 mg, 8.6 μmol). The reaction mixture was stirred at 90° overnight, cooled to r.t and concentrated.

The crude product was purified by silica gel chromatography using a CH$_2$Cl$_2$/MeOH gradient as eluent to provide the title compound (92 mg, 68%) as a white solid. MS (m/e): 476.3 (M+H)$^+$.

Step 3: 4-Fluoro-1-(2-fluoro-4-(methylcarbamoyl) benzyl)-N-((1S,2S)-2-hydroxycyclohexyl)-1H-indole-3-carboxamide To a solution of 4-fluoro-N-((3R,4S)-3-hydroxytetrahydro-2H-pyran-4-yl)-1-(4-(6-methoxy-pyridin-2-yl)benzyl)-1H-indole-3-carboxamide (50 mg, 105 μmol) in acetonitrile (0.6 ml) at r.t under an argon atmosphere was added sodium iodide (23 mg, 155 μmol) and trimethylchlorosilane (17 mg, 20.2 μl, 158 μmol). To this mixture was added dropwise a solution of acetonitrile (0.1 ml)/water (52 μl). The mixture was stirred at 60° for 7 hrs. After cooling to r.t. the mixture was poured on 10% aqueous Na$_2$SO$_3$ solution and extracted with CH$_2$Cl$_2$. The organic phase was washed with water, dried over MgSO$_4$, filtered and concentrated. The crude product was purified by silica gel chromatography using a CH$_2$Cl$_2$/MeOH gradient as eluent to provide the title compound (15 mg, 28%) as a white solid. MS (m/e): 462.3 (M+H)$^+$.

Example 92

2-[4-Fluoro-1-[[2-fluoro-4-(1-methylpyrazol-4-yl)phenyl]methyl]indol-3-yl]-N-[(3R,4S)-3-hydroxyoxan-4-yl]acetamide

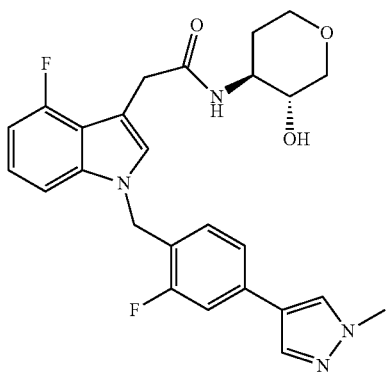 [SMILES: Cn1cc(-c2ccc(Cn3cc(CC(=O)N[C@H]4CCOC[C@@H]4O)c4c(F)cccc43)c(F)c2)cn1]

Step 1: Ethyl 2-(4-fluoro-1H-indol-3-yl)acetate

To a stirred mixture of 4-fluoro-1H-indole (1 g, 7.4 mmol) and ethyl 2-diazoacetate (1.06 g, 973 μl, 925 mmol) in dichloromethane (50 ml) was added at r.t. and under an argon atmosphere copper(II)trifluoromethanesulfonate (134 mg, 370 μmol) (exothermic). The mixture was stirred at r.t overnight, then diluted with CH$_2$Cl$_2$, washed with water, dried over MgSO$_4$, filtered and evaporated. The crude product was purified by silica gel chromatography using a heptane/EtOAc gradient as eluent to obtain the title compound as a mixture with the isomeric ethyl 2-(4-fluoroindol-1-yl)acetate (815 mg) which was used in the next step without further purification. MS (m/e): 222.2 (M+H)$^+$.

Step 2: Ethyl 2-(4-fluoro-1-(2-fluoro-4-(1-methyl-1H-pyrazol-4-yl)benzyl)-1H-indol-3-yl)acetate To a stirred solution of ethyl 2-(4-fluoro-1H-indol-3-yl)acetate (0.8 g, 2.17 mmol) in N,N-dimethylacetamide (10 ml) was added at r.t. and under an argon atmosphere 4-(4-(chloromethyl)-3-fluorophenyl)-1-methyl-1H-pyrazole (487 mg, 2.17 mmol) and cesium carbonate (707 mg, 2.2 mmol). The mixture was stirred at r.t overnight, then diluted with EtOAc and washed with water. The aqueous layer was back extracted with EtOAc. The combined organics were washed with water, dried over MgSO4, filtered and evaporated. The crude product was purified by silica gel chromatography using a heptane/EtOAc gradient as eluent to obtain the title compound (548 mg, 62%) as a colorless viscous oil. MS (m/e): 410.3 (M+H)$^+$.

Step 3: 2-(4-Fluoro-1-(2-fluoro-4-(1-methyl-1H-pyrazol-4-yl)benzyl)-1H-indol-3-yl)acetic acid To a suspension of ethyl 2-(4-fluoro-1-(2-fluoro-4-(1-methyl-1H-pyrazol-4-yl)benzyl)-1H-indol-3-yl)acetate (0.54 g, 1.32 mmol) in MeOH (1.5 ml) and THF (1.5 ml) was added at r.t. and under an argon atmosphere potassium hydroxide solution 1 M in water (2.64 ml, 2.64 mmol). The mixture was stirred at 75° for 4 hrs, then cooled to r.t. 2M HCl in water (2.64 ml, 5.3 mmol) was added under stirring at 0°. The mixture was stirred at r.t for 30 min. The precipitate was filtered, washed with water, collected and dried to provide the title compound (475 mg, 94%) as an off-white solid. MS (m/e): 382.3 (M+H)$^+$.

Step 4: 2-[4-Fluoro-1-[[2-fluoro-4-(1-methylpyrazol-4-yl)phenyl]methyl]indol-3-yl]-N-[(3R,4S)-3-hydroxyoxan-4-yl]acetamide To a solution of 2-(4-fluoro-1-(2-fluoro-4-(1-methyl-1H-pyrazol-4-yl)benzyl)-1H-indol-3-yl)acetic acid (50 mg, 131 μmol) in DMF (1 ml) was added at r.t. and under an argon atmosphere (3R,4S)-4-aminotetrahydro-2H-pyran-3-ol hydrochloride (20.1 mg, 131 μmol), DIEA (50.8 mg, 68.7 μl, 393 μmol) and HATU (59.8 mg, 157 μmol). The yellow solution was stirred at r.t overnight. The mixture was poured on water and extracted with EtOAc. The organic layer was washed with water, dried with MgSO$_4$, filtered and evaporated. The crude product was purified by silica gel chromatography using a CH$_2$Cl$_2$/MeOH gradient as eluent to obtain the title compound (30 mg, 48%) as a white solid. MS (m/e): 481.3 (M+H)$^+$.

Example 93

Preparation of 2-(4-fluoro-1-(2-fluoro-4-(1-methyl-1H-pyrazol-4-yl)benzyl)-1H-indol-3-yl)-N-((1S,2S)-2-hydroxycyclohexyl)acetamide

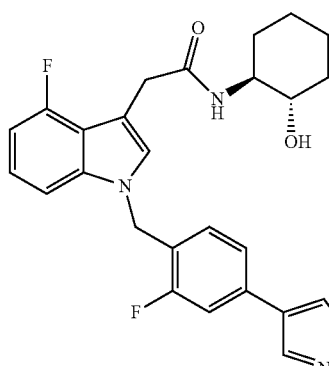

The title compound was obtained in analogy to the procedures described in example 92. Off-white solid. MS (m/e): 479.3 (M+H)$^+$.

Examples 94 to 131

In analogy to example 1, examples 94 to 131 of the following table were prepared by coupling an acid derivative with an amine.

| Example No. | Structure | Systematic Name | Starting materials | MW found (MH+) |
|---|---|---|---|---|
| 94 | 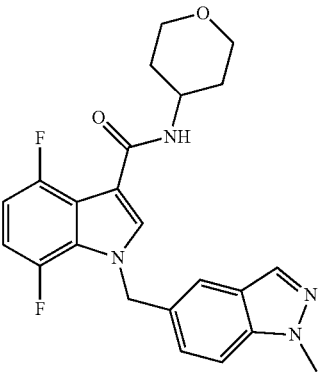 [SMILES: Cn1ncc2cc(Cn3cc(C(=O)NC4CCOCC4)c4c(F)ccc(F)c43)ccc21] | 4,7-difluoro-1-((1-methyl-1H-indazol-5-yl)methyl)-N-(tetrahydro-2H-pyran-4-yl)-1H-indole-3-carboxamide | 4,7-difluoro-1-((1-methyl-1H-indazol-5-yl)methyl)-1H-indole-3-carboxylic acid (example A.17) and tetrahydro-pyran-4-yl-amine | 425.3 |
| 95 | 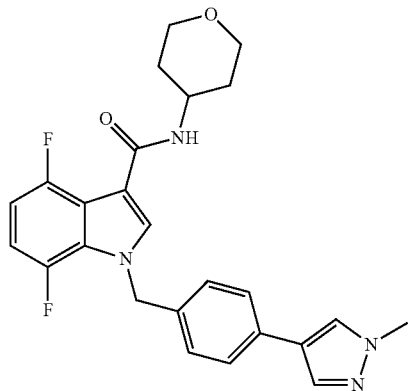 [SMILES: Cn1cc(-c2ccc(Cn3cc(C(=O)NC4CCOCC4)c4c(F)ccc(F)c43)cc2)cn1] | 4,7-difluoro-1-(4-(1-methyl-1H-pyrazol-4-yl)benzyl)-N-(tetrahydro-2H-pyran-4-yl)-1H-indole-3-carboxamide | 4,7-difluoro-1-(4-(1-methyl-1H-pyrazol-4-yl)benzyl)-1H-indole-3-carboxylic acid (example A.18) and tetrahydro-pyran-4-yl-amine | 451.3 |
| 96 | 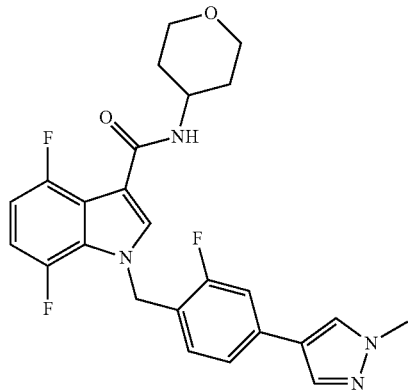 [SMILES: Cn1cc(-c2ccc(Cn3cc(C(=O)NC4CCOCC4)c4c(F)ccc(F)c43)c(F)c2)cn1] | 4,7-difluoro-1-(2-fluoro-4-(1-methyl-1H-pyrazol-4-yl)benzyl)-N-(tetrahydro-2H-pyran-4-yl)-1H-indole-3-carboxamide | 4,7-difluoro-1-(2-fluoro-4-(1-methyl-1H-pyrazol-4-yl)benzyl)-1H-indole-3-carboxylic acid (example A.19) and tetrahydro-pyran-4-yl-amine | 469.3 |

-continued

| Example No. | Structure | Systematic Name | Starting materials | MW found (MH+) |
|---|---|---|---|---|
| 97 | 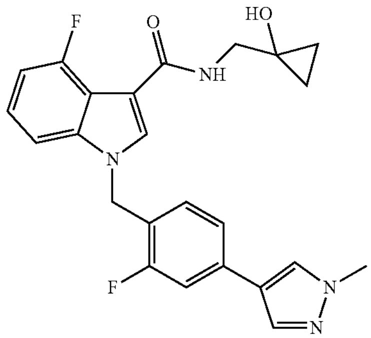 [SMILES: Cn1cc(-c2ccc(Cn3cc(C(=O)NCC4(O)CC4)c4c(F)cccc43)c(F)c2)cn1] | 4-fluoro-1-(2-fluoro-4-(1-methyl-1H-pyrazol-4-yl)benzyl)-N-((1-hydroxycyclopropyl)methyl)-1H-indole-3-carboxamide | 4-fluoro-1-(2-fluoro-4-(1-methyl-1H-pyrazol-4-yl)benzyl)-1H-indole-3-carboxylic acid (example A.1) and (aminomethyl)cyclopropanol | 437.3 |
| 98 | 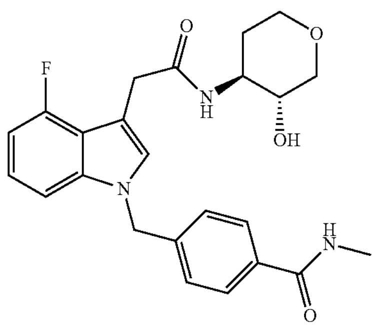 [SMILES: CNC(=O)c1ccc(Cn2cc(CC(=O)N[C@H]3CCOC[C@@H]3O)c3c(F)cccc32)cc1] | 4-((4-fluoro-3-(2-((3R,4S)-3-hydroxytetrahydro-2H-pyran-4-ylamino)-2-oxoethyl)-1H-indol-1-yl)methyl)-N-methylbenzamide | 2-(4-fluoro-1-(4-(methylcarbamoyl)benzyl)-1H-indol-3-yl)acetic acid (example A.20) and 1-(3R,4S)-4-aminotetrahydropyran-3-ol hydrochloride (example C.1) | 440.3 |
| 99 | 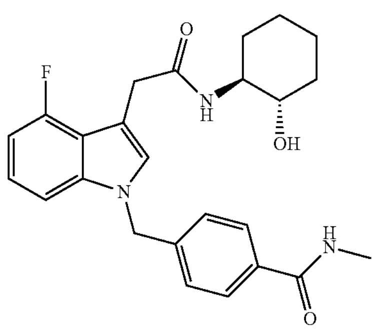 [SMILES: CNC(=O)c1ccc(Cn2cc(CC(=O)N[C@H]3CCCC[C@@H]3O)c3c(F)cccc32)cc1] | 4-((4-fluoro-3-(2-((1S,2S)-2-hydroxycyclohexyl)amino)-2-oxoethyl)-1H-indol-1-yl)methyl)-N-methylbenzamide | 2-(4-fluoro-1-(4-(methylcarbamoyl)benzyl)-1H-indol-3-yl)acetic acid (example A.20) and (3R,4S)-4-aminotetrahydro-2H-pyran-3-ol hydrogen chloride | 438.4 |
| 100 | 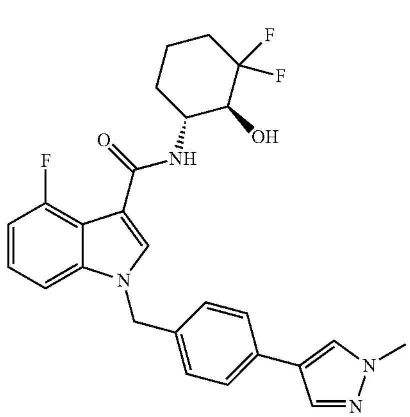 [SMILES: Cn1cc(-c2ccc(Cn3cc(C(=O)N[C@@H]4CCCC(F)(F)[C@H]4O)c4c(F)cccc43)cc2)cn1] | N-((1R,2S)-3,3-difluoro-2-hydroxycyclohexyl)-4-fluoro-1-(4-(1-methyl-1H-pyrazol-4-yl)benzyl)-1H-indole-3-carboxamide | 4-fluoro-1-(4-(1-methyl-1H-pyrazol-4-yl)benzyl)-1H-indole-3-carboxylic acid (example A.9) and (1S,6R)-6-amino-2,2-difluorocyclohexanol (CAS 1109284-40-3) | 483.3 |

| Example No. | Structure | Systematic Name | Starting materials | MW found (MH+) |
|---|---|---|---|---|
| 101 | 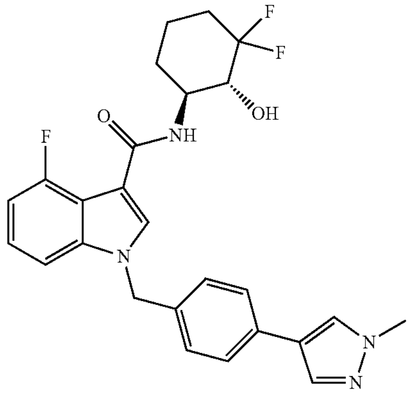 [SMILES: Cn1cc(-c2ccc(Cn3cc(C(=O)N[C@H]4CCCC(F)(F)[C@@H]4O)c4c(F)cccc43)cc2)cn1] | N-((1S,2R)-3,3-difluoro-2-hydroxycyclohexyl)-4-fluoro-1-(4-(1-methyl-1H-pyrazol-4-yl)benzyl)-1H-indole-3-carboxamide | (R)-4-(fluoro-1-(4-(1-methyl-1H-pyrazol-4-yl)benzyl)-1H-indole-3-carboxylic acid (example A.9) and (1R,6S)-6-amino-2,2-difluorocyclohexanol | 483.3 |
| 102 | 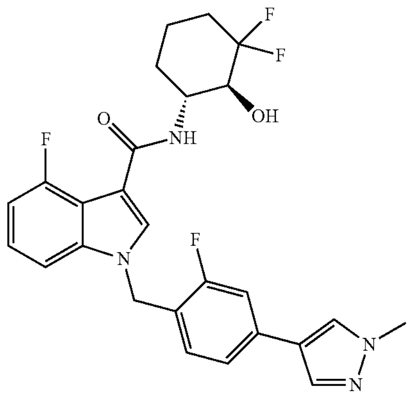 [SMILES: Cn1cc(-c2ccc(Cn3cc(C(=O)N[C@@H]4CCCC(F)(F)[C@H]4O)c4c(F)cccc43)c(F)c2)cn1] | N-((1R,2S)-3,3-difluoro-2-hydroxycyclohexyl)-4-fluoro-1-(2-fluoro-4-(1-methyl-1H-pyrazol-4-yl)benzyl)-1H-indole-3-carboxamide | 4-fluoro-1-(2-fluoro-4-(1-methyl-1H-pyrazol-4-yl)benzyl)-1H-indole-3-carboxylic acid (example A.1) and (1S,6R)-6-amino-2,2-difluorocyclohexanol (CAS 1109284-40-3) | 501.3 |
| 103 | 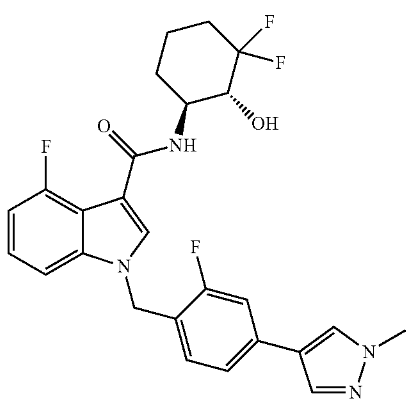 [SMILES: Cn1cc(-c2ccc(Cn3cc(C(=O)N[C@H]4CCCC(F)(F)[C@@H]4O)c4c(F)cccc43)c(F)c2)cn1] | N-((1S,2R)-3,3-difluoro-2-hydroxycyclohexyl)-4-fluoro-1-(2-fluoro-4-(1-methyl-1H-pyrazol-4-yl)benzyl)-1H-indole-3-carboxamide | 4-fluoro-1-(2-fluoro-4-(1-methyl-1H-pyrazol-4-yl)benzyl)-1H-indole-3-carboxylic acid (example A.1) and (1R,6S)-6-amino-2,2-difluorocyclohexanol | 501.3 |

| Example No. | Structure | Systematic Name | Starting materials | MW found (MH+) |
|---|---|---|---|---|
| 104 | 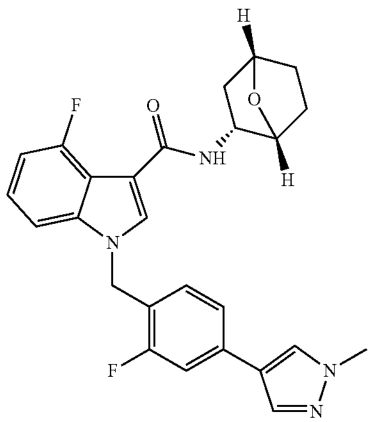 [SMILES: Cn1cc(-c2ccc(Cn3cc(C(=O)N[C@@H]4C[C@@H]5CC[C@H]4O5)c4c(F)cccc43)c(F)c2)cn1] | N-((endo)-7-oxabicyclo[2.2.1]heptan-2-yl)-4-fluoro-1-(2-fluoro-4-(1-methyl-1H-pyrazol-4-yl)benzyl)-1H-indole-3-carboxamide | 4-fluoro-1-(2-fluoro-4-(1-methyl-1H-pyrazol-4-yl)benzyl)-1H-indole-3-carboxylic acid (example A.1) and (endo)-7-oxabicyclo[2.2.1]heptan-2-amine dihydrochloride | 463.2 |
| 105 | 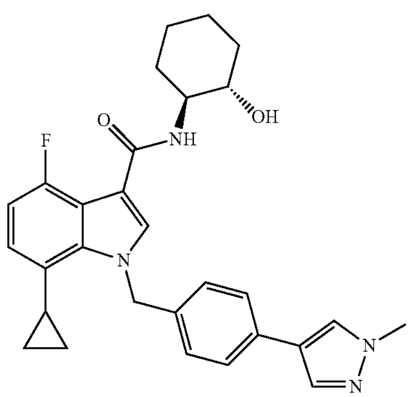 [SMILES: Cn1cc(-c2ccc(Cn3cc(C(=O)N[C@H]4CCCC[C@@H]4O)c4c(F)ccc(C5CC5)c43)cc2)cn1] | 7-cyclopropyl-4-fluoro-N-((1S,2S)-2-hydroxycyclohexyl)-1-(4-(1-methyl-1H-pyrazol-4-yl)benzyl)-1H-indole-3-carboxamide | 7-cyclopropyl-4-fluoro-1-(4-(1-methyl-1H-pyrazol-4-yl)benzyl)-1H-indole-3-carboxylic acid (example A.21) and (3R,4S)-4-aminotetrahydro-2H-pyran-3-ol hydrogen chloride | 487.3 |
| 106 | 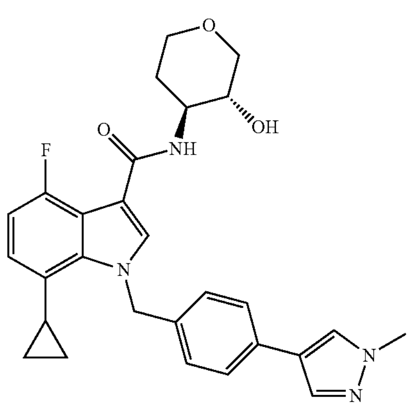 [SMILES: Cn1cc(-c2ccc(Cn3cc(C(=O)N[C@H]4CCOC[C@@H]4O)c4c(F)ccc(C5CC5)c43)cc2)cn1] | 7-cyclopropyl-4-fluoro-N-((3R,4S)-3-hydroxytetrahydro-2H-pyran-4-yl)-1-(4-(1-methyl-1H-pyrazol-4-yl)benzyl)-1H-indole-3-carboxamide | 7-cyclopropyl-4-fluoro-1-(4-(1-methyl-1H-pyrazol-4-yl)benzyl)-1H-indole-3-carboxylic acid (example A.21) and (3R,4S)-4-aminotetrahydropyran-3-ol hydrochloride (example C.1) | 489.3 |

| Example No. | Structure | Systematic Name | Starting materials | MW found (MH+) |
|---|---|---|---|---|
| 107 | 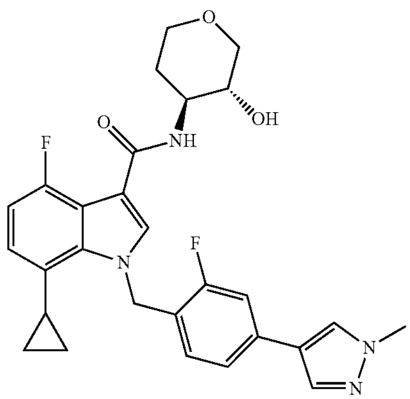 [SMILES: Cn1cc(-c2ccc(Cn3cc(C(=O)N[C@H]4CCOC[C@@H]4O)c4c(F)ccc(C5CC5)c43)c(F)c2)cn1] | 7-cyclopropyl-4-fluoro-1-(2-fluoro-4-(1-methyl-1H-pyrazol-4-yl)benzyl)-N-((3R,4S)-3-hydroxytetrahydro-2H-pyran-4-yl)-1H-indole-3-carboxamide | 7-cyclopropyl-4-fluoro-1-(2-fluoro-4-(1-methyl-1H-pyrazol-4-yl)benzyl)-1H-indole-3-carboxylic acid (example A.22) and (3R,4S)-4-aminotetrahydropyran-3-ol hydrochloride (example C.1) | 507.3 |
| 108 | 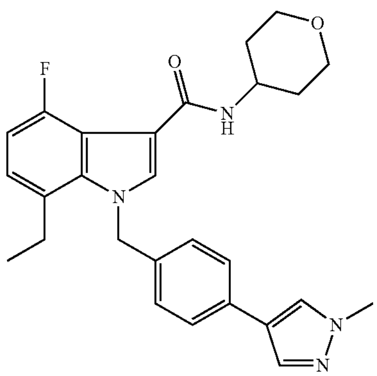 [SMILES: CCc1ccc(F)c2c(C(=O)NC3CCOCC3)cn(Cc3ccc(-c4cnn(C)c4)cc3)c12] | 7-ethyl-4-fluoro-1-(4-(1-methyl-1H-pyrazol-4-yl)benzyl)-N-(tetrahydro-2H-pyran-4-yl)-1H-indole-3-carboxamide | 7-ethyl-4-fluoro-1-(4-(1-methyl-1H-pyrazol-4-yl)benzyl)-1H-indole-3-carboxylic acid (example A.23) and tetrahydro-pyran-4-yl-amine | 461.3 |
| 109 | 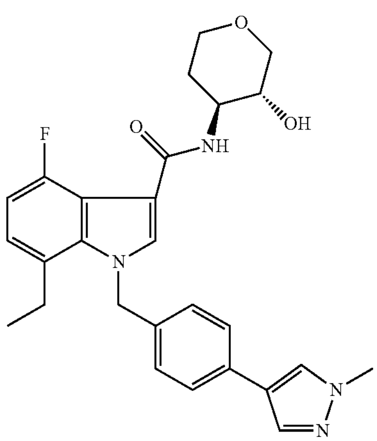 [SMILES: CCc1ccc(F)c2c(C(=O)N[C@H]3CCOC[C@@H]3O)cn(Cc3ccc(-c4cnn(C)c4)cc3)c12] | 7-ethyl-4-fluoro-N-((3R,4S)-3-hydroxytetrahydro-2H-pyran-4-yl)-1-(4-(1-methyl-1H-pyrazol-4-yl)benzyl)-1H-indole-3-carboxamide | 7-ethyl-4-fluoro-1-(4-(1-methyl-1H-pyrazol-4-yl)benzyl)-1H-indole-3-carboyxlic acid (example A.23) and (3R,4S)-4-aminotetrahydropyran-3-ol hydrochloride (example C.1) | 477.3 |
| 110 | 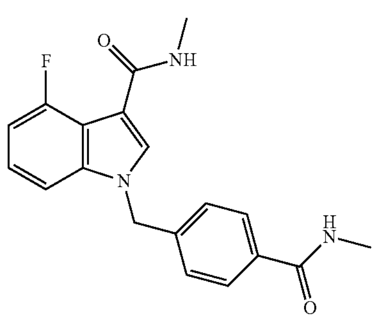 [SMILES: CNC(=O)c1ccc(Cn2cc(C(=O)NC)c3c(F)cccc32)cc1] | 4-fluoro-N-methyl-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and methylamine hydrochloride | 340 |

-continued

| Example No. | Structure | Systematic Name | Starting materials | MW found (MH+) |
|---|---|---|---|---|
| 111 | 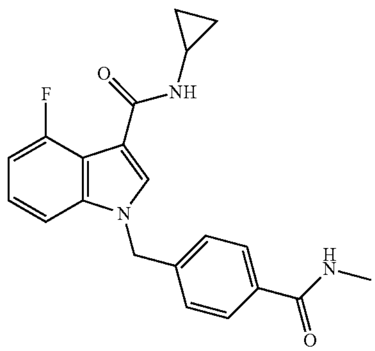 [SMILES: CNC(=O)c1ccc(Cn2cc(C(=O)NC3CC3)c3c(F)cccc32)cc1] | N-cyclopropyl-4-fluoro-1-[[4-(methylcarbamoyl)phenyl]methyl]indol-3-carboxamide | 4-fluoro-1-{[4-(methylcarbamoyl)phenyl]methyl}-1H-indole-3-carboxylic acid (example A.24) and cyclopropylamine | 365.6 |
| 112 | 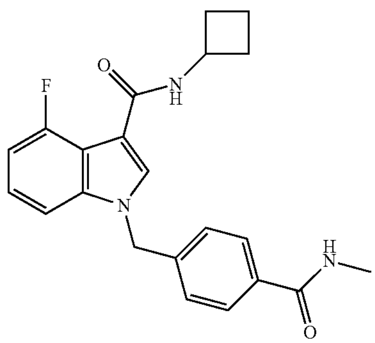 [SMILES: CNC(=O)c1ccc(Cn2cc(C(=O)NC3CCC3)c3c(F)cccc32)cc1] | N-cyclobutyl-4-fluoro-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and cyclobutylamine | 380 |
| 113 | 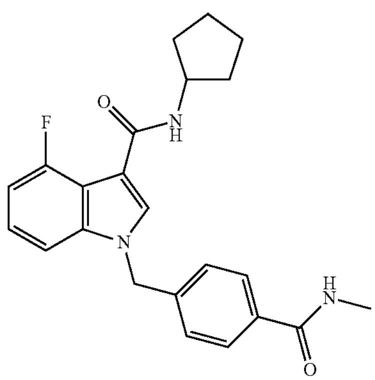 [SMILES: CNC(=O)c1ccc(Cn2cc(C(=O)NC3CCCC3)c3c(F)cccc32)cc1] | N-cyclopentyl-4-fluoro-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and cyclopentylamine | 394 |
| 114 | 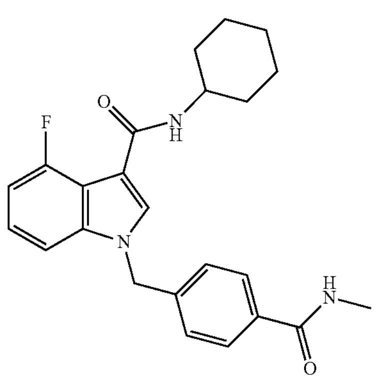 | N-cyclohexyl-4-fluoro-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and cyclohexylamine | 408 |

-continued

| Example No. | Structure | Systematic Name | Starting materials | MW found (MH+) |
|---|---|---|---|---|
| 115 | 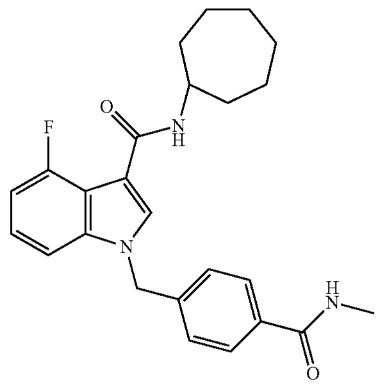 [SMILES: CNC(=O)c1ccc(Cn2cc(C(=O)NC3CCCCCC3)c3c(F)cccc32)cc1] | N-cycloheptyl-4-fluoro-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and cycloheptylamine | 422 |
| 116 | 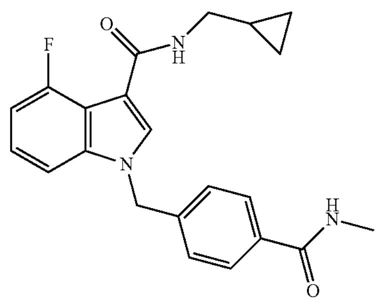 [SMILES: CNC(=O)c1ccc(Cn2cc(C(=O)NCC3CC3)c3c(F)cccc32)cc1] | N-(cyclopropylmethyl)-4-fluoro-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and (cyclopeopylmethyl)amine | 380 |
| 117 | 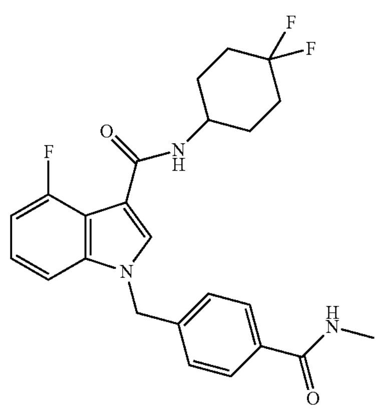 [SMILES: CNC(=O)c1ccc(Cn2cc(C(=O)NC3CCC(F)(F)CC3)c3c(F)cccc32)cc1] | N-(4,4-difluorocyclohexyl)-4-fluoro-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and 4,4-difluorocyclohexan-1-amine | 444 |
| 118 | 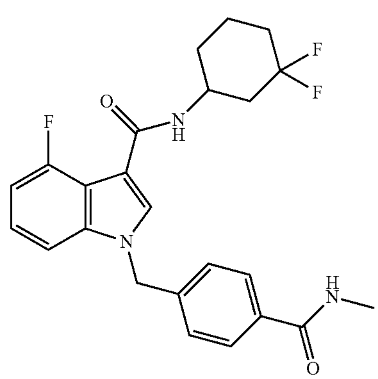 [SMILES: CNC(=O)c1ccc(Cn2cc(C(=O)NC3CCCC(F)(F)C3)c3c(F)cccc32)cc1] | N-(3,3-difluorocyclohexyl)-4-fluoro-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and 3,3-difluorocyclohexan-1-amine hydrochloride | 444 |

-continued

| Example No. | Structure | Systematic Name | Starting materials | MW found (MH+) |
|---|---|---|---|---|
| 119 | 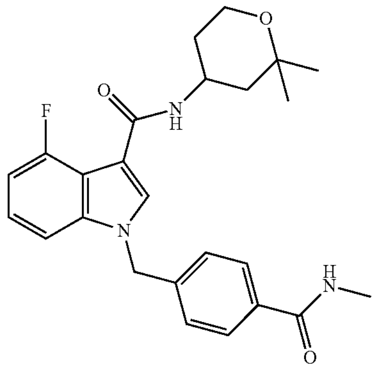 [SMILES: CNC(=O)c1ccc(Cn2cc(C(=O)NC3CCOC(C)(C)C3)c3c(F)cccc32)cc1] | N-(2,2-dimethyloxan-4-yl)-4-fluoro-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and 2,2-dimethyloxan-4-amine | 438 |
| 120 | 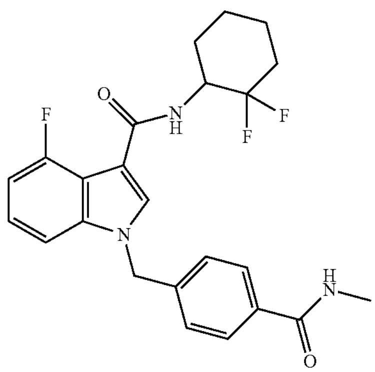 [SMILES: CNC(=O)c1ccc(Cn2cc(C(=O)NC3CCCCC3(F)F)c3c(F)cccc32)cc1] | N-(2,2-difluorocyclohexyl)-4-fluoro-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and 2,2-difluorocyclohexan-1-amine | 444 |
| 121 | 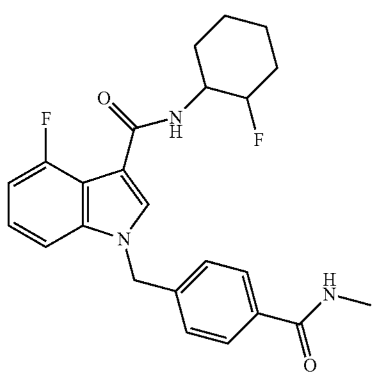 [SMILES: CNC(=O)c1ccc(Cn2cc(C(=O)NC3CCCCC3F)c3c(F)cccc32)cc1] | 4-fluoro-N-(2-fluorocyclohexyl)-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and 2-fluorocyclohexan-1-amine | 426 |
| 122 | 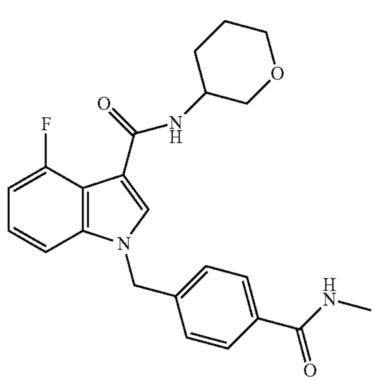 [SMILES: CNC(=O)c1ccc(Cn2cc(C(=O)NC3CCCOC3)c3c(F)cccc32)cc1] | 4-fluoro-1-[[4-(methylcarbamoyl)phenyl]methyl]-N-(oxan-3-yl)indole-3-carboxamide | 4-fluoro-1-{[4-(methylcarbamoyl)phenyl]methyl}-1H-indole-3-carboxylic acid (example A.24) and oxan-3-amine | 410 |

| Example No. | Structure | Systematic Name | Starting materials | MW found (MH+) |
|---|---|---|---|---|
| 123 | 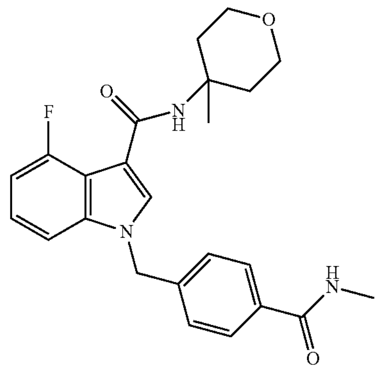 [SMILES: CNC(=O)c1ccc(Cn2cc(C(=O)NC3(C)CCOCC3)c3c(F)cccc32)cc1] | 4-fluoro-1-[[4-(methylcarbamoyl)phenyl]methyl]-N-(4-methyloxan-4-yl)indole-3-carboxamide | 4-fluoro-1-{[4-(methylcarbamoyl)phenyl]methyl}-1H-indole-3-carboxylic acid (example A.24) and 4-methyloxan-4-amine | 424 |
| 124 | 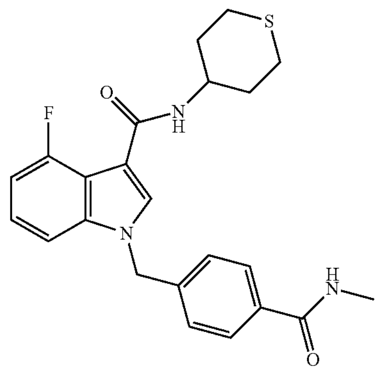 [SMILES: CNC(=O)c1ccc(Cn2cc(C(=O)NC3CCSCC3)c3c(F)cccc32)cc1] | 4-fluoro-1-[[4-(methylcarbamoyl)phenyl]methyl]-N-(thian-4-yl)indole-3-carboxamide | 4-fluoro-1-{[4-(methylcarbamoyl)phenyl]methyl}-1H-indole-3-carboxylic acid (example A.24) and thian-4-amine | 426 |
| 125 | 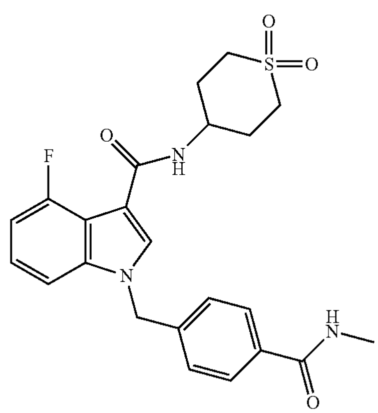 [SMILES: CNC(=O)c1ccc(Cn2cc(C(=O)NC3CCS(=O)(=O)CC3)c3c(F)cccc32)cc1] | N-(1,1-dioxothian-4-yl)-4-fluoro-1-[[4-(methylcarbamoyl)phenyl]methyl]indole-3-carboxamide | 4-fluoro-1-{[4-(methylcarbamoyl)phenyl]methyl}-1H-indole-3-carboxylic acid (example A.24) and 4-aminotetrahydrothiopyrandioxide | 458 |
| 126 | 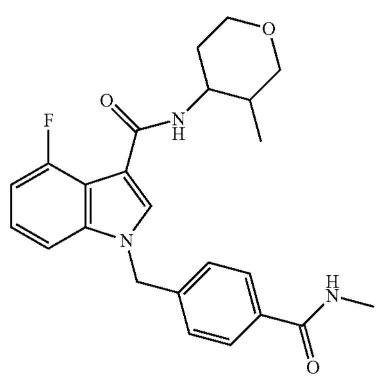 [SMILES: CNC(=O)c1ccc(Cn2cc(C(=O)NC3CCOCC3C)c3c(F)cccc32)cc1] | 4-fluoro-1-[[4-(methylcarbamoyl)phenyl]methyl]-N-(3-methyloxan-4-yl)indole-3-carboxamide | 4-fluoro-1-{[4-(methylcarbamoyl)phenyl]methyl}-1H-indole-3-carboxylic acid (example A.24) and 3-methyloxan-4-amine | 424 |

-continued

| Example No. | Structure | Systematic Name | Starting materials | MW found (MH⁺) |
|---|---|---|---|---|
| 127 | 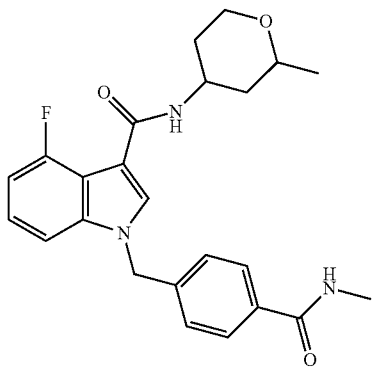 [SMILES: CNC(=O)c1ccc(Cn2cc(C(=O)NC3CCOC(C)C3)c3c(F)cccc32)cc1] | 4-fluoro-1-[[4-(methylcarbamoyl)phenyl]methyl]-N-(2-methyloxan-4-yl)indole-3-carboxamide | 4-fluoro-1-{[4-(methylcarbamoyl)phenyl]methyl}-1H-indole-3-carboxylic acid (example A.24) and 2-methyloxan-4-amine | 424 |
| 128 | 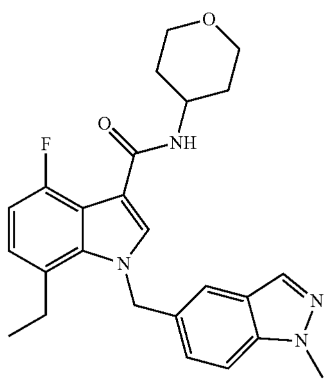 [SMILES: CCc1ccc(F)c2c(C(=O)NC3CCOCC3)cn(Cc3ccc4c(cnn4C)c3)c12] | 7-ethyl-4-fluoro-1-((1-methyl-1H-indazol-5-yl)methyl)-N-(tetrahydro-2H-pyran-4-yl)-1H-indole-3-carboxamide | 7-ethyl-4-fluoro-1-((1-methyl-1H-indazol-5-yl)methyl)-1H-indole-3-carboxylic acid (example A.25) and tetrahydro-pyran-4-yl-amine | 435.4 |
| 129 | 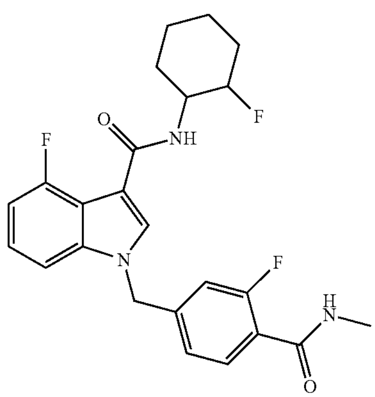 [SMILES: CNC(=O)c1ccc(Cn2cc(C(=O)NC3CCCCC3F)c3c(F)cccc32)cc1F] | 4-fluoro-1-(3-fluoro-4-(methylcarbamoyl)benzyl)-N-(2-fluorocyclohexyl)-1H-indole-3-carboxamide | 4-fluoro-1-(3-fluoro-4-(methylcarbamoyl)benzyl)-1H-indole-3-carboxylic acid (example A.26) and 2-fluorocyclohexan-1-amine | 444.3 |
| 130 | 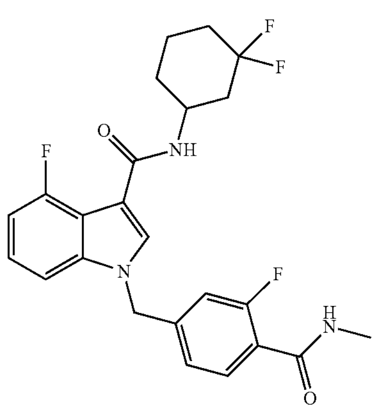 [SMILES: CNC(=O)c1ccc(Cn2cc(C(=O)NC3CCCC(F)(F)C3)c3c(F)cccc32)cc1F] | N-(3,3-difluorocyclohexyl)-4-fluoro-1-(3-fluoro-4-(methylcarbamoyl)benzyl)-1H-indole-3-carboxamide | 4-fluoro-1-(3-fluoro-4-(methylcarbamoyl)benzyl)-1H-indole-3-carboxylic acid (example A.26) and 3,3-difluorocyclohexan-1-amine hydrochloride | 462.3 |

Examples 131 to 154

In analogy to example 26, examples 131 to 154 of the following table were prepared by reaction of the indicated amides with an alkylating agent.

| Example No. | Structure | Systematic Name | Starting materials | MW found (MH+) |
|---|---|---|---|---|
| 131 | 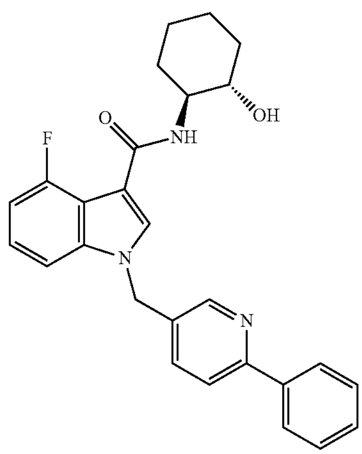 [SMILES: O=C(N[C@H]1CCCC[C@@H]1O)c1cn(Cc2ccc(-c3ccccc3)nc2)c2cccc(F)c12] | 4-fluoro-N-((1S,2S)-2-hydroxycyclohexyl)-1-((6-phenylpyridin-3-yl)methyl)-1H-indole-3-carboxamide | 4-fluoro-N-((1S,2S)-2-hydroxycyclohexyl)-1H-indole-3-carboxamide (example A.6) and 2-chloromethyl-5-phenylpyridine (CAS 146775-28-2) | 444.4 |
| 132 | 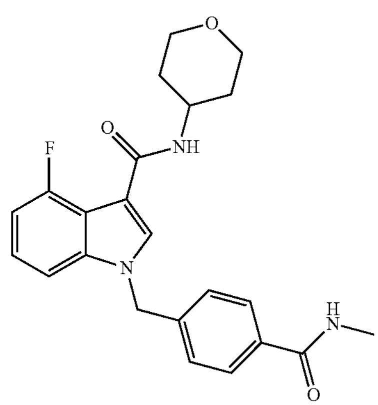 [SMILES: CNC(=O)c1ccc(Cn2cc(C(=O)NC3CCOCC3)c3c(F)cccc32)cc1] | 4-fluoro-1-(4-(methylcarbamoyl)benzyl)-N-(tetrahydro-2H-pyran-4-yl)-1H-indole-3-carboxamide | 4-Fluoro-N-(tetrahydro-2H-pyran-4-yl)-1H-indole-3-carboxamide (example A.8) and 4-(chloromethyl)-N-methylbenzamide (example B.6) | 410.3 |
| 133 | 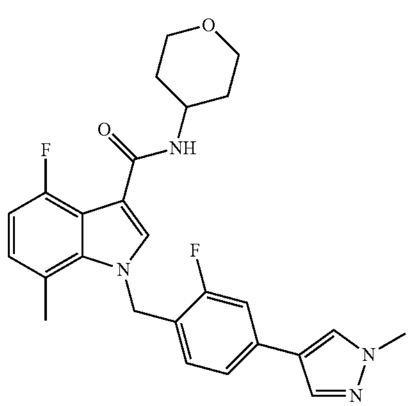 [SMILES: Cc1ccc(F)c2c(C(=O)NC3CCOCC3)cn(Cc3ccc(-c4cnn(C)c4)cc3F)c12] | 4-fluoro-1-(2-fluoro-4-(1-methyl-1H-pyrazol-4-yl)benzyl)-7-methyl-N-(tetrahydro-2H-pyran-4-yl)-1H-indole-3-carboxamide | 4-fluoro-7-methyl-1H-indole-3-carboxylic acid (tetrahydro-pyran-3-yl)-amide (example A.11) and 4-(4-(Chloromethyl)-3-fluorophenyl)-1-methyl-1H-pyrazole (example B.2) | 465.3 |

| Example No. | Structure | Systematic Name | Starting materials | MW found (MH+) |
|---|---|---|---|---|
| 134 | 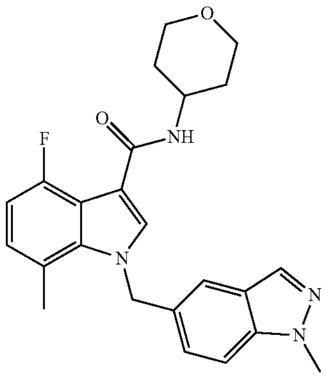 [SMILES: Cc1ccc(F)c2c(C(=O)NC3CCOCC3)cn(Cc3ccc4c(cnn4C)c3)c12] | 4-fluoro-7-methyl-1-((1-methyl-1H-indazol-5-yl)methyl)-N-(tetrahydro-2H-pyran-4-yl)-1H-indole-3-carboxamide | 4-fluoro-7-methyl-1H-indole-3-carboxylic acid (tetrahydro-pyran-3-yl)-amide (example A.11) and 5-methyl-1H-indazole hydrobromide | 421.3 |
| 135 | 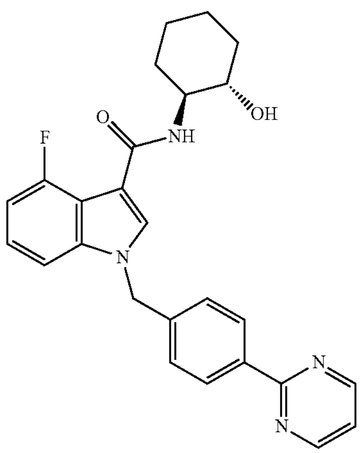 [SMILES: O=C(N[C@H]1CCCC[C@@H]1O)c1cn(Cc2ccc(-c3ncccn3)cc2)c2cccc(F)c12] | 4-fluoro-N-((1S,2S)-2-hydroxycyclohexyl)-1-(4-(pyrimidin-2-yl)benzyl)-1H-indole-3-carboxamide | 4-Fluoro-N-((1S,2S)-2-hydroxycyclohexyl)-1H-indole-3-carboxamide (example A.6) and 2-[4-(chloromethyl)phenyl]pyrimidine | 445.3 |
| 136 | 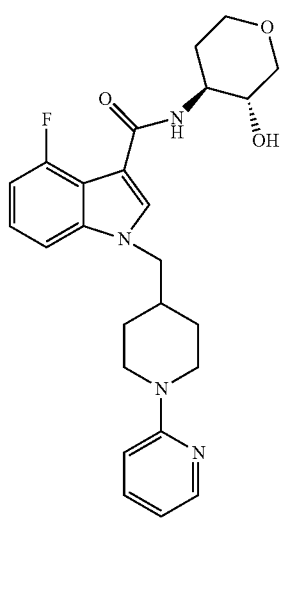 [SMILES: O=C(N[C@H]1CCOC[C@@H]1O)c1cn(CC2CCN(c3ccccn3)CC2)c2cccc(F)c12] | 4-fluoro-N-((3R,4S)-3-hydroxytetrahydro-2H-pyran-4-yl)-1-((1-(pyridin-2-yl)piperidin-4-yl)methyl)-1H-indole-3-carboxamide | 4-Fluoro-N-((3R,4S)-3-hydroxytetrahydro-2H-pyran-4-yl)-1H-indole-3-carboxamide (example A.34) and [1-(2-pyridyl)-4-piperidyl]methyl methanesulfonate (CAS 199117-81-2) | 453.3 |

| Example No. | Structure | Systematic Name | Starting materials | MW found (MH+) |
|---|---|---|---|---|
| 137 | 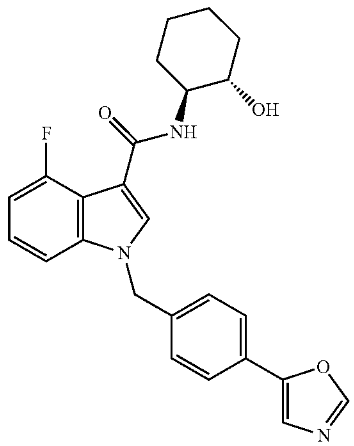 [SMILES: O=C(N[C@H]1CCCC[C@@H]1O)c1cn(Cc2ccc(-c3cnco3)cc2)c2cccc(F)c12] | 4-fluoro-N-((1S,2S)-2-hydroxycyclohexyl)-1-(4-(oxazol-5-yl)benzyl)-1H-indole-3-carboxamide | 4-Fluoro-N-((1S,2S)-2-hydroxycyclohexyl)-1H-indole-3-carboxamide (example A.6) and 5-(4-bromomethyl-phenyl)-oxazole (example B.8) | 434.3 |
| 138 | 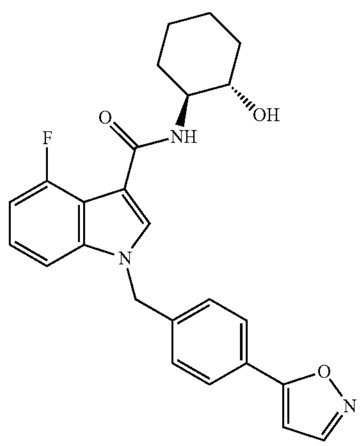 [SMILES: O=C(N[C@H]1CCCC[C@@H]1O)c1cn(Cc2ccc(-c3ccno3)cc2)c2cccc(F)c12] | 4-fluoro-N-((1S,2S)-2-hydroxycyclohexyl)-1-(4-(isoxazol-5-yl)benzyl)-1H-indole-3-carboxamide | 4-Fluoro-N-((1S,2S)-2-hydroxycyclohexyl)-1H-indole-3-carboxamide (example A.6) and 5-(4-bromomethyl-phenyl)-isoxazole (CAS 169547-50-6) | 434.3 |
| 139 | 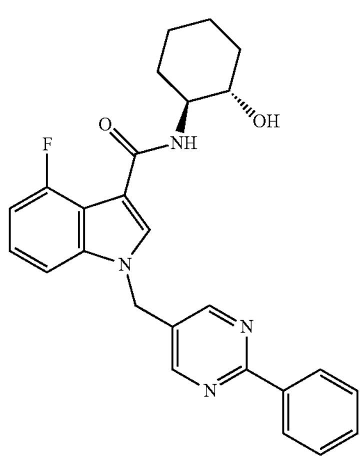 [SMILES: O=C(N[C@H]1CCCC[C@@H]1O)c1cn(Cc2cnc(-c3ccccc3)nc2)c2cccc(F)c12] | 4-fluoro-N-((1S,2S)-2-hydroxycyclohexyl)-1-((2-phenylpyrimidin-5-yl)methyl)-1H-indole-3-carboxamide | 4-Fluoro-N-((1S,2S)-2-hydroxycyclohexyl)-1H-indole-3-carboxamide (example A.6) and 5-(chloromethyl)-2-phenyl-pyrimidine | 445.3 |

| Example No. | Structure | Systematic Name | Starting materials | MW found (MH+) |
|---|---|---|---|---|
| 140 | 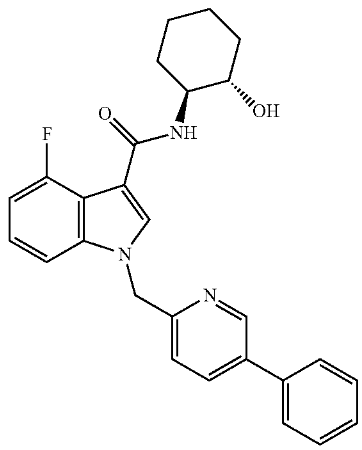 [SMILES: O=C(N[C@H]1CCCC[C@@H]1O)c1cn(Cc2ccc(-c3ccccc3)cn2)c2cccc(F)c12] | 4-fluoro-N-((1S,2S)-02-hydroxycyclohexyl)-1-((5-phenylpyridin-2-yl)methyl)-1H-indole-3-carboxamideyl)benzyl)-1H-indole-3-carboxamide | 4-Fluoro-N-((1S,2S)-2-hydroxycyclohexyl)-1H-indole-3-carboxamide (example A.6) and 2-chloromethyl-5-phenylpyridine (CAS 146775-28-2) | 444.3 |
| 141 | 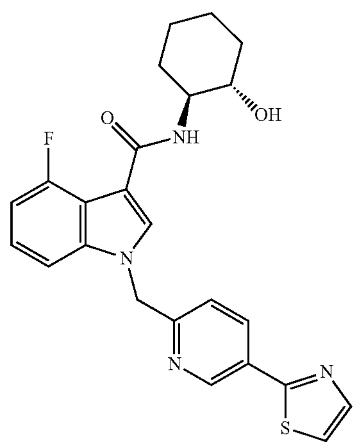 [SMILES: O=C(N[C@H]1CCCC[C@@H]1O)c1cn(Cc2ccc(-c3nccs3)cn2)c2cccc(F)c12] | 4-fluoro-N-((1S,2S)-2-hydroxycyclohexyl)-1-((5-(thiazol-2-yl)pyridin-2-yl)methyl)-1H-indole-3-carboxamide | 4-Fluoro-N-((1S,2S)-2-hydroxycyclohexyl)-1H-indole-3-carboxamide (example A.6) and 2-(4-(chloromethyl)phenyl)thiazole (example B.9) | 451.3 |
| 142 | 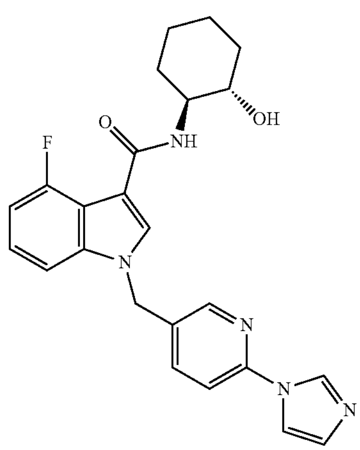 [SMILES: O=C(N[C@H]1CCCC[C@@H]1O)c1cn(Cc2ccc(-n3ccnc3)nc2)c2cccc(F)c12] | 1-((6-(1H-imidazol-1-yl)pyridin-3-yl)methyl)-4-fluoro-N-((1S,2S)-2-hydroxycyclohexyl)-1H-indole-3-carboxamide | 4-Fluoro-N-((1S,2S)-2-hydroxycyclohexyl)-1H-indole-3-carboxamide (example A.6) and 5-(chloromethyl)-2-(1H-imidazol-1-yl)pyridine | 434.2 |

-continued

| Example No. | Structure | Systematic Name | Starting materials | MW found (MH+) |
|---|---|---|---|---|
| 143 | 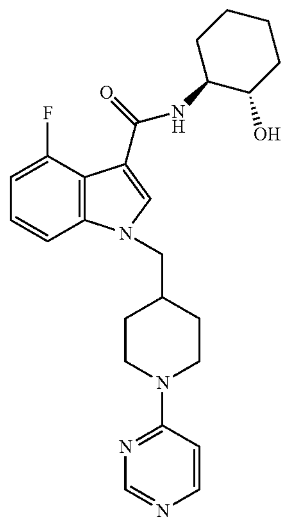 [SMILES: O=C(N[C@H]1CCCC[C@@H]1O)c1cn(CC2CCN(c3ccncn3)CC2)c2cccc(F)c12] | 4-fluoro-N-((1S,2S)-2-hydroxycyclohexyl)-1-((1-(pyrimidin-4-yl)piperidin-4-yl)methyl)-1H-indole-3-carboxamide | 4-Fluoro-N-((1S,2S)-2-hydroxycyclohexyl)-1H-indole-3-carboxamide (example A.6) and (1-(pyrimidin-4-yl)piperidin-4-yl)methyl methanesulfonate (example B.10) | 452.4 |
| 144 | 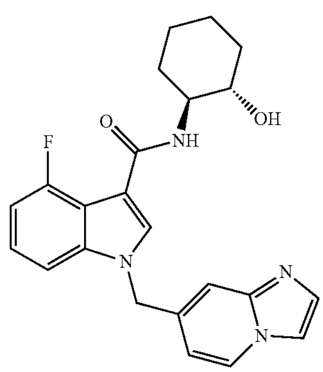 [SMILES: O=C(N[C@H]1CCCC[C@@H]1O)c1cn(Cc2ccn3ccnc3c2)c2cccc(F)c12] | 4-fluoro-N-((1S,2S)-2-hydroxycyclohexyl)-1-(imidazo[1,2-a]pyridin-7-ylmethyl)-1H-indole-3-carboxamide | 4-Fluoro-N-((1S,2S)-2-hydroxycyclohexyl)-1H-indole-3-carboxamide (example A.6) and 7-(chloromethyl)imidazo[1,2-a]pyridine | 407.3 |
| 145 | 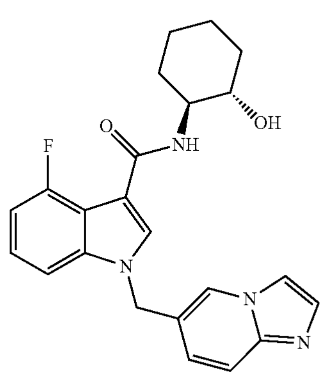 [SMILES: O=C(N[C@H]1CCCC[C@@H]1O)c1cn(Cc2ccc3nccn3c2)c2cccc(F)c12] | 4-fluoro-N-((1S,2S)-2-hydroxycyclohexyl)-1-(imidazo[1,2-a]pyridin-6-ylmethyl)-1H-indole-3-carboxamide | 4-Fluoro-N-((1S,2S)-2-hydroxycyclohexyl)-1H-indole-3-carboxamide (example A.6) and 6-(chloromethyl)imidazo[1,2-a]pyridine hydrochloride | 407.3 |

-continued

| Example No. | Structure | Systematic Name | Starting materials | MW found (MH+) |
|---|---|---|---|---|
| 146 | 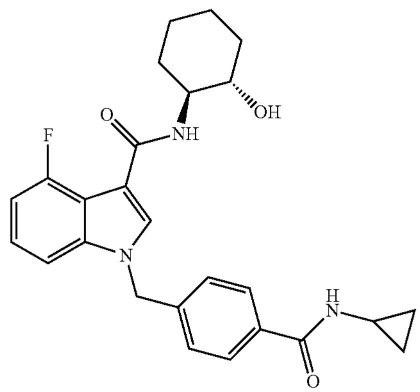 [SMILES: O=C(NC1CC1)c1ccc(Cn2cc(C(=O)N[C@H]3CCCC[C@@H]3O)c3c(F)cccc32)cc1] | 1-(4-(cyclopropylcarbamoyl)benzyl)-4-fluoro-N-((1S,2S)-2-hydroxycyclohexyl)-1H-indole-3-carboxamide | 4-Fluoro-N-((1S,2S)-2-hydroxycyclohexyl)-1H-indole-3-carboxamide (example A.6) and 4-chloromethyl-N-cyclopropyl-benzamide (CAS 873371-67-6) | 450.2 |
| 147 | 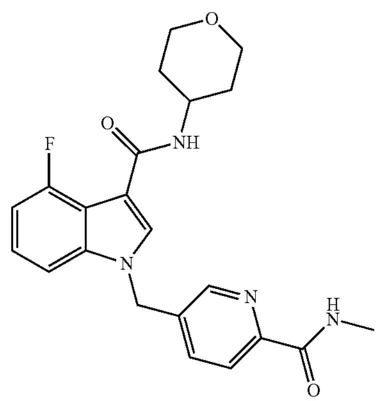 [SMILES: CNC(=O)c1ccc(Cn2cc(C(=O)NC3CCOCC3)c3c(F)cccc32)cn1] | 4-fluoro-1-((6-(methylcarbamoyl)pyridin-3-yl)methyl)-N-(tetrahydro-2H-pyran-4-yl)-1H-indole-3-carboxamide | 4-fluoro-N-(tetrahydro-2H-pyran-4-yl)-1H-indole-3-carboxamide (example A.8) and 5-(chloromethyl)-N-methylpicolinamide (example B.11) | 411.2 |
| 148 | 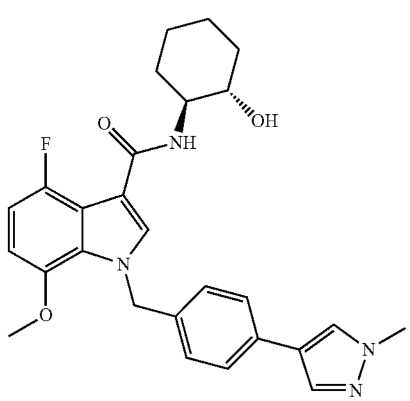 [SMILES: COc1ccc(F)c2c(C(=O)N[C@H]3CCCC[C@@H]3O)cn(Cc3ccc(-c4cnn(C)c4)cc3)c12] | 4-fluoro-N-((1S,2S)-2-hydroxycyclohexyl)-7-methoxy-1-(4-(1-methyl-1H-pyrazol-4-yl)benzyl)-1H-indole-3-carboxamide | 4-fluoro-N-((1S,2S)-2-hydroxycyclohexyl)-7-methoxy-1H-indole-3-carboxamide (example A.27) and 5-(chloromethyl)-2-(1-mehtyl-1H-pyrazol-4-yl)pyridine (example B.1) | 477.3 |
| 149 | 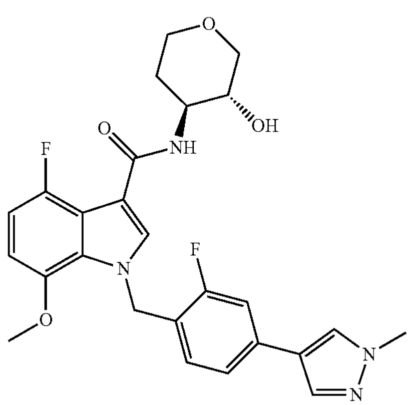 [SMILES: COc1ccc(F)c2c(C(=O)N[C@H]3CCOC[C@@H]3O)cn(Cc3ccc(-c4cnn(C)c4)cc3F)c12] | 4-fluoro-1-(2-fluoro-4-(1-methyl-1H-pyrazol-4-yl)benzyl)-N-((1S,2S)-2-hydroxycyclohexyl)-7-methoxy-1H-indole-3-carboxamide | 4-fluoro-N-((1S,2S)-2-hydroxycyclohexyl)-7-methoxy-1H-indole-3-carboxamide (example A.27) and 4-(4-(chloromethyl)-3-fluorophenyl)-1-methyl-1H-pyrazole (example B.2) | 495.2 |

-continued

| Example No. | Structure | Systematic Name | Starting materials | MW found (MH+) |
|---|---|---|---|---|
| 150 | 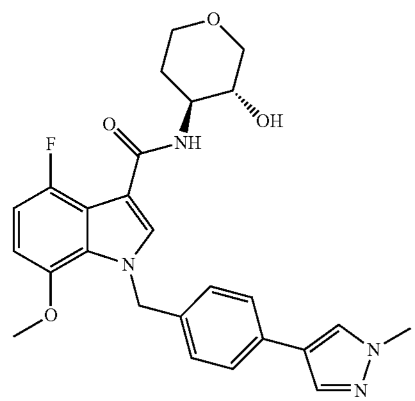 [SMILES: COc1ccc(F)c2c(C(=O)N[C@H]3CCOC[C@@H]3O)cn(Cc3ccc(-c4cnn(C)c4)cc3)c12] | 4-fluoro-N-((3R,4S)-3-hydroxytetrahydro-2H-pyran-4-yl)-7-methoxy-1-(4-(1-methyl-1H-pyrazol-4-yl)benzyl)-1H-indole-3-carboxamide | 4-fluoro-N-((3R,4S)-3-hydroxytetrahydro-2H-pyran-4-yl)-7-methoxy-1H-indole-3-carboxamide (example A.28) and 5-(chloromethyl)-2-(1-methyl-1H-pyrazol-4-yl)pyridine (example B.1) | 479.2 |
| 151 | 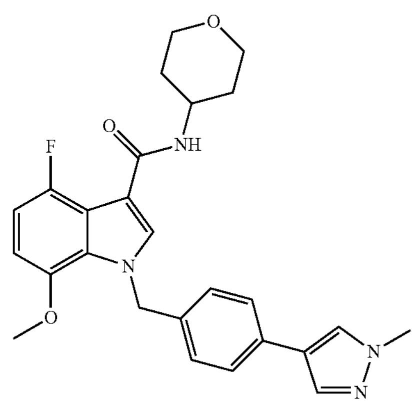 [SMILES: COc1ccc(F)c2c(C(=O)NC3CCOCC3)cn(Cc3ccc(-c4cnn(C)c4)cc3)c12] | 4-fluoro-7-methoxy-1-(4-(1-methyl-1H-pyrazol-4-yl)benzyl)-N-(tetrahydro-2H-pyran-4-yl)-1H-indole-3-carboxamide | 4-fluoro-7-methoxy-N-(tetrahydro-2H-pyran-4-yl)-1H-indole-3-carboxamide (example A.29) and 5-(chloromethyl)-2-(1-methyl-1H-pyrazol-4-yl)pyridine (example B.1) | 463.2 |
| 152 | 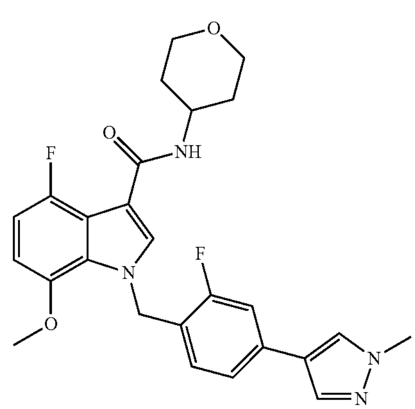 [SMILES: COc1ccc(F)c2c(C(=O)NC3CCOCC3)cn(Cc3ccc(-c4cnn(C)c4)cc3F)c12] | 4-fluoro-1-(2-fluoro-4-(1-methyl-1H-pyrazol-4-yl)benzyl)-7-methoxy-N-(tetrahydro-2H-pyran-4-yl)-1H-indole-3-carboxamide | 4-fluoro-7-methoxy-N-(tetrahydro-2H-pyran-4-yl)-1H-indole-3-carboxamide (example A.29) and 4-(4-(chloromethyl)-3-fluorophenyl)-1-methyl-1H-pyrazole (example B.2) | 481.2 |

-continued

| Example No. | Structure | Systematic Name | Starting materials | MW found (MH+) |
|---|---|---|---|---|
| 153 | 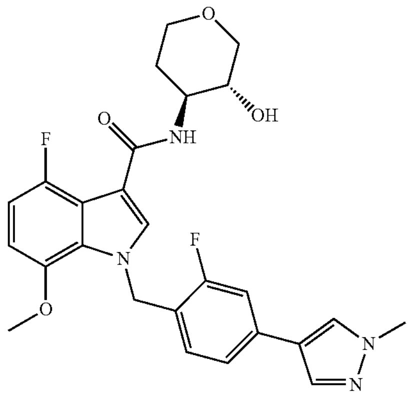 [SMILES: COc1ccc(F)c2c(C(=O)N[C@H]3CCOC[C@@H]3O)cn(Cc3ccc(-c4cnn(C)c4)cc3F)c12] | 4-fluoro-1-(2-fluoro-4-(1-methyl-1H-pyrazol-4-yl)benzyl)-N-((3R,4S)-3-hydroxytetrahydro-2H-pyran-4-yl)-7-methoxy-1H-indole-3-carboxamide | 4-fluoro-N-((3R,4S)-3-hydroxytetrahydro-2H-pyran-4-yl)-7-methoxy-1H-indole-3-carboxamide (example A.28) and 4-(4-(chloromethyl)-3-fluorophenyl)-1-methyl-1H-pyrazole (example B.2) | 497.2 |
| 154 | 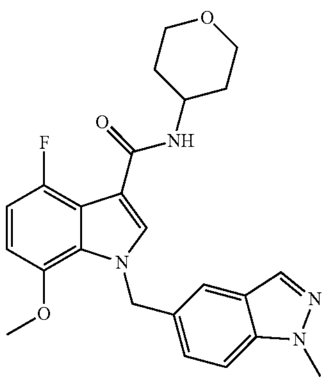 [SMILES: COc1ccc(F)c2c(C(=O)NC3CCOCC3)cn(Cc3ccc4c(cnn4C)c3)c12] | 4-fluoro-7-methoxy-1-((1-methyl-1H-indazol-5-yl)methyl)-N-(tetrahydro-2H-pyran-4-yl)-1H-indole-3-carboxamide | 4-fluoro-7-methoxy-N-(tetrahydro-2H-pyran-4-yl)-1H-indole-3-carboxamide (example A.29) and 5-(bromomethyl)-1-methyl-1H-indazole hydrobromide | 437.2 |

Example 155

1-(4-(1H-Pyrazol-5-yl)benzyl)-4-fluoro-N-((1S,2S)-2-hydroxycyclohexyl)-1H-indole-3-carboxamide Step 1: 4-Fluoro-N-((1S,2S)-2-hydroxycyclohexyl)-1-(4-(1-(4-methoxybenzyl)-1H-pyrazol-5-yl)benzyl)-1H-indole-3-carboxamide In analogy to the procedure described for the synthesis of example 26, the title compound was prepared from 4-fluoro-N-((1S,2S)-2-hydroxycyclohexyl)-1H-indole-3-carboxamide (example A.6) and 5-(4-(chloromethyl)phenyl)-1-(4-methoxybenzyl)-1H-pyrazole (example B.12). White solid. MS (m/e): 553.5 (M+H)+.

Step 2: 1-(4-(1H-pyrazol-5-yl)benzyl)-4-fluoro-N41S,2S)-2-hydroxycyclohexyl)-1H-indole-3-carboxamide A mixture of 4-fluoro-N-((1S,2S)-2-hydroxycyclohexyl)-1-(4-(1-(4-methoxybenzyl)-1H-pyrazol-5-yl)benzyl)-1H-indole-3-carboxamide (95 mg, 172 μmol) and 10% palladium on activated charcoal (91.5 mg, 86.0 μmol) at room temperature in EtOH (3 ml) and acetic acid (3.00 ml) was stirred under a hydrogen atmosphere (balloon pressure) for 17 hours. The catalyst was filtered and rinsed with EtOH. The filtrate was concentrated and the residue was purified with flash column chromatography on silica eluting with a gradient formed from dichloromethane and methanol (0 to 5%) to provide the title compound as a white solid (11.9 mg, 16%). MS (m/e): 433.3 (M+H)+.

Examples 156 and 157

In analogy to the procedures described for the synthesis of example 155, examples 156 and 157 of the following table were prepared by the reaction of the indicated amides with an alkylating agent, followed by hydrogenation.

| Example No. | Structure | Systematic Name | Starting materials | MW found (MH+) |
|---|---|---|---|---|
| 156 | 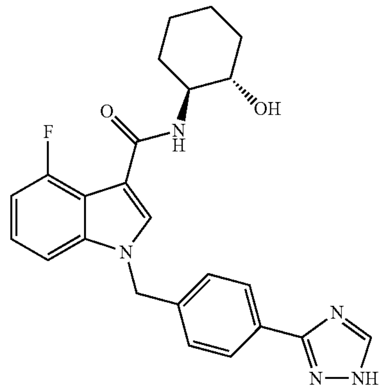 [SMILES: O=C(N[C@H]1CCCC[C@@H]1O)c1cn(Cc2ccc(-c3nc[nH]n3)cc2)c2cccc(F)c12] | 1-(4-(1H-1,2,4-triazol-3-yl)benzyl)-4-fluoro-N-((1S,2S)-2-hydroxycyclohexyl)-1H-indole-3-carboxamide | 4-fluoro-N-((1S,2S)-2-hydroxycyclohexyl)-1H-indole-3-carboxamide (example A.6) and 3-(4-(chloromethyl)phenyl)-1-(4-methoxybenzyl)-1H-1,2,4-triazole (example B.13) | 433.5 |
| 157 | 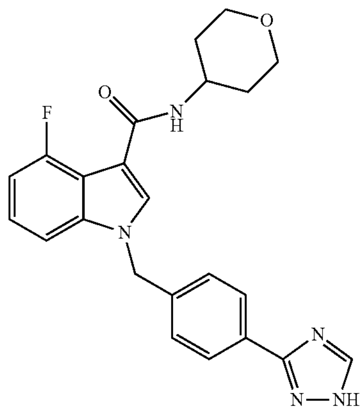 [SMILES: O=C(NC1CCOCC1)c1cn(Cc2ccc(-c3nc[nH]n3)cc2)c2cccc(F)c12] | 1-(4-(1H-1,2,4-triazol-3-yl)benzyl)-4-fluoro-N-(tetrahydro-2H-pyran-4-yl)-1H-indole-3-carboxamide | 4-Fluoro-N-(tetrahydro-2H-pyran-4-yl)-1H-indole-3-carboxamide (example A.8) and 3-(4-(chloromethyl)phenyl)-1-(4-methoxybenzyl)-1H-1,2,4-triazole (example B.13) | 420.3 |

Example 158

4-Fluoro-N-((1S,2S)-2-hydroxycyclohexyl)-1-(4-(pyrimidin-5-yl)benzyl)-1H-indole-3-carboxamide

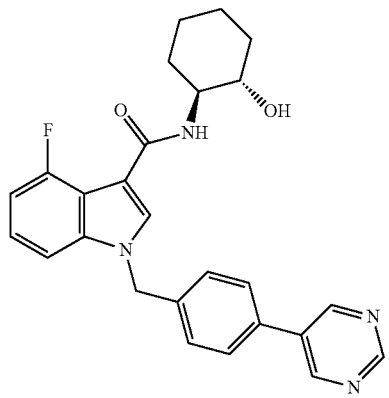 [SMILES: O=C(N[C@H]1CCCC[C@@H]1O)c1cn(Cc2ccc(-c3cncnc3)cc2)c2cccc(F)c12]

To a solution of 1-(4-bromobenzyl)-4-fluoro-N41S,2S)-2-hydroxycyclohexyl)-1H-indole-3-carboxamide (example A.30) (0.1 g, 225 μmol) and pyrimidin-5-ylboronic acid (41.7 mg, 337 μmol) in 1,2-dimethoxyethane (2 ml) under argon was added cesium carbonate (146 mg, 449 μmol), water (0.2 ml) and tetrakis(triphenylphosphine)palladium(0) (7.78 mg, 6.74 μmol). The mixture was stirred at 90° C. for 17 hours, cooled to room temperature and filtered. The cake was rinsed with dchloromethane. The filtrate was concentrated and the residue was purified with flash column chromatography on silica eluting with a gradient formed from dichloromethane and methanol (0 to 5%) to provide the title compound as a white solid (48.3 mg, 43%). MS (m/e): 445.3 (M+H)+.

Example 159

4-Fluoro-N-((1S,2S)-2-hydroxycyclohexyl)-1-(4-(pyridin-3-yl)benzyl)-1H-indole-3-carboxamide

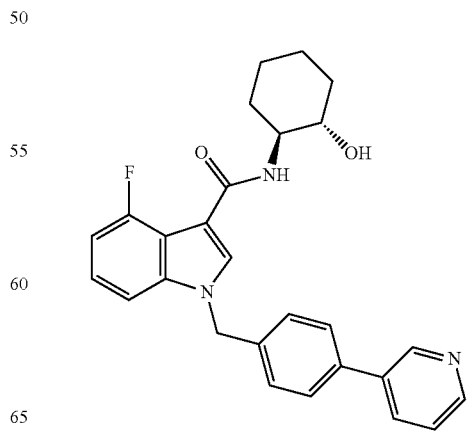

In analogy to the procedure described for the synthesis of example 158, the title compound was prepared by the reaction of 1-(4-bromobenzyl)-4-fluoro-N-((1S,2S)-2-hydroxycyclohexyl)-1H-indole-3-carboxamide (example A.30) and pyridin-3-ylboronic acid. Off-white solid. MS (m/e): 444.3 (M+H)⁺.

Example 160

4-Fluoro-N-((1S,2S)-2-hydroxycyclohexyl)-1-((1-(pyridin-2-yl)piperidin-4-yl)methyl)-1H-indole-3-carboxamide

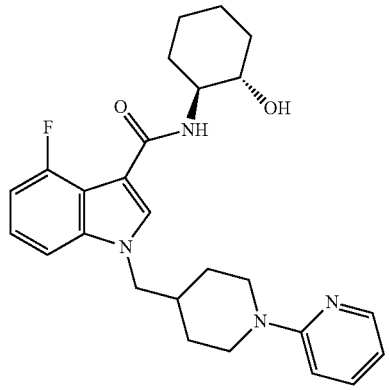 [SMILES: O=C(N[C@H]1CCCC[C@@H]1O)c1cn(CC2CCN(c3ccccn3)CC2)c2cccc(F)c12]

To a stirred mixture of 4-fluoro-N-((1S,2S)-2-hydroxycyclohexyl)-1-(piperidin-4-ylmethyl)-1H-indole-3-carboxamide (example A.31) (150 mg, 402 µmol), 2-bromopyridine (63.5 mg, 38.5 µl, 402 µmol), potassium carbonate (99.9 mg, 723 µmo) and water (15.2 mg, 15.2 µl, 843 µmol) in xylene (9 ml) at room temperature under argon were added palladium(II) acetate (3.61 mg, 16.1 µmol) and 9,9-dimethyl-4,5-bis(diphenylphosphino)xanthene (11.6 mg, 20.1 µmol). The reaction mixture was degassed and back-filled with argon (3 times). The mixture was then heated to 140° C. for 17 hours, cooled to room temperature, diluted with dichloromethane, stirred at room temperature for 5 min and filtered. The filtrate was concentrated and the residue was purified with flash column chromatography on silica eluting with a gradient formed from dichloromethane and methanol (0 to 5%) to provide the title compound as an off-white solid (27 mg, 15%). MS (m/e): 451.3 (M+H)⁺.

Example 161 and 162

In analogy to the procedure described for the synthesis of example 160, examples 161 and 162 of the following table were prepared.

| Example No. | Structure | Systematic Name | Starting materials | MW found (MH⁺) |
|---|---|---|---|---|
| 161 | 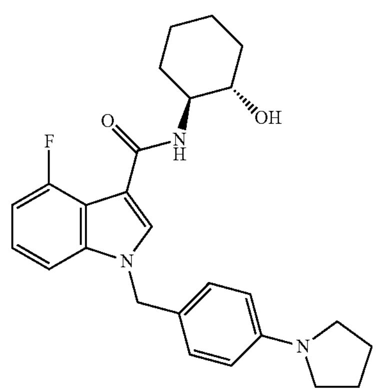 [SMILES: O=C(N[C@H]1CCCC[C@@H]1O)c1cn(Cc2ccc(N3CCCC3)cc2)c2cccc(F)c12] | 4-fluoro-N-((1S,2S)-2-hydroxycyclohexyl)-1-(4-(pyrrolidin-1-yl)benzyl)-1H-indole-3-carboxamide | 1-(4-bromobenzyl)-4-fluoro-N-((1S,2S)-2-hydroxycyclohexyl)-1H-indole-3-carboxamide (example A.30) and pyrrolidine | 436.4 |
| 162 | 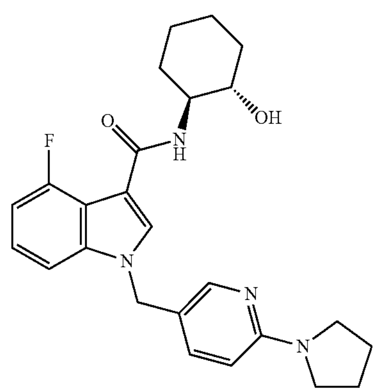 [SMILES: O=C(N[C@H]1CCCC[C@@H]1O)c1cn(Cc2ccc(N3CCCC3)nc2)c2cccc(F)c12] | 4-fluoro-N-((1S,2S)-2-hydroxycyclohexyl)-1-((6-(pyrrolidin-1-yl)pyridin-3-yl)methyl)-1H-indole-3-carboxamide | 1-((6-bromopyridin-3-yl)methyl)-4-fluoro-N-((1S,2S)-2-hydroxycyclohexyl)-1H-indole-3-carboxamide (example A.32) and pyrrolidine | 437.4 |

Example 163

4-Fluoro-1-(3-fluoro-4-(methylcarbamoyl)benzyl)-N-(tetrahydro-2H-pyran-4-yl)-1H-indole-3-carboxamide

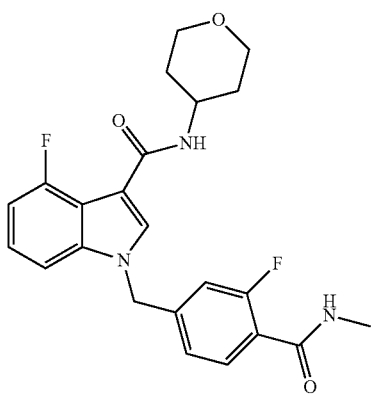 [SMILES: CNC(=O)c1ccc(Cn2cc(C(=O)NC3CCOCC3)c3c(F)cccc32)cc1F]

The title compound was obtained in analogy to the procedure described in example 86, reacting methyl 2-fluoro-4-((4-fluoro-3-(tetrahydro-2H-pyran-4-ylcarbamoyl)-1H-indol-1-yl)methyl)benzoate (example A.33) and methylamine hydrochloride. White solid. MS (m/e): 423.3 (M+H)$^+$.

Example 164

4-Fluoro-1-(2-fluoro-4-(methylcarbamoyl)benzyl)-N-(tetrahydro-2H-pyran-4-yl)-1H-indole-3-carboxamide

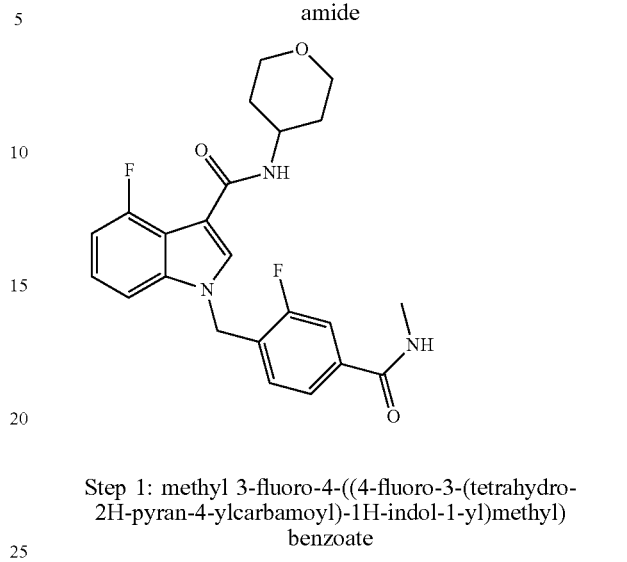

Step 1: methyl 3-fluoro-4-((4-fluoro-3-(tetrahydro-2H-pyran-4-ylcarbamoyl)-1H-indol-1-yl)methyl)benzoate The title compound was obtained in analogy to the procedure described in example 26, reacting 4-fluoro-N-(tetrahydro-2H-pyran-4-yl)-1H-indole-3-carboxamide (example A.8) and methyl 4-(bromomethyl)-3-fluorobenzoate (CAS 128577-47-9). Off-white solid. MS (m/e): 429.3 (M+H)$^+$.

Step 2: 4-Fluoro-1-(2-fluoro-4-(methylcarbamoyl)benzyl)-N-(tetrahydro-2H-pyran-4-yl)-1H-indole-3-carboxamide The title compound was obtained in analogy to the procedure described in example 86, reacting methyl 3-fluoro-4-((4-fluoro-3-(tetrahydro-2H-pyran-4-ylcarbamoyl)-1H-indol-1-yl)methyl)benzoate and methylamine hydrochloride. White solid. MS (m/e): 428.3 (M+H)$^+$.

Examples 165 to 168

In analogy to example 1, examples 165 to 168 of the following table were prepared by coupling an acid derivative with an amine.

| Example No. | Structure | Systematic Name | Starting materials | MW found (MH$^+$) |
|---|---|---|---|---|
| 165 | ![structure] | N-(2,2-difluorocyclohexyl)-4-fluoro-1-(3-fluoro-4-(methy7lcarbamoyl)benzyl)-1H-indole-3-carboxamide | 4-Fluoro-1-(3-fluoro-4-(methylcarbamoyl)benzyl)-1H-indole-3-carboxylic acid (example A.26) and 2,2-difluorocyclohexan-1-amine | 462.2 |

-continued

| Example No. | Structure | Systematic Name | Starting materials | MW found (MH+) |
|---|---|---|---|---|
| 166 | 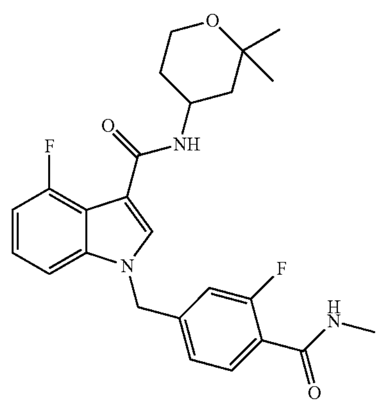 [SMILES: CNC(=O)c1ccc(Cn2cc(C(=O)NC3CCOC(C)(C)C3)c3c(F)cccc32)cc1F] | N-(2,2-dimethyltetrahydro-2H-pyran-4-yl)-4-fluoro-1-(3-fluoro-4-(methylcarbamoyl)benzyl)-1H-indole-3-carboxamide | 4-Fluoro-1-(3-fluoro-4-(methylcarbamoyl)benzyl)-1H-indole-3-carboxylic acid (example A.26) and 2,2-dimethyloxan-4-amine | 456.2 |
| 167 | 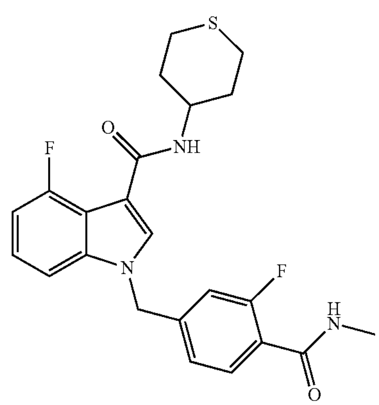 [SMILES: CNC(=O)c1ccc(Cn2cc(C(=O)NC3CCSCC3)c3c(F)cccc32)cc1F] | 4-fluoro-1-(3-fluoro-4-(methylcarbamoyl)benzyl)-N-(tetrahydro-2H-thiopyran-4-yl)-1H-indole-3-carboxamide | 4-FLuoro-1-(3-4-(methylcarbamoyl)benzyl)-1H-indole-3-carboxylic acid (example A.26) and thian-4-amine | 444.2 |
| 168 | 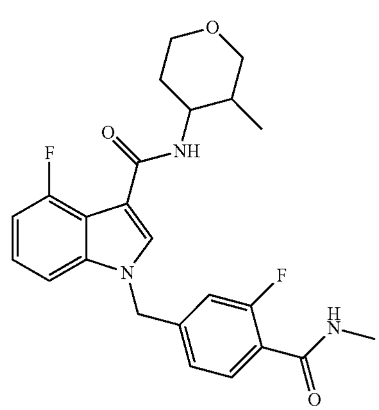 [SMILES: CNC(=O)c1ccc(Cn2cc(C(=O)NC3CCOCC3C)c3c(F)cccc32)cc1F] | 4-fluoro-1-(3-fluoro-4-(methylcarbamoyl)benzyl)-N-(3-methyltetrahydro-2H-pyran-4-yl)-1H-indole-3-carboxamide | 4-FLuoro-1-(3-fluoro-4-(methylcarbamoyl)benzyl)-1H-indole-3-carboxylic acid (example A.26) and 3-methyloxan-4-amine | 442.3 |

The invention claimed is:

1. A compound of formula I

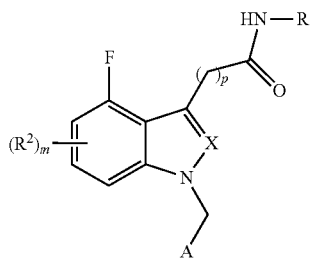

wherein
A is

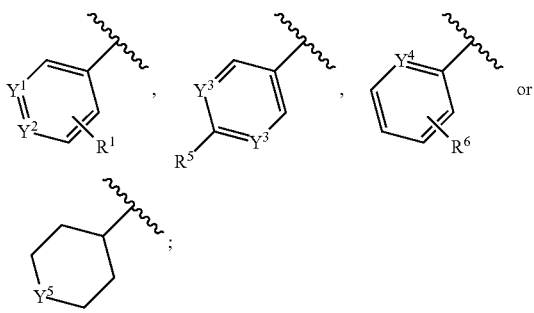

R is lower alkyl, —(CH$_2$)$_z$—C$_{3-7}$-cycloalkyl or —(CH$_2$)$_z$—C$_{4-6}$-heterocycloalkyl, which are optionally substituted by one to tree hydroxy, lower alkyl, lower alkoxy or halogen, or is (endo)-7-oxabicyclo[2.2.1]heptan-2-yl;
X is CH or N;
Y$^1$ is CR$^3$ or N;
Y$^2$ is CR$^4$; or
or Y$^1$ and Y$^2$ may form together with the carbon atoms to which they are attach

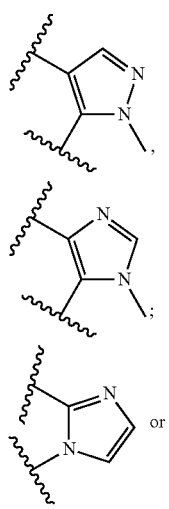

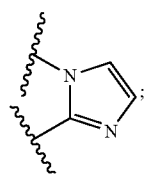

Y$^3$ is N;
Y$^4$ is N;
Y$^5$ is NR$^7$;
R$^1$ is hydrogen or halogen;
R$^2$ is hydrogen, halogen, cycloalkyl, lower alkyl or lower alkoxy;
R$^3$ is hydrogen, halogen,

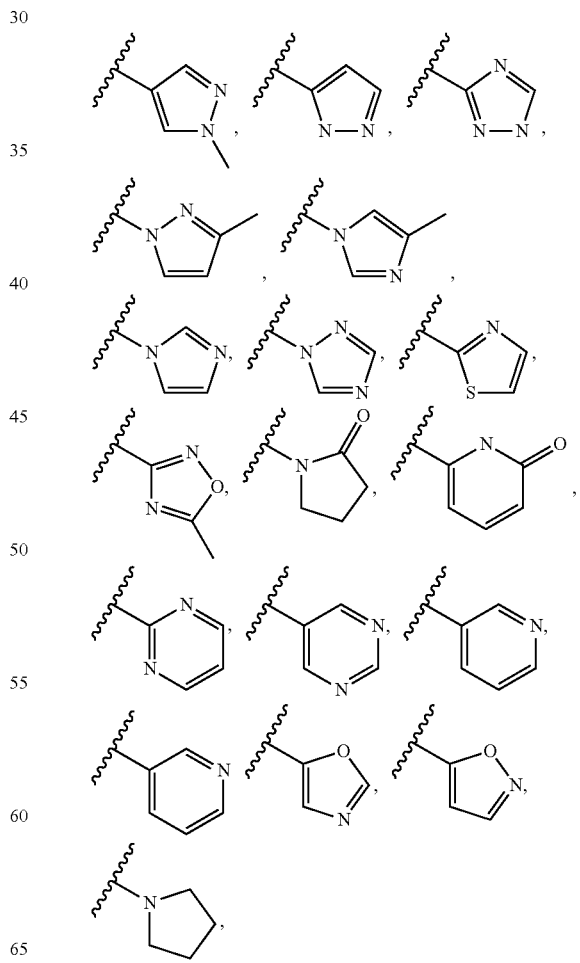

CN, —C(O)NH$_2$, —C(O)NHCH$_3$ or —C(O)N(CH$_3$)$_2$;
R$^4$ is hydrogen, a 5 or 6 membered heteroaryl or heterocyclyl group, selected from the group consisting of or is phenyl, —C(O)NH₂, —CH₂C(O)NH₂, —C(O)NHCH₃, —C(O)NH-cycloalkyl, —C(O)N(CH₃)₂, —NHC(O)O-lower alkyl, CN, lower alkoxy, lower alkoxy substituted by halogen, halogen or S(O)₂CH₃;

R⁵ is phenyl;
R⁶ is phenyl or thiazol-2-yl;
R⁷ is pyridin-2-yl or pyrimidin-4-yl;
p is 0 or 1;
m is 1, 2 or 3;
z is 0 or 1;
or a pharmaceutically acceptable acid addition salt, a racemic mixture or its corresponding enantiomer and/or optical isomers thereof.

2. A compound of formula IA according to claim 1

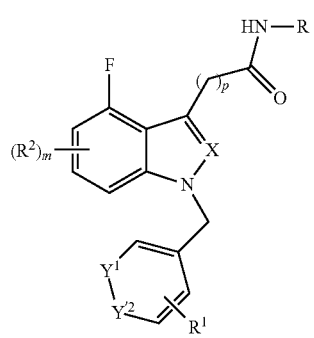

wherein
R is lower alkyl, —(CH₂)_z—C₃₋₇-cycloalkyl or —(CH₂)_z—C₄₋₆-heterocycloalkyl, which are optionally substituted by one to three hydroxy, lower alkyl, lower alkoxy or halogen, or is (endo)-7-oxabicyclo[2.2.1]heptan-2-yl;
X is CH or N;
Y¹ is CR³ or N;
Y² is CR⁴; or
or Y¹ and Y² may form together with the carbon atoms to which they are attach

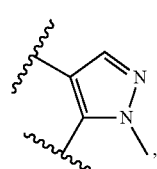

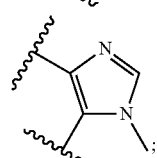

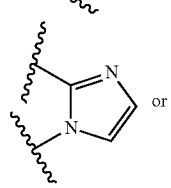 or

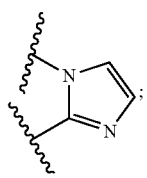

R¹ is hydrogen or halogen;
R² is hydrogen, halogen, cycloalkyl, lower alkyl or lower alkoxy;
R³ is hydrogen, halogen,

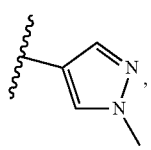 [SMILES: *c1cnn(C)c1]

CN, —C(O)NH₂, —C(O)NHCH₃ or —C(O)N(CH₃)₂;
R⁴ is hydrogen, a 5 or 6 membered heteroaryl or heterocyclyl group, selected from the group consisting of

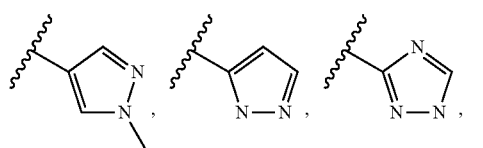

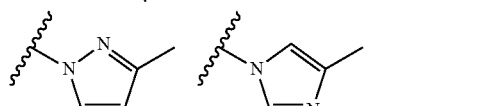

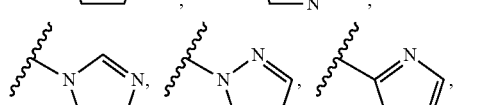

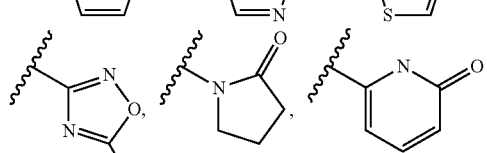

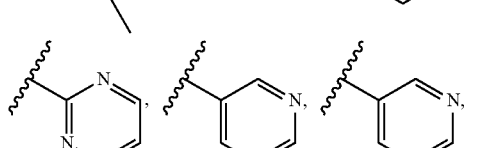

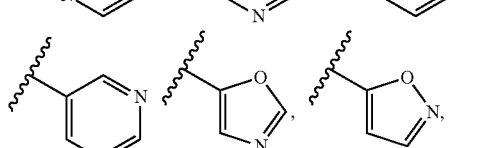

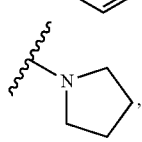

or is phenyl, —C(O)NH₂, —CH₂C(O)NH₂, —C(O)NHCH₃, —C(O)NH-cycloalkyl, —C(O)N(CH₃)₂, —NHC(O)O-lower alkyl, CN, lower alkoxy, lower alkoxy substituted by halogen, halogen or S(O)$_2$CH$_3$;

p is 0 or 1;

m is 1, 2 or 3;

z is 0 or 1;

or a pharmaceutically acceptable acid addition salt, a racemic mixture or its corresponding enantiomer and/or optical isomers thereof.

3. A compound of formula IA according to claim 2, wherein the compound is selected from the group consisting of:

- 4-fluoro-1-(2-fluoro-4-(1-methyl-1H-pyrazol-4-yl)benzyl)-N-((1S,2S)-2-hydroxycyclohexyl)-1H-indole-3-carboxamide;
- 4-fluoro-1-(2-fluoro-4-(1-methyl-1H-pyrazol-4-yl)benzyl)-N-((1R,2R)-2-hydroxycyclohexyl)-1H-indole-3-carboxamide;
- 4-fluoro-1-(2-fluoro-4-(1-methyl-1H-pyrazol-4-yl)benzyl)-N-((1S,2S)-2-hydroxycyclohexyl)-1H-indazole-3-carboxamide;
- 4-fluoro-1-(2-fluoro-4-(1-methyl-1H-pyrazol-4-yl)benzyl)-N-((1R,2R)-2-hydroxycyclohexyl)-1H-indazole-3-carboxamide;
- 4,6-difluoro-1-(2-fluoro-4-(1-methyl-1H-pyrazol-4-yl)benzyl)-N-((1S,2S)-2-hydroxycyclohexyl)-1H-indole-3-carboxamide;
- 4-fluoro-1-(2-fluoro-4-(1-methyl-1H-pyrazol-4-yl)benzyl)-N-((3RS,4RS)-3-hydroxytetrahydro-2H-pyran-4-yl)-1H-indole-3-carboxamide;
- 4-fluoro-1-(2-fluoro-4-(1-methyl-1H-pyrazol-4-yl)benzyl)-N-((3RS,4 SR)-3-hydroxytetrahydro-2H-pyran-4-yl)-1H-indazole-3-carboxamide;
- 4-fluoro-N-[(3 S,4R)-4-methoxyoxolan-3-yl]-1-[[4-(1-methylpyrazol-4-yl)phenyl]methyl]indole-3-carboxamide;
- N-(3,3-difluorocyclobutyl)-4-fluoro-1-(4-(1-methyl-1H-pyrazol-4-yl)benzyl)-1H-indole-3-carboxamide;
- (R)-4-fluoro-1-(4-(1-methyl-1H-pyrazol-4-yl)benzyl)-N-((tetrahydrofuran-2-yl)methyl)-1H-indole-3-carboxamide;
- N-cyclobutyl-4-fluoro-1-(4-(1-methyl-1H-pyrazol-4-yl)benzyl)-1H-indole-3-carboxamide;
- 4-fluoro-1-(4-(1-methyl-1H-pyrazol-4-yl)benzyl)-N-(tetrahydro-2H-pyran-3-yl)-1H-indole-3-carboxamide;
- 4-fluoro-1-(4-(1-methyl-1H-pyrazol-4-yl)benzyl)-N-(oxetan-3-ylmethyl)-1H-indole-3-carboxamide;
- 4-fluoro-1-(4-(1-methyl-1H-pyrazol-4-yl)benzyl)-N-(oxetan-2-ylmethyl)-1H-indole-3-carboxamide;
- 1-(4-carbamoylbenzyl)-4-fluoro-N-((3RS,4SR)-3-hydroxytetrahydro-2H-pyran-4-yl)-1H-indole-3-carboxamide;
- 1-(4-cyanobenzyl)-4-fluoro-N-((3RS,4 SR)-3-hydroxytetrahydro-2H-pyran-4-yl)-1H-indole-3-carboxamide;
- 4-fluoro-1-(2-fluoro-4-(1-methyl-1H-pyrazol-4-yl)benzyl)-N-((1S,2S)-2-hydroxycyclopentyl)-1H-indole-3-carboxamide;
- 4-fluoro-1-(2-fluoro-4-(1-methyl-1H-pyrazol-4-yl)benzyl)-N-((1 SR,2 SR)-2-hydroxy-2-methylcyclohexyl)-1H-indole-3-carboxamide;
- 4-fluoro-1-(2-fluoro-4-(1-methyl-1H-pyrazol-4-yl)benzyl)-N-(tetrahydro-2H-pyran-3-yl)-1H-indole-3-carboxamide;
- N-cyclohexyl-4-fluoro-1-(2-fluoro-4-(1-methyl-1H-pyrazol-4-yl)benzyl)-1H-indole-3-carboxamide;
- 4-fluoro-1-(2-fluoro-4-(1-methyl-1H-pyrazol-4-yl)benzyl)-N-((3 S,4 S)-4-hydroxytetrahydro-2H-pyran-3-yl)-1H-indole-3-carboxamide;
- 4-fluoro-1-(2-fluoro-4-(1-methyl-1H-pyrazol-4-yl)benzyl)-N-(tetrahydro-2H-pyran-4-yl)-1H-indole-3-carboxamide;
- 4-fluoro-1-(2-fluoro-4-(1-methyl-1H-pyrazol-4-yl)benzyl)-N-((1 SR,2RS)-2-hydroxy-2-methylcyclohexyl)-1H-indole-3-carboxamide;
- 4-fluoro-1-(2-fluoro-4-(1-methyl-1H-pyrazol-4-yl)benzyl)-N-((1S,2R)-2-hydroxycyclopentyl)-1H-indole-3-carboxamide;
- N-(2,2-difluorocyclohexyl)-4-fluoro-1-(2-fluoro-4-(1-methyl-1H-pyrazol-4-yl)benzyl)-1H-indole-3-carboxamide;
- 4,5,6,7-tetrafluoro-1-(2-fluoro-4-(1-methyl-1H-pyrazol-4-yl)benzyl)-N-((1S,2S)-2-hydroxycyclohexyl)-1H-indole-3-carboxamide;
- 4,5,6,7-tetrafluoro-N-((1S,2S)-2-hydroxycyclohexyl)-1-((6-(1-methyl-1H-pyrazol-4-yl)pyridine-3-yl)methyl)-1H-indole-3-carboxamide;
- 4-fluoro-1-(2-fluoro-4-methoxybenzyl)-N-((1S,2S)-2-hydroxycyclohexyl)-1H-indole-3-carboxamide;
- 1-(4-(difluoromethoxy)benzyl)-4-fluoro-N-((1S,2S)-2-hydroxycyclohexyl)-1H-indole-3-carboxamide;
- 4-fluoro-N-((1S,2S)-2-hydroxycyclohexyl)-1-((6-(1-methyl-1H-pyrazol-4-yl)pyridine-3-yl)methyl)-1H-indole-3-carboxamide;
- 4-fluoro-N-((1S,2S)-2-hydroxycyclohexyl)-1-(4-methoxybenzyl)-1H-indole-3-carboxamide;
- 1-(4-cyanobenzyl)-4-fluoro-N-((1S,2S)-2-hydroxycyclohexyl)-1H-indole-3-carboxamide;
- 4-fluoro-1-(3-fluoro-4-methoxybenzyl)-N-((1S,2S)-2-hydroxycyclohexyl)-1H-indole-3-carboxamide;
- 4-fluoro-N-((1S,2S)-2-hydroxycyclohexyl)-1-(4-(trifluoromethoxy)benzyl)-1H-indole-3-carboxamide;
- 4-fluoro-N-((1S,2S)-2-hydroxycyclohexyl)-1-(3-(1-methyl-1H-pyrazol-4-yl)benzyl)-1H-indole-3-carboxamide;
- 4-fluoro-N-((1S,2S)-2-hydroxycyclohexyl)-1-(4-(4-methyl-1H-imidazol-1-yl)benzyl)-1H-indole-3-carboxamide;
- 4-fluoro-N-((1S,2S)-2-hydroxycyclohexyl)-1-((1-methyl-1H-indazol-5-yl)methyl)-1H-indole-3-carboxamide;
- 1-(4-chlorobenzyl)-4-fluoro-N-((1S,2S)-2-hydroxycyclohexyl)-1H-indole-3-carboxamide;
- 1-(3-chlorobenzyl)-4-fluoro-N-((1S,2S)-2-hydroxycyclohexyl)-1H-indole-3-carboxamide;
- 1-(3-cyanobenzyl)-4-fluoro-N-((1S,2S)-2-hydroxycyclohexyl)-1H-indole-3-carboxamide;
- 1-(3,4-difluorobenzyl)-4-fluoro-N-((1S,2S)-2-hydroxycyclohexyl)-1H-indole-3-carboxamide;
- 4-fluoro-1-(4-fluorobenzyl)-N-((1S,2S)-2-hydroxycyclohexyl)-1H-indole-3-carboxamide;
- 1-(3,5-difluorobenzyl)-4-fluoro-N-((1S,2S)-2-hydroxycyclohexyl)-1H-indole-3-carboxamide;
- 4-fluoro-N-((1S,2S)-2-hydroxycyclohexyl)-1-(4-(1-methyl-1H-pyrazol-4-yl)benzyl)-1H-indole-3-carboxamide;
- 4-fluoro-1-(2-fluoro-4-(1-methyl-1H-pyrazol-4-yl)benzyl)-N-((1S,2S)-2-hydroxycyclohexyl)-7-methyl-1H-indole-3-carboxamide;
- 4-fluoro-N-((1S,2S)-2-hydroxycyclohexyl)-7-methyl-1-(4-(1-methyl-1H-pyrazol-4-yl)benzyl)-1H-indole-3-carboxamide;

1-benzyl-4-fluoro-N-((1S,2S)-2-hydroxycyclohexyl)-1H-indole-3-carboxamide;
4-fluoro-7-methyl-1-(4-(1-methyl-1H-pyrazol-4-yl)benzyl)-N-(tetrahydro-2H-pyran-3-yl)-1H-indole-3-carboxamide;
4-fluoro-7-methyl-1-(4-(1-methyl-1H-pyrazol-4-yl)benzyl)-N-(tetrahydro-2H-pyran-4-yl)-1H-indole-3-carboxamide;
4-fluoro-N-((1S,2S)-2-hydroxycyclohexyl)-1-(4-(3-methyl-1H-pyrazol-1-yl)benzyl)-1H-indole-3-carboxamide;
4-fluoro-N-((3R,4S) or (3 S,4R)-3-hydroxytetrahydro-2H-pyran-4-yl)-1-(4-(4-methyl-1H-imidazol-1-yl)benzyl)-1H-indole-3-carboxamide;
4-fluoro-N-((3R,4S) or (3 S,4R)-3-hydroxytetrahydro-2H-pyran-4-yl)-1-((1-methyl-1H-indazol-5-yl)methyl)-1H-indole-3-carboxamide;
4,5,6,7-tetrafluoro-N-((1S,2S)-2-hydroxycyclohexyl)-1-(4-(1-methyl-1H-pyrazol-4-yl)benzyl)-1H-indole-3-carboxamide;
1-(4-cyanobenzyl)-4-fluoro-N-((3R,4 S) or (3 S,4R)-3-hydroxytetrahydro-2H-pyran-4-yl)-1H-indole-3-carboxamide;
4-fluoro-N-((3R,4S) or (3 S,4R)-3-hydroxytetrahydro-2H-pyran-4-yl)-1-(4-(1-methyl-1H-pyrazol-4-yl)benzyl)-1H-indole-3-carboxamide;
4-fluoro-N-((1S,2S)-2-hydroxycyclohexyl)-1-((1-methyl-1H-benzo[d]yridine-5-yl)methyl)-1H-indole-3-carboxamide;
4,5-difluoro-N-((1S,2S)-2-hydroxycyclohexyl)-1-(4-(1-methyl-1H-pyrazol-4-yl)benzyl)-1H-indole-3-carboxamide;
4,5-difluoro-N-((1S,2S)-2-hydroxycyclohexyl)-1-((6-(1-methyl-1H-pyrazol-4-yl)pyridine-3-yl)methyl)-1H-indole-3-carboxamide;
4-fluoro-N-((1S,2S)-2-hydroxycyclohexyl)-1-(4-(methylcarbamoyl)benzyl)-1H-indole-3-carboxamide;
4,5-difluoro-N-((1S,2S)-2-hydroxycyclohexyl)-1-(4-(4-methyl-1H-imidazol-1-yl)benzyl)-1H-indole-3-carboxamide;
4,5-difluoro-N-((1S,2S)-2-hydroxycyclohexyl)-1-(4-(3-methyl-1H-pyrazol-1-yl)benzyl)-1H-indole-3-carboxamide;
4,5,6,7-Tetrafluoro-N-((3 S,4R) or (3R,4S))-3-hydroxytetrahydro-2H-pyran-4-yl)-1-(4-(1-methyl-1H-pyrazol-4-yl)benzyl)-1H-indole-3-carboxamide;
4,5,6,7-Tetrafluoro-N-((3R,4 S) or (3 S,4R)-3-hydroxytetrahydro-2H-pyran-4-yl)-1-(4-(1-methyl-1H-pyrazol-4-yl)benzyl)-1H-indole-3-carboxamide;
4,5,6,7-Tetrafluoro-1-(2-fluoro-4-(1-methyl-1H-pyrazol-4-yl)benzyl)-N-((3R,4 S) or (3 S,4R))-3-hydroxytetrahydro-2H-pyran-4-yl)-1H-indole-3-carboxamide;
Fluoro-1-(4-(1-methyl-1H-pyrazol-4-yl)benzyl)-N-(tetrahydro-2H-pyran-4-yl)-1H-indole-3-carboxamide;
4-fluoro-1-((1-methyl-1H-indazol-5-yl)methyl)-N-(tetrahydro-2H-pyran-4-yl)-1H-indole-3-carboxamide;
4-fluoro-1-(4-(4-methyl-1H-imidazol-1-yl)benzyl)-N-(tetrahydro-2H-pyran-4-yl)-1H-indole-3-carboxamide;
4-fluoro-1-((6-(1-methyl-1H-pyrazol-4-yl)yridine-3-yl)methyl)-N-(tetrahydro-2H-pyran-4-yl)-1H-indole-3-carboxamide;
4-fluoro-1-(4-(1-methyl-1H-pyrazol-4-yl)benzyl)-N-(tetrahydro-2H-pyran-4-yl)-1H-indazole-3-carboxamide;
4-fluoro-1-(2-fluoro-4-(1-methyl-1H-pyrazol-4-yl)benzyl)-N-((3 S,4R) or (3R,4 S)-3-hydroxytetrahydro-2H-pyran-4-yl)-1H-indole-3-carboxamide;
4-Fluoro-1-(2-fluoro-4-(1-methyl-1H-pyrazol-4-yl)benzyl)-N-((3R,4 S) or (3 S,4R)-3-hydroxytetrahydro-2H-pyran-4-yl)-1H-indole-3-carboxamide;
4,7-difluoro-1-(2-fluoro-4-(1-methyl-1H-pyrazol-4-yl)benzyl)-N-((1S,2S)-2-hydroxycyclohexyl)-1H-indazole-3-carboxamide;
4,7-difluoro-1-(2-fluoro-4-(1-methyl-1H-pyrazol-4-yl)benzyl)-N-((3R,4 S)-3-hydroxytetrahydro-2H-pyran-4-yl)-1H-indazole-3-carboxamide;
4,7-difluoro-N-((3R,4 S)-3-hydroxytetrahydro-2H-pyran-4-yl)-1-((6-(1-methyl-1H-pyrazol-4-yl)yridine-3-yl)methyl)-1H-indazole-3-carboxamide;
4,7-difluoro-N-((1S,2S)-2-hydroxycyclohexyl)-1-((6-(1-methyl-1H-pyrazol-4-yl)yridine-3-yl)methyl)-1H-indazole-3-carboxamide;
4-fluoro-N-((1S,2S)-2-hydroxycyclohexyl)-1-(4-(methylcarbamoyl)benzyl)-1H-indole-3-carboxamide;
1-(4-carbamoylbenzyl)-4-fluoro-N-((1S,2S)-2-hydroxycyclohexyl)-1H-indole-3-carboxamide;
1-((6-(1H-1,2,4-triazol-1-yl)yridine-3-yl)methyl)-4-fluoro-N-((3R,4 S)-3-hydroxytetrahydro-2H-pyran-4-yl)-1H-indole-3-carboxamide;
4-fluoro-N-((3R,4S)-3-hydroxytetrahydro-2H-pyran-4-yl)-1-(4-(thiazol-2-yl)benzyl)-1H-indole-3-carboxamide;
1-(4-(2-amino-2-oxoethyl)benzyl)-4-fluoro-N-((1S,2S)-2-hydroxycyclohexyl)-1H-indole-3-carboxamide;
1-(3-carbamoylbenzyl)-4-fluoro-N-((1S,2S)-2-hydroxycyclohexyl)-1H-indole-3-carboxamide;
4-fluoro-N-((1S,2S)-2-hydroxycyclohexyl)-1-(4-(methylsulfonyl)benzyl)-1H-indole-3-carboxamide;
4-fluoro-N-((3R,4 S)-3-hydroxytetrahydro-2H-pyran-4-yl)-1-(4-(5-methyl-1,2,4-oxadiazol-3-yl)benzyl)-1H-indole-3-carboxamide;
4-fluoro-N-((3R,4 S)-3-hydroxytetrahydro-2H-pyran-4-yl)-1-(4-(2-oxopyrrolidin-1-yl)benzyl)-1H-indole-3-carboxamide;
ethyl 4-((4-fluoro-3-((1S,2S)-2-hydroxycyclohexyl carbamoyl)-1H-indol-1-yl)methyl)phenylcarbamate;
4-fluoro-1-(2-fluoro-4-(methylcarbamoyl)benzyl)-N-((1S,2S)-2-hydroxycyclohexyl)-1H-indole-3-carboxamide;
4-fluoro-N-((1S,2S)-2-hydroxycyclohexyl)-1-((6-(methylcarbamoyl)pyridin-3-yl)methyl)-1H-indole-3-carboxamide;
4-fluoro-1-(3-fluoro-4-(methylcarbamoyl)benzyl)-N-((1S,2S)-2-hydroxycyclohexyl)-1H-indole-3-carboxamide;
4-fluoro-N-((1S,2S)-2-hydroxycyclohexyl)-1-(3-(methylcarbamoyl)benzyl)-1H-indole-3-carboxamide;
1-(3-(dimethylcarbamoyl)benzyl)-4-fluoro-N-((1S,2S)-2-hydroxycyclohexyl)-1H-indole-3-carboxamide;
4-fluoro-1-(2-fluoro-4-(methylcarbamoyl)benzyl)-N-((1S,2S)-2-hydroxycyclohexyl)-1H-indole-3-carboxamide;
2-[4-fluoro-1-[[2-fluoro-4-(1-methylpyrazol-4-yl)phenyl]methyl]indol-3-yl]-N-[(3R,4S)-3-hydroxyoxan-4-yl]acetamide;
2-(4-fluoro-1-(2-fluoro-4-(1-methyl-1H-pyrazol-4-yl)benzyl)-1H-indol-3-yl)-N-((1S,2S)-2-hydroxycyclohexyl)acetamide;
4,7-difluoro-1-((1-methyl-1H-indazol-5-yl)methyl)-N-(tetrahydro-2H-pyran-4-yl)-1H-indole-3-carboxamide;
4,7-difluoro-1-(4-(1-methyl-1H-pyrazol-4-yl)benzyl)-N-(tetrahydro-2H-pyran-4-yl)-1H-indole-3-carboxamide;

4,7-difluoro-1-(2-fluoro-4-(1-methyl-1H-pyrazol-4-yl)
benzyl)-N-(tetrahydro-2H-pyran-4-yl)-1H-indole-3-
carboxamide;
4,7-difluoro-1-(2-fluoro-4-(1-methyl-1H-pyrazol-4-yl)
benzyl)-N-(tetrahydro-2H-pyran-4-yl)-1H-indole-3-
carboxamide;
4-((4-fluoro-3-(2-((3R,4 S)-3-hydroxytetrahydro-2H-
pyran-4-ylamino)-2-oxoethyl)-1H-indol-1-yl)methyl)-
N-methylbenzamide;
4-((4-fluoro-3-(2-((1S,2S)-2-hydroxycyclohexyl amino)-
2-oxoethyl)-1H-indol-1-yl)methyl)-N-methylbenz-
amide;
N-((1R,2S)-3,3-difluoro-2-hydroxycyclohexyl)-4-fluoro-
1-(4-(1-methyl-1H-pyrazol-4-yl)benzyl)-1H-indole-3-
carboxamide;
N-((1S,2R)-3,3-difluoro-2-hydroxycyclohexyl)-4-fluoro-
1-(4-(1-methyl-1H-pyrazol-4-yl)benzyl)-1H-indole-3-
carboxamide;
N-((1R,2S)-3,3-difluoro-2-hydroxycyclohexyl)-4-fluoro-
1-(2-fluoro-4-(1-methyl-1H-pyrazol-4-yl)benzyl)-1H-
indole-3-carboxamide;
N-((1S,2R)-3,3-difluoro-2-hydroxycyclohexyl)-4-fluoro-
1-(2-fluoro-4-(1-methyl-1H-pyrazol-4-yl)benzyl)-1H-
indole-3-carboxamide;
N-((endo)-7-oxabicyclo[2.2.1]heptan-2-yl)-4-fluoro-1-
(2-fluoro-4-(1-methyl-1H-pyrazol-4-yl)benzyl)-1H-in-
dole-3-carboxamide;
7-cyclopropyl-4-fluoro-N-((1S,2S)-2-hydroxycyclo-
hexyl)-1-(4-(1-methyl-1H-pyrazol-4-yl)benzyl)-1H-in-
dole-3-carboxamide;
7-cyclopropyl-4-fluoro-N-((3R,4 S)-3-hydroxytetra-
hydro-2H-pyran-4-yl)-1-(4-(1-methyl-1H-pyrazol-4-
yl)benzyl)-1H-indole-3-carboxamide;
7-cyclopropyl-4-fluoro-1-(2-fluoro-4-(1-methyl-1H-
pyrazol-4-yl)benzyl)-N-((3R,4 S)-3-hydroxytetra-
hydro-2H-pyran-4-yl)-1H-indole-3-carboxamide;
7-ethyl-4-fluoro-1-(4-(1-methyl-1H-pyrazol-4-yl)ben-
zyl)-N-(tetrahydro-2H-pyran-4-yl)-1H-indole-3-car-
boxamide;
7-ethyl-4-fluoro-N-((3R,4S)-3-hydroxytetrahydro-2H-
pyran-4-yl)-1-(4-(1-methyl-1H-pyrazol-4-yl)benzyl)-
1H-indole-3-carboxamide;
4-fluoro-N-methyl-1-[[4-(methylcarbamoyl)phenyl]
methyl]indole-3-carboxamide;
N-cyclopropyl-4-fluoro-1-[[4-(methylcarbamoyl)phenyl]
methyl]indole-3-carboxamide;
N-cyclobutyl-4-fluoro-1-[[4-(methylcarbamoyl)phenyl]
methyl]indole-3-carboxamide;
N-cyclopentyl-4-fluoro-1-[[4-(methylcarbamoyl)phenyl]
methyl]indole-3-carboxamide;
N-cyclohexyl-4-fluoro-1-[[4-(methylcarbamoyl)phenyl]
methyl]indole-3-carboxamide;
N-cycloheptyl-4-fluoro-1-[[4-(methylcarbamoyl)phenyl]
methyl]indole-3-carboxamide;
N-(cyclopropylmethyl)-4-fluoro-1-[[4-(methylcarbam-
oyl)phenyl]methyl]indole-3-carboxamide;
N-(4,4-difluorocyclohexyl)-4-fluoro-1-[[4-(methylcar-
bamoyl)phenyl]methyl]indole-3-carboxamide;
N-(3,3-difluorocyclohexyl)-4-fluoro-1-[[4-(methylcar-
bamoyl)phenyl]methyl]indole-3-carboxamide;
N-(2,2-dimethyloxan-4-yl)-4-fluoro-1-[[4-(methylcar-
bamoyl)phenyl]methyl]indole-3-carboxamide;
N-(2,2-difluorocyclohexyl)-4-fluoro-1-[[4-(methylcar-
bamoyl)phenyl]methyl]indole-3-carboxamide;
4-fluoro-N-(2-fluorocyclohexyl)-1-[[4-(methylcarbam-
oyl)phenyl]methyl]indole-3-carboxamide;
4-fluoro-1-[[4-(methylcarbamoyl)phenyl]methyl]-N-
(oxan-3-yl)indole-3-carboxamide;
4-fluoro-1-[[4-(methylcarbamoyl)phenyl]methyl]-N-(4-
methyloxan-4-yl)indole-3-carboxamide;
4-fluoro-1-[[4-(methylcarbamoyl)phenyl]methyl]-N-
(thian-4-yl)indole-3-carboxamide;
N-(1,1-dioxothian-4-yl)-4-fluoro-1-[[4-(methylcarbam-
oyl)phenyl]methyl]indole-3-carboxamide;
4-fluoro-1-[[4-(methylcarbamoyl)phenyl]methyl]-N-(3-
methyloxan-4-yl)indole-3-carboxamide;
4-fluoro-1-[[4-(methylcarbamoyl)phenyl]methyl]-N-(2-
methyloxan-4-yl)indole-3-carboxamide;
7-ethyl-4-fluoro-1-((1-methyl-1H-indazol-5-yl)methyl)-
N-(tetrahydro-2H-pyran-4-yl)-1H-indole-3-carboxam-
ide;
4-fluoro-1-(3-fluoro-4-(methylcarbamoyl)benzyl)-N-(2-
fluorocyclohexyl)-1H-indole-3-carboxamide;
N-(3,3-difluorocyclohexyl)-4-fluoro-1-(3-fluoro-4-
(methylcarbamoyl)benzyl)-1H-indole-3-carboxamide;
4-fluoro-N-((1S,2S)-2-hydroxycyclohexyl)-1-((6-phe-
nylpyridin-3-yl)methyl)-1H-indole-3-carboxamide;
4-fluoro-1-(4-(methylcarbamoyl)benzyl)-N-(tetrahydro-
2H-pyran-4-yl)-1H-indole-3-carboxamide;
4-fluoro-1-(2-fluoro-4-(1-methyl-1H-pyrazol-4-yl)ben-
zyl)-7-methyl-N-(tetrahydro-2H-pyran-4-yl)-1H-in-
dole-3-carboxamide;
4-fluoro-7-methyl-1-((1-methyl-1H-indazol-5-yl)
methyl)-N-(tetrahydro-2H-pyran-4-yl)-1H-indole-3-
carboxamide;
4-fluoro-N-((1S,2S)-2-hydroxycyclohexyl)-1-(4-(pyrimi-
din-2-yl)benzyl)-1H-indole-3-carboxamide;
4-fluoro-N-((1S,2S)-2-hydroxycyclohexyl)-1-(4-(oxazol-
5-yl)benzyl)-1H-indole-3-carboxamide;
4-fluoro-N-((1S,2S)-2-hydroxycyclohexyl)-1-(4-(isox-
azol-5-yl)benzyl)-1H-indole-3-carboxamide;
1-((6-(1H-imidazol-1-yl)pyridin-3-yl)methyl)-4-fluoro-
N-((1S,2S)-2-hydroxycyclohexyl)-1H-indole-3-car-
boxamide;
4-fluoro-N-((1S,2S)-2-hydroxycyclohexyl)-1-(imidazo
[1,2-a]pyridin-7-ylmethyl)-1H-indole-3-carboxamide;
4-fluoro-N-((1S,2S)-2-hydroxycyclohexyl)-1-(imidazo
[1,2-a]pyridin-6-ylmethyl)-1H-indole-3-carboxamide;
1-(4-(cyclopropylcarbamoyl)benzyl)-4-fluoro-N-((1S,
2S)-2-hydroxycyclohexyl)-1H-indole-3-carboxamide;
4-fluoro-1-((6-(methylcarbamoyl)pyridin-3-yl)methyl)-
N-(tetrahydro-2H-pyran-4-yl)-1H-indole-3-carboxam-
ide;
4-fluoro-N-((1S,2S)-2-hydroxycyclohexyl)-7-methoxy-
1-(4-(1-methyl-1H-pyrazol-4-yl)benzyl)-1H-indole-3-
carboxamide;
4-fluoro-1-(2-fluoro-4-(1-methyl-1H-pyrazol-4-yl)ben-
zyl)-N-((1S,2S)-2-hydroxycyclohexyl)-7-methoxy-
1H-indole-3-carboxamide;
4-fluoro-N-((3R,4 S)-3-hydroxytetrahydro-2H-pyran-4-
yl)-7-methoxy-1-(4-(1-methyl-1H-pyrazol-4-yl)ben-
zyl)-1H-indole-3-carboxamide;
4-fluoro-7-methoxy-1-(4-(1-methyl-1H-pyrazol-4-yl)
benzyl)-N-(tetrahydro-2H-pyran-4-yl)-1H-indole-3-
carboxamide;
4-fluoro-1-(2-fluoro-4-(1-methyl-1H-pyrazol-4-yl)ben-
zyl)-7-methoxy-N-(tetrahydro-2H-pyran-4-yl)-1H-in-
dole-3-carboxamide;
4-fluoro-1-(2-fluoro-4-(1-methyl-1H-pyrazol-4-yl)ben-
zyl)-N-((3R,4 S)-3-hydroxytetrahydro-2H-pyran-4-yl)-
7-methoxy-1H-indole-3-carboxamide;

4-fluoro-7-methoxy-1-((1-methyl-1H-indazol-5-yl) methyl)-N-(tetrahydro-2H-pyran-4-yl)-1H-indole-3-carboxamide;

1-(4-(1H-Pyrazol-5-yl)benzyl)-4-fluoro-N-((1S,2S)-2-hydroxycyclohexyl)-1H-indole-3-carboxamide;

1-(4-(1H-1,2,4-triazol-3-yl)benzyl)-4-fluoro-N-((1S,2S)-2-hydroxycyclohexyl)-1H-indole-3-carboxamide;

1-(4-(1H-1,2,4-triazol-3-yl)benzyl)-4-fluoro-N-(tetrahydro-2H-pyran-4-yl)-1H-indole-3-carboxamide;

4-Fluoro-N-((1S,2S)-2-hydroxycyclohexyl)-1-(4-(pyrimidin-5-yl)benzyl)-1H-indole-3-carboxamide;

4-Fluoro-N-((1S,2S)-2-hydroxycyclohexyl)-1-(4-(pyridin-3-yl)benzyl)-1H-indole-3-carboxamide;

4-fluoro-N-((1S,2S)-2-hydroxycyclohexyl)-1-(4-(pyrrolidin-1-yl)benzyl)-1H-indole-3-carboxamide;

4-fluoro-N-((1S,2S)-2-hydroxycyclohexyl)-1-((6-(pyrrolidin-1-yl)pyridin-3-yl)methyl)-1H-indole-3-carboxamide;

4-Fluoro-1-(3-fluoro-4-(methylcarbamoyl)benzyl)-N-(tetrahydro-2H-pyran-4-yl)-1H-indole-3-carboxamide;

4-Fluoro-1-(2-fluoro-4-(methylcarbamoyl)benzyl)-N-(tetrahydro-2H-pyran-4-yl)-1H-indole-3-carboxamide;

N-(2,2-difluorocyclohexyl)-4-fluoro-1-(3-fluoro-4-(methylcarbamoyl)benzyl)-1H-indole-3-carboxamide;

N-(2,2-dimethyltetrahydro-2H-pyran-4-yl)-4-fluoro-1-(3-fluoro-4-(methylcarbamoyl)benzyl)-1H-indole-3-carboxamide;

4-fluoro-1-(3-fluoro-4-(methylcarbamoyl)benzyl)-N-(tetrahydro-2H-thiopyran-4-yl)-1H-indole-3-carboxamide; and 4-fluoro-1-(3-fluoro-4-(methylcarbamoyl)benzyl)-N-(3-m ethyltetrahydro-2H-pyran-4-yl)-1H-indole-3-carboxamide.

4. A compound of formula IB according to claim 1,

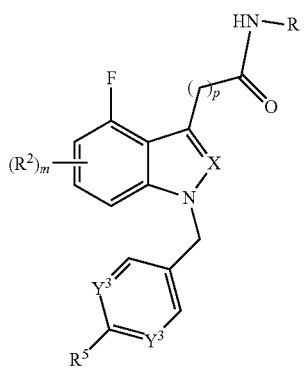

IB wherein
R is lower alkyl, —(CH$_2$)$_z$—C$_{3-7}$-cycloalkyl or —(CH$_2$)$_z$—C$_{4-6}$-heterocycloalkyl, which are optionally substituted by one to tree hydroxy, lower alkyl, lower alkoxy or halogen, or is (endo)-7-oxabicyclo [2.2.1]heptan-2-yl;
X is CH or N;
Y$^3$ is N;
R$^2$ is hydrogen, halogen, cycloalkyl, lower alkyl or lower alkoxy;
R$^5$ is phenyl;
p is 0 or 1;
m is 1, 2 or 3;
z is 0 or 1;

or a pharmaceutically acceptable acid addition salt, a racemic mixture or its corresponding enantiomer and/or optical isomers thereof.

5. A compound of formula IB according to claim 4, wherein compound is:
4-fluoro-N-((1S,2S)-2-hydroxycyclohexyl)-1-((2-phenylpyrimidin-5-yl)methyl)-1H-indole-3-carboxamide.

6. A compound of formula IC according to claim 1

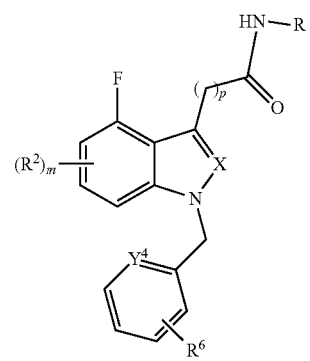

IC wherein
R is lower alkyl, —(CH$_2$)$_z$—C$_{3-7}$-cycloalkyl or —(CH$_2$)$_z$—C$_{4-6}$-heterocycloalkyl, which are optionally substituted by one to tree hydroxy, lower alkyl, lower alkoxy or halogen, or is (endo)-7-oxabicyclo [2.2.1]heptan-2-yl;
X is CH or N;
Y$^4$ is N;
R$^2$ is hydrogen, halogen, cycloalkyl, lower alkyl or lower alkoxy;
p is 0 or 1;
m is 1, 2 or 3;
z is 0 or 1;
or a pharmaceutically acceptable acid addition salt, a racemic mixture or its corresponding enantiomer and/or optical isomers thereof.

7. A compound of formula IC according to claim 6, wherein the compound is:
4-fluoro-N-((1S,2S)-2-hydroxycyclohexyl)-1-((2-phenylpyrimidin-5-yl)methyl)-1H-indole-3-carboxamide, or
4-fluoro-N-((1S,2S)-2-hydroxycyclohexyl)-1-((5-(thiazol-2-yl)pyridin-2-yl)methyl)-1H-indole-3-carboxamide.

8. A compound of formula ID according to claim 1

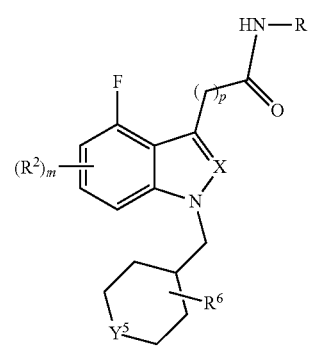

ID wherein

R is lower alkyl, —(CH$_2$)$_z$—C$_{3-7}$-cycloalkyl or —(CH$_2$)$_z$—C$_{4-6}$-heterocycloalkyl, which are optionally substituted by one to tree hydroxy, lower alkyl, lower alkoxy or halogen, or is (endo)-7-oxabicyclo[2.2.1]heptan-2-yl;

X is CH or N;

Y$^5$ is NR$^7$;

R$^2$ is hydrogen, halogen, cycloalkyl, lower alkyl or lower alkoxy;

R$^6$ is phenyl or thiazol-2-yl;

R$^7$ is pyridin-2-yl or pyrimidin-4-yl;

p is 0 or 1;

m is 1, 2 or 3;

z is 0 or 1;

or a pharmaceutically acceptable acid addition salt, a racemic mixture or its corresponding enantiomer and/or optical isomers thereof.

9. A compound of formula ID according to claim 8, selected from the group consisting of:

4-fluoro-N-((3R,4S)-3-hydroxytetrahydro-2H-pyran-4-yl)-1-((1-(pyridin-2-yl)piperidin-4-yl)methyl)-1H-indole-3-carboxamide;

4-fluoro-N-((1S,2S)-2-hydroxycyclohexyl)-1-((1-(pyrimidin-4-yl)piperidin-4-yl)methyl)-1H-indole-3-carboxamide; and 4-Fluoro-N-((1S,2S)-2-hydroxycyclohexyl)-1-((1-(pyridin-2-yl)piperidin-4-yl)methyl)-1H-indole-3-carboxamide.

10. A process for the manufacture of a compound of formula I as defined in claim 1, which process comprises a) reacting a compound of formula

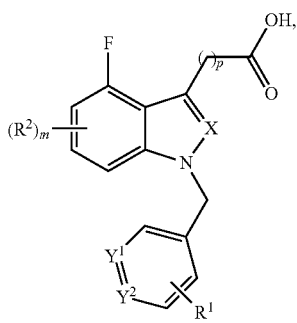

IIA

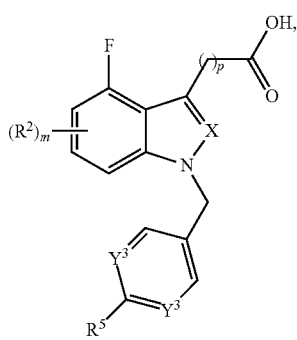

IIB

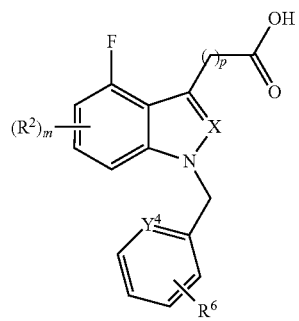

IIC

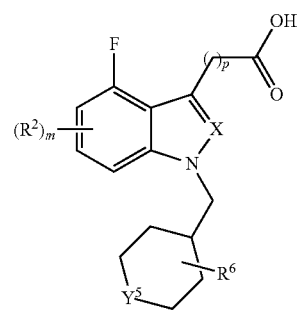

IID with a compound of formula

RNH$_2$ in the presence of BOP (benzotriazol-1-yloxy)tris(dimethylamino)phosphonium hexafluorophosphate or thionyl chloride to yield a compound of formulas

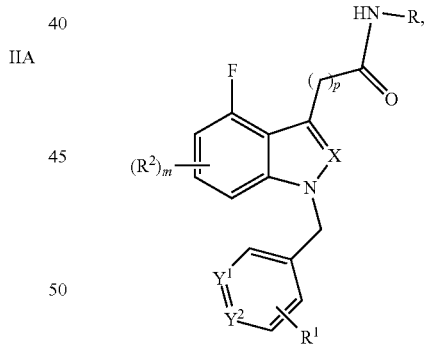

IA

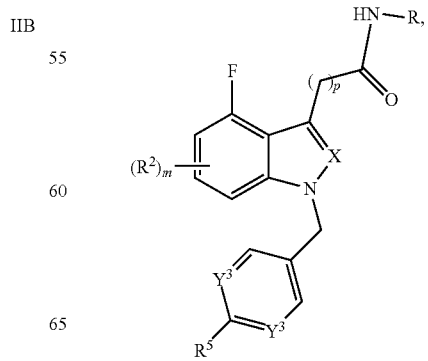

IB

-continued

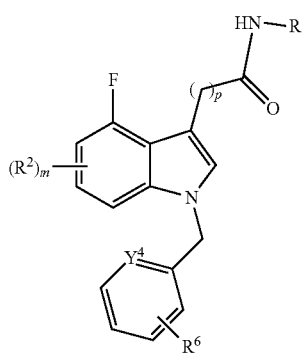

or

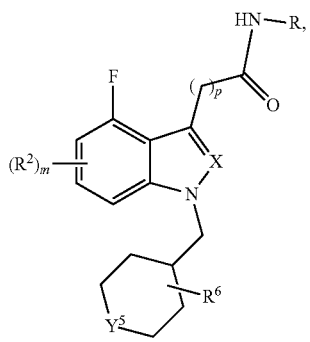

wherein the substituents are as defined in claim 1, or b) reacting a compound of formula

III

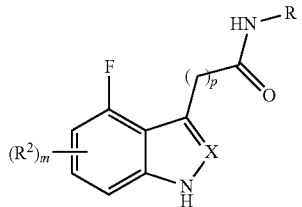

with a compound of formulas

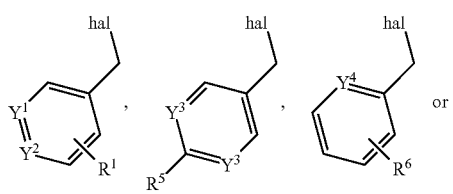

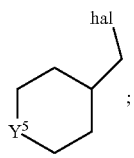

in the presence of base to yield a compound of formulas

IA

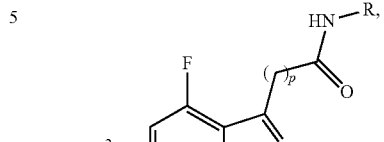

IB

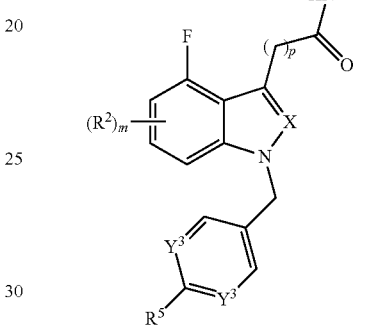

IC

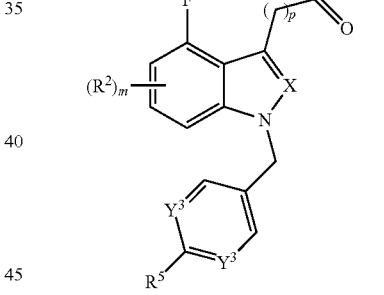

ID

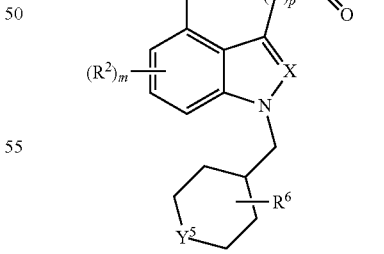

wherein Hal is halogen and the other substituents are as defined in claim 1, and, if desired, converting the compounds obtained into pharmaceutically acceptable acid addition salts.

11. A compound manufactured according a process according to claim 10.

12. A pharmaceutical composition comprising a compound according to claim 1 and a pharmaceutical acceptable carrier and/or adjuvant.

13. A method for the treatment of Alzheimer's disease, cognitive impairment, schizophrenia, pain or sleep disorders, which method comprises administering an effective amount of a compound as defined in claim 1.

\* \* \* \* \*